(12) United States Patent
Fraser et al.

(10) Patent No.: US 6,962,810 B2
(45) Date of Patent: Nov. 8, 2005

(54) METHODS AND COMPOSITIONS FOR TRANSPOSITION USING MINIMAL SEGMENTS OF THE EUKARYOTIC TRANSFORMATION VECTOR PIGGYBAC

(75) Inventors: Malcolm J. Fraser, Granger, IN (US); Xu Li, Notre Dame, IN (US)

(73) Assignee: University of Notre Dame du Lac, Notre Dame, IN (US)

( * ) Notice: Subject to any disclaimer, the term of this patent is extended or adjusted under 35 U.S.C. 154(b) by 360 days.

(21) Appl. No.: 10/001,189

(22) Filed: Oct. 30, 2001

(65) Prior Publication Data

US 2002/0173634 A1 Nov. 21, 2002

Related U.S. Application Data

(60) Provisional application No. 60/244,984, filed on Nov. 1, 2000, and provisional application No. 60/244,667, filed on Oct. 31, 2000.

(51) Int. Cl.$^7$ .................. C12N 15/00; C12N 15/09; C12N 15/63; C12N 15/70; C12N 15/74
(52) U.S. Cl. ............... 435/320.1; 435/455; 435/472; 435/473
(58) Field of Search ................ 435/320.1, 455, 435/472, 473

(56) References Cited

U.S. PATENT DOCUMENTS 6,218,185 B1   4/2001  Shirk et al.
6,551,825 B1 *  4/2003  Shirk et al. .............. 435/348

OTHER PUBLICATIONS

Cary, L.C. et al. (1989) "Transposon Mutagenesis of Baculoviruses: Analysis of Trichoplusia ni Transposon IFP2 Insertions within the FP–Locus of Nuclear Polyhedrosis Viruses." Virology 172:156–169.
Elick, T.A., et al. (1995) "PCR analysis of insertion site specificity, transcription, and structural uniformity of the Lepidopteran transposable element IFP2 in the TN–368 cell genome." Genetica 00:1–13.
Elick, T.A., et al. (1996) "Excision of the piggyBac transposable element in vitro is precise event that is enhanced by the expression of its encoded transposase." Genetica 00:1–100.
Fraser, M.J., et al. (1995) "Assay for Movement of Lipidopteran Transposon IFP2 in Insect Cells Using a Baculovirus Genome as a Target DNA." Virology 211:397–407.
Fraser, M.J. et al. (1996) "Precise excision of TTAA–specific lepidopteran transposons piggyBac (IFP2) and tagalong (TFP3) from the baculovirus genome in cell lines from two species of Lepidoptera." Insect Molecular Biology 5(2):141–151.
Ausubel FM, Brent R, Kingston RE, Moore DD, Seidman JG, Smith JA and Struhl K (1994) Current protocols in molecular biology, John Wiley & Sons, Inc.

Becker HA, Kunze R (1997) Maize Activator transposase has a bipartite DNA binding domain that recognizes subterminal sequences and the terminal inverted repeats, Mol. Gen. Genet. 254(3): pp. 219–230.
Beeman RW, Stauth DM (1997) Rapid cloning of insect transposon insertion junctions using 'universal' PCR, Insect Mol. Biol., 6(1): pp. 83–88.
Berghammer AJ, Klingler M, Wimmer EA (1999) A universal marker for transgenic insects, Nature, 402: pp. 370–371.
Cary LC, Goebel M., Corsaro BG, Wang HG, Rosen E, Fraser MJ Jr (1989) Transposon mutagenesis of baculoviruses: analysis of Trichoplusia ni Transposon IFP2 insertions within the FP–locus of nuclear polyhedrosis viruses, Virology, 172: pp. 156–169.
Elick TA, Bauser CA, Principle NM, Fraser MJ Jr (1996a) PCR analysis of insertion site specificity, transcription, and structural uniformity of the Lepidopteran transposable element IFP2 in the TN–368 cell genome, Genetica., 97(2): pp. 127–139.
Elick TA, Bauser CA, Fraser MJ Jr (1996b) Excision of the piggyBac transposable element in vitro is a precise event that is enhanced by the expression of its encoded transposase, Genetica., 98(1): pp. 33–41.
Elick TA, Lobo N, Fraser MJ Jr (1997) Analysis of the cis–acting DNA elements required for piggyBac transposable element excision, Mol. Gen. Genet., 255(6): pp. 605–610.
Fraser MJ Jr. Smith GB and Summers MD (1983) Acquisition of host cell DNA sequences by baculoviruses: Relationship between host DNA insertions and FP mutants of Autographa californica and Galleria mellonella nuclear polyhedrosis viruses, J. Virol., 47: pp. 287–300.
Fraser MJ Jr, Brusca JS, Smith GE, Summers MD (1985) Transposon–mediated mutagenesis of a baculovirus, Virology, 145(2): pp. 356–361.
Fraser MJ Jr, Cary L, Boonvisudhi K, Wang HG (1995) Assay for movement of Lepidopteran transposon IFP2 in insect cells using a baculovirus genome as a target DNA, Virology, 211(2): pp. 397–407.
Fraser MJ Jr, Ciszczon T, Elick T, Bauser C (1996) Precise excision of TTAA–specific Lepidopteran transposons piggyBac (IFP2) and tagalong (TFP3) from the baculovirus genome in cell lines from two species of Lepidoptera, Insect Mol. Biol., 5(2): pp. 141–151.
Geier and Modrich (1979) Recognition Sequence of the dam Methylase of Escherichia coli K12 and Mode of Cleavage of Dpn 1 Endonuclease, The Journal of Biological Chemistry, 254(4): pp. 1408–1413.

(Continued)

Primary Examiner—Ram R. Shukla
(74) Attorney, Agent, or Firm—Jagtiani + Guttag

(57) ABSTRACT

More efficient transfer of genes into host cells or embryos to transform the cells or embryos is facilitated by transposition vectors using the minimal amount of nucleotide sequences in the transposon piggyBac required for gene transfer. The transformed cells or embryos may be developed into transgenic organisms.

3 Claims, 162 Drawing Sheets

OTHER PUBLICATIONS

Gierl A, Lutticke S, Saedler H (1988) TnpA product encoded by the transposable element En–1 of Zea mays is a DNA binding protein, EMBO J., 7(13): pp. 4045–4053.

Goryshin IY, Kil YV, Reznikoff WS (1994) DNA length, binding, and twisting constraints on IS5O transposition, Proc. Natl. Acad. USA, 91: pp. 10834–10838.

Grossman GL, Rafferty CS, Fraser MJ Jr, Benedict MQ (2000) The piggyBac element is capable of precise excision and transposition in cells and embryos of the mosquito, Anopheles gambiae, Insect Biochem. Mol. Biol., 30(10): pp. 909–914.

Grossman GL, Rafferty CS, Clayton JR, Stevens TK, Mukabayire O, Benedict M (2001) Germline transformation of the malaria vector, Anopheles gambiae, with the piggyBac transposable element, Insect Mol. Biol., 10(6): pp. 597–604.

Grossniklaus U, Pearson RK, Gehring WJ (1992) The Drosophila sloppy paired locus encodes two proteins involved in segmentation that show homology to mammalian transcription factors, Genes Dev., 6(6): pp. 1030–1051.

Handler AM, McCombs SD, Fraser MJ Jr, Saul SH (1998) The Lepidopteran transposon vector, piggyBac, mediates germ–line transformation in the Mediterranean fruit fly, Proc. Natl. Acad. Sci. USA, 95(13): pp. 7250–7555.

Handler AM, Harrell RA $2^{nd}$ (1999) Germline transformation of Drosophila melanogaster with the piggyBac transposon vector, Insect Mol. Biol., 8(4): pp. 449–457.

Handler AM, McCombs SD (2000) The piggyBac transposon germ–like transformation in the Oriental fruit fly and closely related elements exist in its genome, insect Mol. Biol., 9(6): pp. 605–612.

Handler AM, Harrell RA $2^{nd}$ (2001a) Polyubiquitin–regulated DsRed marker for transgenic insects, Biotechniques, 31(4): pp. 824–828.

Handler AM, Harrell RA $2^{nd}$ (2001b) Transformation of the Caribbean fruit fly, Anastrepha suspensa, with a piggyBac vector marked with polyubiquitin–regulated GFP, Insect Biochem. Mol. Biol., 31(2)L pp. 199–205.

Handler AM, (2002) Use of the piggyBac transposon for germ–line transformation of insects, Insect Biochem. Mol. Biol., 32(10): pp. 1211–20.

Hediger M, Niessen M, Wimmer EA, Dubendorfer A, Bopp D (2001) Genetic transformation of the housefly Musca domestica with the Lepidopteran derived transposon piggyback, Insect Mol. Biol., 10(2): pp. 113–119.

Heinrich JC, Li Z, Henry RA, Haack N, Stringfellow L, Heath AC, Scott MJ (2002) Germ–line transformation of the Australian sheep blowfly Lucilia cuprina, Insect Mol. Biol., 11(1): pp. 1–10.

Hirt B (1967) Selective extraction of polyoma DNA from infected mouse cell cultures, J. Miol. Bio., 26: pp. 367–369.

Horn C. Wimmer EA (2000) A versatile vector set for animal transgenesis, Dev. Genes Evol., 210(1): pp. 630–637.

Ivics Z, Hackett PB, Plasterk RH, Izsvak Z (1997) Molecular reconstruction of Sleeping Beauty, a Tc1–like transposon from fish, and its transposition in human cells, Cell, 91(4): pp. 501–510.

Jarvis et al. (1990) Use of early baculovirus promoters for continuous expression and efficient processing of foreign gene products in stably transformed lepidoteran cells, Biotechnology (NY) 10: 950–5. (Abstract).

Jasinskiene N, Coates CJ, James AA (2000) Structure of hermes integrations in the germline of the yellow fever mosquito, Aedes aegypti, Insect Mol. Biol., 9(1): pp. 11–18.

Kaufman PD, Doll RF, Rio DC (1989) Drosophila P element transposase recognizes internal P element DNA sequences, Cell, 59(2): pp. 359–371.

Kokoza V, Ahmed A, Wimmer EA, Raikhel AS (2001) Efficient transformation of the yellow fever mosquito Aedes aegypti using the piggyBac transposable element vector pBac[3xP3–EGFP afm], Insect Biochem. Mol. Biol., 31(12): pp. 1137–1143.

Kunze R, Starlinger P (1989) The putative transposase of transposable element Ac from Zea mays L. interacts with subterminal sequences of Ac, EMBO J., 8(11): pp. 3177–3185.

Li X, Heinrich JC, Scott MJ (2001a) piggyBac–mediated transposition in Drosophila melanogaster: an evaluation of the use of constitutive promoters to control transposase gene expression, Insect Mol. Biol., 10(5): pp. 447–455.

Li X, Lobo N, Bauser CA, Fraser MJ Jr (2001b) The minimum internal and external sequence requirements for transposition of the eukaryotic transformation vector piggyBac, Mol. Genet. Gen., 266(2): pp. 190–198.

Liu D, Mack A, Wang R, Galli M, Belk J, Ketpura NI, Crawford NM (2000) Functional dissection of the cis–acting sequence of the Arabidopsis transposable element Tag1 reveals dissimilar subterminal sequence and minimal spacing requirements for transposition, Genetics, 157(2): pp. 817–830.

Lobo N, Li X, Fraser MJ Jr (1999) Transposition of the piggyBac element in embryos of Drosophilia melanogaster, Aedes aegypti and Trichoplusia ni, Mol. Gen. Genet., 261(4–5): pp. 803–810.

Lobo N, Li X, Hua–Van A, Fraser MJ Jr (2001) Mobility of the piggyBac transposon in embryos of the vectors of Dengue fever (Aedes albopictus) and La Crosse encephalitis (Ae. triseriatus), Mol. Genet. Gen., 265(1): pp. 66–71.

Lobo NF, Hua–Van A, Li X, Nolen BM, Fraser MJ Jr (2002) Germ line transformation of the yellow fever mosquito, Aedes aegypti, mediated by transpositional insertion of a piggyBac vector, Insect Mol. Biol., 11(2): pp. 133–139.

Lohe AR, Hartl DL (2001) Efficient mobilization of mariner in vivo requires multiple internal sequences, Genetics, 160(2): pp. 519–526.

Lozovsky ER, Nurminsky D, Wimmer EA, Hartl DL (2002) Unexpected stability of mariner transgenes in Drosophila, Genetics, 160(2): pp. 527–535.

Mandrioli, et al. "Stable transformation of a Mamestra brassicae (Lepidoptera) cell line with the Lepidopteran–derived transposon piggyback" Insect Biochem. Mol. Bio., vol. 33(1), pp. 1–5, 2002.

Mullins, et al. "cis–acting DNA sequence requirements for P–element transposition" Genes Dev., vol. 3(5), pp. 729–738, 1989.

Nolan, et al. "piggyback–mediated germline transformation of the malaria mosquito Anopheles stephensi using the red fluorescent protein dsRED as a selectable marker" J. Biol. Chem., 277(11), pp. 8759–8762, 2002.

Ochman, et al. "Genetic applications of an inverse polymerase chain reactor" Genetics, vol. 120(3), pp. 621–623, 1988.

Peloquin, et al. "Germ–line transformation of pink bollworm (Lepidopter:gelechiidae) mediated by the piggyback transposable element" Insect Mol. Biol., vol. 9(3), pp. 323–333, 2000.

Perera, et al. "Germ–line transformation of the South American malaria vector, *Anopheles albimanus*, with a *piggyback*/EGFP transposon vector is routine and highly efficient" Insect Mol. Biol., vol. 11(4), pp. 297–297, 2002.

Praffle, et al. Studies on rates of nucleosome formation with DNA under stress.

Rio, et al. "Identification and purification of a *Drosophila* protein that binds to the terminal 31–base–pair inverted repeats of P transposable element" Proc. Natl. Acad. Sci. USA, vol. 85, pp. 8929–8933, 1988.

Rubin, et al. "Genetic transformation of *Drosophila* with transposable element vectors" Science, vol. 218(4570), pp. 348–353, 1982.

Rubin, et al. "Vectors for P element–mediated gene transfer in Drosophila" Nucleic Acids Res., vol. 11(18), pp. 6341–6351, 1983.

Saedler, et al. Transposable Elements. Soringer–Verlag, Berlin. 1996.

Sambrook, et al. Molecular Cloning: A Laboratory Manual. New York: Cold Spring Harbor Press, 1989.

Sarkar A, et al. "Transporation of the *Hermes* element in embryos of the vector mosquito, *Aedes aegypti*," Insect Biochem. Mol. Biol.., 27(5): pp. 359–363, 1997.

Sarkar A, et al. "The Hermes element from Musca domestica can transpose in four families of cyclorrhaphan flies" Genetica., 99(1): pp. 15–29, 1997.

Sarkar A, et al. "Molecular evolutionary analysis of the widespread piggyBac transposon family and related "domesticated" sequences", Mol. Genet. Genomics, 270(2): pp. 173–180, 2003.

Sekar V. "A rapid screening procedure for the identification of recombinant bacterial clones" BioTechniques, 5: pp. 11–13, 1987.

Sumitani, et al. "Germline transformation of the sawfly, Athalia rosae (Hymenoptera: Symphyta), mediated by a piggyBac–derived vector" Insect Biochem. Mol. Biol., 33(4): pp. 449–458, 2003.

Tamura T, et al. "Germline transformation of the silkworm Bombyx mori L. using a piggyBac transposon–derived vector" Nat. Biotechnol. 18(1): pp. 81–84, 2000.

Thibault ST, et al. "Precise excision and transposition of piggyBac in pink bollworm embryos" Insect Mol. Biol., 8(1): pp. 119–123, 1999.

Thomas JL, et al. "3xP3–EGFP marker facilitates screening for transgenic silkworm Bombyx mori L. from the embryonic stage onwards" Insect Biochem. Mol. Biol., 32(3): pp. 247–253, 2002.

Thummel, CS, et al. "New pCaSpeR P element vectors" Dros. Info. Service, 71: pp. 150–150, 1992.

Tosi LR, et al. "cis and trans factor affecting Mos1 mariner evolution and transposition in vitro, and its potential for functional genomics" Nucleic Acids Res., 28(3): pp. 784–790, 2000.

Trentmann SM, et al. "The transposable element En/Spm–encoded TNPA protein contains a DNA binding and a dimerization domain" Mol. Gen. Genet., 238(1–2): pp. 201–208, 1993.

Wang HH, et al. "TTAA serves as the target site for TFP3 Lepidopteran insertions in both nuclear polyhedrosis virus and Trichoplusia ni genomes" Insect Mol. Biol., 1: pp. 109–116, 1993.

Zayed H, et al. "The DNA–bending protein HMGB1 is cellular cofactor of Sleeping Beauty transposition" Nucleic Acids Res., 31(9): pp. 2313–2322, 2003.

* cited by examiner

| PLASMIDS | INSERTION SEQUENCE | IPTA FREQUENCY |
|---|---|---|
| pIAO-P/L-TTAA | TTAA | 0 |
| pIAO-P/L-TTAA2 | TTAATTAA | 0 |
| pIAO-P/L | TTAATCTAGAGGATCCTCTAGATTAA (XbaI/BamHI/XbaI)--(SEQ ID NO:35)-- | $5.4 \times 10^{-3}$ |
| pIAO-P/L-18 bp | TTAATCTAGACGTACGCGGAGCTTAA--(SEQ ID NO:36)-- | $1.0 \times 10^{-6}$ |
| pIAO-P/L-22 bp | TTAATCTAGCTAGTACTAGAACTAGATTAA--(SEQ ID NO:37)-- | $3.6 \times 10^{-6}$ |
| pIAO-P/L-40 bp | TTAATCTAGTTCTAGACGTACGCGGCGCACTAGTACTAGCTAGATTAA--(SEQ ID NO:38)-- | $2.5 \times 10^{-5}$ |
| pIAO-P/L-55 bp | TTAATCTAGTTCTAGACTGCGCGTCTCTAGACGTACGCGGCGCACTA-GTACTAGCTAGATTAA--(SEQ ID NO:39)-- | $1.2 \times 10^{-4}$ |
| pIAO-P/L-73 bp | 63bp of Lambda PvuII fragment between XbaI sites of pIAO-P/L | $1.3 \times 10^{-4}$ |
| pIAO-P/L-212 bp | 63 bp + 141 bp of Lambda PvuII fragment between XbaI sites of pIAO-P/L | $3.1 \times 10^{-4}$ |
| pIAO-P/L-354 bp | 43 bp of Lambda PvuII fragment between XbaI sites of pIAO-P/L | $2.9 \times 10^{-4}$ |
| pIAO-P/L-589 bp | 579 bp of Lambda PvuII fragment between XbaI sites of pIAO-P/L | $3.2 \times 10^{-4}$ |
| pIAO-P/L-2.2 kb | 2.2 kb of Lambda HindIII fragment between XbaI sites of pIAO-P/L | $3.4 \times 10^{-4}$ |

FIG. 2(A)

Sequence Range: 1 to 7670

```
100
AACGGCGCGGGGAGAGGCGGTTTGCGTATTGGGCGCTCTTCCGCTTCCTGCGCTCACTGACTCGCTGCGCTCGGTCGTTCGGCTGCGGCGAGCGGTATCAGC
200
TCACTCAAAGGCGGTAATACGGTTATCCACAGAATCAGGGGATAACGCAGGAAAGAACATGTGAGCAAAAGGCCAGCAAAAGGCCAGGAACCGTAAAAAG
   >Ori
   >──┤
300
GCCGCGTTGCTGGCGTTTTTCCATAGGCTCCGCCCCCCTGACGAGCATCACAAAAATCGACGCTCAAGTCAGAGGTGGCGAAACCCGACAGGACTATAAA
400
GATACCAGGCGTTTCCCCCTGGAAGCTCCCTCGTGCGCTCTCCTGTTCCGACCCTGCCGCTTACCGGATACCTGTCCGCCTTTCTCCCTTCGGGAAGCGT
500
GGCGCTTTCTCAATGCTCACGCTGTAGGTATCTCAGTTCGGTGTAGGTCGTTCGCTCCAAGCTGGGCTGTGTGCACGAACCCCCCGTTCAGCCCGACCGC
600
TGCGCCTTATCCGGTAACTATCGTCTTGAGTCCAACCCGGTAAGACACGACTTATCGCCACTGGCAGCAGCCACTGGTAACAGGATTAGCAGAGCGAGGT
700
ATGTAGGCGGTGCTACAGAGTTCTTGAAGTGGTGGCCTAACTACGGCTACACTAGAAGGACAGTATTTGGTATCTGCGCTCTGCTGAAGCCAGTTACCTT
800
CGGAAAAAGAGTTGGTAGCTCTTGATCCGGCAAACAAACCACCGCTGGTAGCGGTGGTTTTTTTGTTTGCAAGCAGCAGATTACGCGCAGAAAAAAAGGA
900
TCTCAAGAAGATCCTTTGATCTTTTCTACGGGGTCTGACGCTCAGTGGAACGAAAACTCACGTTAAGGGATTTTGGTCATGAGATTATCAAAAAGGATCT
1000
TCACCTAGATCCTTTTAAATTAAAAATGAAGTTTTAAATCAATCTAAAGTATATATGAGTAAACTTGGTCTGACAGTTACCAATGCTTAATCAGTGAGGC
 <W H K I L S A
 <     AMP RESIST
```

FIG. 2(C1)

```
1100 ACCTATCTCAGCGATCTGTCTATTCTTCGTTCATCCATAGTTGCCTGACTCCCCGTCGTGTAGATAACTACGGGAGGCTTACCATCTGGCCCAGT
     <G  I  E  A  I  Q  R  N  R  E  D  M  T  A  Q  S  G  T  T  Y  I  V  V  I  R  S  P  K  G  D  P  G  L
                                        AMP RESIST

1200 GCTGCAATGATGATACCGGAGACCCACGGCTCCACCGGCTCCAGATTTATCAGCAATAAACCAGCCGGAAGGCCGAGCCGCAGAAGTGTCCTGCAACTT
     <A  A  I  I  G  R  S  G  R  E  G  A  G  S  K  D  A  I  F  W  G  A  P  L  A  S  R  L  L  P  G  A  V  K
                                        AMP RESIST

1300 TATCCGGCCTCCATCCAGTCTATTAATTGTTGCGGGAAGTAGTAGTTCGCCAGTTAATAGTTTGCGCAACGTTGTTGCCATTGCTACAGGCAT
     <D  A  E  M  W  D  I  L  Q  Q  R  S  A  L  T  L  L  E  G  T  L  L  K  R  L  T  T  A  M  A  V  P  M
                                        AMP RESIST

1400 CGTGGTGTCACGCTCGTCGTTGGCTTCATTCAGCTCCGGTTCCCAACGATCAAGGCGAGTTACATGATCCCCCATGTGTGCAAAAAAGCGGTT
     <T  T  D  R  E  D  N  P  I  A  E  N  L  E  P  E  W  R  D  L  R  T  V  H  D  G  M  N  H  L  F  A  T
                                        AMP RESIST

1500 AGCTCCTTCGGTCCTCCGATCGTTGTCAGAAGTAAGTTGGCCCAGTGTTATCACTCATGGTTATGGCAGCACTGCATAATTCTCTTACTGTCATGCCAT
     <L  E  K  P  G  G  I  I  T  T  L  L  N  A  A  T  N  D  S  M  T  I  A  A  S  C  L  E  R  V  T  M  G  D
                                        AMP RESIST

1600 CCGTAAGATGCTTTTCTGTGACTGGTGAGTACTCAACCAAGTCATTCTGAGAATAGTGTATGCGGCGACCGAGTTGCTCTTGCCCGGCGTCAATACGGGA
     <T  L  H  K  E  T  V  P  S  Y  E  V  L  D  N  Q  S  Y  H  I  R  R  G  L  Q  E  Q  G  A  D  I  R  S
                                        AMP RESIST

1700 TAATACCGCGCCACATAGCAGAACTTTAAAAGTGCTCATCATTGGAAAACGTTCTTCGGGGGGAAAAACTCTCAAGGATCTTACCGCTGTTGAGATCCAGT
     <L  V  A  G  C  L  L  V  K  F  T  S  M  M  P  F  R  E  E  P  R  F  S  E  L  I  K  G  S  N  L  D  L
                                        AMP RESIST
```

FIG. 2(C1) CONT.

```
1800
TCGATGTAACCCACTCGTGCACCCAACTGATCTTCAGCATCTTTACTTTCACCAGCGTTTCTGGGTGAGCAAAAACAGGAAGGCAAAATGCCGCAAAAA
<E  I  Y  G  V  R  A  G  L  Q  D  E  A  D  K  V  K  V  L  T  E  P  H  A  F  V  P  L  C  F  A  A  F  F
                                          AMP RESIST

1900
AGGGAATAAGGGCGACACGGAAATGTTGAATACTCATACTCTCCTTTTCAATATTATTGAAGCATTTATCAGGGTTATTGTCTCATGAGCGGATACAT
<P  I  L  A  V  R  F  H  Q  I  S  M --(SEQ ID NO:58)--
       AMP RESIST

2000
ATTTGAATGTATTTAGAAAAATAAACAAATAGGGGTTCCGCGCACATTCCCGAAAAGTGCCACCTGACGTCTAAGAAACCATTATTATCATGACATTA
<R  Y  F  Y  A  Y  *  P  A  R  L  H  V  L  Q  *  V  Y  Y  *  S  L  *  R  A  C  A  K  I  V  G  E  R
                                              ORF1 N-TERM [SPLIT]

2100
ACCTATAAAAATAGGCGTATCACGGGGCCCTGAGGTGAACCAATTGTCACGTAATATTACGACAACTACCGTGCACAGGCTTTGATAACTCCTTCACG
<R  Y  F  Y  A  Y  *  P  A  R  L  H  V  L  Q  *  V  Y  Y  *  S  L  *  R  A  C  A  K  I  V  G  E  R
                                              ORF1 N-TERM [SPLIT]

2200
TAGTATTCACCGAGTGGTACTCCGTTGGTCTGTGTTCCCTTCCCAAATAAGGCATTCATTTATCATATACTTCGTACCACTGTCACACATCATGAGGA
<L  I  *  R  T  T  S  R  Q  D  T  N  R  K  G  F  L  A  N  W  K  D  Y  V  E  Y  W  Q  *  V  D  H  P
                                              ORF1 N-TERM [SPLIT]

2300
TTTTTATTCCATACTTACTGGCTTGTTGGGATATACATCCTAAACGGACACCGTCCTCTAAAACCAAGTAACTGTTCATCTATGGTCAAATGAGCCCC
<N  K  N  W  V  *  K  A  Q  K  P  Y  V  D  *  V  S  V  T  R  *  F  W  T  V  T  *  R  H  D  F  S  G  R
                                              ORF1 N-TERM [SPLIT]

2400
TGGAGTGTAATTTTGTATGCACTGATGGATAAAGAGATCCCATATTTTCTAACAGGAGTAAAATACATCGTTTTCTCGAAGTGTGGGCCGTATACTTTG
<S  H  L  K  T  H  V  S  P  Y  L  S  G  M  N  K  *  C  S  Y  I  C  R  K  R  S  T  H  A  T  Y  K  Q
                                              ORF1 N-TERM [SPLIT]
```

```
3300
ATGGAAACCGCTGCGATATTCAGCCATGTGCCTTCTTCCGCGTGCAGCAGATGGCGATGGTTGCTGTTCCATCAGTTGCTGTTGACTGTAGGGCTGATGTTG
<H  E  T  A  R  Y  S  Q  H  V  P  L  L  P  R  V  Q  Q  M  A  M  V  A  V  P  S  V  A  V  D  C  R  A  D  V
 F  G  D  I  N  L  W  T  G  E  E  A  H  L  L  H  R  H  S  T  E  M  L  Q  Q  S  Y  R  S  I  N
                                                    LACZ

3400
AACTGGAAGTCGCCGCGCACTGGTGTGGCGCCATAATTCAATTCGCGCTCCCGCCAGCCGTTTCGCTCGGAAGACGTACGGGTATACATGT
<F  Q  F  D  G  R  W  Q  H  P  G  Y  N  L  E  R  T  G  C  R  L  G  N  E  S  P  F  V  Y  P  T  Y  M  D
                                                    LACZ

3500
CTGACAATGGCAGATCCCAGCGGTCAAAAACAGGCGGTCAGTAGTTTCTTGCGGCCCTAATCCGAGCCAGTTACCGCTCTGCTAC
<S  L  P  L  D  W  R  D  F  C  A  A  T  L  R  D  P  Y  N  E  Q  P  G  L  G  W  N  V  R  E  A  V
                                                    LACZ

3600
CTGCCGCCAGCTGGCAGTTCAGGCCAATCCGCGCCGGATGCGCCACTCGCCACATTGACCACTACCATCAATC
<Q  A  L  Q  C  N  L  G  I  R  A  P  H  P  T  D  S  A  V  E  V  D  V  T  I  A  M  Q  G  S  G  D  I
                                                    LACZ

3700
CGGTAGGTTTTCCGCTGATAAATAAGGTTTCCCCTGATGCTGCCACGCGTGAGCGCGTTGTAATCAGCACCGCATCAGCAAGTGTATCTGCCGTGCACT
<R  Y  T  K  R  S  I  F  L  T  K  G  Q  H  Q  W  A  H  A  T  T  I  L  V  A  D  A  L  T  D  A  T  C  Q
                                                    LACZ

3800
GCAACAAACGCTGCTTCGGCCTGGTAATGCCCAGGCGTTAGGTCGACGCGTTGAATGGGTCGCTTCACTTACGCCAATGTCGTT
<L  L  A  A  E  A  Q  Y  H  G  A  A  K  W  R  E  V  A  N  P  D  I  R  T  A  E  S  V  G  I  D  N
                                                    LACZ

3900
ATCCAGCGGTGCACGGGTGAACTGATCGCAGCGGCGTCAGCAGTTGTTTTTTATCGCCAATCCACATCTGTGAAAGAAAGCCTGACTGGCGGTTAAAT
<D  L  P  A  R  T  F  Q  D  R  L  P  T  L  L  Q  K  K  D  G  I  W  M  Q  S  L  F  G  S  Q  R  N  F
                                                    LACZ
```

```
4000
TGCCAACGCTTATTACCAGCTCGATGCAAAAATCCATTCGCTGGTGTCAGATGCGGGATGGCGTGGACGCGGGGAGCGTCACACTGAGGTTTT
<Q  W  R  K  N  G  L  E  I  C  F  D  M  E  S  T  T  L  H  P  I  A  H  S  A  A  P  L  T  V  S  L  N  E
                                              LACZ

4100
CCGCCAGAGCCACTGCTGCCAGGCGCTGATGTGCCCGGCTTCTGACCATGCCGTTCGGTTGCACTACGGTCACTGTGAGCCAGAGTTGCCCGGC
<A  L  R  W  Q  Q  W  A  S  I  H  G  A  E  S  W  A  T  A  N  P  Q  V  V  R  V  T  L  W  L  Q  G  A
                                              LACZ

4200
GCTCTCCGGCTGCGGTAGTTCAGGCAGTTCAATCAACTGTTTACCTTGTGGAGCGACATCCAGAGGCACTTCACCGCGCTTGCCAGCGTTACCATCCAGC
<S  E  P  P  Q  P  L  E  P  L  E  I  L  Q  K  G  Q  P  A  V  D  L  P  V  E  G  S  A  L  P  K  G  D  L
                                              LACZ

4300
GCTACCATCCAGTGCAGGAGCTGCGGTTATCGCTATGAGACGGAACAGTAGTATTCGCTGGTCACTTCGATGGTTTGCCCGATAAACGGAACTGGAAAAACTGCT
<A  V  M  W  H  L  E  N  D  S  H  R  F  L  Y  E  S  T  V  E  I  T  Q  G  S  L  R  F  Q  F  F  Q  Q
                                              LACZ

4400
GCTGGTGTGTTTTGCTTCCGTCAGCGCTGGATGCGGCTGGATCGGCAAAGACCAGAACCGTTCATACAGAACTGGGCGATCGTTCGGCTATCGCCAAAATC
<Q  H  K  A  E  T  L  A  P  H  P  T  R  D  A  F  V  L  G  N  M  C  F  Q  R  D  N  P  T  D  G  F  D
                                              LACZ

4500
ACCGCCGTAAGCCGACCACGGGTTGCCGTTTCATCATATTTAATCAGCGACTGATCCACCAGTCCCAGACGAAGCCCCTGTAAACGGGATACTGA
<G  G  Y  A  S  W  P  N  G  N  E  D  Y  K  I  L  S  Q  D  V  W  D  W  V  F  G  G  Q  L  R  P  Y  Q
                                              LACZ

4600
CGAAAACGCCTGCCAGTATTAGGCAGAAACCGCCAAGACTGTTACCATCGCGTGGGCGTATTCGCAAAGGATCAGCGGCGTCTCCAGGTAGCGAAA
<R  F  A  Q  W  Y  K  A  F  G  G  L  S  N  G  M  A  H  A  Y  E  C  L  I  L  P  R  T  E  G  P  L  S  L
                                              LACZ
```

```
4700
GCCATTTTTGATGGACCATTTCGGCACAGCCGGGAAGGGCTGGTCGTCTTCATCCACGGCGCCGTACATGGGCAAATAATATCGGTGGCCGTGTGTCGGC
 W  K  K  I  S  W  K  P  V  A  P  F  P  Q  D  E  D  V  R  A  Y  M  P  C  I  I  D  T  A  T  T  D  A
                                              LACZ

4800
TCCGCGCCTTCATACTGCACCGGGCGGGGAAGGATCGACAGATTTGATCCAGCGGATACAGCGGTCGTGATTAGCGCCCTGGCCTGATTCATTCCCAGC
 G  G  E  Y  Q  V  P  R  S  P  D  V  S  K  I  W  R  Y  L  A  D  H  N  A  G  H  G  S  E  N  G  L
                                              LACZ

4900
GACCAGATGATCACACTCGGGTGATTACGATCGCGTGCACCATTCGCGCTTCGCTCATCGCCGGTAGCCAGCGGGATCATCGGTCAGACGAT
 S  W  I  I  V  S  P  H  N  R  D  R  Q  V  M  R  T  V  R  E  S  M  A  P  L  W  R  P  D  D  T  L  R  N
                                              LACZ

5000
TCATTGGCACCATGCCGTGGGTTTCAATATTGGCTTCAGAAGTTGTTCTGCTTAAAGCGGTACACAGCGGTCGCACAGCCGTGTACCACAGCGGATGGTTCGGATAATG
 M  P  V  M  G  H  T  E  I  N  A  E  D  V  V  Y  L  G  Y  R  D  C  L  T  Y  W  L  P  H  N  P  Y  H
                                              LACZ

5100
CGAACAGGCGCACGGCGTTAAGCGCCTCGAATCAGCAACGGCTTGCCGTTCAGCAGCAGGATATCCTGACTGCTCATCCATGACCTGACCTGCTGCTCG
 S  C  R  V  A  N  F  N  Q  K  M  L  L  I  D  Q  V  M  T  Q  E  D  M  V  Q  G  H  L  P  H  H  E
                                              LACZ

5200
TGACGGTTAACGCCTCGAATCAGCAACGGCTTGCCGTTCAGCAGCAGGACCATTTTCAATCCGCACTTGGCGGAAACCGACATCGCAGGCTTCTGCTT
 H  R  N  V  G  R  I  L  L  P  K  G  N  L  L  L  G  N  E  I  R  V  E  R  F  G  V  D  C  A  E  A  E
                                              LACZ

5300
CAATCAGCTGTGCCGTCGGCGTGTGCAGTTCAACCACCGCACGATAGAGATTCGGGATTTCGGGTTTCGACAGTTCGGTTCAGACGTAG
 I  L  T  G  D  A  T  H  L  E  V  V  A  R  Y  L  N  P  I  E  A  S  W  L  K  P  N  E  V  N  L  R  L
                                              LACZ
```

```
6000
CCAGTTTGAGGGGACGACGAGACGGGATCCGTTTTTTTATTACAAAACTGTTACGAAAACAGTAAAATACTTATTATTCGGACCAACAATGTTTATTCTTA
 <V L L T * E *                        S F L L I S I * E S W C   --(SEQ ID NO:60)--
 < ORF1 N-TERM [S
 V
 <W N S P V V V P D T K K N C F Q *
                            LACZ

6100
CCTCTAATAGTCCTCTGTGCCAAGGTCAAGATTCTGTTAGAAGCCAATGAAGAACCTGGTTGTTCAATAACATTTGTTCGTCTAATATTTCACTACGCT
 <R * Y D E T A L D L N Q *   F G I F F R I T * Y C K T R R I N * * A
 < ORF1 N-TERM [SPLIT]
 V

6200
TGACGTTGGCTGACACTTCATGTACCTCATCTATAAACGCTTCTTCTGTATCGCTCTTCACTTACGTGATCTGATATTTCACTGTCAGAATC
 <Q R Q S V S * T G * R Y V S R Y R E P R R * K R S R R I N * Q * F G
 < ORF1 N-TERM [SPLIT]
 V

6300
CTCACCAACAAGCTCGTCATCGCCTTGCAGAGAGCAGAGGATATGCTCATCGTCTAAAGAACATCCCATTTATTATATATTAGTCACGATATCTAT
 <* W C A R * R R A S S C L P Y A * R R F F M G X   --(SEQ ID NO:61)--
 V

6400
AACAAGAAAATATATATATATAATAAGTTATCACGTAAGAACATGAAATATTATCGTATGAGTAAATCTAAAGTCACGTAAAAGAT

6500
AATCGGTCATTTGACTCACGCGGTCGTTATAGTTCAAAATCAGTGACACTTACCGCATTGACAAGCCCTCAGCCGAGCTCCAAGCCGGCGACTG

6600
AGATGTCCTAAAATTGCAAACAGCCACGGATTCGCGCTATTTAGAAAGAGAGCAATATTTCAAGAATGCGTCAATTTTACGCAGACTATCTTTCT

_____ RIGHT TERMINAL REPEAT _____>
```

FIG. 2(C1) CONT.

```
6700
AGGGTTAATCTAGAGAGATCCTCTAGAGATTAACCCTAGAGAAAGATAATCATATTGTGACGTACGTTAAAGATAATCATGCGTAAAATTGACGCATGTGTTTT
       >                                     LEFT TERMINAL REPEAT                                   >
6800
ATCGGCTCTGTATATCGAGGTTTATTTATTATTGAATAGATATTAAGTTTTATTATATATTTACACTTACATACTAATAATAAATTCAACAAACAATTTAT

6900
TTATGTTTATTTATTATTAAAAAAAAAACAGTCATGTTGTATTATAACAAAAATTCTCTAAAGTAACAAACATTCTCTCTTTTACAAAAATAAACTTATTT

7000
TGTACTTTAAAACAGTCATGTTGTATTATAACAAATATAATAGCTTAACTTATACATAATAGAAACAAATTATACTTATTAGTCAGTCCAGAAAACAAC
<D T W F C S
  ORF1 C-TER

7100
TTTGGCACACATATCAATATATGCTCTCGACAAATAACTTTTTGCATTTTTGCACGGATGCATTGCCTTTCGCCTTATTTTAGAGGGGCAGTAAGTACA
<Q C M D I N H E R C I V K K C K K C S A N A K R R I K S P C Y T C
               ORF1 C-TERM

7200
GTAAGTACGTTTTTTCATTACTGGCTCTTCAGTACTGTCATCTGATGTACCAGGCACTTCATTGGCAAAATATTAGAGATATTATCGCGCAAATATCTC
<Y T R K K M V P E E T S D D S T G P V E N P L I N S I N D R L Y R
                       ORF1 C-TERM

7300
TTCAAAAGTAGGAGCTTCTAAAACGGTTACGCATAAACGATGACGTCAGGCTCATGTAAAGGTTTCTCATAAATTTTTTGCGACTTTGAACCTTTCTCCCT
<K L T P A E L R N R M F S S T L S M Y L N R M F K K R S Q V K E G K
                         ORF1 C-TERM
```

FIG. 2(C1) CONT.

```
7400
TGCTACTGACATTATGGCTGTGTATATAAAGAATTTATGCAGGCAATGTTTATCATTCCGTACAATAATGCCATAGCCACTTATTCGTCTTCCTACT
<S  S  V  N  H  S  Y  I  I  F  S  N  I  C  A  I  N  I  M  G  Y  L  L  A  M  P  W  R  N  T  K  R  S
              ORF1 C-TERM

7500
GCAGGTCATCACAGAACACATTTGGTCTAGCGTGTCCACTCCGCCTTTAGTTTGATTATAATACATAACCATTTGCGGTTTACCGGTACTTTCGTTGATA
<C  T  M  V  S  C  M  Q  D  L  T  D  V  G  G  K  T  Q  N  Y  Y  M  V  M  Q  P  K  G  T  S  E  N  I
              ORF1 C-TERM

7600
GAAGCATCCTCATCACAAGATGATAATAAGTATACCATCTTAGCTGGCTTCGGTTTATATGAGACGAGAGTAAGGGGTCCGTCAAAACAAAACATCGATG
<S  A  D  E  D  C  S  S  L  L  Y  V  M  K  A  P  K  P  K  Y  S  V  L  T  L  P  G  D  F  C  F  M  S  T
              ORF1 C-TERM

TTCCCACTGGCCTGGAGGCACTGTTTTTCAGTACTTCCGGTATCTCCGCGTTTGTTTGATCGCACGGTACC --(SEQ ID NO:57)--
<G  V  P  R  S  R  S  N  K  L  V  E  P  I  E  R  K  N  S  R  V  T  G -- (SEQ ID NO:62)--
              ORF1 C-TERM
```

*FIG. 2(C1) CONT.* pIAO-P/L-Lambda-2.2kb
Sequence Range: 1 to 9984

100 AACGCGCGGGGAGAGGCGGTTTGCGTATTGGGCGCTCTTCCGCTTCCTGCTCACTGACTCGCTGCGCTCGGTCGTTCGGCTGCGGCGAGCGGTATCAGC
200 TCACTCAAAGGCGGTAATACGGTTATCCACAGAATCAGGGGATAACGCAGGAAAGAACATGTGAGCAAAAGGCCAGCAAAAGGCCAGGAACCGTAAAAAG
    >Ori
    - -
300 GCCGCGTTGCTGGCGTTTTTCCATAGGCTCCGCCCCCCTGACGAGCATCACAAAAATCGACGCTCAAGTCAGAGGTGGCGAAACCCGACAGGACTATAAA
400 GATACCAGGCGTTTCCCCCTGGAAGCTCCCTCGTGCGCTCTCCTGTTCCGACCCTGCCGCTTACCGGATACCTGTCCGCCTTTCTCCCTTCGGGAAGCGT
500 GGCGCTTTCTCAATGCTCACGCTGTAGGTATCTCAGTTCGGTGTAGGTCGTTCGCTCCAAGCTGGGCTGTGTGCACGAACCCCCCGTTCAGCCCGACCGC
600 TGCGCCTTATCCGGTAACTATCGTCTTGAGTCCAACCCGGTAAGACACGACTTATCGCCACTGGCAGCAGCCACTGGTAACAGGATTAGCAGAGCGAGGT
700 ATGTAGGCGGTGCTACAGAGTTCTTGAAGTGGTGGCCTAACTACGGCTACACTAGAAGGACAGTATTTGGTATCTGCGCTCTGCTGAAGCCAGTTACCTT
800 CGGAAAAAGAGTTGGTAGCTCTTGATCCGGCAAACAAACCACCGCTGGTAGCGGTGGTTTTTTTGTTTGCAAGCAGCAGATTACGCGCAGAAAAAAAGGA
900 TCTCAAGAAGATCCTTTGATCTTTTCTACGGGGTCTGACGCTCAGTGGAACGAAAACTCACGTTAAGGGATTTTGGTCATGAGATTATCAAAAAGGATCT

```
1700
TAATACCGCGCCACATAGCAGAACTTTAAAAGTGCTCATCATTGGAAAACGTTCTTCGGGGCGAAAACTCTCAAGGATCTTACCGCTGTTGAGATCCAGT
<L  V  A  G  C  L  L  V  K  F  T  S  M  M  P  F  R  E  E  P  R  F  S  E  L  I  K  G  S  N  L  D  L
                                      AMP RESIST

1800
TCGATGTAACCCACTCGTGCACCCAACTGATCTTCAGCATCTTTACTTTCACCAGCGTTTCTGGGTGAGCAAAAACAGGAAGGCAAAATGCCGCAAAAA
<E  I  Y  G  V  R  A  G  L  Q  D  E  A  D  K  V  K  V  L  T  E  P  H  A  F  V  P  L  C  F  A  A  F  F
                                      AMP RESIST

1900
AGGGAATAAGGGCGACACGGAAATGTTGAATACTCATACTCTCCTTTTTCAATATTATTGAAGCATTTATCAGGGTTATTGTCTCATGAGCGGATACAT
<P  I  L  A  V  R  F  H  Q  I  S  M --(SEQ ID NO:58)--
      AMP RESIST

2000
ATTTGAATGTATTTAGAAAATAAACAAATAGGGGTTCCGCGCACATTTCCCGAAAAGTGCCACCTGACGTCTAAGAACCATTATTATCATGACATTA

2100
ACCTATAAAAATAGGCGTATCACGGGGCCCTGAGTGAACCAATTGTCACACGTAATATTACGACAACTACCGTGCACAGGCTTTGATAACTCCTTCACG
<R  Y  F  Y  A  Y  *  P  A  R  L  H  V  L  Q  *  V  Y  *  S  L  *  R  A  C  A  K  I  V  G  E  R
                                      ORF1 N-TERM [SPLIT]

2200
TAGTATTCACCGAGTGGTACTCCGTTGGTCTGTGTTCCCTCTTCCCAAATAAGGCATTCCATTTATCATATACTTCGTACCACTGTCACACATCATGAGGA
<L  I  *  R  T  T  S  R  Q  D  T  N  R  K  G  F  L  A  N  W  K  D  Y  V  E  Y  W  Q  *  V  D  H  P
                                      ORF1 N-TERM [SPLIT]

2300
TTTTTATTCCATACTTACTTGGCTTGTTGTTTGGGATATACATCCTAAAACCAAGTAACTGTTCATCTATGGTCAAATGAGCCCC
<N  K  N  W  *  K  A  Q  K  P  Y  Y  V  D  *  V  S  V  T  R  *  F  W  T  V  T  *  R  H  D  F  S  G  R
                                      ORF1 N-TERM [SPLIT]
```

```
3200
ATTTTGACACCAGACCAACTGTAATGGTAGCGACCGGCTCAGTGCTGGAATTCCGCGATACTGACGGGCTCGCCGAGTCGTCGCCACCAATCCCAT
<K  Q  C  W  V  L  Q  Y  H  Y  R  G  A  S  L  Q  F  E  A  S  V  S  P  S  W  S  D  D  G  G  I  G  M
                                                 LACZ

3300
ATGGAAACCGTCGATATTCAGCCATGTGCCTTCTCCGGTGCAGCAGATGGCGATGGTTGTTCCATCAGTTGCTGTTGACTGGCGTAGCGGCTGATGTTG
<H  F  G  D  I  N  L  W  T  G  E  E  A  H  L  L  H  R  H  S  T  E  M  L  Q  Q  Q  S  Y  R  S  I  N
 v                                              LACZ

3400
AACTGGAAGTCGCCCGCCACTGGTCGTGGGCCATAATTCAATTCGCGTCCCGCAGCCGTTTCGCTCGGAAGACCTACGGGGTATACATGT
<F  Q  F  D  G  R  W  Q  H  P  G  Y  N  L  E  R  T  G  C  R  L  G  N  E  S  P  F  V  Y  P  T  Y  M  D
 v                                              LACZ

3500
CTGACAATGGACAGATCCAGGCTCAAAAACAGGCGGTCAATAGTTTTCTTGGCCCTAATCGGCGATAGTTCGAGCCAGTTACCCGCTCTGCTAC
<S  L  P  L  D  W  R  D  F  C  A  A  T  L  R  D  P  Y  N  E  Q  P  G  L  G  L  W  N  V  R  E  A  V
 v                                              LACZ

3600
CTGCCGCCACAGCTGGCAGTTCAGGCCCAATCCGGCCGCCGGATGCGGTGTATCGCCCACTTCAACATCAACGGTAATCGCCACTACCATCAATC
<Q  A  L  Q  C  N  L  G  I  R  A  P  H  P  T  D  S  A  V  E  V  D  V  T  I  A  M  Q  G  S  G  D  I
 v                                              LACZ

3700
CGGTAGGTTTCCGGCTGATAATAAGGTTTCCCTGATGCTGAGCGGTCGTAATCAGCAGCCATCACCGCAAGTGTATCGCCGTGCACT
<R  Y  T  K  R  S  I  F  L  T  K  G  Q  H  Q  W  A  H  A  T  T  I  L  V  A  D  A  L  T  D  A  T  C  Q
 v                                              LACZ

3800
GCAACAACGCTGCTTCGGCTGCTGGTAATGGCCCAGGGCGTTCAGGTCAATGGGTCAAGCGTTAGGGTCAATGCGGTCGCTTCACTTACGCCAATGTCGTT
<L  A  A  E  A  Q  Y  H  G  A  A  K  W  R  E  V  W  A  N  P  D  I  R  T  A  E  S  V  G  I  D  N
 v                                              LACZ
```

*FIG. 2(C2) CONT.*

```
3900 ATCCAGCGGTGCACGGGTGAACTGATCGCGCAGCAGTTGCTTTTATCGCCAATCCACATCTGTGAAAGAAAGCCTGACTGGCGGTTAAAT
     < D  L  P  A  R  T  F  Q  D  R  L  P  T  L  L  Q  K  K  D  G  I  W  M  Q  S  L  F  G  S  Q  R  N  F
     v                                             LACZ

4000 TGCCAACGCTTATTACCCAGCTCGATGCAAAAATCCATTTCGCTGGTGGTCAGATGCGGGATGGCGTGGGGACGCGGGAGCGTCACACTGAGGTTT
     < Q  W  R  K  N  G  L  E  I  C  F  D  M  E  S  T  T  L  H  P  I  A  H  S  A  A  P  L  T  V  S  L  N  E
     v v                                           LACZ

4100 CCGCCAGAGCGCCACTGCTGCCAGGCGCTGATGTGCCCGGCTTCGTTGCACTACGCGGTTCGTGAGCCAGAGTTGCCGGC
     < A  L  R  W  Q  Q  W  A  S  I  H  G  A  E  S  W  A  T  A  N  P  Q  V  V  R  V  T  L  W  L  Q  G  A
     v                                             LACZ

4200 GCTCTCCCGGCTGCGGTAGTTCAGGCAGTTCAATCAACTGTTTACCTTGTGGAGGCGACATCCAGAGGCACTTCACCGGCCTTACCATCCAGC
     < S  E  P  Q  P  L  E  P  P  L  E  I  L  Q  K  G  Q  P  A  V  D  L  P  V  E  G  S  A  L  P  K  G  D  L
     v                                             LACZ

4300 GCCACCATCCAGTGCAGGAGCTCGTTCAGGAGTATTGCGCTGGTTCACTTCGATGTGTTTGCCCGGATAAACGGAACTGGAAAAACTGCT
     < A  V  M  W  H  L  L  E  N  D  S  H  R  R  F  L  Y  E  S  T  V  E  I  T  Q  G  S  L  R  F  Q  F  F  Q
     v                                             LACZ

4400 GCTGGTGTTTGCTTCCGTTCAGCTGACATCCACCCAGTCCCAGACGAAGCCGGCGATCGTTCGGCGTATCGCCAAAATC
     < Q  H  K  A  E  T  L  A  P  H  P  T  R  D  A  F  V  L  G  N  M  C  F  Q  R  D  N  P  T  D  G  F  D
     v v                                           LACZ

4500 ACCGCCGTAAGCCGACCACGGGTTGCCGTTTTCATCATATTTAATCAGCGACTGATCCACCCAGTCCCAGACGAAGCCCTGTAAACGGGATACTGA
     < G  Y  A  S  W  P  N  G  N  E  D  Y  K  I  L  S  Q  D  V  W  D  W  V  F  G  G  Q  L  R  P  Y  Q
     v                                             LACZ
```

*FIG. 2(C2) CONT.*

```
4600
CGAAACGGCCTGCCAGTATTTAGGCGAAAACCGCCAAGACTGTTACCCATCGCGTTGGGCCGTATTCGCAAAGGATCAGCGGGGCCGTCTCTCCAGGTAGCGAAA
 R  F  A  Q  W  Y  K  A  F  G  G  L  S  N  G  M  A  H  A  Y  E  C  L  I  I  P  R  T  E  G  P  L  S  L
                                                LACZ

4700
GCCATTTTTGATGACCATTTCGGCACAGCCGGTGAAGGGCTGGTCTTCATCCCACGCGGCGCAAATAATATCGTGGCCGTGGTGTCGGC
 W  K  K  I  S  W  K  P  V  A  P  F  P  Q  D  E  D  V  R  A  Y  M  P  C  I  I  D  T  A  T  T  D  A
                                                LACZ

4800
TCCGCCGCCTTCATACTGCACCGGGCGGGAAGGATCGACAGATTTGATCCAGGCGTGTGATTAGCGCCGTGATTCATTCCCAGC
 G  G  G  E  Y  Q  V  P  R  S  P  D  V  S  K  I  W  R  Y  L  A  D  H  N  A  G  H  G  S  E  N  G  L
                                                LACZ

4900
GACCAGATGATCACACTCGGGCTGATTACGACGATCGCGCTGCACCATTCGCTTCGCTCATCGCCGGTAGCCGGTTCGCTCATCGCGCTAGCGGTTCGCTCAGACGAT
 S  W  I  I  V  S  P  H  N  R  D  R  Q  V  M  R  T  V  R  E  S  M  A  P  L  W  R  P  D  D  T  L  R  N

5000
TCATTGGCACCACATGCCGGTGGGTTTCAATATTGGCTTCATCCACCACATACAGGCCGTGTACCACAGCGTTTGGCTGTACCACAGCGTGTACCACAGCGGATAATG
 M  P  V  M  G  H  T  E  I  N  A  E  D  V  V  Y  L  G  Y  R  D  C  L  T  Y  W  L  P  H  N  P  Y  H

5100
CGGACAGCAGCACGGCTTGCCGTTAAAGTTGTTCTGCTTCATCAGCAGCAGATATCCTGCACCATCGTCTCCGTCCTCATCCATCGACTGAGAGGATGATGCTCG
 C  R  V  A  N  F  N  N  Q  K  M  L  L  I  D  Q  V  M  T  Q  E  D  M  V  Q  G  H  L  P  H  H  E

5200
TGACGGTTAACGCCTCGAATCAGCAACGGCTTGCCCTTCAGCAGCAGACCATTTCAATCCGCACCTCGCGGAAACCGACATCCGCAGGCTTCTGCTT
 H  R  N  V  G  R  I  L  L  P  K  G  N  L  L  L  G  N  E  I  R  V  E  R  F  G  V  D  C  A  E  A  E
                                                LACZ
```

FIG. 2(C2) CONT.

```
5300
CAATCAGCGGTGCCGTCGGCGGTGTGCAGTTCAACCACCGCACGATAGAGATTCGGGATTTCGGGCGCTCCACAGTTTCGGGTTTTCGACGTTCAGACGTAG
 V  I  L  T  G  D  A  T  H  L  E  V  V  A  R  Y  L  N  P  I  E  A  S  W  L  K  P  N  E  V  N  L  R  L
                                                          LACZ

5400
TGTGACGCGGATCGGCATAACCACGCTCATCGATAATTTCACCGCCGAAAGGCGCCGCTGGCGTGCCGCTGGCGACCTGCGTTTCACCCTGCCATAAAGAAACT
 V  T  V  R  D  A  Y  G  G  R  E  D  I  I  E  G  G  F  P  A  T  G  S  A  V  Q  T  E  G  Q  W  L  S  V
                                                          LACZ

5500
GTTACCCGTAGTAGTCACGCAACTCGGCCGCACATCTGAACTTCAGCCTCCAGTACAGCCTCGAAATCATCATTAAAGGCGAGTGGCAACATGGAAAT
 V  T  V  R  L  Y  D  R  L  E  G  C  M  Q  V  E  A  E  L  V  A  R  S  F  D  D  N  F  R  T  A  V  H  F  D
                                                          LACZ

5600
CGCTGATTTGTGTAGTCGGTTTATGCAGCAACGACGTCGTGGATCGCCGCCTCATCCGAGATAACTGCCGTCACTCCA
 V  S  I  Q  T  T  P  K  H  L  L  S  V  D  R  F  I  G  S  M  R  W  M  D  Q  D  E  L  Y  S  G  D  D  S  W
                                                          LACZ

5700
ACGCAGCACCATCACCGGAGGCGGTTTTCTCCGGCGTAAAAAATGCGCTCAGTCAAATTCAGACGGCAAACGACTGTCCTGGCCGTAACCGACCCAG
 V  R  L  V  M  V  A  L  R  N  E  G  A  R  L  F  A  S  L  D  F  E  S  P  L  R  S  D  Q  G  Y  G  V  W
                                                          LACZ

5800
CGCCCCGTTGCACCACAGATGAAAACGCCGAGTAACGCCATCAAAAATAATTCGCGTCTCCTGTAGCCAGTTTCATCAACATTAAATGTGAGCG
 V  R  G  N  C  W  L  H  F  A  S  N  V  G  D  F  I  I  R  T  Q  G  E  Q  L  W  S  E  D  V  N  F  T  L  S
                                                          LACZ

5900
AGTAACAACCCGTCGGATTCTCCGTGGGAACAAACGGGCGATTGACCGTAATGGGCGCATCGTTGTGTAGATGGGATAGTTACGTTGACGTTAACCGTGCATCTG
 V  Y  C  G  T  P  N  E  T  P  V  F  P  P  N  V  T  I  P  Y  T  V  N  T  Y  I  P  A  D  Y  G  H  M  Q
                                                          LACZ
```

```
6700
AGGGTTAATCTAGCTTTTCTAATTAACCTTTGTCAGGTTACCAACTACTAAGGTTGTAGGCTCAAGAGGGTGTGTCCCTGTCGTAGGTAAATAACTGACC
 <K  R  I  *  G  K  D  P  *  W  S  S  L  N  Y  A  *  S  P  T  D  Q  R  L  Y  I  V  S  R
         EA31 (296); CODON START=1; DB XREF=PID:G215131; TRA [SPLIT]
             MRNA-PL (ALT.; VIA T'J4 TERMINATOR) [SPLIT]
             MRNA-PL (ALT.; VIA T'J3 TERMINATOR) [SPLIT]
             MRNA-PL (ALT.; VIA T'J2 TERMINATOR) [SPLIT]
             MRNA-PL (ALT.; VIA T'J1 TERMINATOR) [SPLIT]
  v v v v

6800
TGTCGAGCTTAATATTCTATATTGTTGTTCTTTCTGCAAAAAAGTGGGAAGTGAGTAATGAAATTATTCTAACATTATCTGCATTATCTGCATCATACCTTCCGAG
 <D  L  K  I  N  *  I  T  T  R  E  A  F  F  H  P  L  S  Y  H  F  *  K  *  C  K  D  A  D  Y  R  G  L
         EA31 (296); CODON START=1; DB XREF=PID:G215131; TRA [SPLIT]
             MRNA-PL (ALT.; VIA T'J4 TERMINATOR) [SPLIT]
             MRNA-PL (ALT.; VIA T'J3 TERMINATOR) [SPLIT]
             MRNA-PL (ALT.; VIA T'J2 TERMINATOR) [SPLIT]
             MRNA-PL (ALT.; VIA T'J1 TERMINATOR) [SPLIT]
  v v v v

6900
CATTATTAAGCATTTCGCTATAAGTTCTCGCTGGAAGAGTAGTTTTTCATTGTACTTTACCTTCATCTCTGTTCATTATCATCGCTTTTAAAACGGT
 <M  *  A  N  R  *  --(SEQ ID NO:64)--
         EA31 (296); CO
 <S  Y  T  R  A  P  L  P  L  K  K  M  T  S  *  R  *  R  Q  E  N  D  D  S  K  F  R  N
         EA59 (525); CODON START=1; DB XREF=PID:G215132; TRA
             MRNA-PL (ALT.; VIA T'J4 TERMINATOR) [SPLIT]
             MRNA-PL (ALT.; VIA T'J3 TERMINATOR) [SPLIT]
             MRNA-PL (ALT.; VIA T'J2 TERMINATOR) [SPLIT]
             MRNA-PL (ALT.; VIA T'J1 TERMINATOR) [SPLIT]
  v v v v
```

*FIG. 2(C2) CONT.*

```
7000
TCGAGCCTTCTAATCCTATCTGACCATTATAATTTTTTAGAATGGTTTCATAAGAAAGCTCTGAATCAACGGACTGCGATAATAAGTGGTGTATCCAGAA
<S  R  R  I  R  D  S  W  *  L  K  K  S  H  N  *  L  F  A  R  F  *  R  V  A  I  I  L  P  P  I  W  F
         EA59 (525); CODON START=1; DB XREF=PID:G215132; TRA
         MRNA-PL (ALT.; VIA T'J4 TERMINATOR) [SPLIT]
         MRNA-PL (ALT.; VIA T'J3 TERMINATOR) [SPLIT]
         MRNA-PL (ALT.; VIA T'J2 TERMINATOR) [SPLIT]
         MRNA-PL (ALT.; VIA T'J1 TERMINATOR) [SPLIT]

7100
TTTGTCACTTCAAGTAAAAACACCTCACGAGTTAAAAACACCCTAAGTTCTCACCGAATGTCTCAATATCCGGACGGATAATATTTATTGCTTCTCTTGACC
<K  D  S  *  T  F  V  G  *  S  N  F  C  R  L  E  *  R  I  D  *  Y  G  S  P  Y  Y  K  N  S  R  K  V
         EA59 (525); CODON START=1; DB XREF=PID:G215132; TRA
         MRNA-PL (ALT.; VIA T'J4 TERMINATOR) [SPLIT]
         MRNA-PL (ALT.; VIA T'J3 TERMINATOR) [SPLIT]
         MRNA-PL (ALT.; VIA T'J2 TERMINATOR) [SPLIT]
         MRNA-PL (ALT.; VIA T'J1 TERMINATOR) [SPLIT]

7200
GTAGGACTTTCCACATGCAGGATTTTGGAACCTCTTGCAGTACTACTGGGGAATGAGTTGCAATTATTGCTACACCATTGCGTGCATCGAGTAAGTCGCT
<T  P  S  E  V  H  L  I  K  S  G  R  A  T  S  S  P  F  S  N  C  N  N  S  C  W  Q  T  C  R  T  L  R  K
         EA59 (525); CODON START=1; DB XREF=PID:G215132; TRA
         MRNA-PL (ALT.; VIA T'J4 TERMINATOR) [SPLIT]
         MRNA-PL (ALT.; VIA T'J3 TERMINATOR) [SPLIT]
         MRNA-PL (ALT.; VIA T'J2 TERMINATOR) [SPLIT]
         MRNA-PL (ALT.; VIA T'J1 TERMINATOR) [SPLIT]
```

*FIG. 2(C2) CONT.*

```
7300
TAATGTTCGTAAAAAGCAGAGAGCAAAGTGGATGCAGATGAACCTCTGTTCATCGAATAAAACTAATGACTTTTCGCCAACGACATCTACTAATCTT
<I  N  T  F  F  C  L  A  F  T  S  A  S  S  G  R  T  *  R  I  F  S  I  V  K  R  W  R  C  R  S  I  K
  EA59 (525); CODON START=1; DB XREF=PID:G215132; TRA
  MRNA-PL (ALT.; VIA T'J4 TERMINATOR) [SPLIT]
  MRNA-PL (ALT.; VIA T'J3 TERMINATOR) [SPLIT]
  MRNA-PL (ALT.; VIA T'J2 TERMINATOR) [SPLIT]
  MRNA-PL (ALT.; VIA T'J1 TERMINATOR) [SPLIT]

7400
GTGATAGTAAATAAAACAATTGCATGTCCAGAGCTCATTCGAAGCAGATATTCTGGATATTGTCATAAAACAATTAGTGAATTATCATCGTCCACTT
<H  Y  Y  I  F  C  N  C  T  W  L  E  N  S  A  S  I  E  P  Y  Q  *  L  V  I  *  H  I  *  R  G  S
  EA59 (525); CODON START=1; DB XREF=PID:G215132; TRA
  MRNA-PL (ALT.; VIA T'J4 TERMINATOR) [SPLIT]
  MRNA-PL (ALT.; VIA T'J3 TERMINATOR) [SPLIT]
  MRNA-PL (ALT.; VIA T'J2 TERMINATOR) [SPLIT]
  MRNA-PL (ALT.; VIA T'J1 TERMINATOR) [SPLIT]

7500
GAATCTGTGTGTTCATTACGTCTTAACTCTTCATATATTTAGAAAATGAGGCTGATGAGTTCCATATATTGAAAAGTTTCATCACTACTTAGTTTTTGATAGC
<S  D  T  T  *  T  K  V  R  *  I  *  F  H  P  Q  H  T  G  Y  K  F  L  K  *  *  K  T  K  Q  Y  S
  EA59 (525); CODON START=1; DB XREF=PID:G215132; TRA
  MRNA-PL (ALT.; VIA T'J4 TERMINATOR) [SPLIT]
  MRNA-PL (ALT.; VIA T'J3 TERMINATOR) [SPLIT]
  MRNA-PL (ALT.; VIA T'J2 TERMINATOR) [SPLIT]
  MRNA-PL (ALT.; VIA T'J1 TERMINATOR) [SPLIT]
```

*FIG. 2(C2) CONT.*

```
7600
TTCAAGCCAGAGTTGTCTTTTTCTATCTCATACAACCAATAAATGCTGAAATGAATTCTAAGGGAGATCGCCTAGTGATTTAAACTATTGCTG
<* A L T T K K * R S E Y L W Y I S F H I R L P S R R T I K F * Q Q
         EA59 (525); CODON START=1; DB XREF=PID:G215132; TRA
         MRNA-PL (ALT.; VIA T'J4 TERMINATOR) [SPLIT]
         MRNA-PL (ALT.; VIA T'J3 TERMINATOR) [SPLIT]
         MRNA-PL (ALT.; VIA T'J2 TERMINATOR) [SPLIT]
         MRNA-PL (ALT.; VIA T'J1 TERMINATOR) [SPLIT]
<v
<v
<v
<v

7700
GCAGCATTCTTGAGTCCAATATAAAAGTATTGTACCTTTTGCTGGGTCAGTTGTTCTTTAGGAGGAGTAAAGGATCAAATGCACTAAACGAAACTG
<C C E Q T W Y L L I T Y R K S P * T T R * S S Y F S * I C * V F S
         EA59 (525); CODON START=1; DB XREF=PID:G215132; TRA
         MRNA-PL (ALT.; VIA T'J4 TERMINATOR) [SPLIT]
         MRNA-PL (ALT.; VIA T'J3 TERMINATOR) [SPLIT]
         MRNA-PL (ALT.; VIA T'J2 TERMINATOR) [SPLIT]
         MRNA-PL (ALT.; VIA T'J1 TERMINATOR) [SPLIT]
<v
<v
<v
<v

7800
AAACAAGCGATCGAAAATATCCCTTTGGGATTCTTGACTCGATAAGTCTATTATTTTCAGAGAAAAAATATTCATTGTTTTCTGGGTTGGTGATTGCACC
<F C A I S F I G K P N K V R Y T * * K * L F F I * Q K R P Q H N C W
         EA59 (525); CODON START=1; DB XREF=PID:G215132; TRA
         MRNA-PL (ALT.; VIA T'J4 TERMINATOR) [SPLIT]
         MRNA-PL (ALT.; VIA T'J3 TERMINATOR) [SPLIT]
         MRNA-PL (ALT.; VIA T'J2 TERMINATOR) [SPLIT]
         MRNA-PL (ALT.; VIA T'J1 TERMINATOR) [SPLIT]
<v
<v
<v
<v
```

FIG. 2(C2) CONT.

```
7900 AATCATTCCATTCAAAATTGTTGTTTTACCACACCCATTCCGCCCGATAAAAGCATGAATGTCTGTGCTGGGCATAGAATTAACCGTCACCTCAAAAGGT
     <D  N  W  E  F  N  N  N  *  W  V  W  E  A  R  Y  F  C  S  H  E  H  Q  A  Y  F  *  G  D  G  *  F  T
            EA59 (525); CODON_START=1; DB_XREF=PID:G215132; TRA
            MRNA-PL (ALT.; VIA T'J4 TERMINATOR) [SPLIT]
            MRNA-PL (ALT.; VIA T'J3 TERMINATOR) [SPLIT]
            MRNA-PL (ALT.; VIA T'J2 TERMINATOR) [SPLIT]
            MRNA-PL (ALT.; VIA T'J1 TERMINATOR) [SPLIT]

8000 ATAGTTAAATCACTGAATCCGGAGCACTTTTTCTATTAAATGAAAAGTGAAATCTGACAATTCTGCAAACCATTAACACACGTGCGAACTGTCCAT
     <Y  N  F  *  Q  I  R  S  C  K  K  *  I  F  L  P  F  R  V  I  R  A  F  W  K  V  C  T  R  V  T  W
            EA59 (525); CODON_START=1; DB_XREF=PID:G215132; TRA
            MRNA-PL (ALT.; VIA T'J4 TERMINATOR) [SPLIT]
            MRNA-PL (ALT.; VIA T'J3 TERMINATOR) [SPLIT]
            MRNA-PL (ALT.; VIA T'J2 TERMINATOR) [SPLIT]
            MRNA-PL (ALT.; VIA T'J1 TERMINATOR) [SPLIT]

8100 GAATTTCTGAAAGAGTTACCCCCTCTAAGTAATGAGGTGTTAAGGACGCTTTCATTTCAATGTCGGCTAATCGATTTGGCCATACTACTAAATCCTGAAT
     <S  N  R  F  S  N  G  R  *  T  I  L  H  *  P  R  K  *  K  *  H  R  S  I  S  K  A  M  S  S  F  G  S  Y
            EA59 (525); CODON_START=1; DB_XREF=PID:G215132; TRA
            MRNA-PL (ALT.; VIA T'J4 TERMINATOR) [SPLIT]
            MRNA-PL (ALT.; VIA T'J3 TERMINATOR) [SPLIT]
            MRNA-PL (ALT.; VIA T'J2 TERMINATOR) [SPLIT]
            MRNA-PL (ALT.; VIA T'J1 TERMINATOR) [SPLIT]
```

*FIG. 2(C2) CONT.*

```
8200
AGCTTAAGAAGGTTATGTTTAAAACCATGCTTAATTGCTGAGATTAACATAGTAGTCAATGCTTTCACCTAAGAAAAAACATTTCAGGGAGTTGA
<S  *  S  P  *  T  *  F  W  R  K  I  Q  Q  S  *  C  L  L  *  H  K  R  L  F  F  V  N  *  P  T  S
        EA59 (525); CODON START=1; DB XREF=PID:G215132; TRA
        MRNA-PL (ALT.; VIA T'J4 TERMINATOR) [SPLIT]
        MRNA-PL (ALT.; VIA T'J3 TERMINATOR) [SPLIT]
        MRNA-PL (ALT.; VIA T'J2 TERMINATOR) [SPLIT]
        MRNA-PL (ALT.; VIA T'J1 TERMINATOR) [SPLIT]

8300
CTGAATTTTTTTATCTATTAATGAATAAGTGCTTACTTCTTCTTTTGACCTACAAAAACCAATTTTAACATTTCCGATATCGCATTTTTCACCATGCTCAT
<Q  I  K  *  R  N  I  F  L  H  K  S  R  R  K  S  R  C  F  W  N  *  C  K  R  Y  R  M  K  *  W  A  *
        EA59 (525); CODON START=1; DB XREF=PID:G215132; TRA
        MRNA-PL (ALT.; VIA T'J4 TERMINATOR) [SPLIT]
        MRNA-PL (ALT.; VIA T'J3 TERMINATOR) [SPLIT]
        MRNA-PL (ALT.; VIA T'J2 TERMINATOR) [SPLIT]
        MRNA-PL (ALT.; VIA T'J1 TERMINATOR) [SPLIT]

8400
CAAAGACAGTAAGATAAACATTGTAACAAAGGAATAGTCATTCCAACCATCTGCTCGTAGGAATGCCTTATTTTTCTACTGCAGGAATATACCCGCC
<*  L  C  Y  S  L  V  N  Y  C  L  F  L  *  E  L  W  R  S  T  P  I  G  *  K  K  R  S  C  S  Y  V  --(SEQ ID NO:65)--
        EA59 (525); CODON START=1; DB XREF=PID:G215132; TRA
        MRNA-PL (ALT.; VIA T'J4 TERMINATOR) [SPLIT]
        MRNA-PL (ALT.; VIA T'J3 TERMINATOR) [SPLIT]
        MRNA-PL (ALT.; VIA T'J2 TERMINATOR) [SPLIT]
        MRNA-PL (ALT.; VIA T'J1 TERMINATOR) [SPLIT]
```

*FIG. 2(C2) CONT.*

8500
TCTTTCAATAACACTAAACTCCAACATATAGTAACCCTTAATTTATTAAAATAACCGCAATTTATTTGGGGGCAACACAGGATCTCTCTTTAAGTTAC
　　　　　MRNA-PL (ALT.; VIA T'J4 TERMINATOR) [SPLIT]
　　　　　MRNA-PL (ALT.; VIA T'J3 TERMINATOR) [SPLIT]
　　　　　MRNA-PL (ALT.; VIA T'J2 TERMINATOR) [SPLIT]
　　　　　MRNA-PL (ALT.; VIA T'J1 TERMINATOR) [SPLIT]

8600
TCTCTATTACATACGTTTTCCATCTAAAAATTAGTAGTATTGAACTTAACGGGGCATCGTATTGTAGTTTTCCATATTTAGCTTTCTGCTTCCTTTTGGA
　　　　　MRNA-PL (ALT.; VIA T'J4 TERMINATOR) [SPLIT]
　　　　　MRNA-PL (ALT.; VIA T'J3 TERMINATOR) [SPLIT]
　　　　　MRNA-PL (ALT.; VIA T'J2 TERMINATOR) [SPLIT]
　　　　　MRNA-PL (ALT.; VIA T'J1 TERMINATOR) [SPLIT]

8700
TAACCCACTGTTATTCATGTTGCATGGTGCACTGTTTATACCAACGATATAGTCTATTAATGCATATATAGTATCGCCGAACGATTAGCTCTTCAGGCTT
　　　　　MRNA-PL (ALT.; VIA T'J4 TERMINATOR) [SPLIT]
　　　　　MRNA-PL (ALT.; VIA T'J3 TERMINATOR) [SPLIT]
　　　　　MRNA-PL (ALT.; VIA T'J2 TERMINATOR) [SPLIT]
　　　　　MRNA-PL (ALT.; VIA T'J1 TERMINATOR) [SPLIT]

8800
CTGAAGAAGCGTTTCAAGTACTAATAAGCCGATAGATAGCCACGGACTTCGTAGCCATTTTTCATAAGTGTTAACTTCCGCTCCTGCTCATAACAGACA
　　　　　MRNA-PL (ALT.; VIA T'J4 TERMINATOR) [SPLIT]
　　　　　MRNA-PL (ALT.; VIA T'J3 TERMINATOR) [SPLIT]
　　　　　MRNA-PL (ALT.; VIA T'J2 TERMINATOR) [SPLIT]
　　　　　MRNA-PL (ALT.; VIA T'J1 TERMINATOR) [SPLIT]

*FIG. 2(C2) CONT.*

```
8900
TTCACTACAGTTATGGGCGAAAGGTATGCATGCTGGGTGTGGGGAAGTCGTGAAAGAAAAGAAGTCAGCTGCGTCGTTTGACATCACTGCTATCTTCTTA
                                 MRNA-PL (ALT.; VIA T'J4 TERMINATOR)   [SPLIT]
                                 MRNA-PL (ALT.; VIA T'J3 TERMINATOR)   [SPLIT]
                                 MRNA-PL (ALT.; VIA T'J2 TERMINATOR)   [SPLIT]
 v  v  v  v                      MRNA-PL (ALT.; VIA T'J1 TERMINATOR)   [SPLIT]

9000
CTGGTTATGCAGGTCGTAGTGGGTGGCACACAAAGCTAGATTAACCCTAGAAAGATAATCATATTGTGACGTACGTTAAAGATAATCATGCGTAAAATTG
 MRNA-PL (ALT.; VIA T'J4 TERM
 MRNA-PL (ALT.; VIA T'J3 TERM
 MRNA-PL (ALT.; VIA T'J2 TERM
 v  v  v  v  MRNA-PL (ALT.; VIA T'J1 TERM                          LEFT TERMINAL REPEAT

9100
ACGCATGTGTTTTATCGGTCTGTGTATATCGAGGTTTATTTATTAATTGAATAGATATTAAGTTTATTATTATTTATTATATTACACTTACATACTAATAATAAATTC
                                                                                          >
      _____

9200
AACAAAACAATTATTATGTTTATTATTTATTAAAAAAAAACAAAAACTCAAAATTCTTCTAAAGTAACAAAACTTTTAAACATTCTCTCTTTTACAA

9300
AAATAAACTTATTTGTACTTTAAAAACAGTCATGTTGTATTATAAATAAGTAATTAGCTTAACTTATACATAATAGAAACAAATTATACTTATTAGTC
                                                                                              <D
                                                                                               v

9400
AGTCCAGAAACAACTTTGGCACATATCAATATTATGCTCTCGACAAATAACTTTTTTGCATTTTTTGCACGATGCATTGCCTTTGCCCTTATTTAGAG
 T   W   F   C   S   Q   C   M   D   I   N   H   E   R   C   I   V   K   K   C   K   K   C   S   A   N   A   K   R   R   I   K   S
                                                        ORF1 C-TERM
 v  v
```

ITR Cartridge Sequence      Sequence Range: 1 to 707

```
                                                    50
GGATCCCATGCGTCAATTTTACGCAGACTATCTTTCTAGGGTTAATCTAG
        ____RIGHT TERMINAL REPEAT_____>
                                                   100
CTGCATCAGGATCATATCGTCGGGTCTTTTTTCCGGCTCAGTCATCGCCC
                                                   150
AAGCTGGCGCTATCTGGGCATCGGGGAGGAAGAAGCCCGTGCCTTTTCCC
                                                   200
GCGAGGTTGAAGCGGCATGGAAAGAGTTTGCCGAGGATGACTGCTGCTGC
                                                   250
ATTGACGTTGAGCGAAAACGCACGTTTACCATGATGATTCGGGAAGGTGT
                                                   300
GGCCATGCACGCCTTTAACGGTGAACTGTTCGTTCAGGCCACCTGGGATA
                                                   350
CCAGTTCGTCGCGGCTTTTCCGGACACAGTTCCGGATGGTCAGCCCGAAG
                                                   400
CGCATCAGCAACCCGAACAATACCGGCGACAGCCGGAACTGCCGTGCCGG
                                                   450
TGTGCAGATTAATGACAGCGGTGCGGCGCTGGGATATTACGTCAGCGAGG
                                                   500
ACGGGTATCCTGGCTGGATGCCGCAGAAATGGACATGGATACCCCGTGAG
                                                   550
TTACCCGGCGGGCGCGCCTCGTTCATTCACGTTTTTGAACCCGTGGAGGA
                                                   600
CGGGCAGACTCGCGGTGCAAATGTGTTTTACAGCGTGATGGAGCAGATGA
                                                   650
AGATGCTCGACACGCTGCAGAACACGCAGCTAGATTAACCCTAGAAAGAT
                                               _____>
                                                   700
AATCATATTGTGACGTACGTTAAAGATAATCATGCGTAAAATTGACGCAT
         _____LEFT TERMINAL REPEAT_____>
GGGATCC --(SEQ ID NO:40)--
_>
```

FIG. 3(C1)

pXL-Bac
Sequence Range: 1 to 3662

100
CTAAATTGTAAGCGTTAATATTTTGTTAAATTCGCGTTAAATTTTGTTAAATCAGCTCATTTTTTAACCAATAGGCCGAAATCGGCAAAATCCCTTAT

200
AAATCAAAAGAATAGACCGAGATAGGGTTGAGTGTTGTTCCAGTTTGGAACAAGAGTCCACTATTAAAGAACGTGGACTCCAACGTCAAAGGGCGAAAAA

300
CCGTCTATCAGGGCGATGGCCCACTACGTGAACCATCACCCTAATCAAGTTTTTTGGGGTCGAGGTGCCGTAAAGCACTAAATCGAACCCTAAAGGGAG

400
CCCCCGATTTAGAGCTTGACGGGGAAAGCCGGCGAACGTGGCGAGAAAGGAAGGGAAGAAAGCGAAAGGAGCGGGCGCTAGGGCGCTGGCAAGTGTAGCG

500
GTCACGCTGCGCGTAACCACCACACCCGCCGCGCTTAATGCGCCGCTACAGGGCGCGTCCCATTCGCCATTCAGGCTGCGCAACTGTTGGGAAGGGCGAT

600
CGGTGCGGGCCTCTTCGCTATTACGCCAGCTGGCGAAAGGGGGATGTGCTGCAAGGCGATTAAGTTGGGTAACGCCAGGGTTTTCCCAGTCACGACGTTG

700
TAAAACGACGGCCAGTGAGCGCGCCTCGTTCATTCACGTTTTTGAACCGTGGAGGACGGGCAGACTCGCGGTGCAAATGTGTTTACAGCGTGATGGAG

800
CAGATGAAGAGATGCTCGACACGCTGCAGAACACGCAGCTAGATTAACCCTAGAAAGATAATCATATTGTGACGTACGTTAAAGATAATCATGCGTAAATT
_____
                                                                    LEFT TERMINAL REPEAT
>MCS_of_pBSII
——|——

900
GACGCCATGGGATCTGTAATACGACTCACTATAGGGCGAATTGGGTACCGGGCCCCCCCTCGAGGTCGACGGTATCGATAAGCTTGATATCGAATTCCTGC
 ^
 |——

*FIG. 3(C2)*

```
1000 AGCCCGGGGGATCCACTAGTTCTAGAGCGGCCGCCACCGCGGTGGAGCTCCAGCTTTGTTCCCTTTAGTGAGGGTTAATTAGATCCCATGCGTCAATTT >
1100 TACGCAGACTATCTTTCTAGGGTTAATCTAGCTGCATCAGGATCATATCGTCGGGTCTCTTTTTCCGGCTCAGTCATCGCCCAAGCTGGGCTATCTGGGC
     RIGHT TERMINAL      >
1200 ATCGGGGAGGAAGAAGCCCGTGCCTTTTCCCGCGAGGTTGAAGCGCATGGAAAGAGTTGCCGAGGATGACTGCTGCTGCATTGACGTTGAGCGAAAAC
1300 GCACGTTTACCATGATGATTCGGGAAGGTGTGGCCATGCACGCCCTTTAACGGTGAACTGTCGTTCAGGCCCACCTGGATACCAGTTCGTCGCGGCTTTT
1400 CCGGACACAGTTCCGGATGGTCAGCCCGAAGGCGCATCAGCAACCGAACAATACCGGCAGCCGGAACTGCCGTGCCGGTGTGCAGATTAATGACAGC
1500 GGTGCGGGCGCTGGGATATTACGTCAGCGAGGACGGGTATCCTGGCTGGATGCCGCAGAAATGGACATGGATACCCCGTGAGTTACCCGGCGGCGCTT
1600 GGCGTAATCATGGTCATAGCTGTTTCCTGTGAAATTGTTATCCGCTCACAATTCCACACAACATACGAGCCGGAAGCATAAAGTGTAAAGCCTGGGGT
1700 GCCTAATGAGTGAGCTAACTCACATTAATTGCGTTGCGCTCACTGCCCGCTTTCCAGTCGGGAAACCTGTCGTGCCAGCTGCATTAATGAATCGGCCAAC
1800 GCGCGGGGAGAGGCGGTTTGCGTATTGGGCGCTCTTCCGCTTCCTCGCTCACTGACTCGCTGCGCTCGGTCGTTCGGCTGCGGCGAGCGGTATCAGCTCA
1900 CTCAAAGGCGGTAATACGGTTATCCACAGAATCAGGGGATAACGCAGGAAAGAACATGTGAGCAAAAGGCCAGCAAAAGGCCAGGAACCGTAAAAAGGCC
2000 GCGTTGCTGGCGTTTTTCCATAGGCTCCGCCCCCCTGACGAGCATCACAAAAATCGACGCTCAAGTCAGAGGTGGCGAAACCCGACAGGACTATAAAGAT
```

*FIG. 3(C2) CONT.*

```
2100
ACCAGGCGGTTTCCCCCTGGAAGCTCCCCTGTTCCGATAGTTACCGGATAAACCTGTCCGCCTTTCTCCCTTCGGGAAGCGTGGC

2200
GCTTTCTCATAGCTCACGCTGTAGGTATCTCAGTTCGGTGTAGGTCGTTCGCTCCAAGCTGGGCTGTGTGCACGAACCCCCCGTTCAGCCCGACCGCTGC

2300
GCCTTATCCGGTAACTATCGTCTTGAGTCCAACCCGGTAAGACACGACTTATCGCCACTGGCAGCAGCCACTGGTAACAGGATTAGCAGAGCGAGGTATG

2400
TAGGCGGTGCTACAGAGTTCTTGAAGTGGTGGCCTAACTACGGCTACACTAGAAGGACAGTATTTGGTATCTGCGCTCTGCTGAAGCCAGTTACCTTCGG

2500
AAAAAGAGTTGGTAGCTCTTGATCCGGCAAACAAACCACCGCTGGTAGCGGTGGTTTTTTTGTTTGCAAGCAGCAGATTACGCGCAGAAAAAAAGGATCT

2600
CAAGAAGATCCTTTGATCTTTTCTACGGGGTCTGACGCTCAGTGGAACGAAAACTCACGTTAAGGGATTTTGGTCATGAGATTATCAAAAAGGATCTTCA
                                                                       <ColE1_origin 2700
CCTAGATCCTTTTAAATTAAAAATGAAGTTTTAAATCAATCTAAAGTATATATGAGTAAACTTGGTCTGACAGTTACCAATGCTTAATCAGTGAGGCACC
                                                                          < AMPCILLIN RESISTAN 2800
TATCTCAGCGATCTGTCTATTTCGTTCATCCATAGTTGCCTGACTCCCCGTCGTGTAGATAACTACGATACGGGAGGGCTTACCATCTGGCCCCAGTGCT
      AMPCILLIN RESISTANCE 2900
GCAATGATACCGCGAGACCCACGCTCACCGGCTCCAGATTTATCAGCAATAAACCAGCCAGCCGGAAGGGCCGAGCGCAGAAGTGGTCCTGCAACTTTAT
       AMPCILLIN RESISTANCE
```

FIG. 3(C2) CONT.

```
3000
CCGCCCTCCATCCAGTCTATTAATTGTTGCCGGGAAGCTAGAGTAAGTAGTTCGCCAGTTAATAGTTTGCGCAACGTTGTTGCCATTGCTACAGGCATCGT
         AMPCILLIN RESISTANCE
3100
GGTGTCACGCTCGTCGTTTGGTATGGCTTCATTCAGCTCCGGTTCCCAACGATCAAGGCGAGTTACATGATCCCCATGTTGTGCAAAAAGCGGTTAGC
         AMPCILLIN RESISTANCE
3200
TCCTTCGGTCCTCCGATCGTTGTCAGAAGTAAGTTGGCCGCAGTGTTATCACTCATGGTTATGGCAGCACTGCATAATTCTCTTACTGTCATGCCATCCG
         AMPCILLIN RESISTANCE
3300
TAAGATGCTTTTCTGTGACTGGTGAGTACTCAACCAAGTCATTCTGAGAATAGTGTATGCGGCGACCGAGTTGCTCTTGCCCGGCGTCAATACGGGATAA
         AMPCILLIN RESISTANCE
3400
TACCGCGCCACATAGCAGAACTTTAAAAGTGCTCATCATTGGAAAACGTTCTTCGGGGCGAAAACTCTCAAGGATCTTACCGCTGTTGAGATCCAGTTCG
         AMPCILLIN RESISTANCE
3500
ATGTAACCCACTCGTGCACCCAACTGATCTTCAGCATCTTTTACTTTCACCAGCGTTTCTGGGTGAGCAAAAACAGGAAGGCAAAATGCCGCAAAAAAGG
         AMPCILLIN RESISTANCE
3600
GAATAAGGGCGACACGGAAATGTTGAATACTCATACTCTTCCTTTTTCAATATTATTGAAGCATTTATCAGGGTTATTGTCTCATGAGCGGATACATATT
         AMPCILLIN RESISTANCE

TGAATGTATTTAGAAAAATAAACAAATAGGGGTTCCGCGCACATTTCCCCGAAAAGTGCCAC --(SEQ ID NO:41)--
```

```
pBSII-hs-orf
Sequence Range: 1 to 5533

100
CTAGAATTGTAAGCGTTAATATATTTGTTAAATTTTGTTAAATCAGCTCATTTTTAACCAATAGGCCGAAATCGGCAAAATCCCTTAT

200
AAATCAAAAGAATAGACCGAGATAGGGTTGAGTGTTGTTCCAGTTTGGAACAAGAGTCCACTATTAAAGAACGTGGACTCCAACGTCAAAGGGCGAAAAA

300
CCGTCTATCAGGGCGATGGCCCACTACGTGAACCATCACCCTAATCAAGTTTTTTGGGGTCGAGGTGCCGTAAAGCACTAAATCGGAACCCTAAAGGGAG

400
CCCCCGATTTAGAGCTTGACGGGGAAAGCCGGCGAACGTGGCGAGAAAGGCGAAAGGGAAGAAAGCGAAAGGAGCGGGGCGCTAGGGCGCTGGCAAGTGTAGCG

500
GTCACGGCTGCGCCGTAACCACCACACCCGCCGCGCTTAATGCCGCCGCTTAATGCCGCTACAGGGCGCGTCCCATTCGCCATTCAGGCTGCGCAACTGTGTGGGAAGGGCGAT

600
CGGTGCGGGCGCTCTTCGCTATTACGCCAGCTGGCGAAAGGGGATGTGCTGCAAGGCGATTAAGTTGGGTAACGCCAGGGTTTTCCCAGTCACGACGTTG

700
TAAAACGACGGCCAGTGAGCGCGCGTAATACGACTCACTATAGGGCGAATTGGGTACCGGGCCCCCCCCTCGAGGTCGACGGTATCGATAAGCTATCCAGT

800
GCAGTAAAACGACGGCCAGTGGAATTGTTTTAGCTTCCACTTAAAAATATGTTTTTTTAAATCTACATTCTCCAAAAAAAGGGTTTATTAACTTACATACTAGAATTGATCCCCGATCCCC

900
CTAGAATCCCAAAACAAACTGGTTATTGTGTAGGTCATTGTTGGCAGAAGAAATTCTCTGGCCGTTATTCGTTATTCTCTCTTTC

1000
TTTTGGGTCTCCCCTCTCTGCACTAATGCTCTCTCACTCTGTCACACAGTAAAGCGGCATACTGCTCTCGTTGGTTCGAGAGAGCGCCGCCTCGAATGTTCG

1100
CGAAAAGAGCGCCGGAGTATAAATAGAGCGCTTCGTCTACGGAGCGACAATTCAATTCAAACAAGCAAAGTGAACACGTCGCTAAGGCGAAAGCTAAGCAA
```

```
1200
ATAAACAAGCGCAGCTGAACAAGCTAAACAATCTGCAGTAAAGTGCAAGTTAAAGTGAATCAATTAAAAGTAACCAGCAACCAAGTAAATCAACTGCAAC
                                                    <hsp70_promoter
1300
TACTGAAATCTGCCAAGAAGTAATTATTGAATACAAGAAGAGAACTCTGAATAGGGAATTGGGAATTCCTGCAGCCCGGGGGATCCTATATAATAAAATG
1400
GGTAGTTCTTTAGATGATGAGCATATCCCTCTGCCTCTTCTGCAAAGGCGATGACGAGCTTGTGGTGAGGATTCTGACAGTGAAATATCAGATCACGTAA
1500
GTGAAGATGACGTCCAGAGCGGATACAGAAGAAGCGTTTATAGATGAGTACATGAAGTGCAGCCAACGTCAAGCGGTAGTGAAATATTAGACGAACAAAA
1600
TGTTATTGAACAACCAGGTTCTTCATTGGCTTCTAACAGAATCTTGACCTTGCCACAGAGGACTATTAGAGGTAAGAATAAACATTGTTGGTCAACTTCA
1700
AAGTCCACGAGGCGTAGCCGAGTCTCTGCACTGAACATTGTCAGATCTCAAAGAGGTCCGACGCGTATGTGCCGAATATATGACCCACTTTTATGCT
1800
TCAAACTATTTTTACTGATGAGATAATTCGGAAATCTATGCTTTCTTTGGTATTCTGGTAATGACAGTGAGAAAAGATAACCACATGTCCACAGATGACCTCTTTGAT
1900
TCGTGACACGAATGAAGATGAAATCTATGCTTTCTTTGGTATTCTGGTAATGACAGTGAGAAAAGATAACCACATGTCCACAGATGACCTCTTTGAT
2000
CGATCTTTGTCAATGGTGTACGTCTCTGTAAGAGTCGTGATCGTTTGATTTTTTGATACGATGTCTTAGAATGGATGACAAAGTATACGGCCCACAC
2100
TTCGAGAAAACGATGTATTACTCCCGTTAGAAAAATAATATGGGATCTCTTTATCCATCAGTGCATACAAAATTACACTCCAGGGGCTCATTTGACCATAGA
2200
TGAACAGTTACTTGGTTTTAGAGGACGGGTGTCCGTTTAGGATGTATATCCCAAACAAGCCAAGTAAGTATGGAATAAAAATCCTCATGATGTGTGACAGT
```

*FIG. 5(B) CONT.*

```
2300
GGTACGAAGTATATGATAAATGGAATGCCTTATTTGGGAAGAGGAACACAGACCAACGGAGTACCACTCGGTGAATACTACGTGAAGGAGTTATCAAAGC
2400
CTGTGCACGGTAGTTGTCGTAATATTACGTGTGACAATTGGTTCACCTCAATCCCTTTGGCAAAAAACTTACTACAAGAACCGTATAAGTAACCATTGT
2500
GGGAACCGTGCGATCAAACAAACGCGAAGTACGGAAGATACCGAAGTACTGAAAAACAGTCGCTTCCAGGCCAGTGGGAACATGATGTTTGTTTGACGGACCCCTT
2600
ACTCTCGTCTCATATAAACCGAAGCCAGCTAAGATGGTATACTTATTATCATCTTGTGATGAGGATGCTTCTATCAACGAAAGTACCGTAAACCGCAAA
2700
TGGTTATGTATTATAATCAAACTAAAGGCGGAGTGGACACGCTAGACCAAATGTGTTCTGTGATGACCTGCAGTAGAAGACGAATAGGTGGCCTATGGC
2800
ATTATTGTACGGAATGATAAACATTGCCTGCATAAATTCTTTATTATATACAGCCATAATGTCAGTAGCAAGGGAGAAAAGGTTCAAAGTCGCAAAAAA
2900
TTTATGAGAAACCTTTACATGAGCCTGACGTCATCGTTTATGCGTAAGCGTTAGAGCTCCTACTTTGAAGAGATATTGCGCGATAATATCTCTAATA
3000
TTTTGCCAAATGAAGTGCCTGGTACATCAGATGACAGTACTGAAGAGCCAGTAATGAAAAAACGTACTTACTGTACTTACTGCCCCTCTAAAATAAGGCG
3100
AAAGGCAAATGCATCGTGCAAAAAATGCAAAAGTTATTGTCGAGCATATATTGATATGTGCCAAAGTGTTTCTGACTGACTAATAAGTATATAT
3200
TTGTTTCTATTATGTATAAGTTAAGCTAATTACTTATTTTATAATACAACATGACTGTTTTTAAGTACAAAATAAGTTTATTTTGTAAAAGAGAGAAT
3300
GTTTAAAAGTTTGTTACTTTAGAGAAATTTGAGTTTTTGTTTTTTTTAATAAATAAATAAATTGTTGTTGAATTGGATCCACTA
3400
GTTCTAGAGCGGCCGCCACCGGTGTGAGCTCCAGCTTTGTTCCCTTTAGTGAGGGTTAATTGCGCGCTTGGCGTAATCATGGTCATAGCTGTTCCTG
```

FIG. 5(B) CONT.

```
3500
TGTGAAATTGTTATCCGCTCACACAATTCCACACAACATATACGAGCCGGAAGCATAAAGTGTAAAGCCTGGGGTGCCTAATGAGTGAGCTAACTCACATTAAT
3600
TGCGTTGCGCTCACTGCCCGCTTTCCAGTCGGGAAACCTGTCGTGCCAGCTGCATTAATGAATCGGCCAACGCGCGGGGAGAGGCGGTTTGCGTATTGGG
3700
CGCTCTTCCGCTTCCTCGCTCACTGACTCGCTGCGCTCGGTCGTTCGGCTGCGGCGAGCGGTATCAGCTCACTCAAAGGCGGTAATACGGTTATCCACAG
3800
AATCAGGGGATAACGCAGGAAAGAACATGTGAGCAAAAGGCCAGCAAAAGGCCAGGAACCGTAAAAAGGCCGCGTTGCTGGCGTTTTTCCATAGGCTCCG
3900
CCCCCCTGACGAGCATCACAAAAATCGACGCTCAAGTCAGAGGTGGCGAAACCCGACAGGACTATAAAGATACCAGGCGTTTCCCCCTGGAAGCTCCCTC
4000
GTGCGCTCTCCTGTTCCGACCCTGCCGCTTACCGGATACCTGTCCGCCTTTCTCCCTTCGGAAGCGTGGCGCTTTCTCATAGCTCACGCTGTAGTATC
4100
TCAGTTCGGTGTAGGTCGTTCGCTCCAAGCTGGGCTGTGTGCACGAACCCCCCGTTCAGCCCGACCGCTGCGCCTTATCCGGTAACTATCGTCTTGAGTC
4200
CAACCCGGTAAGACACGACTTATCGCCACTGGCAGCAGCCACTGGTAACAGGATTAGCAGAGCGAGGTATGTAGGCGGTGCTACAGAGTTCTTGAAGTGG
4300
TGGCCTAACTACGGCTACACTAGAAGGACAGTATTTGGTATCTGCGCTCTGCTGAAGCCAGTTACCTTCGGAAAAAGAGTTGGTAGCTCTTGATCCGGCA
4400
AACAAACCACCGCTGGTAGCGGTGGTTTTTTTGTTTGCAAGCAGCAGATTACGCGCAGAAAAAAAGGATCTCAAGAAGATCCTTTGATCTTTTCTACGGG
4500
GTCTGACGCTCAGTGGAACGAAAACTCACGTTAAGGGATTTTGGTCATGAGATTATCAAAAAGGATCTTCACCTAGATCCTTTTAAATTAAAAATGAAGT
```

*FIG. 5(B) CONT.*

<ColE1_origin
|--|

4600
TTTAAATCAATCTAAAGTATATATGAGTAAACTTGGTCTGACAGTTACCAATGCTTAATCAGTGAGGCACCTATCTCAGCGATCTGTCTATTTCGTTCAT
AMPCILLIN RESISTANCE >

4700
CCATAGTTGCCTGACTCCCCGTCGTGTAGATAACTACGATACGGGAGGGCTTACCATCTGGCCCCAGTGCTGCAATGATACCGCGAGACCCACGCTCACC
AMPCILLIN RESISTANCE >

4800
GGCTCCAGATTTATCAGCAATAAACCAGCCAGCCGGAAGGGCCGAGCGCAGAAGTGGTCCTGCAACTTTATCCGCCTCCATCCAGTCTATTAATTGTTGC
AMPCILLIN RESISTANCE >

4900
CGGGAAGCTAGAGTAAGTAGTTCGCCAGTTAATAGTTTGCGCAACGTTGTTGCCATTGCTACAGGCATCGTGGTGTCACGCTCGTCGTTTGGTATGGCTT
AMPCILLIN RESISTANCE >

5000
CATTCAGCTCCGGTTCCCAACGATCAAGGCGAGTTACATGATCCCCCATGTTGTGCAAAAAAGCGGTTAGCTCCTTCGGTCCTCCGATCGTTGTCAGAAG
AMPCILLIN RESISTANCE >

5100
TAAGTTGGCCGCAGTGTTATCACTCATGGTTATGGCAGCACTGCATAATTCTCTTACTGTCATGCCATCCGTAAGATGCTTTTCTGTGACTGGTGAGTAC
AMPCILLIN RESISTANCE >

5200
TCAACCAAGTCATTCTGAGAATAGTGTATGCGGCGACCGAGTTGCTCTTGCCCGGCGTCAATACGGGATAATACCGCGCCACATAGCAGAACTTTAAAAG
AMPCILLIN RESISTANCE >

5300
TGCTCATCATTGGAAAACGTTCTTCGGGGCGAAAACTCTCAAGGATCTTACCGCTGTTGAGATCCAGTTCGATGTAACCCACTCGTGCACCCAACTGATC
AMPCILLIN RESISTANCE >

*FIG. 5(B) CONT.*

5400
TTCAGCATCTTTTACTTTCACCAGGCGTTTCTGGGTGAGCAAAATGCCCGCAAAAACAGGAAGGCAAAATGCCGCAAAAAAGGGAATAAGGGCGACACGGAAATGTTGAATA
                                                    AMPCILLIN RESISTANCE

5500
CTCATACTCTTCCTTTTTCAATATTATTGAAGCATTTATCAGGGTTATTGTCTCATGAGCGGATACATATTTGAATGTATTTAGAAAAATAAACAAATAG

GGGTTCCGCGCACATTTCCCCGAAAAGTGCCAC --(SEQ ID NO:42)--

FIG. 5(B) CONT.

Sequence Range: 1 to 4971

100
CTAAATTGTAAGCGTTAATATTTTGTTAAATTCGCGTTAAATTTTTGTTAAATCAGCTCATTTTTAACCAATAGGCCGAAATCGGCAAATCCCTTAT

200
AAATCAAAAGAATAGACCGAGATAGGGTTGAGTGTTGTTCCAGTTTGGAACAAGAGTCCACTATTAAAGAACGTGGACTCCAAGCTCAAAGGGCGAAAAA

300
CCGTCTATCAGGGCGATGGCCCACTACGTGAACCATCACCCTAATCAAGTTTTTTGGGGTCGAGGTGCCGTAAAGCACTAAATCGGAACCCTAAAGGGAG

400
CCCCCGATTTAGAGCTTGACGGGGAAAGCCGGCGAACGTGGCGAGAAAGGAAGAAAAGCGAAAGGAGCGGGCGCTAGGGCGCTGGCAAGTGTAGCG

500
GTCACGCTGCGCGCGTAACCACCACACCCGCGCGCTTAATGCGCCGCTACAGGGCCGTCCCATTCAGGCTGCGCAACTGTTGGGAAGGGCGAT

600
CGGTGCGGGCCCTTCGCTATTACGCCAGCTGGGCGAAAGGGGATGTGCTGCAAGGCGATTAAGTTGGGTAACGCCAGGGTTTTCCCAGTCACGACGTTG

700
TAAAACGACGGCCAGTGAGCGCGCGTAATACGACTCACTATAGGGCGAATTGGGTACCGGGCCCCCCCTCGAGGTCGACGGTATCGATAAGCTTGATATC

800
GAATTCCTGCAGCCCGGGGATCCTATATAATAAAATGGGTAGTTCTTTAGACGATGAGCATATCCTCTCGCTCTTCTGCAAAGCGATGACGAGCTTGT

900
TGGTGAGGATTCTGACAGTGAAATATCAGATCACGTAAGTGAAGATGACGTCCAGAGCGATACAGAAGAAGCGTTATAGATGAGGTACATGAAGTGCAG

1000
CCAACGTCAAGCGGTAGTGAAATATTAGACGAACAAAATGTTATTGAACAACCAGGTTCTTCATTGGCTTCTAACAGAATCTTGACCTTGCCACAGAGGA

1100
CTATTAGAGGTAAGAATAAACATTGTTGGTCAACTTCAAAGTCCACGAGGCGTAGCCGAGTCTCTGCACTGAACATTGTCAGATCTCAAAGAGTCCGAC

FIG. 6(B)

```
1200
GCGTATGTGCCCGCAATATATATGACCCACTTTTATGCTTCAAACTATTTTTTACTGATGAGATAATTTCGAAATTGTAAAATGGACAAATGCTGAGATA
1300
TCATTGAAACGTCGGGAATCTATGACAGGTGCTACATTCGTGACACGAATGAAGATGAAATCTATGCTTTCTTTGTATTCGTGGTAATGACAGCAGTGA
1400
GAAAAGATAACCACATGTCCACAGATGACCTCTTTGATCGATCTTTGTCAATGGTGTACGTCTCTGTAATGAGTCGTGATCGTTTTGATTTTTGATACG
1500
ATGTCTTAGAATGGATGACAAAGTATACGGCCCACACTTCGAGAAAACGATGTATTTACTCCCTGTTAGAAAAATATGGATCTCTTATCCATCAGTGC
1600
ATACAAAATTACACTCCAGGGCTCATTGACCATAGATGAACAGTTACTTGGTTTTAGAGGACGGTGTCCGTTAGGATGTATATCCCAAACAAGCCAA
1700
GTAAGTATGGAATAAAATCCTCATGATGTGTGACAGTGGTACGAAGTATATGATAAATGGAATGCCTTATTGGGAAGAGGAACACAGACCAACGGAGT
1800
ACCACTCGGTGAATACTACGTGAAGGAGTTATCAAAGCCTGTGCACGGTAGTTGTCGTAATATTACGTGTGACAATTGTTCACCTCAATCCCTTTGGCA
1900
AAAAACTTACTACAAGAACCGTATAAGTTAACCATTGTGGGAACCGTGCGATCAAACAAACGCGAAGTACTGAAAAACAGTCGCTCCAGGC
2000
CAGTGGGAACATCGATGTTTTGTTTTGACGACCCCTTACTCTCGTCTCATATAAACCGAAGCCAGTCTATACTTATTATCATCTTGTGATGA
2100
GGATGCTTCTATCAACGAAAGTACCGGTAAACCGCTAGACCAAATGTGTTCTGTG
2200
ATGACCTGCAGTAGGAAGACGAATAGGTTCAAAGTGGCCTATGGCATTATTGTACGGAATGATAAACATTGCCTGCATAAATTCTTTTATTATATACAGCCATAATG
2300
TCAGTAGCCAAGGGAGAAAAGGTTCAAAGTCGCAAAAATTATGAGAGAAACCTTTACATGAGCCTGACGTCATCGTTTATGCGTAAGCGTTTAGAAGCTCC
```

*FIG. 6(B) CONT.*

```
2400
TACTTTGAAGAGAGATATTGCGCGATAATATCTCTAATATTTGCCAAATGAAGTGCCTGTACATCAGATGACAGTACTGAAGAGCCAGTAATGAAAAAA
2500
CGTACTTACTGTACTTACTGCCCCTCTAAAATAAGGCGAAAGGCGAAATGCATCGTGTGCAAAAAATGCAAAAAAGTATTGTCGAGAGCATAATATTGATA
2600
TGTGCCAAAGTTGTTTCTGACTGACTAATAAGTATAATTGTTTCTATTATGTATAAGTTAAGCTAATTACTTATTTTATAATACAACATGACTGTTTT
2700
AAAGTACAAAATAAGTTTATTTTGTAAAAGAGAGAATGTTTAAAAGTTTTGTTACTTTAGAAGAAATTTGAGTTTTTGTTTTTTTAATAAATAAAT
2800
AAACATAAATAAATTGTTTGTTGAATTTGGATCCACTAGTTCTAGAGCGGCCGCCACCGCGGTGGAGCTCCAGCTTTTGTTCCCTTTAGTGAGGGTTAAT
2900
TGCGCGCTTGGCGTAATCATGGTCATAGCTGTTTCCTGTGTGAAATTGTTATCCGCTCACAATTCCACACAACATACGAGCCGGAAGCATAAAGTGTAAA
3000
GCCTGGGGTGCCTAATGAGTGAGCTAACTCACATTAATTGCGTTGCGCTCACTGCCCGCTTTCCAGTCGGGAAACCTGTCGTGCCAGCTGCATTAATGAA
>ColE1_origin
3100
TCGGCCAACGCGCGGGGAGAGGCGGTTTGCGTATTGGGCGCTCTTCCGCTTCCTCGCTCACTGACTCGCTGCGCTCGGTCGTTCGGCTGCGGCGAGCGGT
3200
ATCAGCTCACTCAAAGGCGGTAATACGGTTATCCACAGAATCAGGGGATAACGCAGGAAAGAACATGTGAGCAAAAGGCCAGCAAAAGGCCAGGAACCGT
3300
AAAAAGGCCGCGTTGCTGGCGTTTTTCCATAGGCTCCGCCCCCCTGACGAGCATCACAAAAATCGACGCTCAAGTCAGAGGTGGCGAAACCCGACAGGAC
3400
TATAAAGATACCAGGCGTTTCCCCCTGGAAGCTCCCTCGTGCGCTCTCCTGTTCCGACCCTGCCGCTTACCGGATACCTGTCCGCCTTTCTCCCTTCGGG
```

*FIG. 6(B) CONT.*

3500
AAGCGTGGCGCTTTCTCATAGTCTCACGCTGTAGTATCTCAGTTCGGTGTAGTTCGTTCGCTCCAAGCTGGGCTGTGTGCACGAACCCCCCGTTCAGCCC

3600
GACCGCTGCGCCTTATCCGGTAACTATCGTCTTGAGTCCAACCCGGTAAGACACGACTTATCGCCACTGGCAGCAGCCACTGGTAACAGGATTAGCAGAG

3700
CGAGGTATGTAGGCGGTGCTACAGAGTTCTTGAAGTGGTGGCCTAACTACGGCTACACTAGAAGGACAGTATTTGGTATCTGCGCTCTGCTGAAGCCAGT

3800
TACCTTCGGAAAAAGAGTTGGTAGCTCTTGATCCGGCAAACAACCACCGCTGGTAGCGGTGGTTTTTTTGTTTGCAAGCAGCAGATTACGCGCAGAAAA

3900
AAAGGATCTCAAGAAGATCCTTTGATCTTTTCTACGGGTCTGACGCTCAGTGGAACGAAAACTCACGTTAAGGGATTTTGGTCATGAGATTATCAAAAA

4000
GGATCTTCACCTAGATCCTTTTAAATTAAAAATGAAGTTTTAAATCAATCTAAAGTATATATGAGTAAACTTGGTCTGACAGTTACCAATGCTTAATCAG
                >
                _____

4100
TGAGGCACCTATCTCAGCGATCTGTCTATTTCGTTCATCCATAGTTGCCTGACTCCCCGTCGTGTAGATAACTACGATACGGGAGGGCTTACCATCTGGC
                                                    AMPCILLIN RESISTANCE

4200
CCCAGTGCTGCAATGATACCGCGAGACCACGCTCACCGGCTCCAGATTATCAGCAATAAACCAGCCAGCCGGAAGGGCCGAGCGCAGAAGTGGTCCTG
                                                    AMPCILLIN RESISTANCE

4300
CAACTTTATCCGCCTCCATCCAGTCTATTAATTGTTGCCGGGAAGCTAGAGTAAGTAGTTCGCCAGTTAATAGTTTGCGCAACGTTGTTGCCATTGCTAC
                                                    AMPCILLIN RESISTANCE

4400
AGGCATCGTGGTGTCACGCTCGTCGTTTGGTATGGCTTCATTCAGCTCCGGTTCCCAACGATCAAGGCGAGTTACATGATCCCCATGTTGTGCAAAAAA
                                                    AMPCILLIN RESISTANCE

*FIG. 6(B) CONT.*

```
4500
GCGGTTAGCTCCTTCGGTCCTCCGATCGTTGTCAGAAGTAAGTTGGCCGCAGTGTTATCACTCATGGTTATGGCAGCACTGCATAATTCTCTTACTGTCA
                                            AMPCILLIN RESISTANCE                                   >
4600
TGCCATCCGTAAGATGCTTTTCTGTGACTGGTGAGTACTCAACCAAGTCATTCTGAGAATAGTGTATGCGGCGACCGAGTTGCTCTTGCCCGGCGTCAAT
                                     AMPCILLIN RESISTANCE                                          >
4700
ACGGGATAATACCGCGCCACATAGCAGAACTTTAAAAGTGCTCATCATTGGAAAACGTTCTTCGGGGCGAAAACTCTCAAGGATCTTACCGCTGTTGAGA
                                       AMPCILLIN RESISTANCE                                        >
4800
TCCAGTTCGATGTAACCCACTCGTGCACCCAACTGATCTTCAGCATCTTTTACTTTCACCAGCGTTTCTGGGTGAGCAAAAACAGGAAGGCAAAATGCCG
                                       AMPCILLIN RESISTANCE                                        >
4900
CAAAAAAGGGAATAAGGGCGACACGGAAATGTTGAATACTCATACTCTTCCTTTTTCAATATTATTGAAGCATTTATCAGGGTTATTGTCTCATGAGCGG
                  AMPCILLIN RESISTANCE                   >

ATACATATTTGAATGTATTTAGAAAAATAAACAAATAGGGGTTCCGCGCACATTTCCCCGAAAAGTGCCAC --(SEQ ID NO:43)--
```

*FIG. 6(B) CONT.*

Sequence Range: 1 to 5523

100
CTAAATTGTAAGCGTTAATATTTGTTAAATTTTGTTAAATCAGCTCATTTTTAACCAATAGCCGAAATCGGCAAAATCCCTTAT

200
AAATCAAAAGAATAGACCGAGATAGGGTTGAGTGTTGTTCCAGTTTGGAACAAGAGTCCACTATTAAAGAACGTGGACTCCAACGTCAAGGGCGAAAAA

300
CCGTCTATCAGGGCGATGGCCCACTACGTGAACCATCACCCTAATCAAGTTTTTGGGGTCGAGGTGCCGTAAAGCACTAAATCGGAACCCTAAAGGGAG

400
CCCCCGATTTAGAGCTTGACGGGGAAAGCCGGCGAACGTGGCGAGAAAGGAGCGAAAGGAAGAAAGCGAAAGGAGCGGGCGTAGGCGCTGGCAAGTGTAGCG

500
GTCACGCTGCGCGTAACCACCACACCCGCCGCTTAATGCGCCGTACAGGGCGCGTCCCATTCAGCCTGCCAACTGTTGGGAAGGGCGAT

600
CGGTGCGGGCCTCTTCGCTATTACGCCAGCTGGCGAAAGGGGGGATGTGCTGCAAGGCGATTAAGTTGGGTAACGCCAGGGTTTTCCCAGTCACGACGTTG

700
TAAAACGACGGCCAGTGAGCGCGCGTAATACGACTCACTATAGGGCGAATTGGGTACCGGGCCCCCCCTCGAGGTCGACGGTATCGATAAGCTTCGATGT

800
CTTTGTGATGCGCCGACATTTTGTAGGTTATTGATAAATGAACGGATACAGTTGCCCGACATTATCATTAAATCCTTGGCGTAGAATTGTCGGGTCC

900
ATTGTCCGTGTGCGCTAGCATGCCCGCTAACGGACCCTCGTACTTTTGGCTTCAAAGGTTTTGCGCACAGACAAAATGTGCCACACTTGCAGCTCTGCATG

1000
TGTGCGCGTTACCACAAATCCCAACGGCGCCAGTGTACTTGTTGTATGCAAATAAATCTCGATAAGGGCGGCGCGAATGCAGCTGATCACGTACGCT

1100
CCTCGTGTTCCGTTCAAGGACGTGTTATCGACCTCAGATTAAGTTTATCGGCCGACTGTTTCGTATCCGCTCACCAAACGCGTTTTTGCATTAACAT

FIG. 8(B)

1200 TGTATGTCGGCGATGTTCTATATCTAATTTGAATAAAACGATAACCGCGTTGGTTTTAGAGGGCATAATAAAGAAATATTGTATCGTGTTCGCC
1300 ATTAGGGCAGTATAAATTGACGTTCATGTTGGATATTGTTTCAGTTGCAAGTGAATTCCTGCAGCCCGGGGATCCTATATAATAAAATGGTAGTTCTT
1400 TAGACGATGAGCATATCCTCTGCTCTTCTGCAAAGCGATGAGAGCTTGTTGGTGAGGATTCTGACAGTGAAATATCAGATCACGTAAGTGAAGATGA
1500 CGTCCAGAGGATACAGAAGAAGCGTTTATAGAGAGTGCAGCCAACGTCAAGCGGTAGTGAAATATTAGACGAACAAAATGTTATTGAA
1600 CAACCAGTTCTTCATTGGCTTCTAACAGAATCTTGACCTTGTCAGATCTCAAAGAGTCCGACGCGTATGTGCCGCAATATATGACCCACTTTATGCTTCAAACTATT
1700 GGCGTAGCCGAGTCTCTGCACTGAACATTGTAAAATGCTGAGATATCATTGAAACGTCGGGAATCTATGACAGGTGCTACATTTCGTGACACG
1800 TTTTACTGATGAGATAATTTCGGAAATTGTAAAATGGACAAATGCTGAGAATGCAGCAGTGAGAAAAGATAACCACATGTCCACAGATGACCTCTTTGATCGATCTTTGT
1900 AATGAAGATGAAATCTATGCTTTCTTTCTTTGGTATTCTGGTAATGACAGCAGTGAGATGCTTAGATGCGATGACAAAAGTATACGCCCACACTTCGAGAAAA
2000 CAATGGTGTACGTCTCTGTAATGAGTCGTGATCGTTTGATTTTTGATACGATGTCTTAGATGATGACAAAAGTATACGCCCACACTTCGAGAAAA
2100 CGATGTATTACTCCGTTAGAAAAATATGGGATCTCTTTATCCATCAGTCATACAAAATTACACTCCAGGGGCTCATTTGACCATAGATGAACAGTTA
2200 CTTGGTTTTAGAGGACGGTGTCCGTTAGGATGTATATCCCAAACAAGCAAGTAAGTATGAATAAAATCCTCATGATGTGTGACAGTGGTACGAAGT
2300 ATATGATAAATGGAATGCCTTATTTGGGAAGAGAGAACACAGAACCAACGGAGTACCACTCGGTGAATACTACGTGAATAACTACGTGAAGGAGTTATCAAAGCCTGTGCACGG

FIG. 8(B) CONT.

```
2400
TAGTTGTCGTAATATTACGTGTGACAATTGGTTCACCTCAATCCCTTTGGCAAAAAACTTACTACAAGAACCGTATAAGTTAACCATTGTGGAACCGTG
2500
CGATCAAACAACGGAGATACCGGAAGTACTGAAAAACAGTCGCTCCAGGCCAGTGGGAACATCGATGTTTTGTTTGACGGACCCCTTACTCTCGTCT
2600
CATATAAACCGAAGCCAGTAAGATGGTATACTTATTATTATCATCTTGTGATGAGGATGCTTCTATCAACGAAAGTACCGTAAACCGCAAATGGTTATGTA
2700
TTATAATCAAACTAAAGGCGGAGTGTGACACGCTAGACCAAATGTGTTCTGTGATGACCTGCAGTAGGAAGACGAATAGTGGCCTATGGCATTATTGTAC
2800
GGAATGATAAACATTGCCTGCAGTCATCGTTATGCGTAAGCGTTTAGAAGCTCCTACTTTGAAGAGATATTTGCCGATAATATCTCTAATATTTGCCAAA
2900
ACCTTTACATGAGCCTGGTACATCAGATGACAGTACTGAAGAGCCAGTAATGAAAAACGTACTTACTGTACTTACTGCCCCTCTAAAATAAGGCGAAAGGCAAAT
3000
TGAAGTGCCTGGTACATCAGATGACAGTACTGAAGAGCCAGTAATGAAAAACGTACTTACTGTACTTACTGCCAAAGTGTTTCTGACTGACTAATAAGTATAATTTGTTTCTAT
3100
GCATCGTGCAAAAAATGCAAAAAAGTTATTGTGAGAGCATAATATTGTGAGAGCATAATATTGTCGAAAATAAGTTTATTTTGTAAAGAGAATGTTTAAAAGT
3200
TATGTATAAGTTAAGCTAATTACTTATTTTATAATACAAACATGACTGTTTTTAAAGTACAAAATAAGTTTATTTTGTAAAGAGAATGTTTAAAAGT
3300
TTTGTTACTTTAGAAGAATTTTGAGTTTTTGTTTTTTTTTAATAATAAATAAACATAAATAAATTGTTGTTGAATTGGATCCACTAGTTCTAGAGC
3400
GGCCGCCACCGCGGTGGAGCTCCAGCTTTTGTTCCCTTTAGTGAGGGTTAATTGCGCGCTTGGCGTAATCATGGTCATAGCTGTTCCTGTGTGAAATTG
```

*FIG. 8(B) CONT.*

```
3500
TTATCCGGCTCACAATTCCACACAACATACGAGCCGGAAGCATAAAGTGTAAAGCCTGGGGTGCCTAATGAGTGAGCTAACTCACATTAATTGCGTTGCGC
>ColE1_origin
3600
TCACTGCCCGCTTTCCAGTCGGGAAACCTGTCGTGCCAGCTGCATTAATGAATCGGCCAACGCGCGGGGAGAGGCGGTTTGCGTATTGGGCGCTCTTCCG
3700
CTTCCTCGCTCACTGACTCGCTGCGCTCGGTCGTTCGGCTGCGGCGAGCGGTATCAGCTCACTCAAAGGCGGTAATACGGTTATCCACAGAATCAGGGGA
3800
TAACGCAGGAAAGAACATGTGAGCAAAAGGCCAGCAAAAGGCCAGGAACCGTAAAAAGGCCGCGTTGCTGGCGTTTTTCCATAGGCTCCGCCCCCCTGAC
3900
GAGCATCACAAAAATCGACGCTCAAGTCAGAGGTGGCGAAACCCGACAGGACTATAAAGATACCAGGCGTTTCCCCCTGGAAGCTCCCTCGTGCGCTCTC
4000
CTGTTCCGACCCTGCCGCTTACCGGATACCTGTCCGCCTTTCTCCCTTCGGGAAGCGTGGCGCTTTCTCATAGCTCACGCTGTAGGTATCTCAGTTCGGT
4100
GTAGGTCGTTCGCTCCAAGCTGGGCTGTGTGCACGAACCCCCCGTTCAGCCCGACCGCTGCGCCTTATCCGGTAACTATCGTCTTGAGTCCAACCCGGTA
4200
AGACACGACTTATCGCCACTGGCAGCAGCCACTGGTAACAGGATTAGCAGAGCGAGGTATGTAGGCGGTGCTACAGAGTTCTTGAAGTGGTGGCCTAACT
4300
ACGGCTACACTAGAAGGACAGTATTTGGTATCTGCGCTCTGCTGAAGCCAGTTACCTTCGGAAAAAGAGTTGGTAGCTCTTGATCCGGCAAACAAACCAC
4400
CGCTGGTAGCGGTGGTTTTTTTGTTTGCAAGCAGCAGATTACGCGCAGAAAAAAAGGATCTCAAGAAGATCCTTTGATCTTTTCTACGGGGTCTGACGCT
4500
CAGTGGAACGAAAACTCACGTTAAGGGATTTTGGTCATGAGATTATCAAAAAGGATCTTCACCTAGATCCTTTTAAATTAAAAATGAAGTTTTAAATCAA
4600
TCTAAAGTATATATGAGTAAACTTGGTCTGACAGTTACCAATGCTTAATCAGTGAGGCACCTATCTCAGCGATCTGTCTATTTCGTTCATCCATAGTTGC
                                    AMPCILLIN RESISTANCE
                                                          >
```

*FIG. 8(B) CONT.*

```
4700
CTGACTCCCCGTCGTGTAGATAACTACGATACGGGAGGGCTTACCATCTGGCCCCAGTGCTGCAATGATACCGCGAGACCCACGCTCACGGCTCCAGAT
                                                 AMPCILLIN RESISTANCE
4800
TTATCAGCAATAAACCAGCCAGCCGGAAGGGCCAGAAGTGGTCCTGCAACTTTATCCGCCTCCATCCAGTCTATTAATTGTGCCGGGAAGCTA
                                                 AMPCILLIN RESISTANCE
4900
GAGTAAGTAGTTCGCCAGTGTTAATAGTTTGCGCAACGTTGTTGCCATTGCTACAGGCATCGTGGTGTCACGCTCGTCGTTTGGTATGGCTTCATTCAGCTC
                                                 AMPCILLIN RESISTANCE
5000
CGGTTCCCAACGATCAAGGCGAGTACATGATCCCCCATGTTGTGCAAAAAAGCGGTTAGCTCCTTCGGTCCTCCGATCGTTGTCAGAAGTAAGTTGGCC
                                                 AMPCILLIN RESISTANCE
5100
GCAGTGTTATCACTCATGGTTATGGCAGCACTGCATAATTCTCTTACTGTCATGCCATCCGTAAGATGCTTTTCTGTGACTGGTGAGTACTCAACCAAGT
                                                 AMPCILLIN RESISTANCE
5200
CATTCTGAGAATAGTGTATGCGGCGACCGAGTTGCTCTTGCCCCGGCGTCAATACGGGATAATACCGCGCCACATAGCAGAACTTTAAAAGTGCTCATCAT
                                                 AMPCILLIN RESISTANCE
5300
TGGAAAACGTTCTTCGGGGCGAAAACTCTCAAGGATCTTACCGCTGTTGAGATCCAGTTCGATGTAACCCACTCGTGCACCCAACTGATCTTCAGCATCT
                                                 AMPCILLIN RESISTANCE
5400
TTTACTTTCACCAGCGTTTCTGGGTGAGCAAAAACAGGAAGGCAAAATGCCGCAAAAAAGGGAATAAGGGCGACACGGAAATGTTGAATACTCATACTCT
                                                 AMPCILLIN RESISTANCE
5500
TCCTTTTTCAATATTATTGAAGCATTTATCAGGGTTATTGTCTCATGAGCGGATACATATTTGAATGTATTTAGAAAAATAAACAAATAGGGGTTCCGCG
CACATTTCCCCGAAAAGTGCCAC --(SEQ ID NO:44)--
```

*FIG. 8(B) CONT.* p3XP3-DsRed-orf
Sequence Range: 1 to 6984

```
100
TAGTTATTAATAGTAATCAATTACGGGGTCATTAGTTCATAGCCCATATATGGAGTTCCGGGTTACATAACTTACGGTAAATGGCCCGCCTGGCTGACCG
                                         CMV PROMOTER

200
CCCAACGACCCCCGCCCATTGACGTCAATAATGACGTATGTTCCCATAGTAACGCCAATAGGGACTTTCCATTGACGTCAATGGGTGGAGTATTTACGGT
                                         CMV PROMOTER

300
AAACTGCCCACTTGGCAGTACATCAAGTGTATCATATGCCAAGTACGCCCCCTATTGACGTCAATGACGGTAAATGGCCCGCCTGGCATTATGCCCAGTA
                                         CMV PROMOTER

400
CATGACCTTATGGGACTTTCCTACTTGGCAGTACATCTACGTATTAGTCATCGCTATTACCATGGTGATGCGGTTTTGGCAGTACATCAATGGGCGTGGA
                                         CMV PROMOTER

500
TAGCGGTTTGACTCACGGGGATTTCCAAGTCTCCACCCCATTGACGTCAATGGGAGTTTGTTTTGGCACCAAAATCAACGGGACTTTCCAAAATGTCGTA
                                         CMV PROMOTER

600
ACAACTCCGCCCCATTGACGCAAATGGGCGGTAGGCGTGTACGGTGGGAGGTCTATATAAGCAGAGCTGGTTTAGTGAACCGTCAGATCCGCTAGCGCTA
                                         CMV PROMOTER

700
CCGGACTCAGATCCTATATAATAAAGTGGTAGTTCTTTAGACGATGAGCATATCCTCTCTGCTCTTCTGCAAAGCGATGACGAGCTTGTTGGTGAGGAT
                                                                                    PIGGYBAC ORF

800
TCTGACAGTGAAATATCAGATCACGTAAGTGAAGATGACGTTCCAGAGCGATACAGAAGAAGCGTTTATAGATGAGGTACATGAAGTGCAGCCAACGTCAA
                                                                                    PIGGYBAC ORF
```

FIG. 9(B)

```
900
GCGGGTAGTGAAATATTAGACGAACAAAATGTTATTGAACAACCAGTTCTTCATTGGCTTCTCTAACAGAATCTTGACCTTGCCACAGAGGACTATTAGAGG
                                                PIGGYBAC ORF

1000
TAAGAATAAACATTGTTGGTCAACTTCAAAGTCCACGAGGCGTAGCCGAGTCTCTGCACTGAACATTGTCAGATCTCAAAGAGGTCCGACGCGTATGTGC
                                                PIGGYBAC ORF

1100
CGCAATATATATGACCCACTTTTATGCTTCAAACTATTTTTACTGATGAGATAATTTCGGAAATTGTAAAATGCTGAGATATCATTGAAAC
                                                PIGGYBAC ORF

1200
GTCGGGGAATCTATGACAGGTGCTACATTCGTGACACGAATGAAGATGAAATCTATGCTTTCTTCTTTGGTATTCTGGTAATGACAGCAGTGAGAAAGATAA
                                                PIGGYBAC ORF

1300
CCACATGTCCACAGATGACCTCTTTGATCGATCTTGTCAATGGTGTACGTCTCTGTAATGAGTCGTGATCGTTTGATTTTTTGATACGATGTCTTAGA
                                                PIGGYBAC ORF

1400
ATGGATGACAAAGTATACGGGCCCACACTTCGAGAAAACGATGTATTACTCCTGTTTAGAGGACGGTGTCCGTTAGGATGTATATCCCAAACAAGCCAAGTAAGTATGG
                                                PIGGYBAC ORF

1500
ACACTCCAGGGGCTCATTTGACCATAGATGAACAGTGTACTTGGTTGTACGAAGTATATGAACAGCCAACGGAGTACCACTCGGT
                                                PIGGYBAC ORF

1600
AATAAAATCCTCATGATGTGTGACAGTGGTACGAAGTATATGATAAATGAATGCCTTATTGGGAAGAGAACACAGACCAACGGAGTACCACTCGGT
                                                PIGGYBAC ORF

1700
GAATACTACGTGAAGGAGTTATCAAAGCCTGTGCACGGTAGTTGTCGTAATATTACGTGTGACAATTGGTTCACCTCAATCCCTTTGGCAAAAACTTAC
                                                PIGGYBAC ORF
```

*FIG. 9(B) CONT.*

```
1800
TACAAGAGACCGTATAAGTTAACCATTGTGGGAACCTGCGATCAAACAAAACGCGAGATACCGGAAGTACTGAAAACAGTCGCTCCAGGCCAGTGGGAAC
     PIGGYBAC ORF

1900
ATCGATGTTTTGTTTTGACGACCCCTTACTCTCGTCTCATATAAACCGAAGCCAGCTAAGATGGTATACTTATTATCATCTTGTGATGAGGATGCTTCT
     PIGGYBAC ORF

2000
ATCAACGAAAGTACCGGTAAACCGCAAATGGTTATGTATTATAATCAAACTAAAGGGCGAGTGGACACGCGCTAGACCAAATGTGTTCTGTGATGACCTGCA
     PIGGYBAC ORF

2100
GTAGGAAGACGAATAGGTGGCCTATGGCATTATTGTACGGAATGATAAACATTGCCTGCATAAATTCTTTATTATATACAGCCATAATGTCAGTAGCAA
     PIGGYBAC ORF

2200
GGGAGAAAAGGTTCAAAGTCGCAAAAAATTTATGAGAAACCTTTACATGAGCCTGACGTCATCGTTTATGCGTAAGCGTTTAGAGCTCCTACTTTGAAG
     PIGGYBAC ORF

2300
AGATATTGCGCGATAATATCTCTAAATATTTTGCCAAATGAAGTGCCTGGTACATCAGATGACAGTACTGAAGAGCCAGTAATGAAAAACGTACTTACT
     PIGGYBAC ORF

2400
GTACTTACTGCCCCTCTAAAATAAGGCGAAAGGCAAATGCATCGTGCAAAAAAATGCAAAAAAGTTATTTGTCGAGAGCATAATATTGATATGTGCCAAAG
     PIGGYBAC ORF

2500
TTGTTTCTGACTGACTAATAAGTATAATTGTTTCTATTATGTAAGTTAAGCTAATTACTTATTTTATAATACAACATGACTGTTTTAAAGTACAAA
     PIGGYBAC ORF

2600
ATAAGTTTATTTTTGTAAAGAGAGAATGTTTAAAAGTTTGTTACTTAGAAGAAATTTGAGTTTTTTGTTTTTTTTAATAAATAAATAAACATAAAT
     PIGGYBAC ORF
```

*FIG. 9(B) CONT.*

2700
AAATTGTTTGTTGAATTGGATCTCGAGGTTCCCACAATGGTTAATTCGAGCTCGCCCGGGGATCTAATTCAATTAGAGACTAATTCAATTAGAGCTAAT
  PIGGYBAC ORF  >                                             3XP3 PROMOTER        >

2800
TCAATTAGGATCCAAGCTTATCGATTTCGAACCCTCGACCGCCGGAGTATAAATAGAGGGCGCTTCGTCTACGGAGCGACAATTCAATTCAAACAAGCAAA
                                             3XP3 PROMOTER                                      >

2900
GTGAACACGTCGCTAAGGCGAAAGCTAAGCAAATAAACAAGCGCAGCTGAACAAGCTAAACAATCGGGTACCGCTAGAGTCGACGGTACCGCGGGCCCGG
                                       3XP3 PROMOTER                                     >

3000
GATCCACCGGTCGCCACCATGAATTCTGCAGTCGACGGTACCGCGGGCCCGGGATCCACCGGTCGCCACCATGGTGCGCTCCTCCAAGAACGTCATCAAG
   3XP3 PROMOTER     >                                                           DSRED GENE

3100
GAGTTCATGCGCTTCAAGGTGCGCATGGAGGGCACCGTGAACGGCCACGAGTTCGAGATCGAGGGCGAGGGCGAGGGCCGCCCCTACGAGGGCCACAACA
                                             DSRED GENE                                                 >

3200
CCGTGAAGCTGAAGGTGACCAAGGGCGGCCCCCTGCCCTTCGCCTGGGACATCCTGTCCCCCCAGTTCCAGTACGGCTCCAAGGTGTACGTGAAGCACCC
                                           DSRED GENE                                                 >

3300
CGCCGACATCCCCGACTACAAGAAGCTGTCCTTCCCCGAGGGCTTCAAGTGGGAGCGCGTGATGAACTTCGAGGACGGCGGCGTGGTGACCGTGACCCAG
                                           DSRED GENE                                                 >

3400
GACTCCTCCCTGCAGGACGGCTGCTTCATCTACAAGGTGAAGTTCATCGGCGTGAACTTCCCCTCCGACGGCCCCGTAATGCAGAAGAAGACCATGGGCT
                                           DSRED GENE                                                 >

FIG. 9(B) CONT.

```
3500
GGGAGGGCCCTCCACCGAGCGCCTGTACCCCGCGACGGCGTGCTGACGGGCGAGATCCACAAGGCCCTGAAGCTGAAGGACGGCGGCCACTACCTGGTGGA
                                                           DSRED GENE                                  >
3600
GTTCAAGTCCATCTACATGGCCAAGAAGCCCGTGCAGCTGCCCGGCTACTACTACGTGGACTCCAAGCTGGACATCACCTCCCACAACGAGGACTACACC
                                                           DSRED GENE                                  >
3700
ATCGTGGAGCAGTACGAGCGCACCGAGGGCGCCCACCTGTTCCTGTAGCGGCCGACTCTAGATCATAATCAGCCATACCACATTTGTAGAGGTTT
                                   DSRED GENE                          >
3800
TACTTGCTTTAAAAAACCTCCCACACCTCCCCCTGAACCTGAAACATAAAATGAATGCAATTGTTGTTGTTAACTTGTTTATTGCAGCTTATAATGGTTA
3900
CAAATAAAGCAATAGCATCACAAATTTCACAAATAAAGCATTTTTTCACTGCATTCTAGTTGTGGTTTGTCCAAACTCATCAATGTATCTTAAGGCGTA
>f1_single-strand_DNA_origin
4000
AATTGTAAGCGTTAATATTTTGTTAAAATTCGCGTTAAATTTTTGTTAAATCAGCTCATTTTTTAACCAATAGGCCGAAATCGGCAAAATCCCTTATAAA
4100
TCAAAAGAATAGACCGAGATAGGGTTGAGTGTTGTTCCAGTTTGGAACAAGAGTCCACTATTAAAGAACGTGGACTCCAACGTCAAGGGCGAAAAACCG
4200
TCTATCAGGGCGATGGCCCACTACGTGAACCATCACCCTAATCAAGTTTTTTGGGGTCGAGGTGCCGTAAAGCACTAAATCGGAACCCTAAAGGGAGCCC
4300
CCGATTTAGAGCTTGACGGGGAAAGCCGGCGAACGTGGCGAGAAAGGAAGGGAAGAAAGCGAAAGGAGCGGGCGCTAGGGCGCTGGCAAGTGTAGCGGTC
```

*FIG. 9(B) CONT.*

```
4400
ACGCTGGCGCGTAACCACCACACCCGCCGCGCTTAATGCGCCGCGCGCTACAGGGGCGCGTCAGGTGGCACTTTTCGGGGAAATGTGCGGGAACCCCTATTTGTT
>Bacerial_promoter_for_expressioin_of_Kan_resistance_gene 4500
TATTTTTCTAAATACATTCAAATATGTATCCGCTCATGAGACAATAATAACCCTGATAAATGCTTCAATAATATTGAAAAAGGAAGAGTCCTGAGGCGGAAAG
                                            >SV40_early_promoter_and_origin_of_replication 4600
AACCAGCTGTGGAATGTGTGTCAGTTAGGGTGTGGAAAGTCCCCAGGCTCCCCAGCCTCCCCAGCAGGCAGAAGTATGCAAAGCATGCATCTCAATTAGTCAGCAACCA 4700
GGTGTGGAAAGTCCCCAGGCTCCCCAGCAGGCAGAAGTATGCAAAGCATGCATCTCAATTAGTCAGCAACCATAGTCCCGCCCCTAACTCCGCCCATCCC 4800
GCCCCTAACTCCGCCCAGTTCCGCCCATTCTCCGCCCCATGGCTGACTAATTTTTTTTATTTATGCAGAGGCCGAGGCCGCCTCTGAGCTATTC 4900
CAGAAGTAGTGAGGAGGCTTTTTTGGAGGCCTAGGCTTTTGCAAAGATCGATCAAGAGACAGGATGAGGATCGTTTCGCATGATTGAACAAGATGGATTG
                                                                                              ˄

5000
CACGCAGGTTCTCCGGCCGCTTGGGTGGAGAGGCTATTCGGCTATGACTGGGCACAACAGACAATCGGCTGCTCTGATGCCGCCGTGTTCCGGCTGTCAG
                                                      KANAMYCIN RESISTANCE GENE                 ˄

5100
CGCAGGGGCGCCCGGTTCTTTTTGTCAAGACCGACCTGTCCGGTGCCCTGAATGAACTGCAAGACGAGGCAGCGCGGCTATCGTGGCTGGCCACGACGGG
                                       KANAMYCIN RESISTANCE GENE                                ˄

5200
CGTTCCTTGCGCAGCTGTGCTCGACGTTGTCACTGAAGCGGGAAGGGACTGGCTGCTATTGGGCGAAGTGCCGGGGCAGGATCTCCTGTCATCTCACCTT
                        KANAMYCIN RESISTANCE GENE                                                ˄
```

```
5300
GCTCCTGCCGAGAAAGTATCCATCATGGCTGATGCAATGCGGGGCTGCATACGCTTGATCCGGCTACCTGCCCATTCGACCACCAAGCGAAACATCGCA
          KANAMYCIN RESISTANCE GENE

5400
TCGAGCGAGCACGTACTCGGATGGAAGCCGGTCTTGTCGATCAGGATGATCTGGACGAAGAGCATCAGGGGCTCGCGCCAGCCGAACTGTTCGCCAGGCT
         KANAMYCIN RESISTANCE GENE

5500
CAAGGCGAGCATGCCCGACGGCGAGGATCTCGTCGTGACCCATGGCGATGCCTGCTTGCCGAATATCATGTGGAAAATGGCCGCTTTCTGGATTCATC
         KANAMYCIN RESISTANCE GENE

5600
GACTGTGGCCGGCTGGGTGTGGCGGACCGCTATCAGGACATAGCGTTGGCTACCCGTGATATTGCTGAAGAGCTTGGCGGCGAATGGGCTGACCGCTTCC
         KANAMYCIN RESISTANCE GENE

5700
TCGTGCTTTACGGTATCGCCGCTCCCGATTCGCAGCGCATCGCCTTCTATCGCCTTCTTGACGAGTTCTTCTGAGCGGGACTCTGGGGTTCGAAATGACC
         KANAMYCIN RESISTANCE GENE

5800
GACCAAGCGACGCCCAACCTGCCATCACGAGATTTCGATTCCACCGCCGCCTTCTATGAAAGGTTGGGCTTCGGAATCGTTTTCCGGGACGCCGGCTGGA

5900
TGATCCTCCAGCGCGGGGATCTCATGCTGGAGTTCTTCGCCCACCCTAGGGGGAGGCTAACTGAAACACGGAAGGAGACAATACCGGAAGGAACCCGCGC
>Herpes_simplex_virus_(HSV)_thymidine_kinase_(TK)_polyA_signals 6000
TATGACGGCAATAAAAAGACAGAATAAAACGCACGGTGTTGGGTCGTTTGTTCATAAACGCGGGGTTCGGTCCCAGGGCTGGCACTCTGTCGATACCCCA 6100
CCGAGACCCCATTGGGGCCAATACGCCCGCGTTTCTTCCTTTTCCCCACCCCCACCCCCCAAGTTCGGGTGAAGGCCCAGGGCTCGCAGCCAACGTCGGGG
```

*FIG. 9(B) CONT.*

```
6200
CGGCAGGCCCTGCCATAGCCTCAGGTTACTCATATATACTTTAGATTGATTTAAAACTTCATTTTTAAAGGATCTAGGTGAAGATCCTTTTTGA

>pUC_plasmid_replication_origin
                      |—————————————————————————————————|

6300
TAATCTCATGACCAAAATCCCTTAACGTGAGTTTTCGTTCCACTGAGCGTCAGACCCCGTAGAAAAGATCAAAGGATCTCTTGAGATCCTTTTTTTCTG
6400
CGCGTAATCTGCTGCTTGCAAACAAAAAAACCACCGCTACCAGCGGTGGTTTGTTTGCCGGATCAAGAGCTACCAACTCTTTTTCCGAAGGTAACTGGCT
6500
TCAGCAGAGCGCAGATACCAAATACTGTCCTTCTAGTGTAGCCGTAGTTAGGCCACCACTTCAAGAACTCTGTAGCACCGCCTACATACCTCGCTCTGCT
6600
AATCCTGTTACCAGTGGCTGCTGCCAGTGGCGATAAGTCGTGTCTTACCGGGTTGGACTCAAGACGATAGTTACCGGATAAGGCGCAGCGGTCGGGCTGA
6700
ACGGGGGGTTCGTGCACACAGCCCAGCTTGGAGCGAACGACCTACACCGAACTGAGATACCTACAGCGTGAGCTATGAGAAAGCGCCACGCTTCCCGAAG
6800
GGAGAAAGGCGGACAGGTATCCGGTAAGCGGCAGGGTCGGAACAGGAGAGCGCACGAGGGAGCTTCCAGGGGGAAACGCCTGGTATCTTTATAGTCCTGT
6900
CGGGTTTCGCCACCTCTGACTTGAGCGTCGATTTTTGTGATGCTCGTCAGGGGGGCGGAGCCTATGGAAAAACGCCAGCAACGCGGCCTTTTTACGGTTC
CTGGCCTTTTGCTGGCCTTTTGCTCACATGTTCTTTCCTGCGTTATCCCCTGATTCTGTGGATAACCGTATTACCGCCATGCAT --(SEQ ID NO:45)--
```

*FIG. 9(B) CONT.*

Sequence Range: 1 to 4613

100
AGCGGCCCAATACGCCAAACCGCCTCTCCCGCGCGTTGGCCGATTCATTAATGCAGCTGGCACGACAGAGTTCCCGACTGAAAGCGGGCAGTGAGCGCAA

200
CGCAATTAATGTGAGTTAGCTCACTCATTAGGCACCCCAGGCTTTACACTTTATGCTTCCGGCTCGTATGTTGTGTGGAATTGTGAGCGGATAACAATTT

300
CACACAGGAAACAGCTATGACCATGATTACGCCAAGCTTGGTACCGAGCTCGGATCCACTAGTAACGGCCGCCAGTGTGCTGGAATTCGGCTTGGATCCC
>

400
ATGCGTCAATTTACGCAGACTATCTTTCTAGGGTTAATCTAGCTGCATCAGGATCATATCGTCGGGTCTTTTTCCGGCTCAGTCATCGCCCAAGCTGG
L  H  Q  D  H  I  V  G  S  F  F  R  L  S  H  R  P  S  W>
B (CAPSID COMPONENT;533); CODON_START=1; DB_XREF=P >
L  H  Q  D  H  I  V  G  S  F  F  R  L  S  H  R  P  S  W>
     PROCESSED B; CODON_START=1 [SPLIT]
     RIGHT TERMINAL REPEAT        >

500
CGCTATCTGGGCATCGGGGAGGAAGAAGCCCGTGCCTTTTCCCGCGAGGTTGAAGCGGCATGGAAAGAGTTTGCCGAGGATGACTGCTGCTGCATTGACG
R  Y  L  G  I  G  E  E  A  R  A  F  S  R  E  V  E  A  A  W  K  E  F  A  E  D  D  C  C  C  I  D>
B (CAPSID COMPONENT;533); CODON_START=1; DB_XREF=PID:G215108; TRA [SPLIT]
R  Y  L  G  I  G  E  E  A  R  A  F  S  R  E  V  E  A  A  W  K  E  F  A  E  D  D  C  C  C  I  D>
    PROCESSED B; CODON_START=1 [SPLIT]

FIG. 10(B)

```
600
TTGAGCGAAAACGCACGTTTACCATGATGATTCGGGAAGTGTGGCCATGCACGCCCTTTAACGCGTGAACTGTTCGTTCAGGCCACCTGGGATACCAGTTC
 V  E  R  K  R  T  F  T  M  M  I  R  E  G  V  A  M  H  A  F  N  G  E  L  F  V  Q  A  T  W  D  T  S  >
           B (CAPSID COMPONENT;533); CODON_START=1; DB_XREF=PID:G215108; TRA [SPLIT]
 V  E  R  K  R  T  F  T  M  M  I  R  E  G  V  A  M  H  A  F  N  G  E  L  F  V  Q  A  T  W  D  T  S  >
           PROCESSED B; CODON_START=1 [SPLIT]

700
GTCGCGGCTTTTCCGACACAGTTCCGATGGTCAGCCCGAAGCGCATCAGCAACCCGAACAATACCGGCGAACAGCCGGAACTGCCGTGCCGGGTGTGCAG
 S  R  L  F  R  T  Q  F  R  M  V  S  P  K  R  I  S  N  P  N  N  T  G  D  S  R  N  C  R  A  G  V  Q  >
           B (CAPSID COMPONENT;533); CODON_START=1; DB_XREF=PID:G215108; TRA [SPLIT]
 S  R  L  F  R  T  Q  F  R  M  V  S  P  K  R  I  S  N  P  N  N  T  G  D  S  R  N  C  R  A  G  V  Q  >
           PROCESSED B; CODON_START=1 [SPLIT]

800
ATTAATGACAGCGGTGCGGCTGGGAGCTGGGAGATATTACGTCAGGACGGGGTATCCTGGCTGGATGCCGCAGAAATGGACATGGATACCCCGTGAGTTACCCG
 I  N  D  S  G  A  A  L  G  Y  Y  V  S  E  D  G  Y  P  G  W  M  P  Q  K  W  T  W  I  P  P  R  E  L  P  >
           B (CAPSID COMPONENT;533); CODON_START=1; DB_XREF=PID:G215108; TRA [SPLIT]
 I  N  D  S  G  A  A  L  G  Y  Y  V  S  E  D  G  Y  P  G  W  M  P  Q  K  W  T  W  I  P  P  R  E  L  P  >
           PROCESSED B; CODON_START=1 [SPLIT]

900
GCGGGGGCCGGCCCTCGTTCATTCACGTTTTTGAACCCGTGGAGGACGGGCAGACTCGCGGTGCAAATGTGTTTTACAGCCGTGATGGAGCAGATGAAGATGCT
 G  G  R  A  S  F  I  H  V  F  E  P  V  E  D  G  Q  T  R  G  A  N  V  F  Y  S  V  M  E  Q  M  K  M  L  >
           B (CAPSID COMPONENT;533); CODON_START=1; DB_XREF=PID:G215108; TRA [SPLIT]
 G  G  R  A  S  F  I  H  V  F  E  P  V  E  D  G  Q  T  R  G  A  N  V  F  Y  S  V  M  E  Q  M  K  M  L  >
           PROCESSED B; CODON_START=1 [SPLIT]
```

*FIG. 10(B) CONT.*

```
1000
CGACACGCTGCAGAACACGGCAGCTAGATTAACCCTAGAAAGATAATCATATTGTGACGTACGTTAAAGATAATCATGCGTAAAATTGACGCATGGGATCC
 D  T  L  Q  N  T  Q>  --(SEQ ID NO:47)---
 D  T  L  Q  N  T  Q>  --(SEQ ID NO:47)---
 B (CAPSID COMPO     >
 PROCESSED B; CO     >
                                    LEFT TERMINAL REPEAT                                          >

1100
AAGCCCGAATTCTGCAGATATCCATCACACTGGCGGCCGCTCGAGCATGCATCTAGAGGGCCCAATTCGCCCTATAGTGAGTCGTATTACAATTCACTGGC

1200
CGTCGTTTACAACGTCGTGACTGGGAAAACCCTGGCGTTACCCAACTTAATCGCCTTGCAGCACATCCCCCTTTCGCCAGCTGGCGTAATAGCGAAGAG

1300
GCCCGCACCGATCGCCCTTCCCAACAGTTGCGCAGCCTGAATGGCGAATGGGACGCGCCCTGTAGCGGCGCATTAAGCGCGGCGGGTGTGGTGGTTACGC

1400
GCAGCGTGACCGCTACACTTGCCAGCGCCCTAGCGCCCGCTCCTTTCGCTTTCTTCCCTTCCTTTCTCGCCACGTTCGCCGGCTTTCCCCGTCAAGCTCT

1500
AAATCGGGGGCTCCCTTTAGGGTTCCGATTTAGAGCTTTGACGTTGGAGTCCACGTTCTTTAATAGTGGACTCTTGTTCCAAACTGGAACAACACTCAACCCTATCGCGGTCTATT

1600
TGATAGACGGTTTTTCGCCCTTTGACGTTGGAGTCCACGTTCTTTAATAGTGGACTCTTGTTCCAAACTGGAACAACACTCAACCCTATCGCGGTCTATT

1700
CTTTTGATTTATAAGGGATTTTGCCGATTTCGGCCTATTGGTTAAAAAATGAGCTGATTTAACAAATTCAGGGCGCAAGGGCTGCTAAAGGAACCCGGAAC

1800
ACGTAGAAAGCCAGTCCGCAGAAACGGTGCTGACCCCGGATGAATGTCAGCTACTGGGCTATCTGGACAAGGGAAAACGCAAGCGCAAAGAGAAAGCAGG
```

*FIG. 10(B) CONT.*

```
1900 TAGCTTGCAGTGGGCTTACATGGCGATAGCTAGACTGGGCGGTTTTATGGACAGCAAGCGAACCGGAATTGCCAGCTGGGCGCCCTCTGGTAAGGTTGG
2000 GAAGCCCTGCAAAGTAAACTGGATGGCTTTCTTGCCGCCAAGGATCTGATGGCGCAGGGGATCAAGATCTGATCAAGAGACAGGATGAGGATGCGTTTCGC
2100 ATGATTGAACAAGATGGATTGCACGCAGGTTCTCCGGCCGTTCTCCGGCTGGGTGGAGAGGCTATTCGGCTATGACTGGGCACAACAGACAATCGGCTGCTCTGATG
2200 CCGCCGTGTTCCGGCTGTCAGCGCAGGGGCGCCCGGTTCTTTTTGTCAAGACCGACCTGTCCGGTGCCCTGAATGAACTGCAGGACGAGGCAGCGCGGCT
2300 ATCGTGGCTGGCCACGACGGGCGTTCCTTGCGCAGCTGTGCTCGACGTTGTCACTGAAGCGGGAAGGACTGGCTGCTATTGGGCGAAGTGCCGGGCAG
2400 GATCTCCTGTCATCGCCTTGCTCCTGCCGAGAAAGTATCCATCATGGCTGATGCAATGCGGCGGCTGCATACGCTTGATCCGGCTACCTGCCCATTCG
2500 ACCACCAAGCGAAACATCGCATCGAGCGAGCACGTACTCGGATGAAGCCGGTCTTGTCGATCAGGATGATCTGGACGAAGAGCATCAGGGGCTCGCGCC
2600 AGCCGAACTGTTCGCCAGGCTCAAGGCGCGCATGCCCGACGGCGAGGATCTCGTCGTGACCCATGGCGATGCCTGCTTGCCGAATATCATGGTGGAAAAT
2700 GGCCGCTTTTCTGGATTCAACGACTGTGGCCGGCTGGGTGTGGCGGACCGCTATCAGGACATAGCGTTGGATACCCGTGATATTGCTGAAGAGCTTGGCG
2800 GCGAATGGGCTGACCGCTTCCTCGTGCTTTACGGTATCGCCGCTCCCGATTCGCAGCGCATCGCCTTCTATCGCCTTCTTGACGAGTTCTTCTGAATTGA
2900 AAAAGGAAGAGTATGAGTATTCAACATTTCCGTGTCGCCCTTATTCCCTTTTTTGCGGCATTTTGCCTTCCTGTTTTTGCTCACCCAGAAACGCTGGTGA
```

FIG. 10(B) CONT.

```
3000
AAGTAAAAGATGCTGAAGATCAGTTGGGTGCACGAGTGGGTTACATCGAACTGGATCTCAACAGCGGTAAGATCCTTGAGAGTTTTCGCCCCGAAGAACG
3100
TTTTCCAATGATGAGCACTTTTAAAGTTCTGCTATGTCATACACTATTATCCCGTATTGACGCCGGGCAAGAGCAACTCGGTCGCCGGGGCGCGGTATTCT
3200
CAGAATGACTTGGTTGAGTACTCACCAGTCACAGAAAAGCATCTTACGGATGGCATGACAGTAAGAGAATTATGCAGTGCTGCCATAACCATGAGTGATA
3300
ACACTGCGGCCAACTTACTTCTGACAACGATCGGAGGACCGAAGGAGCTAACCGCTTTTTTGCACAACATGGGGATCATGTAACTCGCCTTGATCGTTG
3400
GGAACCGGAGCTGAATGAAGCCATACCAAACGACGAGTGACACCACGATGCCTGTAGCAATGCCAACAACGTTGCGCAAACTATTAACTGGCAACTA
3500
CTTACTCTAGCTTCCCCGCAACAATTAATAGACTGGATGAGGCGGATAAAGTTGCAGGACCACTTCTGCGCTCGGCCCCTTCCGGCTGGCTGGTTTATTG
3600
CTGATAAATCTGGAGCCGGTGAGCGTGGGTCTCGCGGTATCATTGCAGCACTGGGGCCAGATGGTAAGCCCTCCCGTATCGTAGTTATCTCACACGACGGG
3700
GAGTCAGGCAACTATGGATGAACGAAATAGACAGATCGCTGAGATAGGTGCCTCACTGATTAAGCATTGGTAACTGTCAGACCAAGTTTACTCATATATA
3800
CTTTAGATTGATTGAAAACTTCATTTTTAATTTAAAGGATCTAGGTGAAGATCCTTTTTGATAATCTCATGACCAAAATCCCTTAACGTGAGTTTTCGT
3900
TCCACTGAGCGTCAGACCCCGTAGAAAAGATCAAAGGATCTTCTTGAGATCCTTTTTTTTCTGCGCGTAATCTGCTGCTTGCAAACAAAAAAACCACCGCT
4000
ACCAGCGGTGGTTTGTTTGCCGGATCAAGAGCTACCAACTCTTTTTCCGAAGGTAACTGGCTTCAGCAGAGCGCAGATACCAAATACTGTCCTTCTAGTG
```

FIG. 10(B) CONT.

4100
TAGCCGTAGTTAGGCCACCACTTCAAGAACTCTGTAGCACCGCCTACATACCTCGCTCTGCTAATCCTGTTACCAGTGGCTGCTGCCAGTGGGCGATAAGT

4200
CGTGTCTTACCGGGTTGGACTCAAGACGATAGTTACCGGATAAGGCGCAGCGGTCGGGCTGAACGGGGGGTTCGTGCACACAGCCCAGCTTGGAGCGAAC

4300
GACCTACACCGAACTGAGATACCTACAGCGTGAGCATTGAGAAAGCGCCACGCTTCCCGAAGGGAGAAAGGCGACAGGTATCCGTAAGCGGCAGGGTC

4400
GGAACAGGAGAGCGCACGAGGGAGCTTCCAGGGGGAAACGCCTGGTATCTTTATAGTCCTGTCGGGTTTCGCCACCTCTGACTTGAGCGTCGATTTTTGT

4500
GATGCTCGTCAGGGGGGCGGAGCCTATGGAAAAACGCCAGCAACGCGGCCTTTTTACGGTTCCTGGCCTTTGCTCACATGTTCTTTCC

4600
TGCGTTATCCCCTGATTCTGTGGATAACCGTATTACCGCCTTTGAGTGAGCTGATACCGCTCGCCGCAGCCGAACGACCGAGCGCAGCGAGTCAGTGAGC

GAGGAAGCGGAAG -- (SEQ ID NO:46)--

*FIG. 10(B) CONT.* p(PZ)-Bac-EYFP
Sequence Range: 1 to 8999

```
100
ACCGAAGTATACACTTAAATTCAGTGCACGTTTGCTTGTTGAGAGGAAAGGTTGTGTGCGGACGAATTTTTTTGAAAACATTAACCCTTAGTGGAAT
200
AAAAAAAAATGAAATATTGCAAATTTGCTGCAAAGCTGTGACTGGAGTAAAATTAATTCACGTGCCGAAGTGTGCTATTAAGAGAAAATTGTGGGAGCA
300
GAGCCTTGGGTGCAGCCTTGGTGTGAAAACTCCCAAATTTGTGATACCCACTTTAATGATTCGCAGTGGAAGGCTGCACCTGCAAAAGGTCAGACATTTAAA
400
AGGAGGGCGACTCAACGCAGATGCCGTACCTAGTAAAGTGATAGAGCCTGAACCAGAAAAGATAAAGAAGGCTATACCAGTGGGAGTACACAAACAGAGT
500
AAGTTTGAATAGTAAAAAAATCATTTATGTAAACAATAACGTGACTGTGCGTTAGGTCCTGTTCATTGTTAATGAAATAGAGCTTGAGGGAAAAAA
600
TTCGTACTTTGGAGTACGAAATGGCTCGTTTAGAGCAGCAGCCGAATTCACTGCCGTCGTTTACAACGTCGTGACTGGGAAACCCTGGCGTTACCCA
700
ACTTAATCGCCTTGCAGCACATCCCCCTTTCGCCAGCTGGCGTAATAGCGAAGAGGCCCGCACCGATCGCCCTTCCAACAGTTGCGCAGCCTGAATGGC
800
GAATGGCGCTTTGCCTGGTTTCCGGCACCAGAAGCGGTGCCGGAAGCTGGCTGGAGTGCGATCTGTCGTCGTCCCCTCAAACT
900
GGCAGAGATGCACGGTTACGATGCGCCCATCTACACCAACGTAACCTATCCCATTACGGTCAATCCGCCGTTTGTTCCCACGGAGAATCCGACGGGTTGTTA
1000
CTCGCTCACATTTAATGTTGATGAAAGCTGGCTACAGGAAGGCCAGACGCGAATTATTTTTGATGGCGTTAACTCGGCGTTTCATCTGTGGTGCAACGGG
1100
CGCTGGGTCGGTTACGGCCAGGACAGTCGTTTGCCGTCTGAATTTGACCTGAGCGCATTTTTACGCGCCGGAGAAAACCGCCTCGCGGTGATGGTGCTGC
```

FIG. 12(B)

1200
GTTGGAGTGACGGGCAGTTATCTGGAAGATCAGGATATGTGGCGGATGAGCGGCATTTTCCGTGACGTCTCGTTGCTGATAAACCGACTACACAAATCAG

1300
CGATTTCCATGTTGCCACTCGCGCTTAATGATGATTCAGCCGCGCTGTACTGGAGGCTGAAGTTCAGATGTGCGGCGAGTTGCGTGACTACCTACGGTA

1400
ACAGTTTCTTTATGCAGGGTGAAACGCAGGTCGCCAGCGGCCCAGCGGGCCCTTTCGGGGTGAAATTATCGATGAGCGTGGTTATGCCGATCGGCGTCA

1500
CACTACGTCTGAACGTCGAAAACCCGAAACTGTGGAGCGCCCAAATCTCTATCGTGCGGTGGTTGAACTGCACACCGCGCCGACGGGCACGCTGAT

1600
TGAAGCAGAAGCCTGCGATCGGTTCCGCGAGGTGCGGATTGAAAATGTCTGCTGCTGAACCGCAAGCCGTTGCTGATTCGAGGCGTTAACCGT

1700
CACGAGCATCATCCTCGCATGGTCAGTGTCATGATGAGCAGATATCCTGCTGATGAAGCAGCCAATATTGAAACCCACGGCATGGTGCCAAT

1800
CGCATTATCCGAACCATCCGGCCGCTGGCCTACCGGGATGAGCGGCGAACGGTAACGGAATGGTGCAGCCGCGATCGTAATCACCCGAGTGTGATCATCTGG

1900
GAATCGTCTGACCGATGATCGCCGGCCACGGCGCTAATCACGACGCGCTGTATCGCTGGATCAAATCTGTCGATCCTTCCCGCCCGGTGCAGTATGAAGGCGCG

2000
TCGCTGGGAATGAATCAGGCCGCCACCACGGCCACCGATATTATTTGCCCGACTGATCCTTTGCGAATACGCCTGATCCTTTGCGAATACGCCCGATCGTGCCAAATGGTCCATCAAAAATG

2100
GAGCCCGACACCACGGCCCTGGAGAGACGGCCCACGGCGTGGATGAAGACCAGCCCTTCCCGGTCTGTGCCGAAATGGTCCATCAAAAATG

2200
GCTTTCGCTACCTGGAGAGACGGCCCACGGCGTTTACAGGGCGGCTTCGTCTCTGGGACTGGGTGGATCAGTCGCTGATTAAATATGATGAAAACGGCAACCCGTGGTCGGCTTACGGCG

2300
CGTCAGTATCCCCGTTTACAGGGCGGCTTCGTCTCTGGGACTGGGTGGATCAGTCGCTGATTAAATATGATGAAAACGGCAACCCGTGGTCGGCTTACGGCG

FIG. 12(B) CONT.

2400 GTGATTTTGGGCGATACGCCGAACGATCGCCAGTTCTGTATGAACGGTCTGGTCTTTGCCGACCGCACGCCGCATCCAGCGCTGACGGAAGCAAAACACCA
2500 GCAGCAGTTTTTCCAGTTCCGTTTATCGGGCAAACCATCGAAGTGACCAGCGAATACCTGTTCCGTCATAGCGATAACGAGCTCCTGCACTGGATGGTG
2600 GCGCTGGATGGGTAAGCCGCTGGCAAGCGGTGAAGTGCCTCTGGATGTCGCTCCACAAGGTAAACAGTGATTGAACTGCCTGAACTGCCTGAACTACCGCAGCCGGAGA
2700 GCGCCGGGCAACTCTGGCTCACAGTACGCGTAGTGCAACCGAACGGCATGTCAGAAGCCGGGCACATCAGCGCCTGGCAGCAGTGGCGCTGGC
2800 GGAAAAACCTCAGTGTGACGCTCCCCGCCGCGTCCCACGCCATCCCGATCTGACCACCAGCGAAATGGATTTTTGCATGAGCTGGGTAATAAGCGTTGG
2900 CAATTTAACCGCCAGTCAGGCTTTCTTTCACAGATGTGGATTGGCGATAAAAAAACAACTGCTGACGCCGCTGCCGGATCAGTTCACCGTCACCGCTGG
3000 ATAACGACATTGGCGTAAGTGAAGCGACCCGCATTGACCCTAACGCCTGGGTCGAAGCGGCGGGCCATTACCAGCCGGAAGCAGCGGTTGTT
3100 GCAGTGCACGGCAGATACACTTGCTGATGCGGTTGCTGTGATTACGACCGCTCACGCGTGGCAGCATCAGGGGAAAACCTTATTTATCAGCCGGAAAACCTAC
3200 CGGATTGATGTGTAGTGGTCAAATGGGCGATTACCGTTGATGTTGAAGTGGCGAAGAAAACTATCCCGACCGCCCTTACTGCGCCTGTTTTGACCGCTGGGATCTGCCAGCTGGCGC
3300 AGGTAGCAGAGCGGGTAAACTGCTCGGATTAGGGCCGCAAGAAAACGGGTCTGCGCTGCGGGACGCGCGAATTGAATTATGGCCCACACCAGTGGCGCGGCGACTTGTC
3400 AGACATGTATACCCGTACGTTCTTCCCGAGCGAAAACCAGCCATCGCTGCACGCGGAAGAAGGCACATGGCTGAATATCGACGGTTTCCAG
3500 TTCAACATCAGCCGCTACAGTCAACAACAGCCATCGCTGCACGCGGAAGAAGGCACATGGCTGAATATCGACGGTTTCC

*FIG. 12(B) CONT.*

```
3600 ATATGGGGATTGGTGGGCGACGACTCCTGAGCCCGGTCAGTATCGGCGGAATTCCAGCTGAGCGCCGGTCGCTACCATTACCAGTTGGTCTGGTGTCGGGG
3700 ATCCGTCGACTAAGGCCAAAGAGTCTAATTTTGTTCATCAATGGGTTATAACATATGGGTTATATTATAAGTTGTTTAAGTTTTGAGACTGATAAG
3800 AATGTTTCGATCGAATATTCCATAGAACAACATAGTATTACCTAATTACCAAGTCTTAATTTAGCAAAAAATGTTATTGCTTATAGAAAAATAAATTAT
3900 TTATTTGAAAATTAAAGTCAACTTGTCATTTAATGTCTTACGATACAATTAGTATCTAATATACATGGTTCATTCTACAT
4000 TCTATATATTAGTGATGATTCTCTTAGCTAGTAATACATTTAATTATATTCGGCTTTGATGATTTTCTGATTTTTTCCGAACGGATTTCGTAGACCCTTT
4100 CGATCTCATAATGGCTCATTTATTGCGATGACGGTCAGGAGAGCTCCACTTTTGAATTCTGTTGCAGACACCGCATTGTAGCACATAGCCGGGAC
4200 ATCCGGTTGGGAGATTTCCAGTCTCTGTTGCAATGGTTTCGGAATGCGTTCAGGCGCATACGCTCTATATCCTCCGAACGGCGCTGTTGACC
4300 CTAGCATTTACATAAGGATCAGCAGCAAAAATTGCCTCTCCGCCGCACACTCCACACTGATATGTCGCTCGCCGCATATGGATCTTAAGGTCGTTGACTGCACAAAG
4400 GCGAACCGCACACAAAGCTCTCGCCGCACTCCACACTGATATGTCGCTCGCCGCATATGATCTTAAGTCGTTGACTGCACAAAG
4500 CTCTTGCTGCACATTTGCAGGAGTACGGCCTTTGACCCGTGCAATGAGAGATCCCGCCGGAGGATCATCCAGCGGCGTCCCGGAAAACGATTCCGAAGCCCAACCTTTCAT
4600 GGCCGCCCGGGGTGGGCGAAGAACTCGAGAACCGGCGTCGCTTGGTCGTCGGTCATTCGAACCCCAGAGTCCCGCTCAGAAGAACTCGTCAAGA
4700 AGAAGGCGGCGGTGGTGAATCGAAATCTCGTGATGGCAGGTTGGGCGTCGCTTGGTCGTCGGTCATTCGAACCCCAGAGTCCCGCTCAGAAGAACTCGTCAAGA
```

*FIG. 12(B) CONT.*

```
4800
AGGCGATAGAAGGCGATGCGCTGCGAATCGGGAGCGGCGATACCGTAAAGCACGAGGAAGCGGTCAGCCATTCGCCGCCAAGCTCTTCAGCAATATCAC
4900
GGGTAGCCAACGCTATGTCCTGATAGCGGTCCGCCACACCCAGCCGGCCACAGTCGATGAATCCAGAAAAGCGGCCATTTTCCACCATGATATTCGGCAA
5000
GCAGGCATCGGCCATGGGTCACGACGAGATCCTCGCCGTCGGGCATGCGCGTCGGCCTTGAGCCTTCGGCGTGGCGCGAGCCCTGATGCTCTTCG
5100
TCCAGATCATCCTGATCGACAAGACCGGCTTCCATCCGAGTACGTGCTCGCTCGATGCGATGTTCGCTTGGTGGTCGAATGGGCAGTAGCCGGATCAA
5200
GCGTATGCAGCCGCCCGCCATTGCATCAGCCATGATGATACTTTCTCGGCAGGAGCAAGGTGAGATGACAGGAGATCCTGCCCCGGCACTTCGCCCAATAG
5300
CAGCCAGTCCCTTCCCGCTTCAGTGACAACGTCGAGCAGCTGCGCAAGGAACGCCCGTCGTGGCCAGCCACGATAGCCGGCCGCGCTCGTCCTGCAGT
5400
TCATTCAGGGCACCGGACAGGTCGGTCTTGACAAAAGAACCGGGCGCCCCTGCGCTGACAGCCGGAACACGGCGCATCAGAGCAGCCGATTGTCTGTT
5500
GTGCCCAGTCATAGCCGAATAGCCCTCCACCCAAGGCGCCGGAGAACCTGCGTGCAATCCATCTTGTTCAATCATGCGAAACGATCCTCATCCTGTCTC
5600
TTGATCAGATCTTGATCCCCTGCGCCATCAGATCCTTGGGCGCAAGAAAGCCATCCAGTTACTTTGCAGGGCTTCCCAACCTTACCAGAGGGCGGCCCCA
5700
GCTGGCAATTCCGGTTCGCTTGCTGTCCATAAAACCGGCTATCCAGTCTAGCTATCCGCCATGTAAGCCCACTGCAAGCTACCTGCTTTCTCTTTGCGCTTGCGT
5800
TTTCCCTTGTCCAGATAGCCCAGTAGCTAACCGTTCTCGCCGTTTCTGCCGGACTGGCTTTCTACGTGTTCCTTTAGCAGCCCTT
5900
GCGCCCTGAGTGCTTGCGGGCAGCCGTGAAGCTAATTCATGGTTATAAATTTTGTTAAATCAGCTCATTTTTAACCAATAGCCGAAATCGGCAAAATCC
```

*FIG. 12(B) CONT.*

6000
CTTATAAATCAAAAGAATAGCCCGAGATAGGGTTGAGTGTTGTTCCAGTTTGGAACAAGAGTCCACTATTAAAGAACGTGGACTCCAACGTCAAAGGGCG

6100
AAAAACCGTCTATCAGGGCGATGGCCGATCAGCTTATGCGGTGTGAAATACCGCACAGATGCGTAAGGAGAAAATACCGCATCAGGCGCTCTTCCGCTT

6200
CCTCGCTCACTGACTCGCTGCGCTCGGTCGTTCGGCTGCGGCGAGCGGTATCAGCTCACTCAAAGGCGGTAATACGGTTATCCACAGAATCAGGGGATAA

6300
CGCAGGAAAGAACATGTGAGCAAAAGGCCAGCAAAAGGCCAGGAACCGTAAAAAGGCCGCGTTGCTGGCGTTTTTCCATAGGCTCCGCCCCCCTGACGAG

6400
CATCACAAAAATCGACGCTCAAGTCAGAGGTGGCGAAACCCGACAGGACTATAAAGATACCAGGCGTTTCCCCCTGGAAGCTCCCTCGTGCGCTCTCCTG

6500
TTCCGACCCTGCCGCTTACCGGATACCTGTCCGCCTTTCTCCCTTCGGGAAGCGTGGCGCTTTCTCATAGCTCACGCTGTAGGTATCTCAGTTCGGTGTA

6600
GGTCGTTCGCTCCAAGCTGGGCTGTGTGCACGAACCCCCCGTTCAGCCCGACCGCTGCGCCTTATCCGGTAACTATCGTCTTGAGTCCAACCCGGTAAGA

6700
CACGACTTATCGCCACTGGCAGCAGCCACTGGTAACAGGATTAGCAGAGCGAGGTATGTAGGCGGTGCTACAGAGTTCTTGAAGTGGTGGCCTAACTACG

6800
GCTACACTAGAAGGACAGTATTTGGTATCTGCGCTCTGCTGAAGCCAGTTACCTTCGGAAAAAGAGTTGGTAGCTCTTGATCCGGCAAACAAACCACCGC

6900
TGGTAGCGGCGGTTTTTTGTTTGCAAGCAGCAGATTACGCGCAGAAAAAAGGATCTCAAGAAGATCCTTTGATCTTTTCTACTGAACGGTGATCCCCA

7000
CCGGAATTGCCGCGGAATTCTCATGTTTGACAGCTTATCATCGATAAGCTGGCCGCTCTAGAACTAGTGTCCCACAATGGTTAATTCGAGCTCGCC⟩
                                                                                3XP3-EYFP MARKER

7100
CGGGGATCCTAATTCAATTAGAGACTAATTCAATTAGAGCTAATTCAATTAGGATCCAAGCTTATCGATTTCGAACCCTCGACCGCCGGAGTATAAATAGA⟩
3XP3-EYFP MARKER

FIG. 12(B) CONT.

```
7200
GGGCGGCTTCGTCTCTACGGAGGCGACAATTCAATTCAAACAAGCAAAGTGAACACGTCGCTAAGCGAAAGCTAAGCAATAAACAAGGCAGCTGAACAAGCTA
                                                                              3XP3-EYFP MARKER

7300
AACAATCGGGGTACCGCTAGAGTCGACGGTACGATCCACCGGTTGCCACCATGGTGAGCAAGGGCGAGGAGCTGTTCACCGGGGTGGTGCCCATCCTGGT
                                                                              3XP3-EYFP MARKER

7400
CGAGCTGGACGGCGACGTAAACGGCCACAAGTTCAGCGTGTCCGGCGAGGGCGAGGGCGATGCCACCTACGGCAAGCTGACCCTGAAGTTCATCTGCACC
                                                                              3XP3-EYFP MARKER

7500
ACCGGCAAGCTGCCCGTGCCCTGGCCCACCCTCGTGACCACCTTCGGCTACGGCCTGCAGTGCTTCGCCCGCTACCCCGACCACATGAAGCAGCACGACT
                                                                              3XP3-EYFP MARKER

7600
TCTTCAAGTCCGCCATGCCCGAAGGCTACGTCCAGGAGCGCACCATCTTCTTCAAGGACGACGGCAACTACAAGACCCGCGCCGAGGTGAAGTTCGAGGG
                                                                              3XP3-EYFP MARKER

7700
CGACACCCTGGTGAACCGCATCGAGCTGAAGGGCATCGACTTCAAGGAGGACGGCAACATCCTGGGGCACAAGCTGGAGTACAACTACAACAGCCACAAC
                                                                              3XP3-EYFP MARKER

7800
GTCTATATCATGGCCGACAAGCAGAAGAACGGCATCAAGGTGAACTTCAAGATCCGCCACAACATCGAGGACGGCAGCGTGCAGCTCGCCGACCACTACC
                                                                              3XP3-EYFP MARKER

7900
AGCAGAACACCCCCATCGGCGACGGCCCCGTGCTGCTGCCCGACAACCACTACCTGAGCTACCAGTCCGCCCTGAGCAAAGACCCCAACGAGAAGCGCGA
                                                                              3XP3-EYFP MARKER

8000
TCACATGGTCCTGCTGGAGTTCGTGACCGCCGCCGGGATCACTCTCGGCATGACGAGCTGTACAAGTAAAGCGGCCGACTCTAGATCATAATCAGCC
                                                                              3XP3-EYFP MARKER
```

*FIG. 12(B) CONT.*

```
8100
ATACCACATTTGTAGAGGTTTTACTTGCTTTAAAAAACCTCCCCCTGAACCTGAAACATAAATGAATGCAATTGTTGTTGTTAACTTGTT
                                                 3XP3-EYFP MARKER                          >
8200
TATTGCAGCTTATAATGGTTACAAATAAAGCAATTCACAAATAAAGCATTTTTTTCACTGCATTCTAGTGTGTTGTTGGTTTGTCCAAACTC
                                                3XP3-EYFP MARKER                           >
8300
ATCAATGTATCTTAAAGCTTATCGATACCGTCGATTATTACGCATGATTATCTTTAACGTACGTCACAATATGATT
                                                                  LEFT TERMINAL REPEAT
8400
ATCTTTTCTAGGGTTAATCTAGCTCGCTGTGTTCTGCAGGCGTGTCGAGCATCTTCATCTGCTCCATCACGCTGTAAAACACATTTGCACGCCGAGTCTGCCCG
<
8500
TCCTCCACGGGTTCAAAAACGTGAATGAACGAGGCGGCCCGCCGGGTAACTCACGGGTATCCATGTCATTCTGCGGCATCCAGCCAGGATACCCGT
8600
CCTCGCTGACGTAATATCCCAGCGCCGCACCGTCGTCATTAATCTGCACACCGGGCACGGCGAGTTCCGGCTGTGCGCCGGTATTGTTCGGGTTGCTGATGCG
8700
CTTCGGGCTGACCATCCGGAACTGTGTCCGGAAAAGCGTGGCCTGAACGAACAGTGTATCCAGGTGGCCTGAACGAACAGTCACCGTTAAAGGCGTGCATGGCC
8800
ACACCTTCCCGAATCATCATGGTAAACGTGCGTTTTCGCTCAACGTCAATGCAGCAGTCAGTCATCCTCCGGCAAACTCTTTCCATGCCGCTTCAACCTCGC
8900
GGGAAAAGGCACGGGCGCTTCTTCCTCCCCGATGCCCAGATAGCGCCAGCTTGGGCATGGGCGTAAAATTGACGCATGGGATCCCCCGGGCTGCAGGAATTCGATATCAAGCTTATCGATACCGTCGAAGCTT
CTAGATTAACCCTAGAAAGATAGTCTGCGTAAAATTGACGCATGGGATCCCCCGGGCTGCAGGAATTCGATATCAAGCTTATCGATACCGTCGAAGCTTATCGATACCGTCGATGCAG
     RIGHT TERMINAL REPEAT
<                                                                        --(SEQ ID NO:48)--
```

*FIG. 12(B) CONT.*

```
p(P2)-Bac-ECFP
Sequence Range: 1 to 9012

1 ACCGAAGTATACACTTAAATTCAGTGCACGTTTGCTTGTTGAGAGGAAAGGTTGTGTGCGACGAATTTTTTTGAAACATTAACCCTTACGTGGAAT
 100 AAAAAAAATGAAATATTGCAAATTTGCTGCAAAGCTGTGACTGGAGTAAAATTAATTCACGTGCCGAAGTGTGCTATTAAGAGAAAATTGTGGAGCA
 200 GAGCCTTGGGTGCAGCCTTGGTGCGAAAACTCCCAAATTTGTGATACCCACTTTAATGATTCGCAGTGGAAGGCTGCACCTGAAAAGGTCAGACATTTAAA
 300 AGGAGGCGACTCAACGCAGATGCCGTACCTAGTAAAGTGATAGAGCCTGAACCAGAAAAGAAGGCTATACCAGTGGGAGTACACAAACAGAGT
 400 AAGTTTGAATAGTAAAAAAATCATTTATGTAAACAATAACGTGACTGCGTTAGGTCCTGTGTTCATTGTTAATGAAAATAAGAGCTTGAGGGAAAAAA
 500 TTCGTACTTTGGAGTACGAAATGCGTCGTTAGAGCAGCAGCCGAATTCACTGGCCGTCGTTTACAACGTCGTGACTGGGAAAACCCTGGCGTTACCCA
 600 ACTTAATCGCCTTGCAGCACATCCCCCTTTCGCCAGCTGGCGTAATAGCGAAGAGGCCCGCACCGATCGCCCTTCCCAACAGTTGCGCAGCCTGAATGGC
 700 GAATGGCGCTTTGCCTGGTTTCCGGCACCAGAAGCGGTGCCGGAAAGCTGGCTGGAGTGCGATCTTCCTGAGGCCGATACTGTCGTCCCCTCAAACT
 800 GGCAGATGCACGGTTACGATGCGCCCATCTACACCAACGTAACCTATCCCATTACGGTCAATCCGCCGTTTGTTCCCACGGAGAATCCGACGGGTTGTTA
 900 CTCGCTCACATTTAAATGTTGATGAAAGCTGGCTACAGGAAGGCCAGACGCGAATTATTTTTGATGGCGTTAACTCGGCGTTTCATCTGTGGTGCAACGGG
1000 CGCTGGGTCGGTTACGGCCAGGACAGTCGTTTGCCGTCTGAATTTGACCTGAGCGCATTTTACGCGCCGGAGAAAACCGCCTCGCGGTGATGGTGCTGC
```

FIG. 13(B)

```
1200
GTTGGAGTGACGGCAGTTATCTGGAAGATCAGGATATGTGGCGGATGAGCGGCCATTTCCGTGACGTCTCGTTGCTCTGCATAAACCGACTACACAAATCAG
1300
CGGATTTCCATGTTGCCACTCGCTTTAATGATGATTTCAGCCGCGCTGTACTGGAGGCTGAAGTTCAGATGTGCCGGCGAGTTGCGTGACTACCTACGGGTA
1400
ACAGTTTCTTTATGGCAGGGTGAAACCAGGTCGCCAGCGGGCCCTTTCCGGGTGAAATTATCGATGAGCGTGGTGGTTATGCCGATCGCGTCA
1500
CACTACGTCTGAACGTCGAAAACCCGAAACTGTGGAGCCCCGAAATCCGAATCTCTATCGTGCGGGTTGAACTGCACACCGCCGACGGCACGCTGAT
1600
TGAAGCAGAAGCCTGCCGATGTCGGTTTCCGGAGGTGCCGGATTGAAAATGTCTGCTGCTGAACGCAAGCCGTTGCTGATTCGAGGCGTTAACCGT
1700
CACGAGCATCATCCTCGCATGGTCAGGTCATGGATGAGCAGACGATGGTGCAGGATATCCTGCTGATGAAGCAGAACAACTTAACGCCGTGCGCTGTT
1800
CGGCATTATCCGAACCATCCGCTGGTACACGCGTGCCGACCGCTGTGCCGATGAGCCGTAACGCGAATGGTGCAGCGCGATCGTAATCACCGAGTGTGATCATCTGG
1900
GAATCGTCTGACCGATGATCCGCGCTGGCTACCGGGCGATGAGCCGAACGCGTAACGCGCTAATCACGCGCCGATCGTAATCTGTCGATCAAATCTGTGCCGGTGCAGTATGAAGGCGGCG
2000
TCGCTGGGAATGAATCAGGCCACGGCCACCGATATTATTTGCCGATGTACGCCCACGCGATGGGTAACAGTCTTGGCGGTTTCGCTAAATACTGGCAGGCGTT
2100
GAGCCGACACCACGGCCACCGATATTATTTGCCGATGTACGCCCACGCGATGGGTAACAGTCTTGGCGGTTTCGCTAAATACTGGCAGGCGTT
2200
GCTTTCGCTACCTGGAGAGACGCGCCCGTGATCCTTTGCGAATACGCCCACGCGATGGGTAACAGTCTTGGCGGTTTCGCTAAATACTGGCAGGCGTT
2300
CGTCAGTATCCCGTTTACAGGGGGGCTTCGTCTGGGACTGGGTGGATCAGTCGCTGATTAAATATGATGAAAACGGCAACCCGTGGTCGGCTTACGCGG
```

FIG. 13(B) CONT.

2400 GTGATTTTGGCGATACGCCGAACGATCGCCAGTTCTGTATGAACGGTCTGTGTCTTTGCCGACCGCATCCAGCGCTGACGGAAGCAAAACACCA

2500 GCAGCAGTTTTTCCAGTTCCGTTTATCGGGCAAACCATCGAAGTGACCAGCGAATACCTGTTCCGTCATAGCGATAACGAGCTCCTGCACTGGATGGTG

2600 GCGCTGGATGTGAAGCCGTGGCAAGCGGTGAAGTGCCTCTGGATGTCGCTCCACAAGGTAAACAGTTGATTGAACTGCCTGAACTACCGCAGCCGGAGA

2700 GCGCCGGGCAACTCTGGCTCACAGTACGCGTAGTGCAACCGAACGCGACCGCATGGTCAGAAGCCGGGCACATCAGCGCCTGGCAGCAGTGGCGTCTGGC

2800 GGAAAAACCTCAGTGTGACGCTCCCCGCGTCCCACGCGCCATCTGACCAGCCACCAGCGAAATGGATTTTTGCATCGAGCTGGGTAATAAGCGTTGG

2900 CAATTTAACCGCCAGTCAGGCTTTCTTTCACAGATGTGGATAAAAAAACAACTGCTGACGCCCGCTGCCGATCAGTTCACCGTGCACCGCTGG

3000 ATAACGACATTGGCGTAAGTGAAGCGACCCTAACGCCTGGGTCGAACGCTGGGCCCATTACCAGCCGAAGCAGCCGTTGTT

3100 GCAGTGCACGGCAGATACACTTGCTGATGCGGTTGCTGATTACGACCGTTGATGTGAAGTGGCGAGCGATACACCGCATCCGGCGCGATTGGCCTGAACTGCCAGCTGGCGC

3200 CGGATTGATGTAGTGGTCAAATGGCGATTACCGTTGATGTGAAGTGGCGAGCGATTACACCGCATCCGGCGCGATTGGCCTGAACTGCCAGCTGGCGC

3300 AGGTAGCAGAGCGGGTAAACTGGCTCGGATTAGGGCCCGCAAGAAAACTATCCGACCGGCCTTACTGCCGCCTGTTTGACCGCTGGGATCTGCCATTGTC

3400 AGACATGTATACCCCGTACGTCTTCCCGAGCGAAAACGCTCGCCTGCCGGACGCCGAATTGAATTATGGCCCACACCAGTGGCGGGCGACTTCCAG

3500 TTCAACATCAGCCGCTACAGTCAACAGCAACTGATGAAACCAGCCATCGCCATCTGCTGCACGCGGAAGAAGGCACATGGCTGAATATCGACGGTTCC

*FIG. 13(B) CONT.*

```
3600 ATATGGGGATTGGTGTGGCGACGACTCCTGGAGCCCGTCAGTATCGGCGGAATTCCAGCTGAGCGCCGGTGCGCTGCTACCATTACCAGTTGGTCTCGGTGTCGGGG
3700 ATCCGTCGACTAAGGCCAAAGAGTCTAATTTTGTTCATCAATGGGTTATAACATATGGGTTATATATTATAAGTTGTTTTAAGTTTTTGAGACTGATAAG
3800 AATGTTTCGATCGAATATTCCATAGAACAACAATAGTATTACCTAATTACCAAGTCTTAATTTAGCAAAAATGTTATTGCTTATAGAAAAATAAATTAT
3900 TTATTTGAAATTTAAAGTCAACTTGTCATTTAATGTCTTGTAGACTTTTGAAAGTCTTACGATACAATTAGTATCTAATATACATGGTTCATTCTACAT
4000 TCTATATTAGTGATGATTCTTTAGCTAGTAATACATTTAATTATATATTCGGCTTTGATGATTTTCTGATTTTTCCGAACGGATTTTCGTAGACCCTTT
4100 CGATCTCATAATGGCTCCATTTATTGCGATGGACGGTCAGGAGAGAGCTCCACTTTTGAATTCTGTTCCGCAGACACCGCATTGTAGCACATAGCCGGGAC
4200 ATCCGGTTTGGGGAGATTTCCAGTCTCTGTTGCAATTGGTTTCGGGGAATGGCGTTGCAGGCGCATACGCCTCTATATCCTCCGAACGGGCGCTGGTTGACC
4300 CTAGCATTTACATAAGGATCAGCAGAAATTGCCTCTGCTTCATTGCCCGGAATCACAGCAATCAGATGTCCCTTTCGGTTACGATGGATATTCAGGT
4400 GCGAACCGCACACAAAGCTCTCGCCGCACACTCCACACTGATATGGTGTCGCTCCGCCCTGTGGCGCCGCATATGGATCTTAAGGTCGTTGGACTGCACAAAG
4500 CTCTTGCTGCACATTTGCAGAGTACGGCCTTTGACCCGTGTGCAATCGCATGTGTCGCGCCAGCTTGTTCTGCGAAATAAACTTCTTGGAGCAGATGC
4600 GGCCGCCCGGGGTGGGCGAAGAACTCCAGCATGAGATCCCCGCGGAGGATCATCCAGCCGCGGCGTCCCGGAAAACGATTCCGAAGCCCAACCTTTCAT
4700 AGAAGGCGGCGGTGGAATCGAAATCTCGTGATGGCAGGTTGGGCGTCGCTTGGTCGGTCATTTCGAACCCCAGAGTCCCGCTCAGAAGAACTCGTCAAGA
```

*FIG. 13(B) CONT.*

4800
AGGCGATAGAAGGCGATGCGCTGCGAATCGGGAGGCGGCGATACCGTAAAGCACGAGAGAAGCGGTCAGCCCATTCGCCGCCAAGCTCTTCAGCAATATCAC

4900
GGGTAGCCAACGCTATGTCCTGATAGCGGTCCGCCACACCCAGCGGCCACAGTCGATGAATCCAGAAAAGCGGCCATTTCCACCATGATATTCGGCAA

5000
GCAGGCATCGCCATGGGTCACGACGAGATCCTCGCCGTCGGGCATGCGCGCCCTTGAGCCTGGCGAACAGTTCGGCTGGCGCGAGCCCTGATGCTCTTCG

5100
TCCAGATCATCCTGATCGACAAGACCCGGCTTCCATCCGAGTACGTGCTCGCTCGATGCGATGTTTCGCCTTGGTGGTCGAATGGGCAGGTAGCCGATCAA

5200
GCGTATGCAGCCGCCGCATTGCATCAGCCATGATGGATACTTTCTCGGCAGGAGCAAGGTGAGATGACAGGAGATCCTGCCCGGCACTTCGCCCAATAG

5300
CAGCCAGTCCCTTCCCGCTTCAGTGACAACGTCGAGCACAGCTGGCGCAAGGAACCCGTCGTGGCCAGCCACGATAGCCGGCTGCCTCGTCCTGCAGT

5400
TCATTCAGGCACCGACAGGTCGGTCTTGACAAAAGAACCGGCCCCTGCCTGACAGCCGGATCAGAGCAGCCGATTGTCTGTT

5500
GTGCCCAGTCATAGCCGAATAGCCTCTCCACCCAGCGGCCGAGAACCTGCGTGCAATCCATCTTGTTCAATCATGCGAAACGATCCTCATCCTGTCTC

5600
TTGATCAGATCTTGATCCCCTGCGCCATCAGATCCTTGGCGGCAAGAAAGCCATCCAGTTACTTTGCAGGCTTCCCAACCTTACCAGAGGGCGCCCCA

5700
GCTGGCAATTCGGTTCGCTTGCTGTCCATAAAACCGCCAGTCTAGCTATCGCCATGTAAGCCCACTGCAAGCTACCTGCTTTCTCTTTGCGCTTGCGT

5800
TTTCCCTTGTCCAGATAGCCCAGTAGCTGACATTCATCGGGGTCAGCACCGTTTCTCGCGGACTGGCTTTCTACGTGTTCCGCTTCCTTTAGCAGCCCTT

5900
GCGCCCTGAGTGCTGCTTGGCGGCAGCGGTGAAGCTAATTCATGGTTATAAATTTTGTTAAATCAGCTCATTTTTTAACCAATAGGCCGAAATCGGCAAAATCC

*FIG. 13(B) CONT.*

```
6000
CTTATAAATCAAAAGAATAGCCCGAGATAGGGTTGAGTGTTGTTCCAGTTTGGAACAAGAGTCCACTATTAAAGAAGTGGACTCCAACGTCAAAGGGCG
6100
AAAAACCGTCTATCAGGGCGATGGCCGGGATCAGCTTGATGCGGTGTGAAATACCGCACAGATGCGTAAGGAGAAAATACCGCATCAGGCGCTCTTCCGCTT
6200
CCTCGCTCACTGACTCGCTGCGCTCGGTCGTTCGGCTGCGGCGAGCGGTATCAGCTCACTCAAAGGCGGTAATACGGTTATCCACAGAATCAGGGGATAA
6300
CGCAGGAAAGAACATGTGAGCAAAAGGCCAGCAAAAGGCCAGGAACCGTAAAAAGGCCGCGTTGCTGGCGTTTTTCCATAGGCTCCGCCCCCCTGACGAG
6400
CATCACAAAAATCGACGCTCAAGTCAGAGGTGGCGAAACCCGACAGGACTATAAAGATACCAGGCGTTTCCCCCTGGAAGCTCCCTCGTGCGCTCTCCTG
6500
TTCCGACCCTGCCGCTTACCGGATACCTGTCCGCCTTTCTCCCTTCGGGAAGCGTGGCGCTTTCTCATAGCTCACGCTGTAGGTATCTCAGTTCGGTGTA
6600
GGTCGTTCGCTCCAAGCTGGGCTGTGTGCACGAACCCCCCGTTCAGCCCGACCGCTGCGCCTTATCCGGTAACTATCGTCTTGAGTCCAACCCGGTAAGA
6700
CACGACTTATCGCCACTGGCAGCAGCCACTGGTAACAGGATTAGCAGAGCGAGGTATGTAGGCGGTGCTACAGAGTTCTTGAAGTGGTGGCCTAACTACG
6800
GCTACACTAGAAGGACAGTATTTGGTATCTGCGCTCTGCTGAAGCCAGTTACCTTCGGAAAAAGAGTTGGTAGCTCTTGATCCGGCAAACAAACCACCGC
6900
TGGTAGCGGCGGTTTTTTGTTGCAAGCAGCAGATTACGCGCAGAAAAAAAGGATCTCAAGAAGATCCTTTGATCTTTTCTACTGAACGGTGATCCCCA
7000
CCGGAATTGCGGCGGGAATTCTCATGTTGACAGCTTATCATGATAAGCTGGCCGCTCTAGAACTAGTGTCCCACAATGGTTAATTCGAGCTCGCC
                                                                              3XP3-EYFP MARKER
7100
CGGGGATCTAATTAGAGAGACTAATTCAATTAGAGACTAATTCAATTAGAGATCCAAGCTTATCGATTCGAACCCTCGACCGCCGGAGTATAAATAGA
                                                                 3XP3-EYFP MARKER
```

FIG. 13(B) CONT.

```
7200
GGCGCTTCGTCTACGGAGGACAATTCAATTCAAACAAGCAAAGTGAACACGTCGCTAAGCGAAAGCTAAGCAAATAAACAAGGCAGCTGAACAAGCTA
     3XP3-EYFP MARKER                                                                              >
7300
AACAATCGGGTACCGCTAGAGTCGACGGTACGATCCACCGGTCGCCACCATGGTGAGCAAGGGCGAGGAGCTGTTCACCGGGGTGGTGCCCATCCTGGT
     3XP3-EYFP MARKER                                                                              >
7400
CGAGCTGGACGGCGACGTAAACGGCCACAAGTTCAGCGTGTCCGGCGAGGGCGAGGGCGATGCCACCTACGGCAAGCTGACCCTGAAGTTCATCTGCACC
     3XP3-EYFP MARKER                                                                              >
7500
ACCGGCAAGCTGCCCGTGCCCTGGCCCACCCTCGTGACCACCCTGACCTACGGCGTGCAGTGCTTCAGCCGCTACCCCGACCACATGAAGCAGCACGACT
     3XP3-EYFP MARKER                                                                              >
7600
TCTTCAAGTCCGCCATGCCCGAAGGCTACGTCCAGGAGCGCACCATCTTCTTCAAGGACGACGGCAACTACAAGACCCGCGCCGAGGTGAAGTTCGAGGG
     3XP3-EYFP MARKER                                                                              >
7700
CGACACCCTGGTGAACCGCATCGAGCTGAAGGGCATCGACTTCAAGGAGGACGGCAACATCCTGGGGCACAAGCTGGAGTACAACTACATCAGCCACAAC
     3XP3-EYFP MARKER                                                                              >
7800
GTCTATATCACCGCCGACAAGCAGAAGAACGGCATCAAGGCCAACTTCAAGATCCGCCACAACATCGAGGACGGCAGCGTGCAGCTCGCCGACCACTACC
     3XP3-EYFP MARKER                                                                              >
7900
AGCAGAACACCCCCATCGGCGACGGCCCCGTGCTGCTGCCCGACAACCACTACCTGAGCACCCAGTCCGCCCTGAGCAAAGACCCCAACGAGAAGCGCGA
     3XP3-EYFP MARKER                                                                              >
8000
TCACATGGTCCTGCTGGAGTTCGTGACCGCCGCGGGGATCACTCTCGGCATGGACGAGCTGTACAAGTAAAGCGGCCGCGACTCTAGATCATAATCAGCC
     3XP3-EYFP MARKER                                                                              >
```

*FIG. 13(B) CONT.*

```
8100
ATACCACATTTGTAGAGGTTTTTACTTGCTTTAAAAAACCTCCCACACCTCCCCCTGAACCCTGAAACATAAAATGAATGCAATTGTGTGTGTTAACTTGTT
                                                            3XP3-EYFP MARKER

8200
TATTGCAGCTTATAATGGTTACAAATAAAGCATTCACAAATTTCACAAATAAGCATTTTTTTTCACTGCATTCTAGTTGTTGGTTTGTCCAAACTC
                                                            3XP3-EYFP MARKER

8300
ATCAATGTATCTTAAAGCTTATCGATACGCGTACGGCGCGCCTAGGCCGACCGATTGGATCCCATGCGTCAATTTACGCATGATTATCTTTAACGTACG
                3XP3-EYFP MARKER                                                      LEFT TERMINAL REPEAT

8400
TCACAATATGATTATCTTTCTAGGGTTAATCTAGCTGCGTTCTGCAGCGTGTCGAGCATCTTCATCGCTGTAAACACATTTGCACC
    LEFT TERMINAL REPE

8500
GCGAGTCTGCCCGTTCCTCCACGGGTCAAAACGTGAATGAACGAGGCGCGCCCGGGTATCCATGTCCATTTCTGCGGCATCCAG

8600
CCAGGATACCCGTCCTCGCTGACGTAATATCTGCACCGCCACCGGTGTATCCCAGGTGGCCTGAACGAACAGTTCACCGTTAAA

8700
GGTTGCTGATGCGCTTCGGGCTTGACCATCCGGAAAAGCCGGTTTCGCTCAACGTGCGTTTTCGCTCAACGTCAATGCAGCAGCAGTCATCCTCGGCAAACTCTTTCCATGCC

8800
GGCGTGCATGGCCACACCTTCCCGGAAAAGGCACGGGCTTCTTCCTCCCCGATGCCCAGATAGCGCCAGCTTGGGCGATGACTGACCGGAAAAAAGACCCGACGATAT

8900
GCTTCAACCTCGGGAAAAGGCACGGGCTTCTTCCTCCCCGATGCCCAGATAGCGCCAGCTTGGGGATGACTGACCGGAAAAAAGACCCGACGATAT

9000
GATCCCTGATGCAGCTAGATTAACCCTAGAAAGATAGTCTGCGTAAAATTGACGCCATGGGATCCCCCCGGGCTGCAGGAATTCGATATCAAGCTTATCGATA
                            RIGHT TERMINAL REPEAT

CCGTCGAAGCTT --(SEQ ID NO:49)--

FIG. 13(B) CONT.
```

P(PZ)-Bac-EGFP
Sequence Range: 1 to 9013

100
ACCGAAGTATACACTTAAATTCAGTGCACGTTTGCTCTGTTGAGAGGAAAGGTTGTGTGCGGACGAATTTTTTTGAAAACATTAACCCTTACGTGGAAT

200
AAAAAAAATGAAATATTGCAAATTTGCTGCAGTAAAATTAATTCACGTGCCGAAGTGTGCTATTAAGAGAAAATTGTGGGAGCA

300
GAGCCTTGGGTGCAGCCTTGGTGAAAACTCCCAAATTTGTGATACCCACTTTAATGATTCGCAGTGGAAGGCTGCAAAGGTCAGACATTTAAA

400
AGGAGGGCGACTCAACGCAGATGCCGTACCTAGTAAAGTGATAGAGCCTGAACCAGAAAGATAAAAGAAGGCTATACCAGTGGGAGTACACAAACAGAGT

500
AAGTTTGAATAGTAAAAAAATCATTTATGTAAACAATAACGTGACTGTGCGTTAGTTCCTGTTCATTGTTTAATGAAAATAAGAGCTTGAGGGAAAAAA

600
TTCGTACTTTGGAGTACGAAATGCGTCGTTAGAGCAGCCGAATTCACTGGCCGTCGTTTACAACGTCGTGACTGGGAAAACCTGGCGTTACCCA

700
ACTTAATCGCCTTGCAGCACATCCCCCTTTCGCCAGCTGGCGTAATAGCGAAGAGGCCCGCACCGATCGCCCTTCCCAACAGTTGCGCAGCCTGAATGGC

800
GAATGGCGCTTTGCCTGGTTTCCGGCACCAGAAGCGGTGCCGGAAAGCTGGCTGGAGTGCGATCTTCCTGAGGCCGATACTGTCGTCGTCCCCTCAAACT

900
GGCAGATGCACGGTTACGATGCGCCCATCTACACCAACGTAACCTATCCCATTACGGTCAATCCGCCGTTTGTTCCCACGGAGAATCCGACGGGTTGTTA

1000
CTCGCTCACATTTAATGTTGATGAAAGCTGGCTACAGGAAGGCCAGACGCGAATTATTTTTGATGGCGTTAACTCGGCGTTTCATCTGTGGTGCAACGGG

1100
CGCTGGGTCGGTTACGGCCAGGACAGTCGTTTGCCGTCTGAATTTGACCTGAGCGCATTTTTACGCGCCGGAGAAAACCGCCTCGCGGTGATGGTGCTGC

FIG. 14(B)

1200 GTTGGGAGTGACGGCAGTTATCTGGAAGATCAGGATATGTGGCGGATGAGCGGCATTTCCGTGACGTCTCGTTGCTGCATAAACGACTACACAAATCAG
1300 CGATTTCCATGTTGCCACTCGCTTTAATGATGATTCAGCCGCTGTACTGGAGGCTGAAGTTCAGATGTGCGGCGAGTTGCTGACTACCTACGGTA
1400 ACAGTTTCTTTATGCCAGGGTGAAACGCAGTCGCCAGCGGCACCGCCTTTCGGCGGTGAAATTATCGATGAGCGTGGTGTTATGCCGATCGCGTCA
1500 CACTACGGTCTGAACGTCGAAAAACCCGAAACTGTGGAGCGCCGAAATCCCGAATCTCTATCGTGCGGTGGTTGAACTGCACACCGCCGACGGCACGCTGAT
1600 TGAAGCAGAGAAGCCTGCGATGTCGGTTCGCCCGAGGTGCCGATTGAAAATGGTTGCTGCTGAACCGGCAAGCCGTTGCTGATTCGAGGCGTTAACCGT
1700 CACGAGCAGCATCATCCTCTGCATGGTCAGGTCATGGATGAGCAGCAGAGACGATGGTGCAGGATATCCTGCTGATGAAGCAGAACAACTTTAACGCCGTGCCGCTGTT
1800 CGCATTATCCGAACCATCCGCTGTGTACACGGCTGGCCGCTACGGGCGATGAGCGAACGCGTAACGCGGAATGTGCAGCGCGGATCGTAATCACCCGAGTGTGATCATCTGG
1900 GAATCGTCTGACCGATGATCCGCTGGCTACCGGCGATGAGCGAACGCGTAACGCGGAATGTGCAGCGCGGATCGTAATCACCCGAGTGTGATCATCTGG
2000 TCGCTGGGGAATGAATCAGGCCACCGATATTATTTGCCCGCTATCCTTTGCGAATACGCCCACGCGATGGGTAACAGTCTTGGCGGTTTCGCTAAATACTGGCAGGCGTTT
2100 GAGCCCGACACCACGGCCACCGATATTATTTGCCCGCTATCCTTTGCGAATACGCCCACGCGATGGGTAACAGTCTTGGCGGTTTCGCTAAATACTGGCAGGCGTTT
2200 GCTTTCGCTACCTGGAGAGACGCGCCACGCGATCCTTTGCGAATACGCCCACGCGATGGGTAACAGTCTTGGCGGTTTCGCTAAATACTGGCAGGCGTTT
2300 CGTCAGTATCCCCGTTTACAGGGCGGCTTCGTCTGGGACTGGGTGGATCAGTCGCTGATTAAATATGATGAAAACGGCAACCCGTGTCGGCTTACGGCG

*FIG. 14(B) CONT.*

```
2400
GTGATTTGGGCGATACGCCGAACGATCGCCAGTTCTGTATGAACGGTCTGGTCTCTTTGCCGACCGCACGCCGCATCCAGCGCTGACGGAAGCAAAACACCA
2500
GCAGCAGTTTTTCCAGTTCCGTTATCGGGCAAACCATCGAAGTGACCAGCGAATACCTGTTCCGTCATAGCGATAACGAGCTCCTGCACTGGATGGTG
2600
GCGCTGATGGTAAGCCGCTGGCAAGCGGTGAAGTGCCTCTGCGATGTGCTCCACAAGGTAAACAGTGATTGAACTGCCTGAACTACCCGCAGCCGGAGA
2700
GCGCCGGGCAACTCTGGCTCACAGTACGCGTAGTGCAACCGAACGCGACCGCATGGTCAGAGCCGGGCACATCAGGCGCCTGGCAGCAGTGGGCGTCTGGC
2800
GGAAAACCTCAGTGCGCTCCCCGCGCTCCCACGCCATCTGACCACCAGCGAAATGGATTTTTGCATCGAGCTGGGTAATAAGCGTTGG
2900
CAATTTAACCGCAGTCAGGCTTTCTTTCACAGATGGCGATAAAAAACAACTGCTGACGCCGCTGCCGGATCAGTTCACCCGTGCACCGCTGG
3000
ATAACGACATTGGCGTAAGTGAAGCGACCGCATTGACCCTAAGCGCCTGGGTCGAACGCTGGAAGGCGGGCCATTACCAGGCGAAGCAGCGGTTGTT
3100
GCAGTGCACGGCAGATACACTTGCTGATGCGGTGCTGATTACGACCGCTCACGCGTGCAGCATCAGGGCAAAACCTTATTTATCAGCCGGAAAACCTAC
3200
CGGATTGATGGTAGTGGTCAAATGGCGATTACCGTTGATGTTGAAGTGGCGAGCGATACACCGCCATCCGGCGCGGATTGGCCTGAACTGCCAGCTGGCGC
3300
AGGTAGCAGAGCGGGTAAACTGGCTCGGATTAGGGCCGCAAGAAAACTATCCGACCGCCTTACTGCCGCCTGTTTGACCGCTGGGATCGCCATTGTC
3400
AGACATGTATACCCCGTACGTCTTCCCGAGCGACGCGCGAATTGAATTATGCCCACACCAGTGGGCGGGGACTTCCAG
3500
TTCAACATCAGCCGCTACAGTCAACAGCAACTGATGAAACCAGCCATCGCCATCTGCTGCACGCGGAAGAAGGCACATGGCTGAATATCGACGGTTTCC
```

FIG. 14(B) CONT.

```
3600
ATATGGGGATTGGTGGGCGACGACTCCTGGAGCCCGTCAGTATCGGCGGGAATTCCAGTCTGAGCGCCGTCGCTACCATTACCAGTTGGTCTGGTGTCGGGG
3700
ATCCGTCGACTAAGGCCAAAGAGTCTAATTTTGTTCATCAATGGGTTATAACATATGGGTTATATATTAAGTTTGTTTTAAGTTTTTGAGACTGATAAG
3800
AATGTTTCGATCGAATATTCCATAGAACAACAAATAGTATTACCTAATTACCAAGTCTTAATTAGCAAAAATGTTATTGCTTATAGAAAAATAAATTAT
3900
TTATTTGAAATTTAAAGTCAACTTGTCATTTAATGTCTTGTAGACTTTTGAAAGTCTTACGATACAATTAGTATCTAATATACATGGTTCATTCTACAT
4000
TCTATATTAGTGATGATTTCTTTAGCTAGTAATACATTTTAATTATATATTCGGCTTTGATGATTTTCTGATTTTTTCCGAACGGATTTTCGTAGACCCTTT
4100
CGATCTCATAATGGCTCATTTTATTGCGATGACGGTCAGGAGAGCTCCACTTTTGAATTCTGTTCGCAGACACCGCATTGTAGCACATAGCCGGAC
4200
ATCCGGTTTGGGGAGATTTCCAGTCTCTGTTGCAATTGGTTTCGGGAATGCGTTGCAGGCGCATACGCTCTATATCCTCCGAACGGCCTGGTTGACC
4300
CTAGCATTTACATAAGGATCAGCAGTCAAAATTTGCCTCTGCTTCATTGCCCGGAATCACAGCAATCAGATGTCCCTTTCGGTTACGATGGATATTCAGGT
4400
GCGAACCGCACACAAAGCTCTCGCCGCACACTCCACACTGATATGGTCGTCGCCCTGTGGCGCCGCATATGGATCTTAAGGTCGTTGGACTGCACAAAG
4500
CTCTTGCTGCACATTTTGCAGGAGTACGGCCTTTGACCCGTGCAATCGCATGTGTCGCGGCCAGCTTGTTCTGCGAAATAAACTTCTTGGAGCAGATGC
4600
GGCCGCCCGGGGTGGGCGAAGAACTCCAGCATGAGATCCCCGCGCTGAGGATCATCCAGCCGGGCGTCCCGGTCGTCATTTCGAACCCAGAGTCCCGCTGGTCGTCATTTCGAACCCAGAGTCCCGCTTCAT
4700
AGAAGGCGGGCGGTGGGCGGTGAATCGAAATCTCGTGATGCCAGTTGGGCGTCGCTTGGTCGTCATTTCGAACCCAGAGTCCCGCTCAGAAGAACTCGTCAAGA
4800
AGGCGATAGAAGGCGATGCGCTGCGAATCGGGAGCGGCGATACCGTAAAGCACGAGGAAGCGGTCAGCCGCTTCAGCCCATTCGCCGCCAAGCTCTTCAGCAATATCAC
```

*FIG. 14(B) CONT.*

```
4900
GGGTAGCCAACGCTATGTCCTGATAGCGGTCCGCCACACCCAGCCGGCCACAGTCGATGAATCCAGAAAAGCGGCCATTTCCACCATGATATTCGGCAA
5000
GCAGGGCATCGCCATGGGTCACGACGAGATCCCTCGCCCGTCGGGCATGCGCGCCCTTGAGCCTGGCGGAACAGTTCGGCTGGCGGAGCCCCTGATGCTCTTCG
5100
TCCAGATCATCCTGATCGACAGACCGGCTTCCATCCGAGTACGTCGCTCGATGCGATGTTTCGCTTGGTGGTGCGAATGGGCAGGTAGCCGGATCAA
5200
GCGTATGCAGCCGCCCGCCATTGCATCAGCCATGATGGATACTTTCTCGGCAGGAGCAAGGTGAGATGACAGGAGATCCTGCCCGGCACTTCGCCCAATAG
5300
CAGCCAGTCCCTTCCGCTTCAGTGACAAAGAACGCCCGTCGTGGCCAGCACAGCCGGCATCAGAGCAGCCGATTGTCTGTT
5400
TCATTCAGGGCACCGGACAGTCGGTTCTTGACAAAAGAACGGGCGCCCCTGCGCTGACGCCGAACACGGGCGAACACCTGTTCAATCATGCGAAACGATCCTCATCCTGTCTC
5500
GTGCCCAGTCATAGCCGAATAGCCTCTCCACCCAAGCGGCCGGAGAACCTGCGTGCAAGAAAGCCATCCAGTTACTTTGCAGGGCTTCCAACCTTACCAGAGGGCGCCCCA
5600
TTGATCAGATCTTGATCCCCTGCGCCATCAGATCCTTGGCGGCTTGCTGTCCAATAAAACCGCCAGTCTAGCTATCGCCATGTAAGCCCACTGCAAGCTACCTGCTTTCTCTTGCGCTTGCGT
5700
GCTGGCAATTCCGGTTCGCTTGCGCTTGGCGACTAGCTGACATCATCCGGGTCAGCACCGTTCTCGCGACTGGCTTTCTACGTGTTCCGCTCCTTTAGCAGCCCTT
5800
TTTCCCTTGTCCAGATAGCCCAGTAGCTGACATTCATCCGGGTCAGCACCGTTCTCGCGACTGGCTTTCTACGTGTTCCGCTCCTTTAGCAGCCCTT
5900
GCGCCCTGAGTGCTTGCGCAGCGTGAAGCTAATTCATGGTTATAAATTTTGTAAATCAGCTCATTTTTAACCAATAGGCCGAAATCGGCAAAATCC
6000
CTTATAAATCAAAAGAATAGCCCGAGATAGGGTTGAGTGTTGTTCCAGTTTGGAACAAGAGTCCACTATTAAAGAACGTGGACTCCAACGTCAAAGGGCG
6100
AAAAACCGTCTATCAGGGCGATGCCGATCAGCTTATGCGGTGTGAAATACCGCACAGATGCGTAAGGAGAAAATACCGCATCAGGGCGCTCTTCCGCTT
```

*FIG. 14(B) CONT.*

```
6200 CCTCGCTCACTGACTCGCTGCGCCTCGGTCGTCGGCTGCGGCGAGCGGTATCAGCTCACTCAAAGGCGGTAATACGGTTATCCACAGAATCAGGGGATAA
6300 CGCAGGAAAGAACATGTGAGCAAAAGGCCAGCAAAAGGCCAGGAACCGTAAAAAGGCCGCGTTGCTGGCGTTTTTCCATAGGCTCCGCCCCCCTGACGAG
6400 CATCACAAAAATCGACGCTCAAGTCAGAGGTGGCGAAACCCGACAGGACTATAAAGATACCAGGCGTTTCCCCCTGGAAGCTCCCTCGTGCGCTCTCCTG
6500 TTCCGACCCTGCCGCTTACCGGATACCTGTCCGCCTTTCTCCCTTCGGGAAGCGTGGCGCTTTCTCATAGCTCACGCTGTAGGTATCTCAGTTCGGTGTA
6600 GGTCGTTCGCTCCAAGCTGGGCTGTGTGCACGAACCCCCCGTTCAGCCCGACCGCTGCGCCTTATCCGGTAACTATCGTCTTGAGTCCAACCCGGTAAGA
6700 CACGACTTATCGCCACTGGCAGCAGCCACTGGTAACAGGATTAGCAGAGCGAGGTATGTAGGCGGTGCTACAGAGTTCTTGAAGTGGTGGCCTAACTACG
6800 GCTACACTAGAAGGACAGTATTTGGTATCTGCGCTCTGCTGAAGCCAGTTACCTTCGGAAAAAGAGTTGGTAGCTCTTGATCCGGCAAACAAACCACCGC
6900 TGGTAGCGGTGGTTTTTTTGTTTGCAAGCAGCAGATTACGCGCAGAAAAAAAGGATCTCAAGAAGATCCTTTGATCTTTTCTACTGAACGGTGATCCCCA
7000 CCGGAATTGCGGCCGCGGAATTCTCATGTTTGACAGCTTATCATCGATAAGCTGTCCGCCGCTCTAGAACTAGTGTTCCCACAATGGTTAATTCGAGCTCGCC
                                                                                              3XP3-EYFP MARKER
7100 CGGGGATCTAATTCAATTAGAGACTAATTCAATTAGAGATCCAAGCTTATCGATTTCGAACCCCTCGACCCGCCGGAGTATAAATAGA
     3XP3-EYFP MARKER
7200 GGCGCTTCGTCTACGGAGCGACAATTCAATTCAAACAAGCAAAGTGAACACGTCGCTAAGCGAAAGCTAAGCAAATAAACAAGGCGCAGCTGAACAAGCTA
     3XP3-EYFP MARKER
```

*FIG. 14(B) CONT.*

7300
AACAATCGGGGTACCGCTAGAGTCGACGGTACCGCGGGCCCGGGATCCACCGGTCGCCACCATGGTGAGCAAGGGCGAGGAGCTGTTCACCGGGGTGGTG
    3XP3-EYFP MARKER

7400
CCCATCCTGGTCGAGCTGGACGGCGACGTAAACGGCCACAAGTTCAGCGTGTCCGGCGAGGGCGAGGGCGATGCCACCTACGGCAAGCTGACCCTGAAGT
    3XP3-EYFP MARKER

7500
TCATCTGCACCACCGGCAAGCTGCCCGTGCCCTGGCCCACCCTCGTGACCACCCTGACCTACGGCGTGCAGTGCTTCAGCCGCTACCCCGACCACATGAA
    3XP3-EYFP MARKER

7600
GCAGCACGACTTCTTCAAGTCCGCCATGCCCGAAGGCTACGTCCAGGAGCGCACCATCTTCTTCAAGGACGACGGCAACTACAAGACCCGCGCCGAGGTG
    3XP3-EYFP MARKER

7700
AAGTTCGAGGGCGACACCCTGGTGAACCGCATCGAGCTGAAGGGCATCGACTTCAAGGAGGACGGCAACATCCTGGGGCACAAGCTGGAGTACAACTACA
    3XP3-EYFP MARKER

7800
ACAGCCACAACGTCTATATCATGGCCGACAAGCAGAAGAACGGCATCAAGGTGAACTTCAAGATCCGCCACAACATCGAGGACGGCAGCGTGCAGCTCGC
    3XP3-EYFP MARKER

7900
CGACCACTACCAGCAGAACACCCCCATCGGCGACGGCCCCGTGCTGCCCGACAACCACTACCTGAGCACCCAGTCCGCCCTGAGCAAAGACCCCAAC
    3XP3-EYFP MARKER

8000
GAGAAGCGCGATCACATGGTCCTGCTGGAGTTCGTGACCGCCGCGGGATCACTCTCGGCATGGACGAGCTGTACAAGTAAAGCGGCGACTCTAGAT
    3XP3-EYFP MARKER

8100
CATAATCAGCCATACCACATTTGTAGAGGTTTTACTTGCTTTAAAAAACCTCCCACACCTCCCCCTGAACCTGAAACATAAAATGAATGCAATTGTTGTT
    3XP3-EYFP MARKER

*FIG. 14(B) CONT.*

```
8200
GTTAACTTGTTTATTGCAGCTTATAAATGGTTACAAATTTCACAAATAAAGCATTTTTTCACTGCATTCTAGTTGTGGTT
                                                         3XP3-EYFP MARKER

8300
TGTCAAAACTCATCAATGTATCTTAAAGCTTACGATACGCGTACGGGCGCCCTAGTGCGTCAATTTACGCATGATTATCTTTAACGTAC
                                                                       LEFT TERMINAL REPEAT
                        3XP3-EYFP MARKER

8400
GTCACAATATGATTATCTTTCTAGGGTTAATCTAGCTGCGTTCTCGAGCGTGTCGAGCATCTTCATCTGCTCCATCACGCTGTAAACACATTTGCAC
        LEFT TERMINAL REPEA

8500
CGGGAGTCTGCCCGTCCTCCACGGGTTCAAAAACGTGAATGAACGAGGCGCCCGCGGGTATCCATGTCCATTTCTGCGGCATCCA

8600
GCCAGGATACCCGTCCTCGCTGACGTAATATCCCAGCGCCCACCGCTGTCATTAATCTGCACACCGGCAGTTCGGCTGTCGCCGGTATTGTTC

8700
GGGTTGCTGATGCGGCTTCGGGCTGACCATCGTGTCCGGAAAAGCCGCGACGAACTGTATCCCAGGTGGCCTGAACGAACAGTTCACCGTAA

8800
AGGCGTGCATGGCCACACCTTCCCGAATCATCATGGTAAACGTGGCGTTTCGCTCAACGTCAATGCAGCAGTCATCCTCGCAAACTCTTTCCATGC

8900
CGCTTCAACCTCGCGGGAAAAGGCACGGGCTTCTTCCTCCCCCGATGCCCAGATAGCCCAGCTTGGGCGATGACTGAGCCGGAAAAAGACCCGACGATA

9000
TGATCCTGATGCAGCTAGATTAACCCTAGAAAGATAGTCTGCCTAAAATTGACGCATGGGATCCCCCGGGCTGCAGGAATTCGATATCAAGCTTATCGAT
                                                         RIGHT TERMINAL REPEAT

ACCGTCGAAGCTT --(SEQ ID NO:50)--
```

*FIG. 14(B) CONT.* pXL-Bac-EYFP
Sequence Range: 1 to 4951

100
CTAAATTGTAAGCGTTAATATTTTGTTAAATTTCGCGTTAAATTTTTGTTAAATCAGCTCATTTTTTAACCAATAGGCCGAAATCGGCAAAATCCCTTAT

200
AAATCAAAAGAATAGACCGAGATAGGGTTGAGTGTTGTTCCAGTTTGGAACAAGAGTCCACTATTAAAGAACGTGGACTCCAACGTCAAAGGGCGAAAAA

300
CCGTCTATCAGGGCGATGGCCCACTACGTGAACCATCACCCTAATCAAGTTTTTTGGGGTCGAGGTGCCGTAAAGCACTAAATCGAACCCTAAAGGGAG

400
CCCCCGATTTAGAGCTTGACGGGGAAAGCCGGCGAACGTGGCGAGAAAGGAAGGGAAGAAAGCGAAAGGAGCGGGCGCTAGGGCGCTGGCAAGTGTAGCG

500
GTCACGCTGCGCGTAACCACCACACCCGCCGCTTAATGCGCCGCTACAGGGCGCGTCCCATTCGCCATTCAGGCTGCGCAACTGTTGGGAAGGGCGAT

600
CGGTGCGGGCCTCTTCGCTATTACGCCAGCTGGCGAAAGGGGGATGTGCTGCAAGGCGATTAAGTTGGGTAACGCCAGGGTTTTCCCAGTCACGACGTTG

700
TAAAACGACGGCCAGTGAGCGCGCCCGCCCGGGTAACTCACGGGTATCCATGTCCATTTCGCGGCATCCAGCCAGGATACCCGTCCTCGCTGACGTAAT

800
ATCCCAGCGCCCGACCGCTGTCATTAATCTGCACACCGGCAGTTCCGGCTGTGCGCGGTATTGTTCGGTTGCTGATGCGCTTCGGGCTGACCAT

900
CCGGAACTGTGTCCGGAAAGCCGGCGACGAACGTGACCAGTGCCTGAACGAACAGTCACCGTTAAAGGCGTGCATGGCCACACCTTCCCGAATC

1000
ATCATGTGTAAACGTGCGTTTCGCTCAACGTCAATGCAGCAGCAGTCATCCTCGCCTTCAACCTCGGGAAAAGGCACGGG

1100
CTTCTTTCCTCCCCGATGCCACCAGATAGCGCCAGCTTGGGCGATGACTGAGCCGGAAAAAAGACCCGACGATATGATCCTGATGCAGCTAGATTAACCCTAG

1200
AAAGATAGTCTGCGTAAAATTGACGCATGATCTAATTAACCCTCACTAAAGGGAACAAAAGCTGGAGCTCCACCGCGGTGGCGGCCGCTCTAGAACTAGT
< RIGHT TERMINAL REPEAT

FIG. 15(B)

```
1300
GTTCCCACACAATGTTAATTCGAGCTGCCCGGGGATCTAATTCAATTAGAGACTAATTCAATTAGAGATCCAAGCTTATCGATTTC
     3XP3-EYFP MARKER

1400
GAACCCTCGACGCCGGAGTATAAATAGAGGCGCTTCGTCTACGGAGCGACAATTCAAACAAGCAAAGTGAACACGTCGCTAAGCGAAAGCTAAG
     3XP3-EYFP MARKER

1500
CAAATAAACAAGGCGAGCTGAACAAGCTAAACAATCGGGGTACCGCTAGAGTCGACGGTACGATCCACCGGTGCGCCACCATGGTGAGCAAGGGCGAGGAG
     3XP3-EYFP MARKER

1600
CTGTTCACCGGGGTGGTGCCCATCCTGGTCGAGCTGGACGGCGACGTAAACGGCCACAAGTTCAGCGTGTCCGGCGAGGGCGAGGGCGATGCCACCTACG
     3XP3-EYFP MARKER

1700
GCAAGCTGACCCTGAAGTTCATCTGCACCACCGGCAAGCTGCCCGTGCCCTGGCCCACCCTCGTGACCACCTTCGGCTACGGCCTGCAGTGCTTCGCCCG
     3XP3-EYFP MARKER

1800
CTACCCCGACCACATGAAGCAGCACGACTTCTTCAAGTCCGCCATGCCCGAAGGCTACGTCCAGGAGCGCACCATCTTCTTCAAGGACGACGGCAACTAC
     3XP3-EYFP MARKER

1900
AAGACCCGCGCCGAGGTGAAGTTCGAGGGCGACACCCTGGTGAACCGCATCGAGCTGAAGGGCATCGACTTCAAGGAGGACGGCAACATCCTGGGCACA
     3XP3-EYFP MARKER

2000
AGCTGGAGTACAACTACAACAGCCACAAGTCTATATCATGGCCGACAAGCAGAAGAACGGCATCAAGGTGAACTTCAAGATCCGCCACAACATCGAGGA
     3XP3-EYFP MARKER
```

*FIG. 15(B) CONT.*

```
2100
CGGCAGCGTGCAGCTCGCCGACCACTACCAGCAGAACACCCCCATGGGCGACGGCCCCGTGCTGCTGCCCGACAACCACTACCTGAGCTACCAGTCCGCC
                                                      3XP3-EYFP MARKER

2200
CTGAGCAAAGACCCCAACGAGAAGCGCGATCACATGGTCCTGCTGGAGTTCGTGACCGCCGCCGGGATCACTCTCGGCATGGACGAGCTGTACAAGTAAA
                                                      3XP3-EYFP MARKER

2300
GCGGGCCGACTCTAGATCATAATCAGCCATACCACATTTGTAGAGGTTTTACTTGCTTTAAAAAACCTCCCACACCTCCCCCTGAACCTGAAACATAAA
                                                      3XP3-EYFP MARKER

2400
ATGAATGCAATTGTTGTTGTTAACTTGTTTATTGCAGCTTATAATGGTTACAAATAAAGCAATAGCATCACAAATTTCACAAATAAAGCATTTTTTTCAC
                                                      3XP3-EYFP MARKER

2500
TGCATTCTAGTTGTGGTTTGTCCAAACTCATCAATGTATCTTAAAGCTTATCGATACGCGTACGGCGCGCCTAGCACTAGTGGATCCCCCGGGCTGCAG
                                                                                    >

2600
GAATTCGATATCAAGCTTATCGATACCGTCGACCTCGAGGGGGGGCCCGGTACCCAATTCGCCCTATAGTGAGTCGTATTAAGATCACGCGTAGATCCAT
                                                                                                  ˅
2700
GCGTCAATTTTACGCATGATTATCTTTAACGTACGTCACAATATGATGATTATCTTTCTAGGGTTAATCTAGCTGCCGTTCTCAGCGTGTCGAGCATCTTC
                       LEFT TERMINAL REPEAT

2800
ATCTGCTCCATCACGCTGTAAAACACATTTGCACCGCGAGTCTGCCCGTCCTCCACGGGTTCAAAAACGTGAATGAACGAGGCGCCTTGGCGTAATCAT

2900
GGTCATAGCTGTTTCCTGTGTGAAATTGTTATCCGCTCACAATTCCACACAACATACGAGCCGGAAGCATAAAGTGTAAAGCCTGGGGTGCCTAATGAGT
```

*FIG. 15(B) CONT.*

```
3000
GAGCTAACTCACATTAATTGCGTTGCGCTCACTGCCCGCTTTCCAGTCGGGAAACCTGTCGTGCCAGCTGCATTAATGAATCGGCCAACGCGCGGGGAGA
                                  >ColE1_origin
                                  |
3100
GGCGGGTTTGCGTATTGGGCGCTCTTCCGCTTCCTCGCTCACTGACTCGCTGCGCTCGGTCGTTCGGCTGCGGCGAGCGGTATCAGCTCACTCAAAGGCGG
3200
TAATACGGTTATCCACAGAATCAGGGGATAACGCAGGAAAGAACATGTGAGCAAAAGGCCAGCAAAAGGCCAGGAACCGTAAAAAGGCCGCGTTGCTGGC
3300
GTTTTTCCATAGGCTCCGCCCCCCTGACGAGCATCACAAAAATCGACGCTCAAGTCAGAGGTGGCGAAACCCGACAGGACTATAAAGATACCAGGCGTTT
3400
CCCCCCTGGAAGCTCCCTCGTGCGCTCTCCTGTTCCGACCCTGCCGCTTACCGGATACCTGTCCGCCTTTCTCCCTTCGGGAAGCGTGGCGCTTTCTCATA
3500
GCTCACGCTGTAGGTATCTCAGTTCGGTGTAGGTCGTTCGCTCCAAGCTGGGCTGTGTGCACGAACCCCCCGTTCAGCCCGACCGCTGCGCCTTATCCGG
3600
TAACTATCGTCTTGAGTCCAACCCGGTAAGACACGACTTATCGCCACTGGCAGCAGCCACTGGTAACAGGATTAGCAGAGCGAGGTATGTAGGCGGTGCT
3700
ACAGAGTTCTTGAAGTGGTGGCCTAACTACGGCTACACTAGAAGGACAGTATTTGGTATCTGCGCTCTGCTGAAGCCAGTTACCTTCGGAAAAAGAGTTG
3800
GTAGCTCTTGATCCGGCAAACAAACCACCGCTGGTAGCGGTGGTTTTTTTGTTTGCAAGCAGCAGATTACGCGCAGAAAAAAAGGATCTCAAGAAGATCC
3900
TTTGATCTTTTCTACGGGGTCTGACGCTCAGTGGAACGAAAACTCACGTTAAGGGATTTTGGTCATGAGATTATCAAAAAGGATCTTCACCTAGATCCTT
4000
TTAAATTAAAAATGAAGTTTTAAATCAATCTAAAGTATATATGAGTAAACTTGGTCTGACAGTTACCAATGCTTAATCAGTGAGGCACCTATCTCAGCGA
                                                                      AMPCILLIN RESISTANCE ────────>
```

FIG. 15(B) CONT.

```
4100
TCTGTCTATTTCGTTCATCCATAGTTGCCTGACTCCCCGTGTGAGATAACTACGATACGGGAGGGCTTACCATCTGGCCCCAGTGCTGCAATGATACC
                                                  AMPCILLIN RESISTANCE

4200
GCGAGACCCACGCTCACCGGCTCTCAGATTTATCAGCAATAAACCAGCCGGAAGGGCCCGAGCCGCAGAAGTGGTCCTGCAACTTTATCCGCCTCCATC
                                                  AMPCILLIN RESISTANCE

4300
CAGTCTATTAATTGTTGCCGGGAAGCTAGAGTAAGTAGTTCGCCAGTTAATAGTTTGCGCAACGTTGTTGCCATTGCTACAGGCATCGTGGTGTCACGCT
                                                  AMPCILLIN RESISTANCE

4400
CGTCGTTTGGTATGGCTTCATTCAGCTCCGGTTCCCAACGATCAAGGCGAGTTACATGATCCCCCATGTTGTGCAAAAAAGCGGTTAGCTCCTTCGGTCC
                                                  AMPCILLIN RESISTANCE

4500
TCCGATCGTTGTCAGAAGTAAGTTGGCCGCAGTGTTATCACTCATGGTTATGGCAGCACTGCATAATTCTCTTACTGTCATGCCATCCGTAAGATGCTTT
                                                  AMPCILLIN RESISTANCE

4600
TCTGTGACTGGTGAGTACTCAACCAAGTCATTCTGAGAATAGTGTATGCGGCGACCGAGTTGCTCTTGCCCGGCGTCAATACGGATAATACCGCGCCAC
                                                  AMPCILLIN RESISTANCE

4700
ATAGCAGAACTTTAAAAGTGCTCATCATTGGAAAACGTTCTTCGGGGCGAAAACTCTCAAGGATCTTACCGCTGTTGAGATCCAGTTCGATGTAACCCAC
                                                  AMPCILLIN RESISTANCE

4800
TCGTGCACCCAACTGATCTTCAGCATCTTTTACTTTCACCAGCGTTTCTGGGTGAGCAAAAACAGGAAGGCAAAATGCCGCAAAAAAGGGAATAAGGGCG
                                                  AMPCILLIN RESISTANCE

4900
ACACGGAAATGTTGAATACTCATACTCTTCCTTTTTCAATATTATTGAAGCATTATCAGGGTTATTGTCTCATGAGCGGATACATATTTGAATGTATTT
         AMPCILLIN RESISTANCE        >

AGAAAAATAAACAAATAGGGGTTCCGCGCACATTTCCCGAAAAGTGCCAC --(SEQ ID NO:51)--
```

*FIG. 15(B) CONT.* pXL-Bac-EGFP
Sequence Range: 1 to 4952

```
100 CTAAATTGTAAGCGTTAATATTTTGTTAAAATTTTGTTAAATCAGCTCATTTTTTAACCAATAGGCCGAAATCCCTTAT
200 AAATCAAAAGAATAGACCGAGATAGGGTTGAGTGTTGTTCCAGTTTGGAACAAGAGTCCACTATTAAAGAACGTGGACTCCAACGTCAAAGGGCGAAAAA
300 CCGTCTATCAGGGCGATGGCCCACTACGTGAACCATCACCCTAATCAAGTTTTTTGGGGTCGAGGTGCCGTAAAGCACTAAATCGGAACCCTAAAGGGAG
400 CCCCCGATTTAGAGCTTGACGGGGAAAGCCGGCGAACGTGGCGAGAAAGGAAGAAAGCGAAAGGAGCGGGGCGCTAGGGCGCTGGCAAGTGTAGCG
500 GTCACGCTGCGCGTAACCACCACACCCGCGCTTAATGCGCCGCTACAGGGCGCGTCCCATTCGCCATTCAGGCTGCGCAACTGTTGGGAAGGGCGAT
600 CGGTGCGGGCCTCTTCGCTATTACGCCAGCTGGCGAAAGGGGGATGTGCTGCAAGGCGATTAAGTTGGGTAACGCCAGGGTTTTCCCAGTCACGACGTTG
700 TAAAACGACGGCCAGTGAGCGCGCCCGCCGGGTAACTCACGGGTATCCATGTCATTTCTGCGCATCCAGCCAGGATACCCGTCCTGCTGACGTAAT
800 ATCCCAGCGCCGCTGTCATTAATCTGCACACCGGACGAACTGGTATCCCAGTGGCCTGAACGAACAGTTCACCGTTAAAGGCGTGCATGCCACACCTTCCCGAATC
900 CCGGAACTGTGTCCGGAAAAGCCGCTCAACGTCAATGCAGCAGTCATCCTCGGCAAACTCTTTCCATGCCGCTTCAACCTCGCGGGAAAAGGCACGGG
1000 ATCATGGTAAACGTGCGTTTTCGCTCAACGTGCCCAGCTTGGGCGATGACTGAGCCGGAAAAAGACCCGAGACGATATGATCCTGATGCAGCTAGATTAACCCTAG
1100 CTTCTTCCTCCCCGATGCCCAGATAGCGCCAGCTTGGGCGATGACTGAGCCGGAAAAAGACCCGAGACGATATGATCCTGATGCAGCTAGATTAACCCTAG
```

FIG. 16(B)

```
1200
AAAGATAGTCTGCGTAAAATTGACGCATGATCTAATTAACCCTCACTAAAGGGAACAAAAGCTGGAGCTCCACCGGGTGGGGCCGCTCTAGAACTAGT
    RIGHT TERMINAL REPEAT
1300
GCCGTACGCGTATCGATAAGCTTTAAGATACATTGATGAGTTTGGACAAACCACAACTAGAATGCAGTGAAAAAAATGCTTTATTTGTGAAATTTGTGAT
1400
GCTATTGCTTTATTTGTAACCATTATAAGCTGCAATAAACAAGTTAACAACAACAATTGCATTCATTTTATGTTTCAGGTTCAGGGGAGGTGTGGGAGG
                                                    3XP3-EGFP MARKER
1500
TTTTTTAAAGCAAGTAAAACCTCTACAAATGTGGTATGGCTGATTATGATCTAGAGTCGCGGCCGCTTACTTGTACAGCTCGTCCATGCCGAGAGTGAT
                                                    3XP3-EGFP MARKER
1600
CCCGGCGGCGGTCACGAACTCCAGCAGGACCATGTGATCGCGCTTCTCGTTGGGGTCTTTGCTCAGGGCGGACTGGGTGCTCAGGTAGTGGTTGTCGGGC
                                                    3XP3-EGFP MARKER
1700
AGCAGCACGGGCCCGTCGCCGATGGGGGTGTTCTGCTGGTAGTGGTCGGCGAGCTGCACGCTGCCGTCCTCGATGTTGTGGCGGATCTTGAAGTTCACCT
                                                    3XP3-EGFP MARKER
1800
TGATGCCGTTCTTCTGCTTGTCGGCCATGATATAGACGTTGTGGCTGTTGTAGTTGTACTCCAGCTTGTGCCCCAGGATGTTGCCGTCCTCCTTGAAGTC
                                                    3XP3-EGFP MARKER
1900
GATGCCCTTCAGCTCGATGCGGTTCACCAGGGTGTCGCCCTCGAACTTCACCTCGGCGCGGGTCTTGTAGTTGCCGTCGTCCTTGAAGAAGATGGTGCGC
                                                    3XP3-EGFP MARKER
2000
TCCTGGACGTAGCCTTCGGGCATGGCGGACTTGAAGAAGTCGTGCTGCTTCATGTGGTCGGGGTAGCGGCTGAAGCACTGCACGCCGTAGGTCAGGGTGG
                                                    3XP3-EGFP MARKER
2100
TCACGAGGGTGGGCCAGGGCACGGGCAGCTTGCCGGTGGTGCAGATGAACTTCAGGGTCAGCTTGCCGTAGGTGGCATGCCCTCGCCCTCCGCCGGACAC
                                                    3XP3-EGFP MARKER
```

*FIG. 16(B) CONT.*

```
2200
GCTGAACTTGTGGGCCGTTTACGTCGCCGTCCAGCTCGACCAGGATGGGCACCACCCCGGTGAACAGCTCCTCGCCCTTGCTCACCATGGTGGGACCGGT
                                              3XP3-EGFP MARKER
2300
GGATCCCGGGCCCGCGGTACCGTCGACTCGAGCGGTACCCGATTGTTGTTCAGCTTGTTTAGCTTGCGCTTGCGCTTGTTTATTGCTTAGCTTTCGCTTAGCGACGTG
                                              3XP3-EGFP MARKER
2400
TTCACTTTGCTTGTTGAATTGTCGCTCCGTAGACGAAGCGCCTCTATTATACTCCGGCGGTCGAGGGTTCGAAATCGATAAGCTTGGATCCTA
                                              3XP3-EGFP MARKER
2500
ATTGAATTAGCTCTAATTAGTCTCTAATTGAATTAGATCCCCGGGGCGAGCTCGAATTAACCATTGTGGGAACACTAGTGGATCCCCCGGGCTGCA
                           LEFT TERMINAL REPEAT
2600
GGAATTCGATATCAAGCTTATCGATACCGTCGACCTCGAGGGGGGCCCGGTACCCAATTCGCCCTATAGTGAGTCGTATTAAGATCACGCTAGATCCA
2700
TGCGTCAATTTTACGCATGATTATCTTTAACGTACGTCACAATATGATTATCTTTCTAGGGTTAATCTAGCTGCTGTTCTGCAGCGTGTCGAGCATCTT
       LEFT TERMINAL REPEAT
2800
CATCTGCTCCATCACGCTGTAAAACATTTGCACCGTCCGAGTCTGCCCGTCCACGGGTTCAAAAACGTGAATGAAGGAGCGCGCTTGGCGTAATCA
2900
TGGTCATAGCTGTTTCCTGTGAAATTGTTATCCGCTCACAATTCCACACAACATACGAGCCGGAAGCATAAAGTGTAAAGCCTGGGGTGCCTAATGAG
3000
TGAGCTAACTCACATTAATTGCGTTGCGCTCACTGCCCGCTTTCCAGTCGGGAAACCTGTCGTGCCAGCTGCATTAATGAATCGGCCAACGCGCGGGGAG
3100
AGGCGGTTTGCGTATTGGGCGCTCTTCCGCTTCCTCGCTCACTGACTCGCTGCGCTCGGTCGTTCGGCTGCGGCGAGCGGTATCAGCTCACTCAAAGGCG
3200
GTAATACGGTTATCCACAGAATCAGGGGATAACGCAGGAAAGAACATGTGAGCAAAAGGCCAGCAAAAGGCCAGGAACCGTAAAAAGGCCGCGTTGCTGG
       COLE1 ORIGIN
```

FIG. 16(B) CONT.

3300
CGTTTTTTCCATAGGCTCCGCCCCCCTGACGAGCATCACAAAAATGAGCGCTCAAGTCAGAGGTGGCGAAACCCGACAGGACTATAAAGATACCAGGCGTT
        COLE1 ORIGIN

3400
TCCCCCTGGAAGCTCCCTCGTGCGCTCTCCTGTTCCGACCCTGCCGCTTACCGGATACCTGTCCGCCTTTCTCCCTTCGGGAAGCGTGGCGCTTTCTCAT
        COLE1 ORIGIN

3500
AGCTCACGCTGTAGGTATCTCAGTTCGGTGTAGGTCGTTCGCTCCAAGCTGGGCTGTGTGCACGAACCCCCCGTTCAGCCCGACCGCTGCGCCTTATCCG
        COLE1 ORIGIN

3600
GTAACTATCGTCTTGAGTCCAACCCGGTAAGACACGACTTATCGCCACTGGCAGCAGCCACTGGTAACAGGATTAGCAGAGCGAGGTATGTAGGCGGTGC
        COLE1 ORIGIN

3700
TACAGAGTTCTTGAAGTGGTGGCCTAACTACGGCTACACTAGAAGGACAGTATTTGGTATCTGCGCTCTGCTGAAGCCAGTTACCTTCGGAAAAAGAGTT
        COLE1 ORIGIN

3800
GGTAGCTCTTGATCCGGCAAACAAACCACCGCTGGTAGCGGTGGTTTTTTTGTTTGCAAGCAGCAGATTACGCGCAGAAAAAAAGGATCTCAAGAAGATC
        COLE1 ORIGIN

3900
CTTTGATCTTTTCTACGGGGTCTGACGCTCAGTGGAACGAAAACTCACGTTAAGGGATTTTGGTCATGAGATTATCAAAAAGGATCTTCACCTAGATCCT
        COLE1 ORIGIN

4000
TTTAAATTAAAAATGAAGTTTTAAATCAATCTAAAGTATATATGAGTAAACTTGGTCTGACAGTTACCAATGCTTAATCAGTGAGGCACCTATCTCAGCG
        COLE1 ORIGIN                              _____
                                                                                                              AMPICILLIN RESISTANCE

4100
ATCTGTCTATTTCGTTCATCCATAGTTGCCTGACTCCCCGTCGTGTAGATAACTACGATACGGGAGGGCTTACCATCTGGCCCCAGTGCTGCAATGATAC
                                                      AMPICILLIN RESISTANCE

FIG. 16(B) CONT.

```
4200
CGCGAGACCCACGCTCACCGGCTCTCCAGATTTATCAGCAATAAACCAGCCAGCCGGAAGGGCCGAGCCGAGAAGTGTCCTGCAACTTTATCCGCCTCCAT
                                                    AMPCILLIN RESISTANCE                                >
4300
CCAGTCTCTATTAATTGTTGCCGGGAAGCTAGAGTAAGTAGTTCGCCAGTTAATAGTTTGCGCAACGTTGTTGCCATTGCTACAGGCATCGTGGTGTCACGC
                                                    AMPCILLIN RESISTANCE                                >
4400
TCGTGTGTTTGGTATGGCTTCATTCAGCTCCGGTTCCCAACGATCAAGGCGAGTTACATGATCCCCCATGTTGTGCAAAAAAGCGGTTAGCTCCTTCGGTC
                                                    AMPCILLIN RESISTANCE                                >
4500
CTCCGATCGTTGTCAGAAGTAAGTTGGCCGCAGTGTTATCACTCATGGTTATGGCAGCACTGCATAATTCTCTTACTGTCATGCCATCCGTAAGATGCTT
                                                    AMPCILLIN RESISTANCE                                >
4600
TTCTGTGACTGGTGAGTACTCAACCAAGTCATTCTGAGAATAGTGTATGCGGCGACCGAGTTGCTCTTGCCCGGCGTCAATACGGGATAATACCGCGCCA
                                                    AMPCILLIN RESISTANCE                                >
4700
CATAGCAGAACTTTAAAAGTGCTCATCATTGGAAAACGTTCTTCGGGGCGAAAACTCTCAAGGATCTTACCGCTGTTGAGATCCAGTTCGATGTAACCCA
                                                    AMPCILLIN RESISTANCE                                >
4800
CTCGTGCACCCAACTGATCTTCAGCATCTTTTACTTTCACCAGCGTTTCTGGGTGAGCAAAAATGCCGCAAAAAAGGGAATAAGGGC
                                                    AMPCILLIN RESISTANCE                                >
4900
GACACGGAAATGTTGAATACTCATACTCTTCCTTTTTCAATATTATTGAAGCATTTATCAGGGTTATTGTCTCATGAGCGGATACATATTGAATGTATT
                      AMPCILLIN RESISTANCE           >

TAGAAAAATAAACAAATAGGGGTTCCGCGCACATTTCCCCGAAAAGTGCCAC --(SEQ ID NO:52)--
```

FIG. 16(B) CONT.

pXL-Bac-ECFP
Sequence Range: 1 to 4941

```
100 CTAAATTGTAAGCGTTAATATTTTGTTAAATTCGCGTTAAATTTTGTTAAATCAGCTCATTTTTTAACCAATAGGCCGAAATCGGCAAAATCCCTTAT
200 AAATCAAAAGAATAGACCGAGATAGGGTTGAGTGTTGTTCCAGTTTGGAACAAGAGTCCACTATTAAAGAACGTGGACTCCAACGTCAAAGGGCGAAAAA
300 CCGTCTATCAGGGCGATGCCCACTACGTGAACCATCACCCTAATCAAGTTTTTTGGGGTCGAGGTGCCGTAAAGCACTAAATCGGAACCCTAAAGGGAG
400 CCCCCGATTTAGAGCTTGACGGGGAAAGCCGGCGAACGTGGCGAGAAAGGAAGAAAGCGAAAGGAGCGGGCGCTAGGGCGCTGGCAAGTGTAGCG
500 GTCACGCTGCGCGTAACCACCACACCCGCGCGCTTAATGCGCCGCTACAGGGCGCGTCCATTCGCCATTCAGGCTGCGCAACTGTTGGGAAGGGCGAT
600 CGGTGCGGGCCTCTTCGCTATTACGCCAGCTGGCGAAAGGGGGATGTGCTGCAAGGCGATTAAGTTGGGTAACGCCAGGGTTTTCCCAGTCACGACGTTG
700 TAAAACGACGGCCAGTGAGCGCGCCCGGGCTAACTCACGGGGTATCCATGTCCATTTCTGCGCATCCAGCCAGGATACCCGTCCTCGCTGACGTAAT
800 ATCCCAGCGCCGACCGCTGTCATTAATCTGCACACCGGCAGTTCCGCCGTCGCCGGTATTGTTCGGTTGCTGATGCCTTCGGGCTGACCAT
900 CCGGAACTGTGTCCGGAAAAGCCGCGACGAACTGGTATCCCAGTGGCCTGAACGAACAGTTCACCGTTAAAGGCGTGCATGCCACACCTTCCCGAATC
1000 ATCATGGTAAACGTGCGTTTCGCTCAACGTCAAGTCAGCAGCAGTCATCCTCGGCAAACTCTTTCCATGCCGCTTCAACCTCGCGGGAAAGGCACGGG
1100 CTTCTTCCTCCCCGATGCCCAGATAGCGCCAGCTTGGGCGATGACTGAGCCGGATGACTGATCCTGATGCAGCTAGATTAACCCTAG
```

*FIG. 17(B)*

```
1200 AAGATAGTCTGCGGTAAAATTGACGCATGATCTAATTAACCCTCACTAAAGGGAACAAAAGCTGGAGCTCCACCGCGGTGGCGGCCGCTCTAGAACTAGT
     <  RIGHT TERMINAL REPEAT
1300 GTTCCCACAATGGTTAATTCGAGCTCGCCCGGGGATCTAATTCAATTAGAGACTAATTCAATTAGAGCTAATTCAATTAGGATCCAAGCTTATCGATTTC
                                                            3XP3-ECFP MARKER                              >
1400 GAACCCTCGACCGCCGGAGTATAAATAGAGGCGCTTCGTCTACGGAGCCGACAATTCAATTCAAACAAGCAAAGTGAACACGTCGCTAAGCGAAAGCTAAG
                                                            3XP3-ECFP MARKER                              >
1500 CAAATAAACAAGCGCAGCTGAACAAGCTAAACAAGCTAAACAATCGGGGTACCGCTAGAGTCGACGGTACCGCTAGAGTCGACGATCCACCGGTCGCCACCATGGTGAGCAAGGGCGAGGAG
                                                            3XP3-ECFP MARKER                              >
1600 CTGTTCACCGGGGTGGTGCCCATCCTGGTCGAGCTGGACGGCGACGTAAACGGCCACAAGTTCAGCGTGTCCGGCGAGGGCGATGCCACCTACG
                                                            3XP3-ECFP MARKER                              >
1700 GCAAGCTGACCCTGAAGTTCATCTGCACCACCGGCAAGCTGCCCGTGCCCTGGCCCACCCTCGTGACCACCCTGACCTGGGGCGTGCAGTGCTTCAGCCG
                                                            3XP3-ECFP MARKER                              >
1800 CTACCCCGACCACATGAAGCAGCACGACTTCTTCAAGTCCGCGAAGGCTACGTCCAGGAGCGCACCATCTTCTTCAAGGACGACGGCAACTAC
                                                            3XP3-ECFP MARKER                              >
1900 AAGACCCGGCGCGAGGTGAAGTTCGAGGGCGACACCCTGGTGAACCGCATCGAGCTGAAGGGCATCGACTTCAAGGAGGACGGCAACATCCTGGGGCACA
                                                            3XP3-ECFP MARKER                              >
2000 AGCTGGAGTACAACTACAACATCAGCCACAACGTCTATATCACCGCCGACAAGCAGAAGAACGGCATCAAGGCCAACTTCAAGATCCGCCACAACATCGAGGA
                                                            3XP3-ECFP MARKER                              >
```

*FIG. 17(B) CONT.*

```
2100
CGGCAGCGTGCAGCTCGCCGACCACTACCAGCAGAGAACACCCCATCGGGCGACGGCCCCGTGCTGCTGCCCGACAACCACTACCTGAGCACCCAGTCCGCC
                                                 3XP3-ECFP MARKER                                  >
2200
CTGAGCAAAGACCCCAACGAGAAGCGCGATCACATGGTCCTGCTGGAGTTCGTGACCGCCGCCGGGATCACTCTCGGCATGGACGAGCTGTACAAGTAAA
                                       3XP3-ECFP MARKER                                         >
2300
GCGGGCCCGGACTCTAGATCATAATCAGCCATACCACATTTGTAGAGGTTTTACTTGCTTTAAAAAACCTCCCACACCTCCCCCTGAACCTGAAACATAAA
                                       3XP3-ECFP MARKER                                            >
2400
ATGAATGCAATTGTTGTTGTTAACTTGTTTATTGCAGCTTATAATGGTTACAAATAAAGCAATAGCATCACAAATTTCACAAATAAAGCATTTTTTTCAC
                                       3XP3-ECFP MARKER                                          >
2500
TGCATTCTAGTTGTGGTTTGTCCAAACTCATCAATGTATCTTAAAGCTTATCGATACGGCACTAGTGGATCCCCCGGGCTGCAGGAATTCGATA
                                                                                             >
2600
TCAAGCTTATCGATACCGTCGACCTCGAGGGGGGCCCGGTACCCAATTCGCCCTATAGTGAGTCGTATTAAGATCACGGCGTAGATCCATGGCGTCAATTT
                                                                                              ˅
2700
TACGCATGATTATCTTAACGTACGTCACAATATGATTATCTTTCTAGGGTTAATCTAGCTGCGGTGTCGAGCATCTTCATCTGCTCCA
                LEFT TERMINAL REPEAT
2800
TCACGCTGTAAACACATTTGCACCGCGAGTCTGCCCGCTCCTCCACGGGTTCAAAAACGTGGGCGCTTGGCGTAATCATGGTCATAGCT
                                                                                              ˅
2900
GTTTCCTGTGTGAAATTGTTATCCGCTCACAATTCCACACAACATACGAGCCGGAAGCATAAAGTGTAAAGCCTGGGGTGCCTAATGAGTGAGCTAACTC
3000
ACATTAATTGCGTTGCGCTCACTGCCCGCTTTCCAGTCGGGAAACCTGTCGTGCCAGCTGCATTAATGAATCGGCCAACGCGCGGGGAGAGGCGGTTTGC
```

*FIG. 17(B) CONT.*

>ColE1_origin

3100 GTATTGGGCGCTCTTCCGCTTCCTCGCTCACTGACTCGCTGCGCTCGGTCGTTCGGCTGCGGCGAGCGGTATCAGCTCACTCAAAGGCGGTAATACGGTT
3200 ATCCACAGAATCAGGGGATAACGCAGGAAAGAACATGTGAGCAAAAGGCCAGCAAAAGGCCAGGAACCGTAAAAAGGCCGCGTTGCTGGCGTTTTTCCAT
3300 AGGCTCCGCCCCCCTGACGAGCATCACAAAAATCGACGCTCAAGTCAGAGGTGGCGAAACCCGACAGGACTATAAAGATACCAGGCGTTTCCCCCTGGAA
3400 GCTCCCTCGTGCGCTCTCCTGTTCCGACCCTGCCGCTTACCGGATACCTGTCCGCCTTTCTCCCTTCGGGAAGCGTGGCGCTTTCTCATAGCTCACGCTG
3500 TAGGTATCTCAGTTCGGTGTAGGTCGTTCGCTCCAAGCTGGGCTGTGTGCACGAACCCCCCGTTCAGCCCGACCGCTGCGCCTTATCCGGTAACTATCGT
3600 CTTGAGTCCAACCCGGTAAGACACGACTTATCGCCACTGGCAGCAGCCACTGGTAACAGGATTAGCAGAGCGAGGTATGTAGGCGGTGCTACAGAGTTCT
3700 TGAAGTGGTGGCCTAACTACGGCTACACTAGAAGGACAGTATTTGGTATCTGCGCTCTGCTGAAGCCAGTTACCTTCGGAAAAAGAGTTGGTAGCTCTTG
3800 ATCCGGCAAACAAACCACCGCTGGTAGCGGTGGTTTTTTTGTTTGCAAGCAGCAGATTACGCGCAGAAAAAAAGGATCTCAAGAAGATCCTTTGATCTTT
3900 TCTACGGGGTCTGACGCTCAGTGGAACGAAAACTCACGTTAAGGGATTTTGGTCATGAGATTATCAAAAAGGATCTTCACCTAGATCCTTTTAAATTAAA
4000 AATGAAGTTTTAAATCAATCTAAAGTATATATGAGTAAACTTGGTCTGACAGTTACCAATGCTTAATCAGTGAGGCACCTATCTCAGCGATCTGTCTATT

AMPCILLIN RESISTANCE ⟩

*FIG. 17(B) CONT.*

```
4100
TCGTTCATCCATAGTTGCCTGACTCCCCGTCGTGTAGATAACTACGATACGGGAGGGCTTACCATCTGGCCCCAGTGCTGCAATGATACCGGGAGACCCA
     AMPCILLIN RESISTANCE                                                                            >

4200
CGCTCACCGGCTCCAGATTTATCAGCAATAAACCAGCCAGCCGGAAGGGCCGAGCGCAGAAGTGGTCCTGCAACTTTATCCGCCTCCATCCAGTCTATTA
     AMPCILLIN RESISTANCE                                                                            >

4300
ATTGTTGCCGGGAAGCTAGAGTAAGTAGTTCGCCAGTAATAGTTTGCGCAACGTTGTTGCCATTGCTACAGGCATCGTGGTGTCACGCTCGTCGTTTGG
     AMPCILLIN RESISTANCE                                                                          >

4400
TATGGCTTCATTCAGCTCCGGTTCCCAACGATCAAGGCGAGTTACATGATCCCCCATGTTGTGCAAAAAAGCGGTTAGCTCCTTCGGTCCTCCGATCGTT
     AMPCILLIN RESISTANCE                                                                            >

4500
GTCAGAAGTAAGTTGGCCGCAGTGTTATCACTCATGGTTATGGCAGCACTGCATAATTCTCTTACTGTCATGCCATCGTAAGATGCTTTTCTGTGACTG
     AMPCILLIN RESISTANCE                                                                          >

4600
GTGAGTACTCAACCAAGTCATTCTGAGAATAGTGTATGCGGCGACCGAGTTGCTCTTGCCCGGCGTCAATACGGGATAATACCGCGCCACATAGCAGAAC
     AMPCILLIN RESISTANCE                                                                            >

4700
TTTAAAAGTGCTCATCATTGGAAAACGTTCTTCGGGGCGAAAACTCTCAAGGATCTTACCGCTGTTGAGATCCAGTTCGATGTAACCCACTCGTGCACCC
     AMPCILLIN RESISTANCE                                                                            >

4800
AACTGATCTTCAGCATCTTTTACTTTCACCAGCGTTTCTGGGTGAGCAAAAACAGGAAGGCAAAATGCCGCAAAAAAGGGAATAAGGGCGACACGGAAAT
     AMPCILLIN RESISTANCE                                                                            >

4900
GTTGAATACTCATACTCTTCCTTTTTCAATATTATTGAAGCATTTATCAGGGTTATTGTCTCATGAGCGGATACATATTTGAATGTATTTAGAAAAATAA
     AMPCILLIN R  >

ACAAATAGGGGTTCCGCGCACATTTCCCCGAAAGTGCCAC --(SEQ ID NO:53)--
```

FIG. 17(B) CONT.

PBS-ITR-ECFP
Sequence Range: 1 to 4943

100
CACCCTGACGCGCCCTGTAGCGGCGCATTAAGCGCGGCGGGTGTGGTGGTTACGCGCAGCGTGACCGCTACACTTGCCAGCGCCCTAGCGCCCGCTCCTTT

200
CGCTTTCTTCCCTTCCTTTCTCGCCACGTTCGCCGGCTTTCCCCGTCAAGCTCTAAATCGGGGGCTCCCTTTAGGGTTCCGATTTAGTGCTTTACGGCAC

300
CTCGACCCCAAAAAACTTGATTAGGGTGATGGTTCACGTAGTGGGCCATCGCCCTGATAGACGGTTTTTCGCCCTTTGACGTTGGAGTCCACGTTCTTTA

400
ATAGTGGACTCTTGTTCCAAACTGGAACAACACTCAACCCTATCTCGGTCTATTCTTTTGATTTATAAGGGATTTTGCCGATTTCGGCCTATTGGTTAAA

500
AAATGAGCTGATTTAACAAAAATTTAACGCGAATTTTAACGCGTTACAATTTCCATTCGCCATTCAGGCTGCGCAACTGTTGGGAAGGGC

600
GATCGGTGCGGGCCTCTTCGCTATTACGCCAGCTGGCGAAAGGGGGATGTGCTGCAAGGCGATTAAGTTGGGTAACGCCAGGGTTTTCCCAGTCACGACG

700
TTGTAAAACGACGGCCAGTGAATTGTAATACGACTCACTATAGGGCGAATTGGGCCCTCTAGATGCATGCTCGAGCGGCCGCCAGTGTGATGGATATC
                                                                                RIGHT TERMINAL REPEAT ─────>

800
GAATTCCTGCAGCCCGGGGGATCCACTAGTTCTAGAGCGGCCGCCACCGCGGTGGAGCTCCAGCTTTTGTTCCCTTTAGTGAGGGTTAATTCTGAGCTTGGCGTAATCATGGTCATAGCTGTTTCCTGTGTGAAATTGTTATCCGCTCACAATTCCACACAACATACGAGCCGGAAGCATAAAGTGTAAAGCCTGGGGTGCCTAATGAGTGAGCTAACTCACATTAATTGCGTTGCGCTCACTGCCCGCTTTCCAGTCGGGAAACCTGTCGTGCCAGCTGCATTAATGAATCGGCCAACGCGCGGGGAGAGGCGGTTTGCGTATTGGGCGCTCTTCCGCTTCCTCGCTCACTGACTCGCTGCGCTCGGTCGTTCGGCTGCGGCGAGCGGTATCAGCTCACTCAAAGGCGGTAATACGGTTATCCACAGAATCAGGGGATAACGCAGGAAAGAACATGTGAGCAAAAGGCCAGCAAAAGGCCAGGAACCGTAAAAAGGCCGCGTTGCTGGCGTTTTTCCATAGGCTCCGCCCCCCTGACGAGCATCACAAAAATCGACGCTCAAGTCAGAGGTGGCGAAACCCGACAGGACTATAAAGATACCAGGCGTTTCCCCCTGGAAGCTCCCTCGTGCGCTCTCCTGTTCCGACCCTGCCGCTTACCGGATACCTGTCCGCCTTTCTCCCTTCGGGAAGCGTGGCGCTTTCTCATAGCTCACGCTGTAGGTATCTCAGTTCGGTGTAGGTCGTTCGCTCCAAGCTGGGCTGTGTGCACGAACCCCCCGTTCAGCCCGACCGCTGCGCCTTATCCGGTAACTATCGTCTTGAGTCCAACCCGGTAAGACACGACTTATCGCCACTGGCAGCAGCCACTGGTAACAGGATTAGCAGAGCGAGGTATGTAGGCGGTGCTACAGAGTTCTTGAAGTGGTGGCCTAACTACGGCTACACTAGAAGGACAGTATTTGGTATCTGCGCTCTGCTGAAGCCAGTTACCTTCGGAAAAAGAGTTGGTAGCTCTTGATCCGGCAAACAAACCACCGCTGGTAGCGGTGGTTTTTTTGTTTGCAAGCAGCAGATTACGCGCAGAAAAAAAGGATCTCAAGAAGATCCTTTGATCTTTTCTACGGGGTCTGACGCTCAGTGGAACGAAAACTCACGTTAAGGGATTTTGGTCATGAGATTATCAAAAAGGATCTTCACCTAGATCCTTTTAAATTAAAAATGAAGTTTTAAATCAATCTAAAGTATATATGAGTAAACTTGGTCTGACAGTTACCAATGCTTAATCAGTGAGGCACCTATCTCAGCGATCTGTCTATTTCGTTCATCCATAGTTGCCTGACTCCCCGTCGTGTAGATAACTACGATACGGGAGGGCTTACCATCTGGCCCCAGTGCTGCAATGATACCGCGAGACCCACGCTCACCGGCTCCAGATTTATCAGCAATAAACCAGCCAGCCGGAAGGGCCGAGCGCAGAAGTGGTCCTGCAACTTTATCCGCCTCCATCCAGTCTATTAATTGTTGCCGGGAAGCTAGAGTAAGTAGTTCGCCAGTTAATAGTTTGCGCAACGTTGTTGCCATTGCTACAGGCATCGTGGTGTCACGCTCGTCGTTTGGTATGGCTTCATTCAGCTCCGGTTCCCAACGATCAAGGCGAGTTACATGATCCCCCATGTTGTGCAAAAAAGCGGTTAGCTCCTTCGGTCCTCCGATCGTTGTCAGAAGTAAGTTGGCCGCAGTGTTATCACTCATGGTTATGGCAGCACTGCATAATTCTCTTACTGTCATGCCATCCGTAAGATGCTTTTCTGTGACTGGTGAGTACTCAACCAAGTCATTCTGAGAATAGTGTATGCGGCGACCGAGTTGCTCTTGCCCGGCGTCAATACGGGATAATACCGCGCCACATAGCAGAACTTTAAAAGTGCTCATCATTGGAAAACGTTCTTCGGGGCGAAAACTCTCAAGGATCTTACCGCTGTTGAGATCCAGTTCGATGTAACCCACTCGTGCACCCAACTGATCTTCAGCATCTTTTACTTTCACCAGCGTTTCTGGGTGAGCAAAAACAGGAAGGCAAAATGCCGCAAAAAAGGGAATAAGGGCGACACGGAAATGTTGAATACTCATACTCTTCCTTTTTCAATATTATTGAAGCATTTATCAGGGTTATTGTCTCATGAGCGGATACATATTTGAATGTATTTAGAAAAATAAACAAATAGGGGTTCCGCGCACATTTCCCCGAAAAGTGCCACCTGACGTCTAAGAAACCATTATTATCATGACATTAACCTATAAAAATAGGCGTATCACGAGGCCCTTTCGTC

FIG. 18(B)

```
1200
     CCGGAACTGCCGTGCCGGTGTGCAGATTAATGACAGGGTGCGGCGCTGGGATATTACGTCAGCGAGGACGGGTATCCTGGCTGATGCCGAGAAATGG
1300
     ACATGGATACCCCGTGAGTTACCGGCGCTCGTTCATTCACGTTTTTGAACCCTGGAGGACGGCAGACTCCGCGGTGCAAATGTGTTTACAGCGTGA
1400
     TGGAGCAGATGAAGATGCTCGACACGCTAGAGAACGCAGCTAGATTAACCCTAGAAAGATAATCATATTGTGACGTACGTTAAAGATAATCATGCGTA
                                                                                 LEFT TERMINAL REPEAT
1500
     AAATTGACGCATGGAATCCACTAGTGTTCCCACAATGTGTAATTCGAGCTCGCCCCGGGATCTAATTCAATTAGAGACTAATTCAATTAGAGCTAATTCA
                                                          3XP3-ECFP MARKER
1600
     ATTAGGATCCAAGCTTATCGATTTCGAACCCTCGACCGCCGGAGTATAAATAGAGGGCGCTTCGTCTACGGAGCGACAATTCAAACAAGCAAAGTG
                                                                                      3XP3-ECFP MARKER
1700
     AACACGTCGCTAAGCGAAAGCTAAGCAAATAAACAAGCTGAACAAGCAGCTAAACAATCGGGGTACCGCTAGAGTCGACGGTACGATCCACCGGTCGC
                            3XP3-ECFP MARKER
1800
     CACCATGGTGAGCAAGGGCGAGGAGCTGTTCACCGGGGTGGTGCCCATCCTGGTCGAGCTGGACGGCGACGTAAACGGCCACAAGTTCAGCGTGTCCGGC
                            3XP3-ECFP MARKER
1900
     GAGGGCGAGGGCGATGCCACCTACGGCAAGCTGACCCTGAAGTTCATCTGCACCACCGGCAAGCTGCCCGTGCCCTGGCCCACCCTCGTGACCACCCTGA
                            3XP3-ECFP MARKER
2000
     CCTGGGGCGTGCAGTGCTTCAGCCGCTACCCCGACCACATGAAGCAGCACGACTTCTTCAAGTCCGCCATGCCCGAAGGCTACGTCCAGGAGCGCACCAT
                            3XP3-ECFP MARKER
2100
     CTTCTTCAAGGACGACGGCAACTACAAGACCCGCGCCGAGGTGAAGTTCGAGGGCGACACCCTGGTGAACCGCATCGAGCTGAAGGGCATCGACTTCAAG
                            3XP3-ECFP MARKER
```

*FIG. 18(B) CONT.*

```
2200
GAGGAGGCGGCAACATCCTGGGGCACAAGCTGGAGTACAACTACATCAGCCACAAGCTCTATATCACCGCCGACAAGCAGAGAACGGCATCAAGGCCAACT
                                                                    3XP3-ECFP MARKER                >

2300
TCAAGATCCGCCACAACATCGAGGAGGACGGCAGCGTGCAGCTCGCCGACCACTACCAGCAGAACACCCCCATCGGCGACGGCCCCGTGCTGCTGCCCGACAA
                                                                    3XP3-ECFP MARKER                >

2400
CCACTACCTGAGCACCCAGTCCGCCCTGAGCAAAGACCCCAACGAGAAGCGCGATCACATGGTCCTGCTGGAGTTCGTGACCGCCGCCGGGATCACTCTC
                                                                    3XP3-ECFP MARKER                >

2500
GGCATGGACGAGCTGTACAAGTAAAGCGGCCGCGACTCTAGATCATAATCAGCCATACCACCACATTTGTAGAGGTTTTACTTGCTTTAAAAAACCTCCCACA
                                                                    3XP3-ECFP MARKER                >

2600
CCTCCCCCTGAACCTGAAACATAAAATGAATGCAATTGTTGTTGTTAACTTGTTATTGCAGCTTATAATGTTACAAATAAAGCAATAGCATCACAAAT
                                                                    3XP3-ECFP MARKER                >

2700
TTCACAAATAAAGCATTTTTTCACTGCATTCTAGTTGTGGTTTGTCCAAACTCATCAATGTATCTTAAAGCTTATCGATACGCGTACGGCGCCTAGG
                                                                    3XP3-ECFP MARKER                >

2800
CCGGCCGATACTAGTTCTAGAGCGGCCGCCACCGGGTGGAGCTCCAGCTTTTGTTCCCTTTAGTGAGGGTTAATTTCGAGCTTGGCGTAATCATGGTCA
                    >

2900
TAGCTGTTTCCTGTGTGAAATTGTTATCCGCTCACAATTCCACACAACATACGAGCCGGAAGCATAAAGTGTAAAGCCTGGGGTGCCTAATGAGTGAGCT

3000
AACTCACATTAATTGCGTTGCGCTCACTGCCCGCTTTCCAGTCGGGAAACCTGTCGTGCCAGCTGCATTAATGAATCGGCCAACGCGCGGGGAGAGGCGG
```

*FIG. 18(B) CONT.*

>ColE1_origin

```
3100 TTTGCGTATTGGGCGCTCTTCCGCTTCCTCGCTCACTGACTCGCTGCGCTCGGTCGTTCGGCTGCGGCGAGCGGTATCAGCTCACTCAAAGGCGGTAATA
3200 CGGTTATCCACAGAATCAGGGGATAACGCAGGAAAGAACATGTGAGCAAAAGGCCAGCAAAAGGCCAGGAACCGTAAAAAGGCCGCGTTGCTGGCGTTTT
3300 TCCATAGGCTCCGCCCCCCTGACGAGCATCACAAAAATCGACGCTCAAGTCAGAGGTGGCGAAACCCGACAGGACTATAAAGATACCAGGCGTTTCCCCC
3400 TGGAAGCTCCCTCGTGCGCTCTCCTGTTCCGACCCTGCCGCTTACCGGATACCTGTCCGCCTTTCTCCCTTCGGGAAGCGTGGCGCTTTCTCATAGCTCA
3500 CGCTGTAGGTATCTCAGTTCGGTGTAGGTCGTTCGCTCCAAGCTGGGCTGTGTGCACGAACCCCCCGTTCAGCCCGACCGCTGCGCCTTATCCGGTAACT
3600 ATCGTCTTGAGTCCAACCCGGTAAGACACGACTTATCGCCACTGGCAGCAGCCACTGGTAACAGGATTAGCAGAGCGAGGTATGTAGGCGGTGCTACAGA
3700 GTTCTTGAAGTGGTGGCCTAACTACGGCTACACTAGAAGGACAGTATTTGGTATCTGCGCTCTGCTGAAGCCAGTTACCTTCGGAAAAAGAGTTGGTAGC
3800 TCTTGATCCGGCAAACAAACCACCGCTGGTAGCGGTGGTTTTTTTGTTTGCAAGCAGCAGATTACGCGCAGAAAAAAGGATCTCAAGAAGATCCTTTGA
3900 TCTTTTCTACGGGGTCTGACGCTCAGTGGAACGAAAACTCACGTTAAGGGATTTTGGTCATGAGATTATCAAAAAGGATCTTCACCTAGATCCTTTTAAA
4000 TTAAAAATGAAGTTTTAAATCAATCTAAAGTATATATGAGTAAACTTGGTCTGACAGTTACCAATGCTTAATCAGTGAGGCACCTATCTCAGCGATCTGT
     AMPCILLIN RESISTANCE                                                                                 ^
4100 CTATTTCGTTCATCCATAGTTGCCTGACTCCCCGTCGTGTAGATAACTACGATACGGGAGGGCTTACCATCTGGCCCCAGTGCTGCAATGATACCGCGAG
     AMPCILLIN RESISTANCE                                                                                 ^
```

FIG. 18(B) CONT.

4200
ACCCACGCTCACCGGCTCCAGATTTATCAGCAATAAACCAGCCAGCCGGAGGGCCGAGGCGCAGAAGTGGTCCTGCAACTTTATCCGCCTCCATCCAGTC
　　　　　AMPCILLIN RESISTANCE

4300
TATTAATTGTTGCCGGGAAGCTAGAGTAAGTAGTTCGCCAGTTAATAGTTGCGCAACGTTGTTGCCATTGCTACAGGCATCGTGGTGTCACGCTCGTCG
　　　　　AMPCILLIN RESISTANCE

4400
TTTGGTATGGCTTCATTCAGCTCCGGTTCCCAACGATCAAGGCGAGTTACATGATCCCCCATGTTGTGCAAAAAGCGGTTAGCTCCTTCGGTCCTCCGA
　　　　　AMPCILLIN RESISTANCE

4500
TCGTTGTCAGAAGTAAGTTGGCCGCAGTGTTATCACTCATGGTTATGGCAGCACTGCATAATTCTCTTACTGTCATGCCATCGTAAGATGCTTTTCTGT
　　　　　AMPCILLIN RESISTANCE

4600
GACTGGTGAGTACTCAACCAAGTCATTCTGAGAATAGTGTATGCGGCGACCGAGTTGCTCTTGCCCGGCGTCAATACGGGATAATACCGCCACATAGC
　　　　　AMPCILLIN RESISTANCE

4700
AGAACTTTAAAAGTGCTCATCATTGGAAAACGTTCTTCGGGGCGAAAACTCTCAAGGATCTTACCGCTGTTGAGATCCAGTTCGATGTAACCCACTCGTG
　　　　　AMPCILLIN RESISTANCE

4800
CACCCAACTGATCTTCAGCATCTTTTACTTTCACCAGCGTTTCTGGGTGAGCAAAAACAGGAAGGCAAAATGCCGCAAAAAAGGGAATAAGGGCGACACG
　　　　　AMPCILLIN RESISTANCE

4900
GAAATGTTGAATACTCATACTCTTCCTTTTTCAATATTATTGAAGCATTTATCAGGGTTATTGTCTCATGAGCGGATACATATTTGAATGTATTTAGAAA
　　　　　AMPCILLIN RESISTANCE

AATAAACAAATAGGGGTTCCGCGCACATTTCCCCGAAAAGTGC --(SEQ ID NO:54)--

*FIG. 18(B) CONT.*

PBS-ITR-EGFP
Sequence Range: 1 to 4944

100
CACCTGACGCGCCCTGTAGCGGCGCATTAAGCGCGGCGGGTGTGGTGGTTACGCGCAGCGTGACCGCTACACTTGCCAGCGCCCTAGCGCCCGCTCCTTT

200
CGCTTTCTTCCCTTCCTTTCTCGCCACGTTCGCCGGCTTTCCCCGTCAAGCTCTAAATCGGGGGCTCCCTTTAGGGTTCCGATTTAGTGCTTTACGGCAC

300
CTCGACCCCAAAAAACTTGATTAGGGTGATGGTTCACGTAGTGGGCCATCGCCCTGATAGACGGTTTTTCGCCCTTTGACGTTGGAGTCCACGTTCTTTA

400
ATAGTGGACTCTTGTTCCAAACTGGAACAACACTCAACCCTATCGGTCTATTCTTTTGATTTATAAGGATTTTGCCGATTTCGGCCTATTGGTTAAA

500
AAATGAGCTGATTTAACAAAAATTTAACGCGAATTTTAACAAATTTCATTCGCCATTCAGGCTGCGCAACTGTTGGGAAGGGC

600
GATCGGTGCGGGCCTCTTCGCTATTACGCCAGCTGGCGAAAGGGGGATGTGCTGCAAGGCGATTAAGTTGGGTAACGCCAGGGTTTTCCCAGTCACGACG

700
TTGTAAAACGACGGCCAGTGAATTGTAATACGACTCACTATAGGGCGAATTGGGTACCGGGCCCCCCCTCGAGGTCGACGGTATCGATAAGCTTGATATC

800
                                                          RIGHT TERMINAL REPEAT
GAATTCCTGCAGCCCGGGGATCCACCATGCGTCAATTTTACGCAGACTATCTTTCTAGGGTTAATCTAGCTGCATCAGGATCATATCGTCGGGTCTTTTT ──────>

900
CCGGCTCAGTCATCGCCAAGCTGGCGCTATCTGGGCATCGGGAGGAAGAAGCCCGTGCCTTTTCCCGGAGGTTGAAGCGGCATGAAAGAGTTTGCC

1000
GAGGATGACTGCTGCTGCATTGACGTTGAGCGAAAACGCACGTTAAGCGCCTTAACGTGAACTGTTCG

1100
TTCAGGCCACCTGGGATACCAGTTCGTCGCGGCTTTTCCGGACACAGTTCGGATGGTCAGCCGAAGCGCATCAGCAGCAATCCGAACAATACCGGCGACAG

FIG. 19(B)

```
1200
CCGGAACTGCCGTGCCGGTGTGCAGATTAATGACAGCGGTGCGGCCTGGGATATTACGTCAGCGAGGACGGGTATCCTGGCTGGATGCCGCAGAAATGG

1300
ACATGGATACCCCGTGAGTTACCCGGGGCTCGTTCATTCACGTTTTTGAACCCGTGGAGGACGGGCAGACTCGCGGTGCAAATGTGTTTTACAGCGTGA

1400
TGGAGCAGATGAAGATGCTCGACACGCTGACAGTTAACCCTAGAAAGATAAATCATATTGTGACGTACGTTAAAGATAATCATGCGTA
                                                                        LEFT TERMINAL REPEAT    >

1500
AAATTGACGCATGGGATCCACTAGTGTTCCCACAATGTGTTAATTCGAGCTCGCCCGGGGATCTAATTCAATTAGAGACTAATTCAATTAGAGCTAATTCA
                                                                          3XP3-EGFP MARKER        >

1600
ATTAGGATCCAAGCTTATCGATTTCGAACCCTCGACCGCCGGAGTATAAATAGAGGCGCTTCGTCTACGGAGCGACAATTCAATTCAAACAAGCAAAGTG
                                                                          3XP3-EGFP MARKER        >

1700
AACACGTCGCTAAGCGAAAGCTAAGCAAATAAACAATCGGGGTACCGCTAGAGTCGACGGTACCGCGGGCCCGGGAT
                                                                          3XP3-EGFP MARKER        >

1800
CCACCGGTCGCCACCATGGTGAGCAAGGGCGAGGAGCTGTTCACCGGGGTGGTGCCCATCCTGGTCGAGCTGGACGGCGACGTAAACGGCCACAAGTTCA
                                                                          3XP3-EGFP MARKER        >

1900
GCGTGTCCGGCGAGGGCGAGGGCGATGCCACCTACGGCAAGCTGACCCTGAAGTTCATCTGCACCACCGGCAAGCTGCCCGTGCCCTGGCCCACCCTCGT
                                                                          3XP3-EGFP MARKER        >

2000
GACCACCCTGACCTACGGCGTGCAGTGCTTCAGCCGCTACCCCGACCACATGAAGCAGCACGACTTCTTCAAGTCCGCCATGCCCGAAGGCTACGTCCAG
                                                                          3XP3-EGFP MARKER        >

2100
GAGCGCACCATCTTCTTCAAGGACGACGGCAACTACAAGACCCGCGCCGAGGTGAAGTTCGAGGGCGACACCCTGGTGAACCGCATCGAGCTGAAGGGCA
                                                                          3XP3-EGFP MARKER        >
```

*FIG. 19(B) CONT.*

2200
TCGACTTCAAGGAGGACGGCAACATCCTGGGGCACAAGCTGGAGTACAACTACAACAGCCACAACGTCTATATCATGGCCGACAAGCAGAAGAACGGCAT
                                                                                 3XP3-EGFP MARKER

2300
CAAGGTGAACTTCAAGATCCGCCACAACATCGAGGACGGCAGCGTGCAGCTCGCCGACCACTACCAGCAGAACACCCCCATCGGCGACGGCCCCGTGCTG
                                     3XP3-EGFP MARKER

2400
CTGCCCGACAACCACTACCTGAGCACCCAGTCCGCCCTGAGCAAAGACCCCAACGAGAAGCGCGATCACATGGTCCTGCTGGAGTTCGTGACCGCCGCCG
                                     3XP3-EGFP MARKER

2500
GGATCACTCTCGGCATGGACGAGCTGTACAAGTAAAGCGGCCGACTCTAGATCATAATCAGCCATACCACATTGTAGAGGTTTTACTTGCTTTAAAA
                                     3XP3-EGFP MARKER

2600
AACCTCCCACACCTCCCCCTGAACCTGAAACATAAAATGAATGCAATTGTTGTTGTTAACTTGTTTATTGCAGCTTATAATGTTACAAATAAAGCAATA
                                     3XP3-EGFP MARKER

2700
GCATCACAAATTTCACAAATAAAGCATTTTTTTCACTGCATTCTAGTTGTGGTTTGTCCAAACTCATCAATGTATCTTAAAGCTTATCGATACGGCTACG
                                     3XP3-EGFP MARKER

2800
GCGCGCCTAGACTAGTTCTAGAGCGGCCGCCACCGCGGTGGAGCTCCAGCTTTTGTTCCCTTTAGTGAGGGTTAATTCGAGCTTGGCGTAATCATGGTC
                ^

2900
ATAGCTGTGTTCCTGTGTGAAATTGTTATCCGCTCACAATTCCACACAACATACGAGCCGGAAGCATAAAGTGTAAAGCCTGGGGTGCCTAATGAGTGAGC

3000
TAACTCACATTAATTGCGTTGCGCTCACTGCCCGCTTTCCAGTCGGGAAACCTGTCGTGCCAGCTGCATTAATGAATCGGCCAACGCGCGGGGAGAGGCG

*FIG. 19(B) CONT.*

>ColE1_origin

```
3100 GTTTGCGGTATTGGGCGCTCTTCCGCTTCCTCGCTCACTGACTCGCTGCGCTCGGTCGTTCGGCTGCGGCGAGCGGTATCAGCTCACTCAAAGGCGGTAAT
3200 ACGGTTATCCACAGAATCAGGGGATAACGCAGGAAAGAACATGTGAGCAAAAGGCCAGCAAAAGGCCAGGAACCGTAAAAAGGCCGCGTTGCTGGCGTTT
3300 TTCCATAGGCTCCGCCCCCCTGACGAGCATCACAAAAATCGACGCTCAAGTCAGAGGTGGCGAAACCCGACAGGACTATAAAGATACCAGGCGTTTCCCC
3400 CTGGAAGCTCCCTCGTGCGCTCTCCTGTTCCGACCCTGCCGCTTACCGGATACCTGTCCGCCTTTCTCCCTTCGGGAAGCGTGGCGCTTTCTCATAGCTC
3500 ACGCTGTAGGTATCTCAGTTCGGTGTAGGTCGTTCGCTCCAAGCTGGGCTGTGTGCACGAACCCCCCGTTCAGCCCGACCGCTGCGCCTTATCCGGTAAC
3600 TATCGTCTTGAGTCCAACCCGGTAAGACACGACTTATCGCCACTGGCAGCAGCCACTGGTAACAGGATTAGCAGAGCGAGGTATGTAGGCGGTGCTACAG
3700 AGTTCTTGAAGTGGTGGCCTAACTACGGCTACACTAGAAGGACAGTATTTGGTATCTGCGCTCTGCTGAAGCCAGTTACCTTCGGAAAAAGAGTTGGTAG
3800 CTCTTGATCCGGCAAACAAACCACCGCTGGTAGCGGTGGTTTTTTTGTTTGCAAGCAGCAGATTACGCGCAGAAAAAAGGATCTCAAGAAGATCCTTTG
3900 ATCTTTTCTACGGGGTCTGACGCTCAGTGGAACGAAAACTCACGTTAAGGGATTTTGGTCATGAGATTATCAAAAAGGATCTTCACCTAGATCCTTTTAA
4000 ATTAAAAATGAAGTTTTAAATCAATCTAAAGTATATATGAGTAAACTTGGTCTGACAGTTACCAATGCTTAATCAGTGAGGCACCTATCTCAGCGATCTG
     AMPCILLIN RESISTANCE
4100 TCTATTTCGTTCATCCATAGTTGCCTGACTCCCCGTCGTGTAGATAACTACGATACGGGAGGGCTTACCATCTGGCCCCAGTGCTGCAATGATACCGCGA
     AMPCILLIN RESISTANCE
```

FIG. 19(B) CONT.

```
4200
GACCCACGCTCACCGGCTCCAGATTTATCAGCAATAAACCAGCAGCCGGAAGGGCCGAGCGCAGAAGTGGTCCTGCAACTTTATCGCCTCCATCCAGT
                              AMPCILLIN RESISTANCE                                                >
4300
CTATTAATTGTTGCCGGGAAGCTAGAGTAAGTAGTTCGCCAGTTAATAGTTTGCGCAACGTTGTTGCCATTGCTACAGGCATCGTGGTGTCACGCTCGTC
                              AMPCILLIN RESISTANCE                                                >
4400
GTTTGGTATGGCTTCATTCAGCTCCGGTTCCCAACGATCAAGGCGAGTTACATGATCCCCCATGTTGTGCAAAAAAGCGGTTAGCTCCTTCGGTCCTCCG
                              AMPCILLIN RESISTANCE                                                >
4500
ATCGTTGTCAGAAGTAAGTTGGCCGCAGTGTTATCACTCATGGTTATGGCAGCACTGCATAATTCTCTTACTGTCATGCCATCCGTAAGATGCTTTTCTG
                              AMPCILLIN RESISTANCE                                                >
4600
TGACTGGTGAGTACTCAACCAAGTCATTCTGAGAATAGTGTATGCGGCGACCGAGTTGCTCTTGCCCGGCGTCAATACGGGATAATACCGCGCCACATAG
                              AMPCILLIN RESISTANCE                                                >
4700
CAGAACTTTAAAAGTGCTCATCATTGGAAAACGTTCTTCGGGGCGAAAACTCTCAAGGATCTTACCGCTGTTGAGATCCAGTTCGATGTAACCCACTCGT
                              AMPCILLIN RESISTANCE                                                >
4800
GCACCCAACTGATCTTCAGCATCTTTTACTTTCACCAGCGTTTCTGGGTGAGCAAAAACAGGAAGGCAAAATGCCGCAAAAAAGGGAATAAGGGCGACAC
                              AMPCILLIN RESISTANCE                                                >
4900
GGAAATGTTGAATACTCATACTCTTCCTTTTTCAATATTATTGAAGCATTTATCAGGGTTATTGTCTCATGAGCGGATACATATTTGAATGTATTTAGAA
        AMPCILLIN RESISTANCE     >

AAATAAACAAATAGGGGTTCCGCGCACATTTCCCCGAAAAGTGC  -- (SEQ ID NO:55) --
```

FIG. 19(B) CONT.

pBS-ITR-EYFP
Sequence Range: 1 to 4944

```
     CACCCTGACGCGCCCTGTAGCGCGCATTAAGCGCGGCGGGTGTGGTGGTTACGCGCAGCGTGACCGCTACACTTGCCAGCGCCCTAGCGCCCGCTCCTTT
100
     CGCTTTCTTCCCTTCCTTTCTCGCCACGTTCGCCGGCTTTCCCCGTCAAGCTCTAAATCGGGGGCTCCCTTTAGGGTTCCGATTTAGTGCTTTACGGCAC
200
     CTCGACCCCAAAAACTTGATTAGGGTGATGGTTCACGTAGTGGGCCATCGCCCTGATAGACGGTTTTTCGCCCTTTGACGTTGGAGTCCACGTTCTTTA
300
     ATAGTGGACTCTTGTTCCAAACTGGAACAACACTCAACCCTATCTCGGTCTATTCTTTGATTTATAAGGGATTTTGCCGATTTCGGCCTATTGGTTAAA
400
     AAATGAGCTGATTTAACAAAAATTTAACGCGAATTTTAACAAAATATTAACGCTTACAATTTCCATTCGCCATTCAGGCTGCGCAACTGTTGGGAAGGGC
500
     GATCGGTGCGGGCCTCTTCGCTATTACGCCAGCTGGCGAAAGGGGGATGTGCTGCAAGGCGATTAAGTTGGGTAACGCCAGGGTTTTCCCAGTCACGACG
600
     TTGTAAAACGACGGCCAGTGAATTGTAATACGACTCACTATAGGGCGAATTGGGTACCGGGCCCCCCCTCGAGGTCGACGGTATCGATAAGCTTGATATC
700
     GAATTCCTGCAGCCCGGGGATCCACTAGTTCTAGAGCGGCCGCCACCGCGGTGGAGCTCCAGCTTTTGTTCCCTTTAGTGAGGGTTAATTCTGAGCTTGG
800
               CGTAATCATGGTCATAGCTGTTTCCTGTGTGAAATTGTTATCCGCTCACAATTCCACACAACATACGAGCCGGAAGCATAAAGTGTAA
                                      RIGHT TERMINAL REPEAT
     CCGGCTCAGTCATCGCCCAAGCTGGCGCTATCTGGGCATCCGCTTACATTGACGTCAATAATGACGTATGTTCCCATAGTAACGCCAATAGGGACTTTCC
900
     GAGGATGACTGCTGCTGCATTGACGTTGAGCGGAAAACGCACGTTTACCATGATGATTCGGGAAGGCGGTGTGGCCATGCACGCCTTTAACGGTGAACTGTTCG
1000
     TTCAGGCCACCTGGGATACCAGTTCGTCGCGGCTTTTCCGGACACAGTTCCGCGATGGTCAGCCCGACACTAACGGCGCATCAGCAACCCGAACAATACCGGCGACAG
1100
```

*FIG. 20(B)*

```
1200
CCGGAACTGCCCGTGCCGGTGTGCAGATTAATGACAGCGGTGCGGGCGCTGGGATATTACGTCAGCGAGGACGGGTATCCTGGCTGCTGGATGCCGCAGAAATGG

1300
ACATGGATACCCCGTGAGTTACCCGGGCTCGTTCATTCACGTTTTTGAACCCGTGGAGGACCGGGCAGAGACTCGCCGGTGCAAATGTGTTTTACAGCGTGA
                                                                                          LEFT TERMINAL REPEAT
1400
TGGAGCAGAGATGAAGATGCTCGACACGCTGCAGAACACGCAGCTAGATTAACCCTAGAAAGATAATCATATTGTGACGTACGTTAAAGATAATCATGCGTA >
                                                        LEFT TERMINAL REPEAT
1500
AAATTGACGCATGGGATCCACTAGTGTTCCCACAATGGTTAATTCGAGCTCGCCCGGGATCTAATTCAATTAGAGACTAATTCAATTAGAGCTAATTCA >
                                                 3XP3-EYFP MARKER
1600
ATTAGGATCCAAGCTTATCGATTTCGAACCCTCGACCCGCCGAGTATAAATAGAGGGCGCTTCGTCTACGGAGCCGACAATTCAATTCAAACAAGCAAAGTG >
                             3XP3-EYFP MARKER
1700
AACACGTCGCTAAGGCGAAAGCTAAGCAAATAAACAAGCAGCTGAACAAGCTAAACAATCGGGGTACCGCTAGAGTCGACGTACGATCCACCGGTCGC >
                     3XP3-EYFP MARKER
1800
CACCATGGTGAGCAAGGGCGAGGAGCTGTTCACCGGGGTGGTGCCCATCCTGGTCGAGCTGGACGGCGACGTAAACGGCCACAAGTTCAGCGTGTCCGGC >
                     3XP3-EYFP MARKER
1900
GAGGGCGAGGGCGATGCCACCTACGGCAAGCTGACCCTGAAGTTCATCTGCACCACCGGCAAGCTGCCCGTGCCCTGGCCCACCCTCGTGACCACCTTCG >
                     3XP3-EYFP MARKER
2000
GCTACGGCCTGCAGTGCTTCGCCCGCTACCCCGACCACATGAAGCAGCACGACTTCTTCAAGTCCGCCATGCCCGAAGGCTACGTCCAGGAGCGCACCAT >
                     3XP3-EYFP MARKER
2100
CTTCTTCAAGGACGACGGCAACTACAAGACCCGCGCCGAGGTGAAGTTCGAGGGCGACACCCTGGTGAACCGCATCGAGCTGAAGGGCATCGACTTCAAG >
                     3XP3-EYFP MARKER
```

FIG. 20(B) CONT.

```
2200
GAGGACGGCAACATCCTGGGCACAAGCTGGAGTACAACTACAACAGCCACAAGTCTATATCATGGCCGACAAGCAGAAGAACGGCATCAAGGTGAACT
                                                            3XP3-EYFP MARKER                        >

2300
TCAAGATCCCGCCACAACATCGAGGACGGCAGCGTGCAGCTCGCCGACCACTACCAGCAGAACACCCCCATCGGCGACCCCGTGCTGCTGCCCGACAA
                                                            3XP3-EYFP MARKER                        >

2400
CCACTACCTGAGCTACCAGTCCGCCCTGAGCAAAGACCCCAACGAGAAGCGCGATCACATGGTCCTGCTGGAGTTCGTGACCGCCGCCGGGATCACTCTC
                                                            3XP3-EYFP MARKER                        >

2500
GGCATGGACGAGCTGTACAAGTAAAGGCCGCGACTCTAGATCATAATCAGCCATACCACACATTTGTAGAGGTTTTACTTGCTTTAAAAAACCTCCCACA
                                                            3XP3-EYFP MARKER                        >

2600
CCTCCCCCTGAACCTGAAACATAAAATGAATGCAATTGTTGTTGTTAACTTGTTTATTGCAGCTTATAATGGTTACAAATAAAGCAATAGCATCACAAAT
                                                            3XP3-EYFP MARKER                        >

2700
TTCACAAATAAAGCATTTTTTCACTGCATTCTAGTTGTTGGTTTGTCCAAACTCATCAATGTATCTTAAAGCTTATCGATACGGCTACGCGGCCCTAGG
                                                            3XP3-EYFP MARKER                        >

2800
CCGGCCGATCACTAGTTCTAGAGCGGCCGCCACCGGGTGGAGCTCCAGCTTTTGTTCCCTTTAGTGAGGGTTAATTCGAGCTTGGCGTAATCATGGTC
         >

2900
ATAGCTGTTTCCTGTGTGAAATTGTTATCCGCTCACAATTCCACACAACATACGAGCCGGAAGCATAAAGTGTAAAGCCTGGGGTGCCTAATGAGTGAGC

3000
TAACTCACATTAATTGCGTTGCGCTCACTGCCCGCTTTCCAGTCGGGAAACCTGTCGTGCCAGCTGCATTAATGAATCGGCCAACGCGCGGGGAGAGGCG
```

*FIG. 20(B) CONT.*

>ColE1_origin

3100 GTTTGCGTATTGGGCGCTCTTCCGCTTCCTCGCTCACTGACTCGCTGCGCTCGGTCGTTCGGCTGCGGCGAGCGGTATCAGCTCACTCAAAGGCGGTAAT
3200 ACGGTTATCCACAGAATCAGGGGATAACGCAGGAAAGAACATGTGAGCAAAAGGCCAGCAAAAGGCCAGGAACCGTAAAAAGGCCGCGTTGCTGGCGTTT
3300 TTCCATAGGCTCCGCCCCCCTGACGAGCATCACAAAAATCGACGCTCAAGTCAGAGGTGGCGAAACCCGACAGGACTATAAAGATACCAGGCGTTTCCCC
3400 CTGGAAGCTCCCTCGTGCGCTCTCCTGTTCCGACCCTGCCGCTTACCGGATACCTGTCCGCCTTTCTCCCTTCGGGAAGCGTGGCGCTTTCTCATAGCTC
3500 ACGCTGTAGGTATCTCAGTTCGGTGTAGGTCGTTCGCTCCAAGCTGGGCTGTGTGCACGAACCCCCCGTTCAGCCCGACCGCTGCGCCTTATCCGGTAAC
3600 TATCGTCTTGAGTCCAACCCGGTAAGACGACTTATCGCCACTGGCAGCAGCCACTGGTAACAGGATTAGCAGAGCGAGGTATGTAGGCGGTGCTACAG
3700 AGTTCTTGAAGTGGTGGCCTAACTACGGCTACACTAGAAGGACAGTATTTGGTATCTGCGCTCTGCTGAAGCCAGTTACCTTCGGAAAAAGAGTTGGTAG
3800 CTCTTGATCCGGCAAACAAACCACCGCTGGTAGCGGTGGTTTTTTTGTTTGCAAGCAGCAGATTACGCGCAGAAAAAAAGGATCTCAAGAAGATCCTTTG
3900 ATCTTTTCTACGGGGTCTGACGCTCAGTGGAACGAAAACTCACGTTAAGGGATTTTGGTCATGAGATTATCAAAAAGGATCTTCACCTAGATCCTTTTAA
4000 ATTAAAAATGAAGTTTTAAATCAATCTAAAGTATATATGAGTAAACTTGGTCTGACAGTTACCAATGCTTAATCAGTGAGGCACCTATCTCAGCGATCTG
AMPCILLIN RESISTANCE
4100 TCTATTTCGTTCATCCATAGTTGCCTGACTCCCCGTCGTGTAGATAACTACGATACGGGAGGGCTTACCATCTGGCCCCAGTGCTGCAATGATACCGGGA
AMPCILLIN RESISTANCE

FIG. 20(B) CONT.

4200
GACCCACGCTCACCGGCTCCAGATTTATCAGCAATAAACCAGCCAGCCGGAAGGGCCGAGCCGCAGAAGTGTCCTGCAACTTATCCGCCTCCATCCAGT
AMPCILLIN RESISTANCE

4300
CTATTAATTGTTGCGGGAAGCTAGAGTAAGTAGTTCGCCAGTTAATAGTTGCGCAACGTTGTTGCCATTGCTACAGGCATCGTGGTGTCACGCTCGTC
AMPCILLIN RESISTANCE

4400
GTTTGGTATGGCTTCATTCAGCTCCGGTTCCCAACGATCAAGGCGAGTACATGATCCCCATGTTGTGCAAAAAAGCGGTTAGCTCCTTCGGTCCTCCG
AMPCILLIN RESISTANCE

4500
ATCGTTGTCAGAAGTAAGTTGGCCGCAGTGTTATCACTCATGGTTATGGCAGCACTGCATAATTCTCTTACTGTCATGCCATCCGTAAGATGCTTTCTG
AMPCILLIN RESISTANCE

4600
TGACTGGTGAGTACTCAACCAAGTCATTCTGAGAATAGTGTATGCGGGCGACCGAGTTGCTCTTGCCCGGCGTCAATACGGGATAATACCGCGCCACATAG
AMPCILLIN RESISTANCE

4700
CAGAACTTTAAAAGTGCTCATCATTGGAAAACGTTCTTCGGGGCGAAAACTCTCAAGGATCTTACCGCTGTTGAGATCCAGTTCGATGTAACCCACTCGT
AMPCILLIN RESISTANCE

4800
GCACCCAACTGATCTTCAGCATCTTTTACTTTCACCAGCGTTTCTGGGTGAGCAAAAACAGGAAGGCAAAATGCCGCAAAAAAGGGAATAAGGGCGACAC
AMPCILLIN RESISTANCE

4900
GGAAATGTTGAATACTCATACTCTTCCTTTTTCAATATATTATTGAAGCATTTATCAGGGTTATTGTCTCATGAGCGGATACATATTTGAATGTATTTAGAA
AMPCILLIN RESISTANCE

AAATAAACAAATAGGGGTTCCGCGCACATTTCCCCGAAAAGTGC---(SEQ ID NO:56)--

*FIG. 20(B) CONT.*

```
pBSII-Act5c-orf
Sequence Range: 1 to 7411

100
CTAAATTGTAAGCGTTAATATTTTGTTAAATTCGCGTTAAATTTTTGTTAAATCAGCTCATTTTTAACCAATAGGCCGAAATCGGCAAAATCCCTTAT
     200
AAATCAAAAGAGATAGACCGAGATAGGGTTGAGTGTTGTTCCAGTTTGGAACAAGAGTCCACTATTAAAGAACGTGGACTCCAACGTCAAAGGGCGAAAAA
     300
CCGTCTATCAGGGCGATGGCCCACTACGTGAACCATCACCCTAATCAAGTTTTTGGGGTCGAGGTGCCGTAAAGCACTAAATCGGAACCCTAAAGGAG
     400
CCCCGATTTAGAGCTTGACGGGGAAAGCCGGCGAACGTGGCGAGAAAGGAAGAAAAGCGAAAGGAGCGGGCGCTAGGGCGCTGGCAAGTGTAGCG
     500
GTCACGCTGCGCGTAACCACCACACCCGCCGCTTAATGCGCCGCTACAGGGCGCGTCCCATTCGCCATTCAGGCTGCGCAACTGTTGGGAAGGGCGAT
     600
CGGTGCGCGGGCCTCTTCGCTATTACGCCAGCTGGCGAAAGGGGGATGTGCTGCAAGGCGATTAAGTTGGGTAACGCCAGGGTTTTCCCAGTCACGACGTTG
     700
CGGTGCGCGGGCCTCTTCGCTATTACGCCAGCTGGCGAAAGGGGGATGTGCTGCAAGGCGATTAAGTTGGGTAACGCCAGGGTTTTCCCAGTCACGACGTTG
     800
GAATTCTAAAAAAAATCATGAATGCATCAACTCTGAATCAAATCTTTGCAGATGCACCTACTTCTCATTTCCACTGTCACATCATTTTTCCAGATCTCG
     900
CTGCCTGTTATGTGGCCCACAAACCAAGACACGTTTTATGGCCATTAAAGCTGGCTGATCGTGCGCCAAACACCAAATACATATCAATATGTACATTCGAG
                                ————————————————————
                                  ACTIN 5C PROMOTER
    1000
AAAGAAGCGATCAAAGAGAAGGCGTCTTCGGGCGAGTAGGAGAATGCGGAGGAAGGAGAACGAGCTGATCTAGTATCTCTCCACAATCCAATGCCAACTGA
                                ————————————————————
                                  ACTIN 5C PROMOTER
```

*FIG. 21(B)*

```
1100
CCAACTGGCCATATTCGGAGCAATTTGAAGCCAATTTCCATCGCCTGGCGATCGCTCCATTCTTGGCTATATGTTTTCACCGTTCCCGGGGCCATTTC
         ACTIN 5C PROMOTER

1200
AAAGACTCGTCGGTAAGATAAGATTGTGTCACTCGCTGTCTCCTCTTCATTGTCGAAGAATGCTGAGGAATTCGCGATGACGTCGGCGAGTATTTGAA
         ACTIN 5C PROMOTER

1300
GAATGAGAATAATTTGTATTTATACGAAAATCAGTAGTGGAATTTTCTACAAAAACATGTTATCTATAGATAATTTTGTTGCAAAATATGTTGACTATG
         ACTIN 5C PROMOTER

1400
ACAAAAGATTGTATGTATATACCTTTAATGTATTCTCATTTTCTTATGTATTTATAATGGCAATGATGATACTGATGATATTTAAGATGATGCCAGACCA
         ACTIN 5C PROMOTER

1500
CAGGCTGATTCTGGCTCTTTGCCGAAGCAGTGCATGTGCGGTTGTGTGTTTTGGAATAGTTTCAATTTTCGGACTGTCCGCTTTGATTTCAGTTTC
         ACTIN 5C PROMOTER

1600
TTGGCTTATTCAAAAAGCAAAGTAAAGCCAAAAAAAGCGAGATGGCAATACCAAATGCGGCAAAAACGGTAGTGGAAGGAAAGCGGTGCGGGGCAGCGGAAG
         ACTIN 5C PROMOTER

1700
GAAGGGTGGGGCGGGGGTCTGTGGCTGCGCGACGTCACCGACGTTGGAGCCCACTCCTTTGACCATGTGTGCCGTGTGTGTATTATTCGTG
         ACTIN 5C PROMOTER

1800
TCTCGGCCACTCGCCGGTTGTTTTTCTTTTTATCTCGCTCTCTAGCGCCATCTCGTACGCATGCTCAACGCACCGCATGTTGCCGTGTCCTTTATGC
         ACTIN 5C PROMOTER

1900
GTCATTTTGGCTCGAAATAGGCAATTATTTAAACAAAGATTAGTCAACGAAAACGCTAAAATAAGTCTACAATATGGTTACTTATTGCCATGTGTG
         ACTIN 5C PROMOTER
```

*FIG. 21(B) CONT.*

```
2000
TGCAGCCAACGATAGCAACAAAAGCAACAACACAGTGGCTTTCCCTCTTTCACTTTTTGTTTGCAAGCGCGTGCGAGCAAGACGGCACGACCGGCAAACG
     ACTIN 5C PROMOTER

2100
CAATTACGCTGACAAAGAGCAGAGCGAAGTTTTGGCCGAAAAACATCAAGGCGCCTGATACGAATGCATTTGCAATAACAATTGCGATATTTAATATTGTT
     ACTIN 5C PROMOTER

2200
TATGAAGCTGTTTGACTTCAAAACACACAAAAAAAAATAAACAAATTATTTGAAAGAGAATTAGGAATCGGACAGCTTATCGTTACGGGCTAACAGC
     ACTIN 5C PROMOTER

2300
ACACCGAGACGAAATAGCTTACCTGACGTCACAGCCTCTGAAGAACTGCCGCCAAGCAGACGATGCAGAGGACGACACATAGAGTAGCGGAGTAGGCCA
     ACTIN 5C PROMOTER

2400
GCGTAGTACGCATGTGCTTGTGTGTGAGGCGTCTCTCTCTTCGTCTCTGTTGCGCAAACGCATAGACTGCACTGAGAAATCGATTACCTATTTTTA
     ACTIN 5C PROMOTER

2500
TGAATGAATATTTGCACTATTACTATTCAAAACTATTAAGATAGCAATCACATTCAATAGCCAAATACTATACCACCTGAGCGATGCAACGAAATGATCA
     ACTIN 5C PROMOTER

2600
ATTTGAGCAAAAATGCTGCATATTAGGACGGCATCATTATAGAAATGCTTCTGCTGTGTACTTTTCTCTCGCTCTGGACAGCTGTTTCGCCGTTATTGTT
     ACTIN 5C PROMOTER

2700
AAAACCGGCTTAAGTGTTAGGTGTGTTTTCTACGACTAGTGATGCCCCTACTAGAAGATGTGTTGCACAAATGTCCCTGAATAACCAATTGAAGTGCAG
     ACTIN 5C PROMOTER

2800
ATAGCAGTAAAACGTAAGCTAATATGAATGTTTAATATCGCTGGACATTACTAATAAACCCACTATAAACACATGTACATATGT
     ACTIN 5C PROMOTER
```

FIG. 21(B) CONT.

```
2900
ATGTTTTGGCATACAATGAGTAGTTGGGAAAAAATGTGTAAAGCACCGTGACCATCACAGCATAAAGATAACCAGCTGAAGTATCGAATATGAGTAAC
                                                 ACTIN 5C PROMOTER                                     >
3000
CCCCAAATTGAATCACATGCCGCAACTGATAGGAGACCCATGGAAGTACACTCTTCATGGCGATATACAAGACACACACAAGCACGAACACCCAGTTGCCGGA
                                                 ACTIN 5C PROMOTER                                      >
                           >CCATATATGG element
                                       ⎯
3100
GGAAATTCTCCGTAAATGAAAACCCAATCGGCGAACAATTCATACCCATATATGGTAAAAGTTTTGAACGCGACTTGAGAGCCGGAGAGCATTGCGGCTGA
                                                 ACTIN 5C PROMOTER                                      >
          >TATA-box
                ⎯
3200
TAAGGTTTTAGCGCTAAGCGGGCTTTATAAACGGGCTGCGGGACCAGTTTTCATATCGGATCCTATATAATAAAATGGGTAGTTCTTTAGACGATGAGC
             ACTIN 5C PROMOTER                >           IFP2 ORF BAMHI CARTRIDGE                      >
3300
ATATCCCTCTCTGCTCTTCTGCAAAGCGATGACGAGCTTGTTGGTGAGGATTCTGACAGTGAAATATCAGATCACGTAAGTGAAGATGACGTCCAGAGCGA
                                   IFP2 ORF BAMHI CARTRIDGE
3400
TACAGAGAAGCGTTTATAGATGAGTACATGAAGTGCAGCCAAGCGGTAGTGAAATATTAGACGAACAAAATGTTATTGAACAACCAGGTTCT
                                   IFP2 ORF BAMHI CARTRIDGE
3500
TCATTGGCTTCTAACAGAGAATCTTGACCTTGCCACAGAGGACTATTAGAGGTAAGAATAAACATTGTTGGTCAACTTCAAAGTCCACGAGGCGTAGCCGAG
                                   IFP2 ORF BAMHI CARTRIDGE
```

FIG. 21(B) CONT.

```
3600
TCTCTGCACTGAACATTGTCAGATCTCAAAGAGGTCCGACGCGTATGTGCCGCAATATATGACCCACTTTTATGCTTCAAACTATTTTTACTGATGA
         IFP2 ORF BAMHI CARTRIDGE

3700
GATAATTTCGGAAATTGTAAAATGGACAAATGCTGAGATATCATTGAAACGTCGGGAATCTATGACAGTGCTACATTTCGTGACACGAATGAAGATGAA
         IFP2 ORF BAMHI CARTRIDGE

3800
ATCTATGCTTTCTTTGGTATTCTGGTAATGACAGCAGTGAGAAAAGATAACCACATGTCCACAGATGACCTCTTTGATCGATCTTTGTCAATGGTGTACG
         IFP2 ORF BAMHI CARTRIDGE

3900
TCTCTGTAATGAGTCGTGATCGTTTGATTTTTTGATACGATGTCTTAGAATGGATGACAAAAGTATACGGCCCCACACTTCGAGAAAACGATGTATTTAC
         IFP2 ORF BAMHI CARTRIDGE

4000
TCCTGTTAGAAAAATATGGATCTCTTTATCCATCAGTGCATACAAAATTACACTCCAGGGCTCATTTGACCATAGATGAACAGTTACTTGGTTTTTAGA
         IFP2 ORF BAMHI CARTRIDGE

4100
GGACGGTGTCCGTTAGGATGTATATCCAAACAAGCCAAGTAAGTATGGAATAAAAATCCTCATGATGTGTGACAGTGGTACGAAGTATATGATAAATG
         IFP2 ORF BAMHI CARTRIDGE

4200
GAATGCCTTATTTGGAAGAGGAACACAGACCAACGGAGTACCACTCGGTGAATACTACGTGAAGGAGTTATCAAAGCCTGTGCACGGTAGTTGTCGTAA
         IFP2 ORF BAMHI CARTRIDGE

4300
TATTACGTGTGACAATTGGTTCACCTCAATCCCTTTGGCAAAAAACTTACTACAAGAACCGTATAAGTTAACCATTGTGGGAACCGTGCGATCAAACAAA
         IFP2 ORF BAMHI CARTRIDGE

4400
CGCGAGAGATACCGGAAGTACTGAAAACAGTCGCTCCAGGCCAGTGGAACATCGATGTTTGTTTGACGACCCCTTACTCTCGTCTCATATAAACCGA
         IFP2 ORF BAMHI CARTRIDGE
```

*FIG. 21(B) CONT.*

```
4500
AGCCAGCTAAGATGGTATACTTATTATCATCTTGTGATGAGGATGCTTCTATCAACGAAAGTACCGGTAAACCGCAAATGGTTATGTATTATAATCAAAC
              IFP2 ORF BAMHI CARTRIDGE                                                              ^
4600
TAAAGGGCGGAGTGGACACGCTAGACCAAATGTGTTCTGTGATGACCTGCAGTAGGAAGACGAATAGGTTGGCCTATGGCATTATTGTACGGAATGATAAAC
              IFP2 ORF BAMHI CARTRIDGE                                                              ^
4700
ATTGCCTGCATAAATTCTTTATTATATACAGCCATAATGTCAGTAGCAAGGGAGAAAAAGGTTCAAAGTCGCAAAAAATTTATGAGAAACCTTTACATGA
              IFP2 ORF BAMHI CARTRIDGE                                                              ^
4800
GCCTGACGTCATCGTTATGCGTAAGCGTTTAGAGAAGCTCCCTACTTTGAAGAGATATTTGCGCGATAATATCTCTAATATTTGCCAAATGAAGTGCCTGG
              IFP2 ORF BAMHI CARTRIDGE                                                              ^
4900
TACATCAGATGACAGTACTGAAGAGCCAGTAATGAAAAAACGTACTACTGCCCCTCTAAAATAAGGCGAAAGGCAAATGCATCGTGTGCAAA
              IFP2 ORF BAMHI CARTRIDGE                                                              ^
5000
AATGCAAAAAAGTTATTTGTCGAGAGCATAATATTGATATGTGCCAAAGTTGTTTCTGACTGACTAATAAGTATAATTGTTCTATTATGTATAAGTT
              IFP2 ORF BAMHI CARTRIDGE                                                              ^
5100
AAGCTAATTACTTATTTTATAATACAACATGACTGTTTAAAGTACAAAATAAGTTATTTTGTAAAAGAGAGAATGTTTAAAAGTTTTGTTACTTTA
              IFP2 ORF BAMHI CARTRIDGE                                                              ^
5200
GAAGAAATTTGAGTTTGTTTTGTTTTTTTAATAAATAAAACATAAATAAATTGTTGTTGAATTTGGATCCACTAGTTCTAGAGCGGCCGCCACCGC
              IFP2 ORF BAMHI CARTRIDGE                       ^
5300
GGTGGAGCTCCAGCTTTTGTTCCCTTTAGTGAGGGTTAATTGCGCGCTTGGCGTAATCATGGTCATAGCTGTTTCCTGTGTGAAATTGTTATCCGCTCAC
```

FIG. 21(B) CONT.

```
5400
AATTCCACACAACATACGAGCCGGAAGCATAAAGTGTAAAGCCTGGGGTGCCTAATGAGTGAGCTAACTCACATTAATTGCGTTGCGCTCACTGCCCGCT
5500
TTCCAGTCGGGAAACCTGTCGTGCCAGCTGCATTAATGAATCGGCCAACGCGCGGGGAGAGGCGGTTTGCGTATTGGGCGCTCTTCCGCTTCCTCGCTCA
5600
CTGACTCGCTGCGCTCGGTCGTTCGGCTGCGGCGAGCGGTATCAGCTCACTCAAAGGCGGTAATACGGTTATCCACAGAATCAGGGGATAACGCAGGAAA
5700
GAACATGTGAGCAAAAGGCCAGCAAAAGGCCAGGAACCGTAAAAAGGCCGCGTTGCTGGCGTTTTTCCATAGGCTCCGCCCCCCTGACGAGCATCACAAA
5800
AATCGACGCTCAAGTCAGAGGTGGCGAAACCCGACAGGACTATAAAGATACCAGGCGTTTCCCCCTGGAAGCTCCCTCGTGCGCTCTCCTGTTCCGACCC
5900
TGCCGCTTACCGGATACCTGTCCGCCTTTCTCCCTTCGGGAAGCGTGGCGCTTTCTCATAGCTCACGCTGTAGGTATCTCAGTTCGGTGTAGGTCGTTCG
6000
CTCCAAGCTGGGCTGTGTGCACGAACCCCCCGTTCAGCCCGACCGCTGCGCCTTATCCGGTAACTATCGTCTTGAGTCCAACCCGGTAAGACACGACTTA
6100
TCGCCACTGGCAGCAGCCACTGGTAACAGGATTAGCAGAGCGAGGTATGTAGGCGGTGCTACAGAGTTCTTGAAGTGGTGGCCTAACTACGGCTACACTA
6200
GAAGGACAGTATTTGGTATCTGCGCTCTGCTGAAGCCAGTTACCTTCGGAAAAAGAGTTGGTAGCTCTTGATCCGGCAAACAAACCACCGCTGGTAGCGG
6300
TGGTTTTTTTGTTTGCAAGCAGCAGATTACGCGCAGAAAAAAAGGATCTCAAGAAGATCCTTTGATCTTTTCTACGGGGTCTGACGCTCAGTGGAACGAA
6400
AACTCACGTTAAGGGATTTTGGTCATGAGATTATCAAAAAGGATCTTCACCTAGATCCTTTTAAATTAAAAATGAAGTTTTAAATCAATCTAAAGTATAT
6500
ATGAGTAAACTTGGTCTGACAGTTACCAATGCTTAATCAGTGAGGCACCTATCTCAGCGATCTGTCTATTTCGTTCATCCATAGTTGCCTGACTCCCCGT
```

*FIG. 21(B) CONT.*

6600 CGTGTAGATAACTACGATACGGAGGGCTTACCATCTGGCCCCAGTGCTGCAATGATACCGGAGACCCACGCTCACCGGCTCCAGATTTATCAGCAATA
6700 AACCAGCCCAGCCGAAGGGCCGAGCGCAGAAGTGGTCCTGCAACTTTATCCGCCTCCATCCAGTCTATTAATTGTTGCCGGGAAGCTAGAGTAAGTAGTT
6800 CGCCAGTTAATAGTTTGCGCAACGTTGTTGTGCCATTGCTACAGGCATCGTGGTGTCACGCTCGTCGTTGGTATGGCTTCATTCAGCTCCGGTTCCCAACG
6900 ATCAAGGCGAGTTACATGATCCCCCATGTGTGTGCAAAAAAGCGGTTAGCTCCCTTCGGTCCCTCCGATCGTTGTCAGAAGTAAGTTGGCCGCAGTGTTATCA
7000 CTCATGGTTATGGCAGCACTGCATAATTCTCTTACTGTCATGCCATTCCGTAAGATGCTTTTCTGTGACTGGTGAGTACTCAACCAAGTCATTCTGAGAAT
7100 AGTGTATGCGGCGACCGAGTTGCTCTTGCCCGGCGTCAATAACCGCGCCACATAGCAGAACTTAAAAGTGCTCATCATTGGAAAACGTTC
7200 TTCGGGGCGAAAACTCTCAAGGATCTTACCGCTGTTGAGATCCAGTTCGACTGTAACCCACTCGTGCACCCAACTGATCTTCAGCATCTTTTACTTTCACC
7300 AGCGTTTCTCGGGTGAGCAAAAACAGGAAGGCAAATGCCGCAAAAAAGGGAATAAGGGCGACACGGAAATGTTGAATACTCATACTCTTCCTTTTTCAAT
7400 ATTATTGAAGCATTTATCAGGGTTATTGTCTCATGAGCGGATACATATTTGAATGTATTTAGAAAAATAAACAAATAGGGGTTCCGCGCACATTTCCCG

AAAAGTGCCAC --(SEQ ID NO:67)--

*FIG. 21(B) CONT.*

Sequence Range: 1 to 10333

100
AAGCTTGGGCTGCAGTCGACGATCCAAATTCAACAAACAATTTATTTATTGTTTATTTATTATTAAAAAAAAACAAAACTCAAAATTTCTTCTAAAG

200
TAACAAAACTTTAAACATTCTCTCTTTACAAAAATAAACTTATTTGTACTTTAAAAACAGTCATGTTGTATTATAAATAAGTAATTAGCTTAACTT

300
ATACATAATAAAAGAAACAAATTATACTTAGTCAGTCAGAAACAACTTGGCACATATCAATATTATGCTCTCGACAAATAACTTTTTGCATTTTTGC
         PIGGYBAC ORF

400
ACGATGCATTTGCCCTTTCGCCCTTATTTAGAGGGGCAGTAAGTACAGTAAGTACGTTTTTCATTACTGGCTCTTCAGTACTGTCATCGATGTACCAGG
         PIGGYBAC ORF

500
CACTTCATTTGGCAAAATATTAGAGATATTATCGCGCAAATATCTCTTCAAAGTAGGAGCTTCTAAACGCTTACGCATAAACGATGAGCTCAGGCTCATG
         PIGGYBAC ORF

600
TAAAGGTTTCTCATAAATTTTTTGCGACTTTTGAACCTTTTTCTCCCTTGCTACTGACATTATGGCTGTATATAATAAAAGAATTTATGCAGGCAATGTTTA
         PIGGYBAC ORF

700
TCATTCCGTACAATAATGCCATAGGCCACCTATTCGTCTTCCTACTGCAGGTCATCGAGAAGCATCCTCATCACAGAACACATTTGGTCTAGCGTGTCCACTCCGCCTTTAGTTTG
         PIGGYBAC ORF

800
ATTATAATACATAACCATTGCGGTTACCGGTACTTTCGTTGATAGAAGCATCCTCATCACAAGATGATAATAAGTATACCATCTTAGCTGGCTTCGGT
         PIGGYBAC ORF

900
TTATATGAGACGAGAGTAAGGGGTCCGTCAAAACAAAACATCGATGTTCCCACTGGCCTGGAGGCGACTGTTTTTCAGTACTTCCGGTATCTCGCGTTTGT
         PIGGYBAC ORF

FIG. 22

```
1000
TTGATCGCACGGTTCCCACAATGGTTAACTTATACGGTTCTTGTAGTAAGTTTTTGCCAAAGGGATTGAGGTGAACCAATTGTCACACGTAATATATTACG
     v                                   PIGGYBAC ORF
1100
ACAACTACCGTGCACAGGCTTTGATAACTCCTTCACGTAGTATTCACCGAGTGGTACTCCGTTGGCTCTGTGTTCCTCTGTTCCCAAATAAGGCATTCCATTT
     v                                   PIGGYBAC ORF
1200
ATCATATATACTTCGTACCACTGTCACACATCATGAGGATTTTTATTCCATACTTACTTGGCTTGTTGTTTGGGATATACATCCTAAACGGACACCGTCCTCTAA
     v                                   PIGGYBAC ORF
1300
AACCAAGTAACTGTTCATCTATGGTCAAATGAGCCCCTGGAGTGTAATTTTGTATGCACTGATGGATAAAGAGATCCCATATTTTTCTAACAGGAGTAAA
     v                                   PIGGYBAC ORF
1400
TACATCGTTTTCTCGAAGTGTGGGCCCGTATACTTTTGTCATCCATTCTTAAGACACATGCTATCAAAAAATCAAAACGATCACGACTCATTACAGAGACGTAC
     v                                   PIGGYBAC ORF
1500
ACCATTGACAAAGATCGATCAAAGAGGTCATCTGTGGACATGTGGTTATCTTTTCTCACTGCTGTCATTACCAGAATACCAAAGAAAGCATAGATTTCAT
     v                                   PIGGYBAC ORF
1600
CTTCATTCGTGTCACGAAATGTAGCACCTGTCATAGATTCCCGACGTTTCAATGATATCTCAGCATTGTCCATTTTACAATTCCGAAATTATCTCATC
     v                                   PIGGYBAC ORF
1700
AGTAAAAAATAGTTTGAAGCATAAAGTGGGTCATATATATATTGCGGCACATACGCGTCGGACCTCTTTGAGATCTGACAATGTTCAGTGCAGAGACTCGG
     v                                   PIGGYBAC ORF
1800
CTACGCCCTCGTGGACTTTGAAGTTGACCAACAATGTTTATTCTTACCTTCTAATAGTCCTCTGTGGCAAGGTCAAGATTCTGTTAGAAGCCAATGAAGAAC
     v                                   PIGGYBAC ORF
```

*FIG. 22 CONT.*

```
1900
CTGGTTGTTCAATAACATTTGTTCGTCTAATATTTCACTACCGCTTGACGTTGGCTGCACTTCATGTACCTCATCTATAAACGCTTCTCTGTATCGCT
         PIGGYBAC ORF
2000
CTGGACGTCATCTTCACTTACGTGATCTGATATTTCACTGTCAGAATCCTCACCAACAAGCTCGTCATCGCTTTGCAGAAGAGCAGAGAGGATATGCTCA
         PIGGYBAC ORF
2100
TCGTCTAAAGAACTACCCATTTTATTATATAGGATCCCCGACACCAGACCAACTGGTAATGTAGCGACCGGCGCTCAGCTGAATTAGGCCTTCTAGAC
       PIGGYBAC ORF
2200
CGCGGCCGCAGATCTGTTAACGAATCCCAATTCCCTATTCAGAGTTCTCTTGTATTCAATAATTACTTCTTGGCAGATTCAGTAGTTGCAGTTGA
                          HSP 70 PROMOTER
2300
TTTACTTGGTTGCTGGTTACTTTTAATTGATTCACTTAACTTGCACTTTACTGCAGATTGTTTAGCTTGTGTTCAGCTGCGCTTGTTTATTTGCTTAGCTT
                          HSP 70 PROMOTER
2400
TCGCTTAGCGACGTGTTCACTTGCTTCGTTTGAATTGAATTGCTCCGTAGACGAAGCGCTCTATTTATACTCCGGCGCTCTTTTCGCGAACATTCGA
                          HSP 70 PROMOTER
2500
GGCGCGCTCTCTCGAACGAGAGCAGTATGCGCGTTACTGTGACAGAGTGAGAGAGCATTAGTGCAGAGAGGGAGACCCAAAAGAAAAGAGAGA
                          HSP 70 PROMOTER
2600
ATAACGAATAACGGCCAGAGAAATTTCCGAGTTTCTTGTTTTGGGATTCTAGGGGGATCGGGG
                          HSP 70 PROMOTER
2700
ATCAATTCTAGTATGTATGTAAGTTAATAAAAACCCTTTTTTGGAGAATGTAGATTAAAAAAACATATTTTTTTATTTTTTACTGCACTGGATATCA
```

*FIG. 22 CONT.*

2800
TTGAACTTATCTGATCAGTTTTAAATTTACTTCGATTACCTCTCACTCAAAATGACATTCCACTCAA

2900
AGTCAGCGCTGTTGCCTCCTTCTCTGTCCACAGAAATATCGCCGTCTCTTTCGCCGCTCCGTTGTAGCGTTACCTA

3000
GCGTCAAATGCCGCCTTCAGTTGCCACTTTGTCAGCGGTTTCGCAGCGGTTTACGCCATCAATTAAACACAAAGTGCTGTGCCAAAACT

3100
CCCTCGCTTCTTATTTTGTTTGTTTTTGAGTGATTGGGGTGGTGTTTGGGTGGGTAAGCAGGGGAAAGTGTGAAAAATCCCGCAATGGGC

3200
CAAGAGGATCAGGAGCTATTAATTCGCGAGGCAGCAAACACCCATCTGCCGAGCATCTGAACAATGTGAGTAGTACATGTGCATACATCTTAAGTTCAC

3300
TTGATCTATAGGAACTGCGATTGCAACATCAAATTGTCTGCGCTCGCTATATAAGACAATTTTTAAGCTGATCCTAGATGCACAAAAATAATAAACCTACTTCGTAGGATACTTCGTTTT

3400
ACGAAACAGATTATTCTGGTAGCTGTGCTCGCTATATAAGACAATTTTTAAGCTGATCCTAGATGCACAAAAATAATAAACCTACTTCGTAGGATACTTCGTTTT

3500
CTTTTTTACAAAAATATAACAACCAGATATTTAAGCTGATCCTAGATGCACAAAAATAATAAACCTACTTCGTAGGATACTTCGTTTT

3600
GTTCGGGGTTAGATGAGCATAACGCTTGTAGTTGATATTTGAGATCCCCTATCATTGCAGGGTGACAGCGGCTTCGCAGAGCTGCATTAACCAGG

3700
GCTTCGGGCAGGCCAAAAACTACGCACGCTCCTGCACCCAGTCGCCGGAGGACTCCGGTTCAGGAGCGCCAACTAGCCGGACTATTCTGCAACGAGCGACAC

3800
CTGGCACAATATGGACATCTTTGGGGCGGTCAATCAGCGGGCTCCGGATGGGCAGCTGGTCAACGGCGGACTGTTCTGCAACGAGGAGGACAC

3900
ATACCGGGCGCCCAGGAAACATTGCTCAAGAAGCGGTGAGTTTCTATTCGCAGTCGGCTGATCTGTGTGAAATCTTAATAAAGGGTCCAATTACCAATTTG

*FIG. 22 CONT.*

```
4000
AAACTCAGTTTGCGGGCGTGGCCTATCCGGGCGAACTTTTGGCCGTGATGGGCCAGTTCCGGTGCCGGAAAGACGACCCTGCTGAATGCCCTGCCTTTCGA
4100
TCGCCGCAGGGCATCCAAGTATCGCCATCCGGGATGCGACTGCTCAATGGCCAACCTGTGGACGCCAAGGAGATGCAGGCCAAGGTGCCGCTATGTCCAGC
4200
AGGATGACCTCTTTATCGGCTCCCTAACGGCCAGGGAACACCTGATTTTCCAGGCCATGTGCCACGACATCTGACCTATCGGCAGCGAGTGGC
4300
CCGCGTGATCAGGTGATCCAGGAGCTTTCGCTCAGCAAATGTCAGCACACGATCATCGGTGTGCCCGGCAGGGTGAAAGGTCTGTCCGGCGGAGAAAGG
4400
AAGCCGTCTGGCATTCGCCTCCGAGGCACTAACCGATCCGCCCTTCTGATCTGCGATGAGCCCACCTCCGGACTGACTCATTTACCGCCACAGCGTCG
4500
TCCAGGTGCTGAAGAAGCTGTCCGCAGGGTAGCTTTCTTGGGCACTCCCAGGTGCCCCAGTGTCCTACCAACTACAATCCGGCGGACTTTTACGTACAGGTGATGTGTTATTAAGGGTATCTAGCATTA
4600
GATGGGCCGAGGGCAGGGTAGCTTTCTTGGGCACTCCCAGGTGCCCCAGTGTCCTACCAACTACAATCCGGCGGACTTTTACGTACAGGTGTTGCCCGGTTGTGCCCGGACGG
4700
CATTACATCTCAACTCCTATCCAGCGGGATCGGATCGCCAAGATATGCGACAATTTGCTATTAGCAAAGTAGCCCGGATATGGAGCAGTTGTTGGCCACCAAAAATTTGG
4800
GAGAATCGAGTCCCGTGATCGGATCGCCAAGATATGCGACAATTTGCTATTAGCAAAGTAGCCCGGATATGGAGCAGTTGTTGGCCACCAAAAATTTGG
4900
AGAAGCCACTGGAGCAGCCGGAGAATGGGTACACCTACAAGGCCACTGGTTCATGCAGTTCCGGGCGTCCTGTGGCGATCCTGGCTGTCGGTGCTCAA
5000
GGAACCACTCCTCGTAAAAGTGCGACTTATTCAGACAACGGTGAGTGGTTCCAGTGGAAACAAATGATATAACGCTTACAATTCTTGGAAACAAATTCGC
5100
TAGATTTTAGTTAGAATTGCCTGATTCCACACCCTTCTTAGTTTTTTCAATGAGATGTATAGTTTATAGTTTTGCAGAAAATAAATAAATTTCATTTAA
```

FIG. 22 CONT.

```
5200 CTCGGCGAACATGTTGAAGATATGAATATTAATGAGATGCGAGTAACATTTAATTTGCAGATGGTTGCCATCTTGATTGGCCTCATCTTTTTGGGCCAAC
5300 AACTCACGCAAGTGGGCGTGATGAATATCAACGAGCCATCTTCCCTCTTCCTGACCAACATGACCTTTCAAAACGTCTTTGCCACGATAAATGTAAGTCT
5400 TGTTTAGAATACATTTGCATATTAATAATTTACTAACTTTCTAATGAATCGATTCGATTTAGGTGTGTTCACCTCAGAGCTGCCAGTTTTTATGAGGGAGGC
5500 CCGAAGTCGACTTTATCGCTGTGACACATACTTTCTGGGCAAAACGATTGCCGAATTACCGCTTTTTCTCACAGTGCCACGCTGGTCTTCACGGGCGATTGCC
5600 TATCCGATGATCGGACTGCCGGGCCGGAGTGCTGCACTTCTTCAACTGCCTGGTCACTCTGGTGGCCAATGTGTCAACGTCCTTCGGATATCTAA
5700 TATCCTGGCCCAGCTCCCTCGACCTCGATGGCGCTCCGCTGTCTGTGGGTCCGCCGGTTATCATACCATTCCTGCTCTTTGGCGGCTTCTTCTTGAACTCGGGCTC
5800 GGTGCCAGTATACCTCAAATGGTTGTCGTACCTTCATGGTTCCGTACGCCAACGAGGGTCTGCTGATTAACCAATGGGCGACGTGGAGCCGGGCGAA
5900 ATTAGCTGCACACTGCGAACATCGTCGAGCTTCCGGTGCTCGGGGCAAGGTCATCCTGGAGACGCTTAACTTCTCCGAGCCCCGACGCAAGGAGTAGCCGACTATATCCGAAATAACTG
6000 GTCTGGCCATTCCTCATCGTGAGCTTCCGGTGCTCGCATATCTGGCTCTCTGTGTTATTGCCCCCCTCAAAAGCTAATGTAATTATATTTGTGCAATAAAAACAAGATATGA
6100 CTTGTTTTTTTTTTTTACCATTATTACCATGCGTGTTTACTGTTATTGCCCCACAAGTAGACTTTGGATTTGTCTTCTAACCAAAAGACTTACACACCTGCATACCTTACATCAA
6200 CCTATAGAATACAAGTATTCCCCTTCGAACATCCCCACAAGTAGACTTTGGATTTGTCTTCTAACCAAAAGACTTACACACCTGCATACCTTACATCAA
6300 AAACTCGTTTATGCTACATAAAACACCGGGATATATTTTTATATACATACTTTCAAATCGCGCCCCTCTTCATAATTCACCTCCACCACACCACGT
```

FIG. 22 CONT.

6400 TTCGTAGTTGCTCTCTTCGCTGTCTCCCACCCGCTCTCCGCAACACATTCACCTTTGTTCGACGACCTTGGAGCGACTGTCGTTAGTTCCGCGGATTCG
6500 GTTCGCTCAAATGGTTCCGAGTGGTTCATTTCGTCTCAATAGAAATTAGTAATAAATATTGTATGTACAATTTATTGCTCCAATATATTTGTATATAT
6600 TCCCCTCACAGCTATATTTATTCTAATTTAATATATTTAAGGTAATTTTTGTGACCTGTTCGGAGTGATTAGCGTTACAATTTGAACTGAAA
6700 GTGACATCCAGTGTGTTGTTCCTTGTGTAGATGCATCTCAAAAAAAATGGTGGGCATAATAGTGTTGTTATATATATCAAAAATAACAACTATAATAATAA
6800 GAATACAATTAATTAGAAAAATGCTTGGATTTCACTGGAACTAGAATTAATTCGGCTCTAAACGACGCATTCGTACTCCCAAAGTACGAATTT
6900 TTCCCTCAAGCTCTTATTTCATTAAACAATGAACAGGACCTAACGCACAGTCACGTTATTGTTTACATAAATGATTTTTTTACTATTCAAACTTACTC
7000 TGTTTGTGTACTCCCACTGGTATAGCCTTCTTTATCTTTTCTGGTTCAGGCTCTATCACTTTACTAGTACGGCATCTCGCGTTGAGTCGCCTCCTTTTA
7100 AATGTCTGACCTTTTGCAGGTGCAGCCTTCCACTGCGAATCTTTAAAGTGGGTATACACAAATTTGGGAGTTTTCACCAAGGCTGCACCCAAGGCTCTGCT
7200 CCCACAATTTCTCTTAATAGCACACTTCGGCACGTGAATTAATTTTACTCCAGTCACAGCTTTGCAGCAAAATTTGCAATATTTCATTTTTTTTTATTC
7300 CACGTAAGGGTTAATGTTTTCAAAAAAAAAATTCGTCCGCACACAAACCTTTCCTCTCAACAAGCAAACGTGCACTGAATTAAGTGTATACTTCGGTAAGC
7400 TTCGGCTATCGACGGGACCACCTTATGTTATTTCATCATGGGCCAGAGACCCACGTAGTCCAGCGGCAGATCGGCGGCGGAGAAGTTAAGCGTCTCCAGGAT
7500 GACCTTGCCCGAACTGGGGCACGTGGTGTTCGACGATGTGCAGCTAATTCGCCCGGCTCCACGTCCGCCCATTGGTTAATCAGCAGAGACCCTCGTTGGCG

*FIG. 22 CONT.*

7600
TAACGGAACCATGAGAGTACGACAACCATTTGAGTATACTGCACCGAGCCCGAGTTCAAGAGAAGAGGCGTTTTCCATAGGCTCCGCCCCCTGACG

7700
AGCATCACAAAAATCGACGCTCAAGTCAGAGGTGGCGAAACCCGACAGGACTATAAAGATACCAGGCGTTTCCCCCTGGAAGCTCCCTGCGCTCTCC

7800
TGTTCCGACCCTGCCGCTTACCGGATACCTGTCCGCCTTTCTCCCTTCGGGAAGCGTGGGCGCTTTCTCAATGCTCACGCTGTAGGTATCTCAGTTCGGTG

7900
TAGGTCGTTCGCTCCAAGCTGGGCTGTGTGCACGAACCCCCGTTCAGCCCGACCGTGCGCCTTATCCGGTAACTATCGTCTTGAGTCCAACCCGGTAA

8000
GACACGACTTATCGCCACTGGCAGCAGCCACTGGTAACAGGATTAGCAGAGCGAGGTATGTAGGCGGTGCTACAGAGTTCTTGAAGTGGTGGCCTAACTA

8100
CGGCTACACTAGAAGGACAGTATTTGGTATCTGCGCTCTGCTGAAGCCAGTTACCTTCGGAAAAAGAGTTGGTAGCTCTTGATCCGGCAAACAAACCACC

8200
GCTGGTAGCGGTGGTTTTTTGTTTGCAAGCAGCAGATTACGCGCAGAAAAAAAGGATCTCAAGAAGATCCTTTGATCTTTTCTACGGGGTCTGACGCTC

8300
AGTGGAACGAAAACTCACGTTAAGGGATTTTGGTCATGAGATTATCAAAAAGGATCTTCACCTAGATCCTTTTAAATTAAAAATGAAGTTTTAAATCAAT

8400
CTAAAGTATATATGAGTAAACTTGGTCTGACAGTTACCAATGCTTAATCAGTGAGGCACCTATCTCAGCGATCTGTCTATTTCGTTCATCCATAGTTGCC

8500
TGACTCCCCGTCGTGTAGATAACTACGATACGGGAGGGCTTACCATCTGGCCCCAGTGCTGCAATGATACCGCGAGACCCACGCTCACCGGCTCCAGATT

8600
TATCAGCAATAAACCAGCCAGCCGGAAGGGCCGAGCGCAGAAGTGGTCCTGCAACTTTATCCGCCTCCATCCAGTCTATTAATTGTTGCCGGGAAGCTAG

8700
AGTAAGTAGTTCGCCAGTTAATAGTTTGCGCAACGTTGTTGCCATTGCTACAGGCATCGTGGTGTCACGCTCGTCGTTTGGTATGGCTTCATTCAGCTCC

*FIG. 22 CONT.*

8800 GGTTCCCAACGATCAAGGCGAGTTACATGATCCCCATGTTGTGCAAAAAGCGGTTAGCTCCTTCGGTCCTCCTCCGATCGTTGTCAGAAGTAAGTTGGCCG
8900 CAGTGTTATCACTGTTATGGCAGCACTGCATAATTCTCTTACTGTCATGCCATCCGTAAGATGCTTTTCTGTGACTGGTGAGTACTCAACCAAGTC
9000 ATTCTGAGAATAGTGTATGCGGGCGACCGAGTTGCTCTTGCCCGGCGTCAATACGGGATAATACCGCGCCACATAGCAGAACTTTAAAAGTGCTCATCATT
9100 GGAAAACGTTCTTCGGGGCGAAAACTCTCAAGGATCTTACCGCTGTTGAGATCCAGTTCGATGTAACCCACTCGTGCACCCAACTGATCTTCAGCATCTT
9200 TTACTTTCACCAGCGTTTCTGGGTGAGCAAAAACAGGAAGGCAAAATGCCGCAAAAAAGGGAATAAGGGCGACACGGAAATGTTGAATACTCATACTCTT
9300 CCTTTTTCAATATTATTGAAGCATTTATCAGGGTTATTGTCTCATGAGCGGATACATATTTGAATGTATTAGAAAAATAAACAAATAGGGGTTCCGCGC
9400 ACATTTCCCCGAAAAGTGCCACCTGACGTCTAAGAAACCATTATTATCATGACATTAACCTATAAAAATAGGCGTATCACGAGGCCCTTTCGTCTCGCGC
9500 GTTTCGGTGATGACGGTGAAAACCTCTGACACATGCAGCTCCCGGAGACGGTCACAGCTTGTCTGTAAGCGGATGCCGGGAGCAGACAAGCCCGTCAGG
9600 CGCGTCAGCGGGTGTTGGCGGGTGTCGGGGCTGGCTTAACTATGCGGCATCAGAGCAGATTGTACTGAGAGTGCACCATATGCGGTGTGAAATACCGCAC
9700 CGAATCGGCGCGGAACTAACGACAGTGCGCTCCAAGGTCGTCGAACAAAAGGTGAATGTGTTGCGGAGAGCAGCGAAAGAGCAACTACGAA
9800 ACGTGGTGTGGTGGAGGTGAATTATGAAGAGGGGCGCGGATTTGAAAGTAGTATATAAAAATATGTATATAAAAATATATCCCGGTGTTTATGTAGCGATAAACGAGTTT
9900 TTGATGTAAGGTATGCAGGTGTGTAAGTCTTTTGGTTAGAAGACAAATCCAAAGTCTACTTGTGGGGATGTTCGAAGGGGAAATACTTGTATTCTATAGG

*FIG. 22 CONT.*

10000
TCATATCTTGTTTTATTGGCACAAATATAATTACATTAGCTTTTTGAGGGGCAATAAACAGTAAACACGATGGTAATAATGGTAAAAAAAAACAAG

10100
CAGTTATTTCGGATATATGTCGGCTACTCCCTTGCGTCGGGCCCGAAGTCTTAGAGCCAGATATGCGAGCACCCGAAGCTCACGATGAGAATGGCCAGAC

10200
CATGATGAAATAACATAAGGTGGTCCCGTCGGCAAGAGACATCCACTTAACGTATGCTTGCAATAAGTGCGAGTGAAAGGAATAGTATTCTGAGTGTCGT

10300
ATTGAGTCTGAGTGAGACAGCCGATATGATTGTTGATTAACCCTTAGCATGTCCGTGGGTTTGAATTAACTCATAATATTAATTAGACGAAATTATTTT

AAAGTTTTATTTTAATAATTGCGAGTACGCA -- (SEQ ID NO:68)--

*FIG. 22 CONT.*

|     | Natural piggyBac orf | 1 | ATGGGTAGTT | CTTTAGACGA | TGAGCATATC | CTCTCTGCTC | TTCTGCAAAG |
|---|---|---|---|---|---|---|---|
|     | Optimized piggyBac orf | 1 | ATGGGTAGCa | gccTgGAtGA | TGAaCATATC | CTgagcGCgC | TgCTGCAgAG |
|     | Natural piggyBac orf | 51 | CGATGACGAG | CTTGTTGGTG | AGGATTCTGA | CAGTGAAATA | TCAGATCACG |
|     | Optimized piggyBac orf | 51 | CGAcGAcGAa | CTgGTTGGTG | AaGATAgcGA | CAGcGAAATc | agcGATCACG |
|     | Natural piggyBac orf | 101 | TAAGTGAAGA | TGACGTCCAG | AGCCATACAG | AAGAAGCGTT | TATAGATGAG |
|     | Optimized piggyBac orf | 101 | TgAGCGAAGA | cGAcGTtCAG | AGCCGATACCG | AAGAAGCGTT | cATcGAcGAa |
|     | Natural piggyBac orf | 151 | GTACATGAAG | TGCAGCCAAC | GTCAAGCGGT | AGTGAAATAT | TAGACGAACA |
|     | Optimized piggyBac orf | 151 | GTtCACGAAG | TGCAGCCGAC | cagcAGCGGT | AGCGAAATcc | TgGAtGAACA |
|     | Natural piggyBac orf | 201 | AAATGTTATT | GAACAACCAG | GTTCTTCATT | GGCTTCTAAC | AGAATCTTGA |
|     | Optimized piggyBac orf | 201 | gAAcGTTATc | GAACAgCCGg | GTagcagccT | GGCgagcAAC | cGtATCcTGA |
|     | Natural piggyBac orf | 251 | CCTTGCCACA | GAGGACTATT | AGAGGTAAGA | ATAAACATTG | TTGGTCAACT |
|     | Optimized piggyBac orf | 251 | CCCcTGCCgCA | GCGcACcATc | cGtGGTAAaA | AcAAACAcTG | TTGGagcACc |
|     | Natural piggyBac orf | 301 | TCAAAGTCCA | CGAGGCGTAG | CCGAGTCTCT | GCACTGAACA | TTGTCAGATC |
|     | Optimized piggyBac orf | 301 | agcAAaagCA | CCCGcCGTAG | CCGtGTtagc | GCgCTGAACA | TTGTtcGtag |
|     | Natural piggyBac orf | 351 | TCAAAGAGGT | CCGACGCGTA | TGTGCCGCAA | TATATATGAC | CCACTTTTAT |
|     | Optimized piggyBac orf | 351 | cCAgcGtGGT | CCGACCCGTA | TGTGCCGCAA | cATcTAcGAt | CCgCTgcTgT |
|     | Natural piggyBac orf | 401 | GCTTCAAACT | ATTTTTTACT | GATGAGATAA | TTTCGGAAAT | TGTAAAATGG |
|     | Optimized piggyBac orf | 401 | GCTTCAAACT | gTTcTTcACc | GATGAaATcA | TcagcGAAAT | cGTgAAATGG |

FIG. 23

```
Natural piggyBac orf      451  ACAAATGCTG AGATATCATT GAAACGTCGG GAATCTATGA CAGGTGCTAC
Optimized piggyBac orf    451  ACCAACGCCG AaATcagccT GAAACGTCGc GAAagcATGA CCGGcGGcgAC Natural piggyBac orf      501  ATTTCGTGAC ACGAATGAAG ATGAAATCTA TGCTTTCTTT GGTATTCTGG
Optimized piggyBac orf    501  cTTcCGcGAt ACCAACGAaG ATGAaATCTA cGCcTTCTTc GGTATcCTGG Natural piggyBac orf      551  TAATGACAGC AGTGAGAAAA GATAACCACA TGTCCACAGA TGACCTCTTT
Optimized piggyBac orf    551  TgATGACCGC gGTGcGtAAA GATAACCACA TGagCACcGA TGAtCTgTTT Natural piggyBac orf      601  GATCGATCTT TGTCAATGGT GTACGTCTCT GTAATGAGTC GTGATCGTTT
Optimized piggyBac orf    601  GATCGtagcc TGagcATGGT tTACGTtagc GTtATGAGcc GtGAcCGTTT Natural piggyBac orf      651  TGATTTTTTG ATACGATGTC TTAGAATGGA TGACAAAAGT ATACGGCCCA
Optimized piggyBac orf    651  cGATTTtcTG ATCCGtTGTC TgcGtATGGA TGAtAAAAGc ATCCGcCCgA Natural piggyBac orf      701  CACTTCGAGA AAACGATGTA TTTACTCCTG TTAGAAAAAT ATGGGATCTC
Optimized piggyBac orf    701  CcCTgCGcGA AAACGATGTg TTcACcCCgG TTcGCAAAAT cTGGGATCTg Natural piggyBac orf      751  TTTATCCATC AGTGCATACA AAATTACACT CCAGGGGCTC ATTTGACCAT
Optimized piggyBac orf    751  TTcATCCAcC AGTGCATcCA gAACTACACc CCgGGCGCGc AcCTGACCAT Natural piggyBac orf      801  AGATGAACAG TTACTTGGTT TTAGAGGACG GTGTCCGTTT AGGATGTATA
Optimized piggyBac orf    801  cGATGAACAG cTgCTgGGTT TTcGtGGtCG cTGTCCGTTT cGtATGTAcA Natural piggyBac orf      851  TCCCAAACAA GCCAAGTAAG TATGGAATAA AAATCCCTCAT GATGTGTGAC
Optimized piggyBac orf    851  TCCCgAACAA aCCgAGCAAa TACGGtATcA AAATCCCTgAT GATGTGTGAC
```

*FIG. 23 CONT.*

```
Natural piggyBac orf     901  AGTGGTACGA AGTATATGAT AAATGGAATG CCTTATTTGG GAAGAGGAAC
Optimized piggyBac orf   901  AGcGGTACcA AgTAcATGAT caAcgGTaTG CCgTATcTGG GTcGTGGTAC Natural piggyBac orf     951  ACAGACCAAC GGAGTACCAC TCGGTGAATA CTACGTGAAG GAGTTATCAA
Optimized piggyBac orf   951  cCAGACCAAC GGtGTgCCgC TgGGTGAATA CTACGTGAAa GAacTgagcA Natural piggyBac orf    1001  AGCCTGTGCA CGGTAGTTGT CGTAATATTA CGTGTGACAA TTGGTTCACC
Optimized piggyBac orf  1001  AaCCgGTGCA CGGTAGcTGT CGTAACATcA CCTGTGAcAA cTGGTTCACC Natural piggyBac orf    1051  TCAATCCCTT TGGCAAAAAA CTTACTACAA GAACCGTATA AGTTAACCAT
Optimized piggyBac orf  1051  agcATCCCgc TGGCgAAAAA CCTgCTgCAg GAACCGTATA AacTgACCAT Natural piggyBac orf    1101  TGTGGGAACC GTGCGATCAA ACAAAACGCGA GATACCCGGAA GTACTGAAAA
Optimized piggyBac orf  1101  cGTGGGtACC GTcCGtagcA ACAAAACGtGA aATcCCGGAA GTgCTGAAAA Natural piggyBac orf    1151  ACAGTCGCTC CAGGCCAGTG GGAACATCGA TGTTTTGTTT TGACGGACCC
Optimized piggyBac orf  1151  ACAGcCCGtag CCgTcCGGTG GGcACCagcA TGTTcTGTTTcGAtGGTcCg Natural piggyBac orf    1201  CTTACTCTCG TCTCATATAA ACCGAAGCCA CTTCTATCAA GCTAAGATGG TATACTTATT
Optimized piggyBac orf  1201  CTgACcCTgG TtagcTAcAA ACCGAAaCCG CgagcATCAA GCgAAaATGG TgTACCTgcT Natural piggyBac orf    1251  ATCATCTTGT GATGAGGATG CTTCTATCAA CGAAAGTACC GGTAAACCGC
Optimized piggyBac orf  1251  gagcagcTGc GACGAaGACG CgagcATCAA CGAAAGCACC GGTAAACCGC Natural piggyBac orf    1301  AAATGGTTAT GTATTATAAT CAAACTAAAG GCGGAGTGGA CACGCTAGAC
Optimized piggyBac orf  1301  AgATGGTTAT GTAcTAcAAc CAgACCAAAG GCGGtGTGGA CAcCcTGgAt
```

*FIG. 23 CONT.*

```
Natural piggyBac orf       1351  CAAATGTGTT CTGTGATGAC CTGCAGTAGG AAGACGAATA GGTGGCCTAT
Optimized piggyBac orf     1351  CAgATGTGCa gCGTtATGAC CTGCAGccGc AAaACCAAcc GCTGGCCgAT Natural piggyBac orf       1401  GGCATTATTG TACGGAATGA TAAACATTGC CTGCATAAAT TCTTTTATTA
Optimized piggyBac orf     1401  GGCgcTgcTG TACGGtATGA TcAACATcGC CTGCATcAAc agcTTTATcA Natural piggyBac orf       1451  TATACAGCCA TAATGTCAGT AGCAAGGGAG AAAAGGTTCA AAGTCGCAAA
Optimized piggyBac orf     1451  TcTACAGCCA TAAcGTtAGc AGCAAaGGtG AAAAgGTTCA gAGCCGCAAA Natural piggyBac orf       1501  AAATTTATGA GAAACCTTTA CATGAGCCTG ACGTCATCGT TTATGCGTAA
Optimized piggyBac orf     1501  AAATTTATGc GtAACCTgTA CATGAGCCTG ACcagcagcT TcATGCGTAA Natural piggyBac orf       1551  GCGTTTAGAA GCTCCTACTT TGAAGAGATA TTTGCGCGAT AATATCTCTA
Optimized piggyBac orf     1551  aCGTcTggAA GCcCCgAccc TGAAacGtTA TcTGCGCGAT AAcATCagcA Natural piggyBac orf       1601  ATATTTTGCC AAATGAAGTG CCTGGTACAT CAGATGACAG TACTGAAGAG
Optimized piggyBac orf     1601  AcATccTGCC gAACGAAGTG CCgGGTACCa gCGATGAtAG cACCGAAGAa Natural piggyBac orf       1651  CCAGTAATGA AAAAACGTAC TTACTGTACT TACTGCCCCT CTAAAATAAG
Optimized piggyBac orf     1651  CCgGTgATGA AAAAACGTAC cTACTGTACC TACTGCCCga gcAAAATccG Natural piggyBac orf       1701  GCGAAAGGCA AATGCATCGT GCAAAAAATG CAAAAAAGTT ATTTGTCGAG
Optimized piggyBac orf     1701  cCGtAAaGCg AAcGCgagcT GCAAAAAATG CAAAAAAGTT ATcTGTCGtG Natural piggyBac orf       1751  AGCATAATAT TGATATGTGC CAAAGTTGTT TCTGA-- (SEQ ID NO:69)--
Optimized piggyBac orf     1751  AaCATAAcAT cGATATGTGC CAgAGCTGTT TCTGA-- (SEQ ID NO:70)--
```

*FIG. 23 CONT.*

SEQUENCE LISTING

<160> NUMBER OF SEQ ID NOS: 70

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 1
ggatcccatg cgtcaatttt acgca                                          25

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 2
acgactagtg ttcccacaat ggttaattcg                                     30

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 3
acgactagtg ccgtacgcgt atcgataagc                                     30

<210> SEQ ID NO 4
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 4
gcttgataag aagag                                                     15

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 5
gcatgttgct tgctatt                                                   17

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 6
acgtaagctt cgatgtcttt gtgatgcgcc                                     30

<210> SEQ ID NO 7
<211> LENGTH: 31

```
<212> TYPE: DNA
<213> ORGANISM: Artificial Sequence
<220> FEATURE:
<223> OTHER INFORMATION: Description of Artificial Sequence: Primer

<400> SEQUENCE: 7
acggaattca cttgcaactg aaacaatatc c                                    31

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 8
actctcgagg ttcccacaat ggttaattcg                                      30

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 9
actgaattca tggtggcgac cggtggatcg                                      30

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 10
ggatcctcta gattaaccct agaaagata                                       29

<210> SEQ ID NO 11
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 11
gaaagggccc gtgatacgcc tatttttata ggtt                                 34

<210> SEQ ID NO 12
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 12
aatcggtacc aacgcgcggg gagaggcggt ttgcg                                35

<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 13
```

```
ccaagggccc tgacgtgaac cattgtcaca cgt                            33
```

<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 14

```
tgtgggtacc gtcgatcaaa caaacgcgag ataccg                         36
```

<210> SEQ ID NO 15
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15

```
cgtcaatttt acgcagacta tctttctagg g                              31
```

<210> SEQ ID NO 16
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16

```
ttaaccctag aaagatagtc tgcgtaaaat tgacgcatg                      39
```

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17

```
gtacgtcaca atatgattat ctttctaggg                                30
```

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18

```
ttaaccctag aaagataatc atattgtgac                                30
```

<210> SEQ ID NO 19
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 19

```
ttaattaacc ctagaaagat agtctgcgta aaattgacgc atg                 43
```

```
<210> SEQ ID NO 20
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 20
ttaattaacc ctagaaagat aatcatattg tgac                                34

<210> SEQ ID NO 21
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ctagtactag tgcgccgcgt acgtctagag acgcgcagtc tagaad                   46

<210> SEQ ID NO 22
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ttctagactg cgcgtctcta gacgtacgcg gcgcactagt actagd                   46

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 23
gatgacctgc agtaggaaga cgd                                            23

<210> SEQ ID NO 24
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 24
gactctagac gtacgcggag cttaaccta gaaagatad                            39

<210> SEQ ID NO 25
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ggattccatg cgtcaatttt acgcad                                         26

<210> SEQ ID NO 26
<211> LENGTH: 35
<212> TYPE: DNA
<213> ORGANISM: Artificial Sequence
```

```
<220> FEATURE:
<223> OTHER INFORMATION: Description of Artificial Sequence: Primer

<400> SEQUENCE: 26
ggatcctcga tatacagacc gataaaaaca catgd                          35

<210> SEQ ID NO 27
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 27
ggtaccattg caaacagcga cggattcgcg ctatd                          35

<210> SEQ ID NO 28
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 28
acgcgtagat cttaatacga ctcactatag gg                             32

<210> SEQ ID NO 29
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 29
acgcgtagat ctaattaacc ctcactaaag gg                             32

<210> SEQ ID NO 30
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 30
cctcgatata cagaccgata aaacacatg                                 29

<210> SEQ ID NO 31
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 31
gcacgcctca gccgagctcc aagggcgac                                 29

<210> SEQ ID NO 32
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 32
ggatccctca aaatttcttc taaagta                                   27
```

<210> SEQ ID NO 33
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 33
ggatccctca aaatttcttc taaagta                                       27

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 34
gcacgcctca gccgagctcc aagcggcgac                                    30

<210> SEQ ID NO 35
<211> LENGTH: 26
<212> TYPE: DNA
<213> ORGANISM: Artificial Sequence
<220> FEATURE:
<223> OTHER INFORMATION: Description of Artificial Sequence: Plasmid
      insertion sequence

<400> SEQUENCE: 35
ttaatctaga ggatcctcta gattaa                                        26

<210> SEQ ID NO 36
<211> LENGTH: 26
<212> TYPE: DNA
<213> ORGANISM: Artificial Sequence
<220> FEATURE:
<223> OTHER INFORMATION: Description of Artificial Sequence: Plasmid
      insertion sequence

<400> SEQUENCE: 36
ttaatctaga cgtacgcgga gcttaa                                        26

<210> SEQ ID NO 37
<211> LENGTH: 30
<212> TYPE: DNA
<213> ORGANISM: Artificial Sequence
<220> FEATURE:
<223> OTHER INFORMATION: Description of Artificial Sequence: Plasmid
      insertion sequence

<400> SEQUENCE: 37
ttaatctagc tagtactaga actagattaa                                    30

<210> SEQ ID NO 38
<211> LENGTH: 48
<212> TYPE: DNA
<213> ORGANISM: Artificial Sequence
<220> FEATURE:
<223> OTHER INFORMATION: Description of Artificial Sequence: Plasmid
      insertion sequence

<400> SEQUENCE: 38
ttaatctagt tctagacgta cgcggcgcac tagtactagc tagattaa                48

<210> SEQ ID NO 39
<211> LENGTH: 63

<210> SEQ ID NO 39
<211> LENGTH: 63
<212> TYPE: DNA
<213> ORGANISM: Artificial Sequence
<220> FEATURE:
<223> OTHER INFORMATION: Description of Artificial Sequence: Plasmid insertion sequence

<400> SEQUENCE: 39

```
ttaatctagt tctagactgc gcgtctctag acgtacgcgg cgcactagta ctagctagat    60
taa                                                                  63
```

<210> SEQ ID NO 40
<211> LENGTH: 707
<212> TYPE: DNA
<213> ORGANISM: Artificial Sequence
<220> FEATURE:
<223> OTHER INFORMATION: Description of Artificial Sequence: ITR Cartridge sequence

<400> SEQUENCE: 40

```
ggatcccatg cgtcaatttt acgcagacta tctttctagg gttaatctag ctgcatcagg    60
atcatatcgt cggtctttt  ttccggctca gtcatcgccc aagctggcgc tatctgggca   120
tcggggagga agaagcccgt gccttttccc gcgaggttga agcggcatgg aaagagtttg   180
ccgaggatga ctgctgctgc attgacgttg agcgaaaacg cacgtttacc atgatgattc   240
gggaaggtgt ggccatgcac gcctttaacg gtgaactgtt cgttcaggcc acctgggata   300
ccagttcgtc gcggcttttc cggacacagt tccggatggt cagcccgaag cgcatcagca   360
acccgaacaa taccggcgac agccggaact gccgtgccgg tgtgcagatt aatgacagcg   420
gtgcggcgct gggatattac gtcagcgagg acgggtatcc tggctggatg ccgcagaaat   480
ggacatggat accccgtgag ttacccggcg ggcgcgcctc gttcattcac gtttttgaac   540
ccgtggagga cgggcagact cgcggtgcaa atgtgtttta cagcgtgatg gagcagatga   600
agatgctcga cacgctgcag aacacgcagc tagattaacc ctagaaagat aatcatattg   660
tgacgtacgt taaagataat catgcgtaaa attgacgcat gggatcc                  707
```

<210> SEQ ID NO 41
<211> LENGTH: 3662
<212> TYPE: DNA
<213> ORGANISM: Artificial Sequence
<220> FEATURE:
<223> OTHER INFORMATION: Description of Artificial Sequence: pXL-Bac sequence

<400> SEQUENCE: 41

```
ctaaattgta agcgttaata tttttgttaaa attcgcgtta aatttttgtt aaatcagctc    60
attttttaac caataggccg aaatcggcaa atcccttat  aaatcaaaag aatagaccga   120
gatagggttg agtgttgttc cagtttggaa caagagtcca ctattaaaga acgtggactc   180
caacgtcaaa gggcgaaaaa ccgtctatca gggcgatggc ccactacgtg aaccatcacc   240
ctaatcaagt ttttggggt  cgaggtgccg taaagcacta atcggaacc  ctaaagggag   300 cccccgattt agagcttgac ggggaaagcc ggcgaacgtg gcgagaaagg aagggaagaa   360
agcgaaagga gcgggcgcta gggcgctggc aagtgtagcg gtcacgctgc gcgtaaccac   420
cacacccgcc gcgcttaatg cgccgctaca gggcgcgtcc cattcgccat tcaggctgcg   480
caactgttgg gaagggcgat cggtgcgggc ctcttcgcta ttacgccagc tggcgaaagg   540
gggatgtgct gcaaggcgat taagttgggt aacgccaggg ttttcccagt cacgacgttg   600
taaaacgacg gccagtgagc gcgcctcgtt cattcacgtt tttgaacccg tggaggacgg   660
```

```
gcagactcgc ggtgcaaatg tgttttacag cgtgatggag cagatgaaga tgctcgacac    720
gctgcagaac acgcagctag attaacccta gaaagataat catattgtga cgtacgttaa    780
agataatcat gcgtaaaatt gacgcatggg atctgtaata cgactcacta tagggcgaat    840
tgggtaccgg gccccccctc gaggtcgacg gtatcgataa gcttgatatc gaattcctgc    900
agcccggggg atccactagt tctagagcgg ccgccaccgc ggtggagctc cagcttttgt    960
tccctttagt gagggttaat tagatcccat gcgtcaattt tacgcagact atctttctag   1020
ggttaatcta gctgcatcag gatcatatcg tcggtctttt tttccggctc agtcatcgcc   1080
caagctggcg ctatctgggc atcggggagg aagaagcccg tgccttttcc cgcgaggttg   1140
aagcggcatg gaaagagttt gccgaggatg actgctgctg cattgacgtt gagcgaaaac   1200
gcacgtttac catgatgatt cgggaaggtg tggccatgca cgcctttaac ggtgaactgt   1260
tcgttcaggc cacctgggat accagttcgt cgcggctttt ccggacacag ttccggatgg   1320
tcagcccgaa gcgcatcagc aacccgaaca ataccggcga cagccggaac tgccgtgccg   1380
gtgtgcagat taatgacagc ggtgcggcgc tgggatatta cgtcagcgag gacgggtatc   1440
ctggctggat gccgcagaaa tggacatgga taccccgtga gttacccggc gggcgcgctt   1500
ggcgtaatca tggtcatagc tgtttcctgt gtgaaattgt tatccgctca caattccaca   1560
caacatacga gccggaagca taaagtgtaa agcctggggt gcctaatgag tgagctaact   1620
cacattaatt gcgttgcgct cactgcccgc tttccagtcg ggaaacctgt cgtgccagct   1680
gcattaatga atcggccaac gcgcggggag aggcggtttg cgtattgggc gctcttccgc   1740
ttcctcgctc actgactcgc tgcgctcggt cgttcggctg cggcgagcgg tatcagctca   1800
ctcaaaggcg gtaatacggt tatccacaga atcaggggat aacgcaggaa agaacatgtg   1860
agcaaaaggc cagcaaaagg ccaggaaccg taaaaaggcc gcgttgctgg cgttttttcca   1920 taggctccgc cccctgacg agcatcacaa aaatcgacgc tcaagtcaga ggtggcgaaa   1980
cccgacagga ctataaagat accaggcgtt tcccctggaa gctccctcg tgcgctctcc   2040 tgttccgacc ctgccgctta ccggatacct gtccgccttt ctcccttcgg gaagcgtggc   2100
gctttctcat agctcacgct gtaggtatct cagttcggtg taggtcgttc gctccaagct   2160
gggctgtgtg cacgaacccc ccgttcagcc cgaccgctgc gccttatccg gtaactatcg   2220
tcttgagtcc aacccggtaa gacacgactt atcgccactg gcagcagcca ctggtaacag   2280
gattagcaga gcgaggtatg taggcggtgc tacagagttc ttgaagtggt ggcctaacta   2340
cggctacact agaaggacag tatttggtat ctgcgctctg ctgaagccag ttaccttcgg   2400
aaaaagagtt ggtagctctt gatccggcaa acaaaccacc gctggtagcg gtggtttttt   2460
tgtttgcaag cagcagatta cgcgcagaaa aaaaggatct caagaagatc ctttgatctt   2520
ttctacgggg tctgacgctc agtggaacga aaactcacgt taagggattt tggtcatgag   2580
attatcaaaa aggatcttca cctagatcct tttaaattaa aaatgaagtt ttaaatcaat   2640
ctaaagtata tatgagtaaa cttggtctga cagttaccaa tgcttaatca gtgaggcacc   2700
tatctcagcg atctgtctat ttcgttcatc catagttgcc tgactccccg tcgtgtagat   2760
aactacgata cgggagggct taccatctgg ccccagtgct gcaatgatac cgcgagaccc   2820
acgctcaccg gctccagatt tatcagcaat aaaccagcca gccggaaggg ccgagcgcag   2880
aagtggtcct gcaactttat ccgcctccat ccagtctatt aattgttgcc gggaagctag   2940
agtaagtagt tcgccagtta atagtttgcg caacgttgtt gccattgcta caggcatcgt   3000
```

```
ggtgtcacgc tcgtcgtttg gtatggcttc attcagctcc ggttcccaac gatcaaggcg    3060
agttacatga tccccccatgt tgtgcaaaaa agcggttagc tccttcggtc ctccgatcgt    3120
tgtcagaagt aagttggccg cagtgttatc actcatggtt atggcagcac tgcataattc    3180
tcttactgtc atgccatccg taagatgctt ttctgtgact ggtgagtact caaccaagtc    3240
attctgagaa tagtgtatgc ggcgaccgag ttgctcttgc ccggcgtcaa tacgggataa    3300
taccgcgcca catagcagaa ctttaaaagt gctcatcatt ggaaaacgtt cttcggggcg    3360
aaaactctca aggatcttac cgctgttgag atccagttcg atgtaaccca ctcgtgcacc    3420
caactgatct tcagcatctt ttactttcac cagcgtttct gggtgagcaa aaacaggaag    3480
gcaaaatgcc gcaaaaaagg gaataagggc gacacggaaa tgttgaatac tcatactctt    3540 ccttttttcaa tattattgaa gcatttatca gggttattgt ctcatgagcg gatacatatt    3600
tgaatgtatt tagaaaaata aacaaatagg ggttccgcgc acatttcccc gaaaagtgcc    3660
ac                                                                    3662

<210> SEQ ID NO 42
<211> LENGTH: 5533
<212> TYPE: DNA
<213> ORGANISM: Artificial Sequence
<220> FEATURE:
<223> OTHER INFORMATION: Description of Artificial Sequence:
      pBSII-hs-orf sequence

<400> SEQUENCE: 42
ctaaattgta agcgttaata ttttgttaaa attcgcgtta aatttttgtt aaatcagctc      60
attttttaac caataggccg aaatcggcaa aatcccttat aaatcaaaag aatagaccga    120
gatagggttg agtgttgttc cagtttggaa caagagtcca ctattaaaga acgtggactc    180
caacgtcaaa gggcgaaaaa ccgtctatca gggcgatggc ccactacgtg aaccatcacc    240
ctaatcaagt ttttttgggt cgaggtgccg taaagcacta atcggaacc ctaaagggag    300 cccccgattt agagcttgac ggggaaagcc ggcgaacgtg gcgagaaagg aagggaagaa    360
agcgaaagga gcgggcgcta gggcgctggc aagtgtagcg gtcacgctgc gcgtaaccac    420
cacacccgcc gcgcttaatg cgccgctaca gggcgcgtcc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgcgtaata cgactcacta gggcgaatt gggtaccgg      660 gccccccctc gaggtcgacg gtatcgataa gctatccagt gcagtaaaaa ataaaaaaaa    720
aatatgtttt tttaaatcta cattctccaa aaagggttt tattaactta catacatact    780
agaattgatc cccgatcccc ctagaatccc aaaacaaact ggttattgtg gtaggtcatt    840
tgtttggcag aagaaaactc gagaaatttc tctggccgtt attcgttatt ctctcttttc    900
tttttgggtc tccctctctg cactaatgct ctctcactct gtcacacagt aaacggcata    960
ctgctctcgt tggttcgaga gagcgcgcct cgaatgttcg cgaaaagagc gccggagtat   1020
aaatagagcg cttcgtctac ggagcgacaa ttcaattcaa acaagcaaag tgaacacgtc   1080
gctaagcgaa agctaagcaa ataaacaagc gcagctgaac aagctaaaca atctgcagta   1140
aagtgcaagt taaagtgaat caattaaaag taaccagcaa ccaagtaaat caactgcaac   1200
tactgaaatc tgccaagaag taattattga atacaagaag agaactctga atagggaatt   1260
gggaattcct gcagcccggg ggatcctata taataaaatg ggtagttctt tagacgatga   1320
```

```
gcatatcctc tctgctcttc tgcaaagcga tgacgagctt gttggtgagg attctgacag    1380
tgaaatatca gatcacgtaa gtgaagatga cgtccagagc gatacagaag aagcgtttat    1440
agatgaggta catgaagtgc agccaacgtc aagcggtagt gaaatattag acgaacaaaa    1500
tgttattgaa caaccaggtt cttcattggc ttctaacaga atcttgacct tgccacagag    1560
gactattaga ggtaagaata acattgttg gtcaacttca aagtccacga ggcgtagccg     1620
agtctctgca ctgaacattg tcagatctca aagaggtccg acgcgtatgt gccgcaatat    1680
atatgaccca cttttatgct tcaaactatt ttttactgat gagataattt cggaaattgt    1740
aaaatggaca aatgctgaga tatcattgaa acgtcgggaa tctatgacag gtgctacatt    1800
tcgtgacacg aatgaagatg aaatctatgc tttctttggt attctggtaa tgacagcagt    1860
gagaaaagat aaccacatgt ccacagatga cctctttgat cgatctttgt caatggtgta    1920
cgtctctgta atgagtcgtg atcgttttga ttttttgata cgatgtctta aatggatga    1980
caaaagtata cggcccacac ttcgagaaaa cgatgtattt actcctgtta gaaaatatg     2040
ggatctcttt atccatcagt gcatacaaaa ttacactcca ggggctcatt tgaccataga    2100
tgaacagtta cttggtttta gaggacggtg tccgtttagg atgtatatcc caaacaagcc    2160
aagtaagtat ggaataaaaa tcctcatgat gtgtgacagt ggtacgaagt atatgataaa    2220
tggaatgcct tatttgggaa gaggaacaca gaccaacgga gtaccactcg gtaatacta    2280
cgtgaaggag ttatcaaagc ctgtgcacgg tagttgtcgt aatattacgt gtgacaattg    2340
gttcacctca atccctttgg caaaaaactt actacaagaa ccgtataagt taaccattgt    2400
gggaaccgtg cgatcaaaca aacgcgagat accggaagta ctgaaaaaca gtcgctccag    2460
gccagtggga acatcgatgt tttgttttga cggacccctt actctcgtct catataaacc    2520
gaagccagct aagatggtat acttattatc atcttgtgat gaggatgctt ctatcaacga    2580
aagtaccggt aaaccgcaaa tggttatgta ttataatcaa actaaaggcg gagtggacac    2640
gctagaccaa atgtgttctg tgatgacctg cagtaggaag acgaataggt ggcctatggc    2700
attattgtac ggaatgataa acattgcctg cataaattct tttattatat acagccataa    2760
tgtcagtagc aagggagaaa aggttcaaag tcgcaaaaaa tttatgagaa acctttacat    2820
gagcctgacg tcatcgttta tgcgtaagcg tttagaagct cctactttga agagatattt    2880
gcgcgataat atctctaata ttttgccaaa tgaagtgcct ggtacatcag atgacagtac    2940
tgaagagcca gtaatgaaaa aacgtactta ctgtacttac tgcccctcta aaataaggcg    3000
aaaggcaaat gcatcgtgca aaaatgcaa aaaagttatt tgtcgagagc ataatattga     3060
tatgtgccaa agttgtttct gactgactaa taagtataat ttgtttctat tatgtataag    3120
ttaagctaat tacttatttt ataatacaac atgactgttt ttaaagtaca aaataagttt    3180
atttttgtaa aagagagaat gtttaaaagt tttgttactt tagaagaaat tttgagtttt    3240
tgttttttt taataaataa ataaacataa ataaattgtt tgttgaattt ggatccacta    3300
gttctagagc ggccgccacc gcggtggagc tccagctttt gttcccttta gtgagggtta    3360
attgcgcgct tggcgtaatc atggtcatag ctgtttcctg tgtgaaattg ttatccgctc    3420
acaattccac acaacatacg agccggaagc ataaagtgta aagcctgggg tgcctaatga    3480
gtgagctaac tcacattaat tgcgttcgc tcactgcccg ctttccagtc gggaaacctg     3540
tcgtgccagc tgcattaatg aatcggccaa cgcgcgggga gaggcggttt gcgtattggg    3600
cgctcttccg cttcctcgct cactgactcg ctgcgctcgg tcgttcggct gcggcgagcg    3660
gtatcagctc actcaaaggc ggtaatacgg ttatccacag aatcagggga taacgcagga    3720
```

-continued

```
aagaacatgt gagcaaaagg ccagcaaaag gccaggaacc gtaaaaaggc cgcgttgctg    3780 gcgttttttcc ataggctccg ccccctgac gagcatcaca aaaatcgacg ctcaagtcag    3840
aggtggcgaa acccgacagg actataaaga taccaggcgt ttccccctgg aagctccctc    3900
gtgcgctctc ctgttccgac cctgccgctt accggatacc tgtccgcctt tctcccttcg    3960
ggaagcgtgg cgctttctca gctcacgc tgtaggtatc tcagttcggt gtaggtcgtt     4020
cgctccaagc tgggctgtgt gcacgaaccc cccgttcagc ccgaccgctg cgccttatcc    4080
ggtaactatc gtcttgagtc caacccggta agacacgact tatcgccact ggcagcagcc    4140
actggtaaca ggattagcag agcgaggtat gtaggcggtg ctacagagtt cttgaagtgg    4200
tggcctaact acggctacac tagaaggaca gtatttggta tctgcgctct gctgaagcca    4260
gttaccttcg gaaaaagagt tggtagctct tgatccggca acaaaccac cgctggtagc    4320 ggtggttttt ttgttttgcaa gcagcagatt acgcgcagaa aaaaggatc tcaagaagat    4380 cctttgatct tttctacggg gtctgacgct cagtggaacg aaaactcacg ttaagggatt    4440
ttggtcatga gattatcaaa aaggatcttc acctagatcc ttttaaatta aaaatgaagt    4500
tttaaatcaa tctaaagtat atatgagtaa acttggtctg acagttacca atgcttaatc    4560
agtgaggcac ctatctcagc gatctgtcta tttcgttcat ccatagttgc ctgactcccc    4620
gtcgtgtaga taactacgat acgggagggc ttaccatctg gccccagtgc tgcaatgata    4680
ccgcgagacc cacgctcacc ggctccagat ttatcagcaa taaaccagcc agccggaagg    4740
gccgagcgca gaagtggtcc tgcaacttta tccgcctcca tccagtctat taattgttgc    4800
cgggaagcta gagtaagtag ttcgccagtt aatagtttgc gcaacgttgt tgccattgct    4860
acaggcatcg tggtgtcacg ctcgtcgttt ggtatggctt cattcagctc cggttcccaa    4920
cgatcaaggc gagttacatg atcccccatg ttgtgcaaaa aagcggttag ctccttcggt    4980
cctccgatcg ttgtcagaag taagttggcc gcagtgttat cactcatggt tatggcagca    5040
ctgcataatt ctcttactgt catgccatcc gtaagatgct tttctgtgac tggtgagtac    5100
tcaaccaagt cattctgaga atagtgtatg cggcgaccga gttgctcttg cccggcgtca    5160
atacgggata taccgcgcc acatagcaga actttaaaag tgctcatcat tggaaaacgt    5220
tcttcggggc gaaaactctc aaggatctta ccgctgttga tccagttc gatgtaaccc    5280 actcgtgcac ccaactgatc ttcagcatct tttactttca ccagcgtttc tgggtgagca    5340
aaaacaggaa ggcaaaatgc cgcaaaaaag ggaataaggg cgacacggaa atgttgaata    5400
ctcatactct ccttttttca atattattga agcatttatc agggttattg tctcatgagc    5460
ggatacatat ttgaatgtat ttagaaaaat aaacaaatag gggttccgcg cacatttccc    5520
cgaaaagtgc cac                                                      5533
```

<210> SEQ ID NO 43
<211> LENGTH: 4971
<212> TYPE: DNA
<213> ORGANISM: Artificial Sequence
<220> FEATURE:
<223> OTHER INFORMATION: Description of Artificial Sequence:
      pBSII-IFP2-orf sequence

<400> SEQUENCE: 43

```
ctaaattgta agcgttaata ttttgttaaa attcgcgtta aattttttgtt aaatcagctc      60 atttttttaac cataggccg aaatcggcaa atcccttat aaatcaaaag aatagaccga     120
gatagggttg agtgttgttc cagtttggaa caagagtcca ctattaaaga acgtggactc     180
```

-continued

```
caacgtcaaa gggcgaaaaa ccgtctatca gggcgatggc ccactacgtg aaccatcacc    240
ctaatcaagt ttttgggggt cgaggtgccg taaagcacta aatcggaacc ctaaagggag    300
cccccgattt agagcttgac ggggaaagcc ggcgaacgtg gcgagaaagg aagggaagaa    360
agcgaaagga gcggcgcta gggcgctggc aagtgtagcg gtcacgctgc gcgtaaccac    420
cacacccgcc gcgcttaatg cgccgctaca gggcgcgtcc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgcgtaata cgactcacta tagggcgaat gggtaccgg     660 gccccccctc gaggtcgacg gtatcgataa gcttgatatc gaattcctgc agcccggggg    720
atcctatata ataaaatggg tagttcttta gacgatgagc atatcctctc tgctcttctg    780
caaagcgatg acgagcttgt tggtgaggat tctgacagtg aaatatcaga tcacgtaagt    840
gaagatgacg tccagagcga tacagaagaa gcgtttatag atgaggtaca tgaagtgcag    900
ccaacgtcaa gcggtagtga aatattagac gaacaaaatg ttattgaaca accaggttct    960
tcattggctt ctaacagaat cttgaccttg ccacagagga ctattagagg taagaataaa   1020
cattgttggt caacttcaaa gtccacgagg cgtagccgag tctctgcact gaacattgtc   1080
agatctcaaa gaggtccgac gcgtatgtgc cgcaatatat atgacccact tttatgcttc   1140
aaactatttt ttactgatga gataatttcg gaaattgtaa aatggacaaa tgctgagata   1200
tcattgaaac gtcgggaatc tatgacaggt gctacatttc gtgacacgaa tgaagatgaa   1260
atctatgctt tctttggtat tctggtaatg acagcagtga gaaaagataa ccacatgtcc   1320
acagatgacc tcttttgatcg atctttgtca atggtgtacg tctctgtaat gagtcgtgat   1380
cgttttgatt ttttgatacg atgtcttaga atggatgaca aaagtatacg cccacactt    1440 cgagaaaacg atgtatttac tcctgttaga aaaatatggg atctctttat ccatcagtgc   1500
atacaaaatt acactccagg ggctcatttg accatagatg aacagttact tggttttaga   1560
ggacggtgtc cgtttaggat gtatatccca aacaagccaa gtaagtatgg aataaaaatc   1620
ctcatgatgt gtgacagtgg tacgaagtat atgataaatg gaatgcctta tttgggaaga   1680
ggaacacaga ccaacggagt accactcggt gaatactacg tgaaggagtt atcaaagcct   1740
gtgcacggta gttgtcgtaa tattacgtgt gacaattggt tcacctcaat ccctttggca   1800
aaaaacttac tacaagaacc gtataagtta accattgtgg gaaccgtgcg atcaaacaaa   1860
cgcgagatac cggaagtact gaaaaacagt cgctccaggc cagtgggaac atcgatgttt   1920
tgttttgacg gacccttac tctcgtctca tataaaccga agccagctaa gatggtatac    1980
ttattatcat cttgtgatga ggatgcttct atcaacgaaa gtaccggtaa accgcaaatg   2040
gttatgtatt ataatcaaac taaaggcgga gtggacacgc tagaccaaat gttgttctgtg  2100 atgacctgca gtaggaagac gaataggtgg cctatggcat tattgtacgg aatgataaac   2160
attgcctgca taaattcttt tattatatac agccataatg tcagtagcaa gggagaaaag   2220
gttcaaagtc gcaaaaaatt tatgagaaac ctttacatga gcctgacgtc atcgtttatg   2280
cgtaagcgtt tagaagctcc tactttgaag agatatttgc gcgataatat ctctaatatt   2340
ttgccaaatg aagtgcctgg tacatcagat gacagtactg aagagccagt aatgaaaaaa   2400
cgtacttact gtacttactg cccctctaaa ataaggcgaa aggcaaatgc atcgtgcaaa   2460
aaatgcaaaa aagttatttg tcgagagcat aatattgata tgtgccaaag ttgtttctga   2520
```

-continued

```
ctgactaata agtataattt gtttctatta tgtataagtt aagctaatta cttattttat    2580
aatacaacat gactgttttt aaagtacaaa ataagtttat ttttgtaaaa gagagaatgt    2640
ttaaagtttt tgttacttta gaagaaattt tgagttttg ttttttttta ataaataaat     2700
aaacataaat aaattgtttg ttgaatttgg atccactagt tctagagcgg ccgccaccgc    2760
ggtggagctc cagcttttgt tccctttagt gagggttaat tgcgcgcttg gcgtaatcat    2820
ggtcatagct gtttcctgtg tgaaattgtt atccgctcac aattccacac aacatacgag    2880
ccggaagcat aaagtgtaaa gcctggggtg cctaatgagt gagctaactc acattaattg    2940
cgttgcgctc actgcccgct ttccagtcgg gaaacctgtc gtgccagctg cattaatgaa    3000
tcggccaacg cgcggggaga ggcggtttgc gtattggcg ctcttccgct tcctcgctca     3060
ctgactcgct gcgctcggtc gttcggctgc ggcgagcggt atcagctcac tcaaaggcgg    3120
taatacggtt atccacagaa tcaggggata acgcaggaaa gaacatgtga gcaaaaggcc    3180
agcaaaaggc caggaaccgt aaaaaggccg cgttgctggc gtttttccat aggctccgcc    3240
cccctgacga gcatcacaaa aatcgacgct caagtcagag gtggcgaaac ccgacaggac    3300
tataaagata ccaggcgttt ccccctggaa gctccctcgt gcgctctcct gttccgaccc    3360
tgccgcttac cggatacctg tccgcctttc tcccttcggg aagcgtggcg ctttctcata    3420
gctcacgctg taggtatctc agttcggtgt aggtcgttcg ctccaagctg gctgtgtgc    3480
acgaaccccc cgttcagccc gaccgctgcg ccttatccgg taactatcgt cttgagtcca    3540
acccggtaag acacgactta tcgccactgg cagcagccac tggtaacagg attagcagag    3600
cgaggtatgt aggcggtgct acagagttct tgaagtggtg gcctaactac ggctacacta    3660
gaaggacagt atttggtatc tgcgctctgc tgaagccagt taccttcgga aaaagagttg    3720
gtagctcttg atccggcaaa caaaccaccg ctggtagcgg tggtttttt gtttgcaagc    3780
agcagattac gcgcagaaaa aaggatctca agaagatcc tttgatcttt tctacgggt     3840
ctgacgctca gtggaacgaa aactcacgtt aagggatttt ggtcatgaga ttatcaaaaa    3900
ggatcttcac ctagatcctt ttaaattaaa aatgaagtt taaatcaatc taaagtatat     3960
atgagtaaac ttggtctgac agttaccaat gcttaatcag tgaggcacct atctcagcga    4020
tctgtctatt tcgttcatcc atagttgcct gactccccgt cgtgtagata actacgatac    4080
gggagggctt accatctggc cccagtgctg caatgatacc gcgagaccca cgctcaccgg    4140
ctccagattt atcagcaata aaccagccag ccggaagggc cgagcgcaga agtggtcctg    4200
caactttatc cgcctccatc cagtctatta attgttgccg ggaagctaga gtaagtagtt    4260
cgccagttaa tagtttgcgc aacgttgttg ccattgctac aggcatcgtg gtgtcacgct    4320
cgtcgtttgg tatggcttca ttcagctccg gttcccaacg atcaaggcga gttacatgat    4380
cccccatgtt gtgcaaaaaa gcggttagct ccttcggtcc tccgatcgtt gtcagaagta    4440
agttggccga gtgttatca ctcatggtta tggcagcact gcataattct cttactgtca     4500
tgccatccgt aagatgcttt tctgtgactg gtgagtactc aaccaagtca ttctgagaat    4560
agtgtatgcg gcgaccgagt tgctcttgcc cggcgtcaat acgggataat accgcgccac    4620
atagcagaac tttaaaagtg ctcatcattg gaaaacgttc ttcggggcga aaactctcaa    4680
ggatcttacc gctgttgaga tccagttcga tgtaacccac tcgtgcaccc aactgatctt    4740
cagcatcttt tactttcacc agcgtttctg ggtgagcaaa aacaggaagg caaaatgccg    4800
caaaaaaggg aataagggcg acacggaaat gttgaatact catactcttc cttttttcaat   4860
attattgaag catttatcag ggttattgtc tcatgagcgg atacatattt gaatgtattt    4920
```

```
agaaaaataa acaaataggg gttccgcgca catttccccg aaaagtgcca c            4971

<210> SEQ ID NO 44
<211> LENGTH: 5523
<212> TYPE: DNA
<213> ORGANISM: Artificial Sequence
<220> FEATURE:
<223> OTHER INFORMATION: Description of Artificial Sequence:
      pBSII-IEI-orf sequence

<400> SEQUENCE: 44
ctaaattgta agcgttaata ttttgttaaa attcgcgtta aattttgtt aaatcagctc      60 atttttaac caataggccg aaatcggcaa atcccttat aaatcaaaag aatagaccga     120 gataggttg agtgttgttc cagtttggaa caagagtcca ctattaaaga acgtggactc     180
caacgtcaaa gggcgaaaaa ccgtctatca gggcgatggc ccactacgtg aaccatcacc     240
ctaatcaagt tttttggggt cgaggtgccg taaagcacta atcggaacc ctaaagggag     300 cccccgattt agagcttgac ggggaaagcc ggcgaacgtg gcgagaaagg aagggaagaa     360
agcgaaagga gcgggcgcta gggcgctggc aagtgtagcg gtcacgctgc gcgtaaccac     420
cacacccgcc gcgcttaatg cgccgctaca gggcgcgtcc cattcgccat tcaggctgcg     480
caactgttgg gaagggcgat cggtgcgggc ctcttcgcta ttacgccagc tggcgaaagg     540
gggatgtgct gcaaggcgat taagttgggt aacgccaggg ttttcccagt cacgacgttg     600
taaaacgacg gccagtgagc gcgcgtaata cgactcacta gggcgaat tgggtaccgg     660 gccccccctc gaggtcgacg gtatcgataa gcttcgatgt ctttgtgatg cgccgacatt     720
tttgtaggtt attgataaaa tgaacggata cagttgcccg acattatcat taaatccttg     780
gcgtagaatt tgtcgggtcc attgtccgtg tgcgctagca tgcccgctaa cggacctcgt     840
acttttggct tcaaaggttt tgcgcacaga caaaatgtgc cacacttgca gctctgcatg     900
tgtgcgcgtt accacaaatc ccaacggcgc agtgtacttg ttgtatgcaa ataaatctcg     960
ataaaggcgc ggcgcgcgaa tgcagctgat cacgtacgct cctcgtgttc cgttcaagga    1020
cggtgttatc gacctcagat taatgtttat cggccgactg ttttcgtatc cgctcaccaa    1080
acgcgttttt gcattaacat tgtatgtcgg cggatgttct atatctaatt tgaataaata    1140
aacgataacc gcgttggttt tagagggcat aataaaagaa atattgttat cgtgttcgcc    1200
attagggcag tataaattga cgttcatgtt ggatattgtt tcagttgcaa gtgaattcct    1260
gcagcccggg ggatcctata taataaaatg ggtagttctt tagacgatga gcatatcctc    1320
tctgctcttc tgcaaagcga tgacgagctt gttggtgagg attctgacag tgaaatatca    1380
gatcacgtaa gtgaagatga cgtccagagc gatacagaag aagcgtttat agatgaggta    1440
catgaagtgc agccaacgtc aagcggtagt gaaatattag acgaacaaaa tgttattgaa    1500
caaccaggtt cttcattggc ttctaacaga atcttgacct tgccacagag gactattaga    1560
ggtaagaata acattgttg gtcaacttca aagtccacga ggcgtagccg agtctctgca    1620
ctgaacattt tcagatctca aagaggtccg acgcgtatgt gccgcaatat atatgaccca    1680
cttttatgct tcaaactatt ttttactgat gagataattt cggaaattgt aaaatggaca    1740
aatgctgaga tatcattgaa acgtcggaa tctatgacag gtgctacatt tcgtgacacg    1800
aatgaagatg aaatctatgc tttctttggt attctggtaa tgacagcagt gagaaaagat    1860
aaccacatgt ccacagatga cctctttgat cgatctttgt caatggtgta cgtctctgta    1920
atgagtcgtg atcgttttga tttttttgata cgatgtctta gaatggatga caaaagtata    1980
```

-continued

```
cggcccacac ttcgagaaaa cgatgtattt actcctgtta gaaaaatatg ggatctcttt    2040
atccatcagt gcatacaaaa ttacactcca ggggctcatt tgaccataga tgaacagtta    2100
cttggtttta gaggacggtg tccgtttagg atgtatatcc caaacaagcc aagtaagtat    2160
ggaataaaaa tcctcatgat gtgtgacagt ggtacgaagt atatgataaa tggaatgcct    2220
tatttgggaa gaggaacaca gaccaacgga gtaccactcg gtgaatacta cgtgaaggag    2280
ttatcaaagc ctgtgcacgg tagttgtcgt aatattacgt gtgacaattg gttcacctca    2340
atccctttgg caaaaaactt actacaagaa ccgtataagt taaccattgt gggaaccgtg    2400
cgatcaaaca aacgcgagat accggaagta ctgaaaaaca gtcgctccag gccagtggga    2460
acatcgatgt tttgttttga cggacccctt actctcgtct catataaacc gaagccagct    2520
aagatggtat acttattatc atcttgtgat gaggatgctt ctatcaacga agtaccggt     2580 aaaccgcaaa tggttatgta ttataatcaa actaaaggcg gagtggacac gctagaccaa    2640
atgtgttctg tgatgacctg cagtaggaag acgaataggt ggcctatggc attattgtac    2700
ggaatgataa acattgcctg cataaattct tttattatat acagccataa tgtcagtagc    2760
aagggagaaa aggttcaaag tcgcaaaaaa tttatgagaa acctttacat gagcctgacg    2820
tcatcgttta tgcgtaagcg tttagaagct cctactttga agagatattt gcgcgataat    2880
atctctaata ttttgccaaa tgaagtgcct ggtacatcag atgacagtac tgaagagcca    2940
gtaatgaaaa aacgtactta ctgtacttac tgcccctcta aaataaggcg aaaggcaaat    3000
gcatcgtgca aaaaatgcaa aaaagttatt tgtcgagagc ataatattga tatgtgccaa    3060
agttgtttct gactgactaa taagtataat ttgtttctat tatgtataag ttaagctaat    3120
tacttatttt ataatacaac atgactgttt ttaaagtaca aaataagttt attttttgtaa   3180 aagagagaat gtttaaaagt tttgttactt tagaagaaat tttgagtttt tgttttttt     3240 taataaataa ataaacataa ataaattgtt tgttgaattt ggatccacta gttctagagc    3300
ggccgccacc gcggtggagc tccagctttt gttcccttta gtgagggtta attgcgcgct    3360
tggcgtaatc atggtcatag ctgtttcctg tgtgaaattg ttatccgctc acaattccac    3420
acaacatacg agccggaagc ataaagtgta aagcctgggg tgcctaatga gtgagctaac    3480
tcacattaat tgcgttgcgc tcactgcccg ctttccagtc gggaaacctg tcgtgccagc    3540
tgcattaatg aatcggccaa cgcgcgggga gaggcggttt gcgtattggg cgctcttccg    3600
cttcctcgct cactgactcg ctgcgctcgg tcgttcggct gcggcgagcg gtatcagctc    3660
actcaaaggc ggtaatacgg ttatccacag aatcagggga taacgcagga agaacatgt     3720 gagcaaaagg ccagcaaaag gccaggaacc gtaaaaaggc cgcgttgctg cgttttttcc    3780
ataggctccg ccccctgac gagcatcaca aaaatcgacg ctcaagtcag aggtggcgaa     3840
acccgacagg actataaaga taccaggcgt ttccccctgg aagctccctc gtgcgctctc    3900
ctgttccgac cctgccgctt accggatacc tgtccgcctt tctcccttcg ggaagcgtgg    3960
cgctttctca tagctcacgc tgtaggtatc tcagttcggt gtaggtcgtt cgctccaagc    4020
tgggctgtgt gcacgaaccc cccgttcagc ccgaccgctg cgccttatcc ggtaactatc    4080
gtcttgagtc aacccggta agacacgact tatcgccact ggcagcagcc actggtaaca    4140
ggattagcag agcgaggtat gtaggcggtg ctacagagtt cttgaagtgg tggcctaact    4200
acggctacac tagaaggaca gtatttggta tctgcgctct gctgaagcca gttaccttcg    4260
gaaaaagagt tggtagctct tgatccggca aacaaaccac cgctggtagc ggtggttttt    4320
```

-continued

```
ttgtttgcaa gcagcagatt acgcgcagaa aaaaggatc tcaagaagat cctttgatct      4380
tttctacggg gtctgacgct cagtggaacg aaaactcacg ttaagggatt ttggtcatga      4440
gattatcaaa aaggatcttc acctagatcc ttttaaatta aaaatgaagt tttaaatcaa      4500
tctaaagtat atatgagtaa acttggtctg acagttacca atgcttaatc agtgaggcac      4560
ctatctcagc gatctgtcta tttcgttcat ccatagttgc ctgactcccc gtcgtgtaga      4620
taactacgat acgggagggc ttaccatctg gccccagtgc tgcaatgata ccgcgagacc      4680
cacgctcacc ggctccagat ttatcagcaa taaaccagcc agccggaagg gccgagcgca      4740
gaagtggtcc tgcaacttta tccgcctcca tccagtctat taattgttgc cgggaagcta      4800
gagtaagtag ttcgccagtt aatagtttgc gcaacgttgt tgccattgct acaggcatcg      4860
tggtgtcacg ctcgtcgttt ggtatggctt cattcagctc cggttcccaa cgatcaaggc      4920
gagttacatg atcccccatg ttgtgcaaaa aagcggttag ctccttcggt cctccgatcg      4980
ttgtcagaag taagttggcc gcagtgttat cactcatggt tatggcagca ctgcataatt      5040
ctcttactgt catgccatcc gtaagatgct tttctgtgac tggtgagtac tcaaccaagt      5100
cattctgaga atagtgtatg cggcgaccga gttgctcttg cccggcgtca atacgggata      5160
ataccgcgcc acatagcaga actttaaaag tgctcatcat tggaaaacgt tcttcggggc      5220
gaaaactctc aaggatctta ccgctgttga gatccagttc gatgtaaccc actcgtgcac      5280
ccaactgatc ttcagcatct tttactttca ccagcgtttc tgggtgagca aaaacaggaa      5340
ggcaaaatgc cgcaaaaaag ggaataaggg cgacacggaa atgttgaata ctcatactct      5400 tccttttca atattattga agcatttatc agggttattg tctcatgagc ggatacatat      5460
ttgaatgtat ttagaaaaat aaacaaatag gggttccgcg cacatttccc cgaaaagtgc      5520
cac                                                                    5523
```

<210> SEQ ID NO 45
<211> LENGTH: 6984
<212> TYPE: DNA
<213> ORGANISM: Artificial Sequence
<220> FEATURE:
<223> OTHER INFORMATION: Description of Artificial Sequence:
    pBXP3-DsRed-orf sequence

<400> SEQUENCE: 45

```
tagttattaa tagtaatcaa ttacggggtc attagttcat agcccatata tggagttccg       60
cgttacataa cttacggtaa atggcccgcc tggctgaccg cccaacgacc cccgcccatt      120
gacgtcaata atgacgtatg ttcccatagt aacgccaata gggactttcc attgacgtca      180
atgggtggag tatttacggt aaactgccca cttggcagta catcaagtgt atcatatgcc      240
aagtacgccc cctattgacg tcaatgacgg taaatggccc gcctggcatt atgcccagta      300
catgacctta tgggactttc ctacttggca gtacatctac gtattagtca tcgctattac      360
catggtgatg cggttttggc agtacatcaa tgggcgtgga tagcggtttg actcacgggg      420
atttccaagt ctccacccca ttgacgtcaa tgggagtttg ttttggcacc aaaatcaacg      480
ggactttcca aaatgtcgta acaactccgc cccattgacg caaatgggcg gtaggcgtgt      540
acggtgggag gtctatataa gcagagctgg tttagtgaac cgtcagatcc gctagcgcta      600
ccggactcag atcctatata ataaaatggg tagttctta gacgatgagc atatcctctc      660
tgctcttctg caaagcgatg acgagcttgt tggtgaggat tctgcacgtg aaatatcaga      720
tcacgtaagt gaagatgacg tccagagcga tacagaagaa gcgtttatag atgaggtaca      780
```

-continued

```
tgaagtgcag ccaacgtcaa gcggtagtga aatattagac gaacaaaatg ttattgaaca      840
accaggttct tcattggctt ctaacagaat cttgaccttg ccacagagga ctattagagg      900
taagaataaa cattgttggt caacttcaaa gtccacgagg cgtagccgag tctctgcact      960
gaacattgtc agatctcaaa gaggtccgac gcgtatgtgc cgcaatatat atgacccact     1020
tttatgcttc aaactatttt ttactgatga gataatttcg gaaattgtaa aatggacaaa     1080
tgctgagata tcattgaaac gtcgggaatc tatgacaggt gctacatttc gtgacacgaa     1140
tgaagatgaa atctatgctt tctttggtat tctggtaatg acagcagtga gaaaagataa     1200
ccacatgtcc acagatgacc tctttgatcg atctttgtca atggtgtacg tctctgtaat     1260
gagtcgtgat cgttttgatt ttttgatacg atgtcttaga atggatgaca aaagtatacg     1320
gcccacactt cgagaaaacg atgtatttac tcctgttaga aaaatatggg atctctttat     1380
ccatcagtgc atacaaaatt acactccagg ggctcatttg accatagatg aacagttact     1440
tggttttaga ggacggtgtc cgtttaggat gtatatccca aacaagccaa gtaagtatgg     1500
aataaaaatc ctcatgatgt gtgacagtgg tacgaagtat atgataaatg gaatgcctta     1560
tttgggaaga ggaacacaga ccaacggagt accactcggt gaatactacg tgaaggagtt     1620
atcaaagcct gtgcacggta gttgtcgtaa tattacgtgt gacaattggt tcacctcaat     1680
ccctttggca aaaaacttac tacaagaacc gtataagtta accattgtgg gaaccgtgcg     1740
atcaaacaaa cgcgagatac cggaagtact gaaaaacagt cgctccaggc cagtgggaac     1800
atcgatgttt tgttttgacg gacccttac tctcgtctca tataaaccga agccagctaa     1860
gatggtatac ttattatcat cttgtgatga ggatgcttct atcaacgaaa gtaccggtaa     1920
accgcaaatg gttatgtatt ataatcaaac taaaggcgga gtggacacgc tagaccaaat     1980
gtgttctgtg atgacctgca gtaggaagac gaataggtgg cctatggcat tattgtacgg     2040
aatgataaac attgcctgca taaattcttt tattatatac agccataatg tcagtagcaa     2100
gggagaaaag gttcaaagtc gcaaaaaatt tatgagaaac ctttacatga gcctgacgtc     2160
atcgtttatg cgtaagcgtt tagaagctcc tactttgaag agatatttgc gcgataatat     2220
ctctaatatt ttgccaaatg aagtgcctgg tacatcagat gacagtactg aagagccagt     2280
aatgaaaaaa cgtacttact gtacttactg cccctctaaa ataaggcgaa aggcaaatgc     2340
atcgtgcaaa aaatgcaaaa aagttatttg tcgagagcat aatattgata tgtgccaaag     2400
ttgtttctga ctgactaata agtataattt gtttctatta tgtataagtt aagctaatta     2460
cttattttat aatacaacat gactgttttt aaagtacaaa ataagtttat ttttgtaaaa     2520
gagagaatgt ttaaaagttt tgttacttta gaagaaattt tgagtttttg ttttttttta     2580
ataaataaat aaacataaat aaattgtttg ttgaatttgg atctcgaggt tcccacaatg     2640
gttaattcga gctcgcccgg ggatctaatt caattagaga ctaattcaat tagagctaat     2700
tcaattagga tccaagctta tcgatttcga accctcgacc gccggagtat aaatagaggc     2760
gcttcgtcta cggagcgaca attcaattca acaagcaaa gtgaacacgt cgctaagcga     2820
aagctaagca aataaacaag cgcagctgaa caagctaaac aatcgggta ccgctagagt     2880 cgacggtacc gcgggcccgg gatccaccgg tcgccaccat gaattctgca gtcgacggta     2940
ccgcgggccc gggatccacc ggtcgccacc atggtgcgct cctccaagaa cgtcatcaag     3000
gagttcatgc gcttcaaggt gcgcatggag ggcaccgtga acggccacga gttcgagatc     3060
gagggcgagg gcgagggccg cccctacgag ggcacaaaca ccgtgaagct gaaggtgacc     3120
aagggcggcc ccctgccctt cgcctgggac atcctgtccc ccagttcca gtacggctcc     3180
```

-continued

```
aaggtgtacg tgaagcaccc cgccgacatc cccgactaca agaagctgtc cttccccgag    3240
ggcttcaagt gggagcgcgt gatgaacttc gaggacggcg gcgtggtgac cgtgacccag    3300
gactcctccc tgcaggacgg ctgcttcatc tacaaggtga agttcatcgg cgtgaacttc    3360
ccctccgacg gccccgtaat gcagaagaag accatgggct gggaggcctc caccgagcgc    3420 ctgtacccccc gcgacggcgt gctgaagggc gagatccaca aggccctgaa gctgaaggac    3480
ggcggccact acctggtgga gttcaagtcc atctacatgg ccaagaagcc cgtgcagctg    3540
cccggctact actacgtgga ctccaagctg acatcaccct cccacaacga ggactacacc    3600
atcgtggagc agtacgagcg caccgagggc cgccaccacc tgttcctgta gcggccgcga    3660
ctctagatca taatcagcca taccacattt gtagaggttt tacttgcttt aaaaaacctc    3720
ccacacctcc ccctgaacct gaaacataaa atgaatgcaa ttgttgttgt taacttgttt    3780
attgcagctt ataatggtta caaataaagc aatagcatca caatttcac aaataaagca    3840 ttttttttcac tgcattctag ttgtggtttg tccaaactca tcaatgtatc ttaaggcgta    3900
aattgtaagc gttaatattt tgttaaaatt cgcgttaaat ttttgttaaa tcagctcatt    3960
ttttaaccaa taggccgaaa tcggcaaaat cccttataaa tcaaagaat agaccgagat    4020 agggttgagt gttgttccag tttggaacaa gagtccacta ttaaagaacg tggactccaa    4080
cgtcaaaggg cgaaaaaccg tctatcaggg cgatggccca ctacgtgaac catcacccta    4140
atcaagtttt tgggtcga ggtgccgtaa agcactaaat cggaaccta aagggagccc    4200 ccgatttaga gcttgacggg gaaagccggc gaacgtggcg agaaaggaag ggaagaaagc    4260
gaaaggagcg ggcgctaggg cgctggcaag tgtagcggtc acgctgcgcg taaccaccac    4320
acccgccgcg cttaatgcgc cgctacaggg cgcgtcaggt ggcactttc ggggaaatgt    4380 gcgcggaacc cctatttgtt tatttttcta aatacattca aatatgtatc cgctcatgag    4440
acaataaccc tgataaatgc ttcaataata ttgaaaaagg aagagtcctg aggcggaaag    4500
aaccagctgt ggaatgtgtg tcagttaggg tgtggaaagt ccccaggctc cccagcaggc    4560
agaagtatgc aaagcatgca tctcaattag tcagcaacca ggtgtggaaa gtccccaggc    4620
tccccagcag gcagaagtat gcaaagcatg catctcaatt agtcagcaac catagtcccg    4680
cccctaactc cgcccatccc gcccctaact ccgcccagtt ccgcccattc tccgccccat    4740
ggctgactaa ttttttttat ttatgcagag gccgaggccg cctcggcctc tgagctattc    4800
cagaagtagt gaggaggctt ttttggaggc ctaggctttt gcaaagatcg atcaagagac    4860
aggatgagga tcgtttcgca tgattgaaca agatggattg cacgcaggtt ctccggccgc    4920
ttgggtggag aggctattcg gctatgactg gcacaacag acaatcggct gctctgatgc    4980
cgccgtgttc cggctgtcag cgcaggggcg cccggttctt tttgtcaaga ccgacctgtc    5040
cggtgccctg aatgaactgc aagacgagg agcgcggcta tcgtggctgg ccacgacggg    5100
cgttccttgc gcagctgtgc tcgacgttgt cactgaagcg ggaagggact ggctgctatt    5160
gggcgaagtg ccggggcagg atctcctgtc atctcacctt gctcctgccg agaaagtatc    5220
catcatggct gatgcaatgc ggcggctgca tacgcttgat ccggctacct gcccattcga    5280
ccaccaagcg aaacatcgca tcgagcgagc acgtactcgg atggaagccg gtcttgtcga    5340
tcaggatgat ctggacgaag agcatcaggg gctcgcgcca gccgaactgt tcgccaggct    5400
caaggcgagc atgcccgacg gcgaggatct cgtcgtgacc catggcgatg cctgcttgcc    5460
gaatatcatg gtggaaaatg gccgcttttc tggattcatc gactgtggcc ggctgggtgt    5520
```

| | |
|---|---:|
| ggcggaccgc tatcaggaca tagcgttggc tacccgtgat attgctgaag agcttggcgg | 5580 |
| cgaatgggct gaccgcttcc tcgtgcttta cggtatcgcc gctcccgatt cgcagcgcat | 5640 |
| cgccttctat cgccttcttg acgagttctt ctgagcggga ctctgggggtt cgaaatgacc | 5700 |
| gaccaagcga cgcccaacct gccatcacga gatttcgatt ccaccgccgc cttctatgaa | 5760 |
| aggtttgggct tcggaatcgt tttccgggac gccggctgga tgatcctcca gcgcggggat | 5820 |
| ctcatgctgg agttcttcgc ccaccctagg gggaggctaa ctgaaacacg aaggagaca | 5880 |
| ataccggaag gaacccgcgc tatgacggca ataaaaagac agaataaaac gcacggtgtt | 5940 |
| gggtcgtttg ttcataaacg cggggttcgg tcccagggcg ggcactctgt cgataccca | 6000 |
| ccgagacccc attggggcca atacgcccgc gtttcttcct tttccccacc ccaccccca | 6060 |
| agttcgggtg aaggcccagg gctcgcagcc aacgtcgggg cggcaggccc tgccatagcc | 6120 |
| tcaggttact catatatact ttagattgat ttaaaacttc attttaatt taaaaggatc | 6180 |
| taggtgaaga tccttttga taatctcatg accaaaatcc cttaacgtga gttttcgttc | 6240 |
| cactgagcgt cagaccccgt agaaaagatc aaaggatctt cttgagatcc ttttttctg | 6300 |
| cgcgtaatct gctgcttgca acaaaaaaa ccaccgctac cagcggtggt ttgtttgccg | 6360 |
| gatcaagagc taccaactct ttttccgaag gtaactggct tcagcagagc gcagatacca | 6420 |
| aatactgtcc ttctagtgta gccgtagtta ggccaccact tcaagaactc tgtagcaccg | 6480 |
| cctacatacc tcgctctgct aatcctgtta ccagtggctg ctgccagtgg cgataagtcg | 6540 |
| tgtcttaccg ggttggactc aagacgatag ttaccggata aggcgcagcg tcgggctga | 6600 |
| acgggggggtt cctgcacaca gcccagcttg gagcgaacga cctacaccga actgagatac | 6660 |
| ctacagcgtg agctatgaga aagcgccacg cttcccgaag ggagaaaggc ggacaggtat | 6720 |
| ccggtaagcg gcagggtcgg aacaggagag cgcacgaggg agcttccagg gggaaacgcc | 6780 |
| tggtatcttt atagtcctgt cgggtttcgc cacctctgac ttgagcgtcg atttttgtga | 6840 |
| tgctcgtcag gggggcggag cctatggaaa aacgccagca acgcggcctt tttacggttc | 6900 |
| ctggcctttt gctggccttt tgctcacatg ttctttcctg cgttatcccc tgattctgtg | 6960 |
| gataaccgta ttaccgccat gcat | 6984 |

<210> SEQ ID NO 46
<211> LENGTH: 4613
<212> TYPE: DNA
<213> ORGANISM: Artificial Sequence
<220> FEATURE:
<223> OTHER INFORMATION: Description of Artificial Sequence: pCRII-ITR
       sequence
<220> FEATURE:
<221> NAME/KEY: CDS
<222> LOCATION: (344)..(922)

<400> SEQUENCE: 46

| | |
|---|---:|
| agcgcccaat acgcaaaccg cctctccccg cgcgttggcc gattcattaa tgcagctggc | 60 |
| acgacaggtt tcccgactgg aaagcgggca gtgagcgcaa cgcaattaat gtgagttagc | 120 |
| tcactcatta ggcaccccag gctttacact ttatgcttcc ggctcgtatg ttgtgtggaa | 180 |
| ttgtgagcgg ataacaattt cacacaggaa acagctatga ccatgattac gccaagcttg | 240 |
| gtaccgagct cggatccact agtaacggcc gccagtgtgc tggaattcgg cttggatccc | 300 |
| atgcgtcaat tttacgcaga ctatctttct agggttaatc tag ctg cat cag gat | 355 |
| | Leu His Gln Asp |
| | 1 |
| cat atc gtc ggg tct ttt ttc cgg ctc agt cat cgc cca agc tgg cgc | 403 |

|  |  |
|---|---:|
| His Ile Val Gly Ser Phe Phe Arg Leu Ser His Arg Pro Ser Trp Arg<br>5                        10                   15                    20 |  |
| tat ctg ggc atc ggg gag gaa gaa gcc cgt gcc ttt tcc cgc gag gtt<br>Tyr Leu Gly Ile Gly Glu Glu Glu Ala Arg Ala Phe Ser Arg Glu Val<br>                      25                   30                   35 | 451 |
| gaa gcg gca tgg aaa gag ttt gcc gag gat gac tgc tgc tgc att gac<br>Glu Ala Ala Trp Lys Glu Phe Ala Glu Asp Asp Cys Cys Cys Ile Asp<br>                  40                   45                    50 | 499 |
| gtt gag cga aaa cgc acg ttt acc atg atg att cgg gaa ggt gtg gcc<br>Val Glu Arg Lys Arg Thr Phe Thr Met Met Ile Arg Glu Gly Val Ala<br>         55                   60                   65 | 547 |
| atg cac gcc ttt aac ggt gaa ctg ttc gtt cag gcc acc tgg gat acc<br>Met His Ala Phe Asn Gly Glu Leu Phe Val Gln Ala Thr Trp Asp Thr<br>     70                  75                   80 | 595 |
| agt tcg tcg cgg ctt ttc cgg aca cag ttc cgg atg gtc agc ccg aag<br>Ser Ser Ser Arg Leu Phe Arg Thr Gln Phe Arg Met Val Ser Pro Lys<br>85                    90                   95                 100 | 643 |
| cgc atc agc aac ccg aac aat acc ggc gac agc cgg aac tgc cgt gcc<br>Arg Ile Ser Asn Pro Asn Asn Thr Gly Asp Ser Arg Asn Cys Arg Ala<br>                   105                  110                115 | 691 |
| ggt gtg cag att aat gac agc ggt gcg gcg ctg gga tat tac gtc agc<br>Gly Val Gln Ile Asn Asp Ser Gly Ala Ala Leu Gly Tyr Tyr Val Ser<br>         120                   125                 130 | 739 |
| gag gac ggg tat cct ggc tgg atg ccg cag aaa tgg aca tgg ata ccc<br>Glu Asp Gly Tyr Pro Gly Trp Met Pro Gln Lys Trp Thr Trp Ile Pro<br>               135                  140                145 | 787 |
| cgt gag tta ccc ggc ggg cgc gcc tcg ttc att cac gtt ttt gaa ccc<br>Arg Glu Leu Pro Gly Gly Arg Ala Ser Phe Ile His Val Phe Glu Pro<br>150                    155                  160 | 835 |
| gtg gag gac ggg cag act cgc ggt gca aat gtg ttt tac agc gtg atg<br>Val Glu Asp Gly Gln Thr Arg Gly Ala Asn Val Phe Tyr Ser Val Met<br>165                      170                  175              180 | 883 |
| gag cag atg aag atg ctc gac acg ctg cag aac acg cag ctagattaac<br>Glu Gln Met Lys Met Leu Asp Thr Leu Gln Asn Thr Gln<br>               185                  190 | 932 |
| cctagaaaga taatcatatt gtgacgtacg ttaaagataa tcatgcgtaa aattgacgca | 992 |
| tgggatccaa gccgaattct gcagatatcc atcacactgg cggccgctcg agcatgcatc | 1052 |
| tagagggccc aattcgccct atagtgagtc gtattacaat tcactggccg tcgttttaca | 1112 |
| acgtcgtgac tgggaaaacc ctggcgttac ccaacttaat cgccttgcag cacatccccc | 1172 |
| tttcgccagc tggcgtaata gcgaagaggc ccgcaccgat cgcccttccc aacagttgcg | 1232 |
| cagcctgaat ggcgaatggg acgcgccctg tagcggcgca ttaagcgcgg cgggtgtggt | 1292 |
| ggttacgcgc agcgtgaccg ctacacttgc cagcgcccta gcgcccgctc ctttcgcttt | 1352 |
| cttcccttcc tttctcgcca cgttcgccgg ctttccccgt caagctctaa atcggggct | 1412 |
| cccttt aggg ttccgattta gagctttacg gcacctcgac cgcaaaaaac ttgatttggg | 1472 |
| tgatggttca cgtagtgggc catcgccctg atagacggtt tttcgccctt tgacgttgga | 1532 |
| gtccacgttc tttaatagtg gactcttgtt ccaaactgga acaacactca acctatcgc | 1592 |
| ggtctattct tttgatttat aagggatttt gccgatttcg gcctattggt taaaaatga | 1652 |
| gctgatttaa caaattcagg gcgcaagggc tgctaaagga accggaacac gtagaaagcc | 1712 |
| agtccgcaga aacggtgctg accccggatg aatgtcagct actgggctat ctggacaagg | 1772 |
| gaaaacgcaa gcgcaaagag aaagcaggta gcttgcagtg gcttacatg gcgatagcta | 1832 |
| gactgggcgg tttatggac agcaagcgaa ccggaattgc cagctgggc gccctctggt | 1892 |

```
aaggttggga agccctgcaa agtaaactgg atggctttct tgccgccaag gatctgatgg    1952 cgcagggat caagatctga tcaagagaca ggatgaggat cgtttcgcat gattgaacaa     2012
gatggattgc acgcaggttc tccggccgct tgggtggaga ggctattcgg ctatgactgg    2072
gcacaacaga caatcggctg ctctgatgcc gccgtgttcc ggctgtcagc gcaggggcgc    2132
ccggttcttt ttgtcaagac cgacctgtcc ggtgccctga atgaactgca ggacgaggca    2192
gcgcggctat cgtggctggc cacgacgggc gttccttgcg cagctgtgct cgacgttgtc    2252
actgaagcgg gaagggactg gctgctattg ggcgaagtgc cggggcagga tctcctgtca    2312
tctcgccttg ctcctgccga gaagtatcc atcatggctg atgcaatgcg gcggctgcat     2372
acgcttgatc cggctacctg cccattcgac caccaagcga acatcgcat cgagcgagca     2432 cgtactcgga tggaagccgg tcttgtcgat caggatgatc tggacgaaga gcatcagggg    2492
ctcgcgccag ccgaactgtt cgccaggctc aaggcgcgca tgcccgacgg cgaggatctc    2552
gtcgtgatcc atggcgatgc ctgcttgccg aatatcatgg tggaaaatgg ccgcttttct    2612
ggattcaacg actgtggccg gctgggtgtg gcggaccgct atcaggacat agcgttggat    2672
acccgtgata ttgctgaaga gcttggcggc gaatgggctg accgcttcct cgtgctttac    2732
ggtatcgccg ctcccgattc gcagcgcatc gccttctatc gccttcttga cgagttcttc    2792
tgaattgaaa aaggaagagt atgagtattc aacatttccg tgtcgccctt attcccttt    2852 ttgcggcatt ttgccttcct gttttgctc acccagaaac gctggtgaaa gtaaaagatg     2912
ctgaagatca gttgggtgca cgagtgggtt acatcgaact ggatctcaac agcggtaaga    2972
tccttgagag ttttcgcccc gaagaacgtt ttccaatgat gagcactttt aaagttctgc    3032
tatgtcatac actattatcc cgtattgacg ccgggcaaga gcaactcggt cgccgggcgc    3092
ggtattctca gaatgacttg gttgagtact caccagtcac agaaaagcat cttacggatg    3152
gcatgacagt aagagaatta tgcagtgctg ccataaccat gagtgataac actgcggcca    3212
acttacttct gacaacgatc ggaggaccga aggagctaac cgcttttttg cacaacatgg    3272
gggatcatgt aactcgcctt gatcgttggg aaccggagct gaatgaagcc ataccaaacg    3332
acgagagtga caccacgatg cctgtagcaa tgccaacaac gttgcgcaaa ctattaactg    3392
gcgaactact tactctagct tcccggcaac aattaataga ctggatggag gcggataaag    3452
ttgcaggacc acttctgcgc tcggcccttc cggctggctg gtttattgct gataaatctg    3512
gagccggtga gcgtgggtct cgcggtatca ttgcagcact ggggccagat ggtaagccct    3572
cccgtatcgt agttatctac acgacgggga gtcaggcaac tatggatgaa cgaaatagac    3632
agatcgctga gataggtgcc tcactgatta agcattggta actgtcagac caagtttact    3692
catatatact ttagattgat ttaaaacttc attttttaatt taaaaggatc taggtgaaga    3752
tcctttttga taatctcatg accaaaatcc cttaacgtga gttttcgttc cactgagcgt    3812
cagaccccgt agaaaagatc aaaggatctt cttgagatcc ttttttctg cgcgtaatct     3872 gctgcttgca acaaaaaaa ccaccgctac cagcggtggt ttgtttgccg gatcaagagc    3932
taccaactct ttttccgaag gtaactggct tcagcagagc gcagatacca atactgtcc     3992 ttctagtgta gccgtagtta ggccaccact tcaagaactc tgtagcaccg cctacatacc    4052
tcgctctgct aatcctgtta ccagtggctg ctgccagtgg cgataagtcg tgtcttaccg    4112
ggttggactc aagacgatag ttaccggata aggcgcagcg gtcgggctga acggggggtt    4172
cgtgcacaca gcccagcttg gagcgaacga cctacaccga actgagatac ctacagcgtg    4232
agcattgaga aagcgccacg cttcccgaag ggagaaaggc ggacaggtat ccggtaagcg    4292
```

-continued

```
gcagggtcgg aacaggagag cgcacgaggg agcttccagg gggaaacgcc tggtatctttt    4352 atagtcctgt cgggtttcgc cacctctgac ttgagcgtcg attttttgtga tgctcgtcag    4412 gggggcggag cctatggaaa aacgccagca acgcggcctt tttacggttc ctggccttt     4472 gctggccttt tgctcacatg ttctttcctg cgttatcccc tgattctgtg ataaccgta     4532 ttaccgcctt tgagtgagct gataccgctc gccgcagccg aacgaccgag cgcagcgagt    4592
cagtgagcga ggaagcggaa g                                               4613
```

<210> SEQ ID NO 47
<211> LENGTH: 193
<212> TYPE: PRT
<213> ORGANISM: Artificial Sequence
<220> FEATURE:
<223> OTHER INFORMATION: Description of Artificial Sequence: pCRII-ITR
      amino acid sequence

<400> SEQUENCE: 47

```
Leu His Gln Asp His Ile Val Gly Ser Phe Phe Arg Leu Ser His Arg
  1               5                  10                  15

Pro Ser Trp Arg Tyr Leu Gly Ile Gly Glu Glu Glu Ala Arg Ala Phe
             20                  25                  30

Ser Arg Glu Val Glu Ala Ala Trp Lys Glu Phe Ala Glu Asp Asp Cys
         35                  40                  45

Cys Cys Ile Asp Val Glu Arg Lys Arg Thr Phe Thr Met Met Ile Arg
     50                  55                  60

Glu Gly Val Ala Met His Ala Phe Asn Gly Glu Leu Phe Val Gln Ala
 65                  70                  75                  80

Thr Trp Asp Thr Ser Ser Arg Leu Phe Arg Thr Gln Phe Arg Met
                 85                  90                  95

Val Ser Pro Lys Arg Ile Ser Asn Pro Asn Asn Thr Gly Asp Ser Arg
            100                 105                 110

Asn Cys Arg Ala Gly Val Gln Ile Asn Asp Ser Gly Ala Ala Leu Gly
        115                 120                 125

Tyr Tyr Val Ser Glu Asp Gly Tyr Pro Gly Trp Met Pro Gln Lys Trp
    130                 135                 140

Thr Trp Ile Pro Arg Glu Leu Pro Gly Gly Arg Ala Ser Phe Ile His
145                 150                 155                 160

Val Phe Glu Pro Val Glu Asp Gly Gln Thr Arg Gly Ala Asn Val Phe
                165                 170                 175

Tyr Ser Val Met Glu Gln Met Lys Met Leu Asp Thr Leu Gln Asn Thr
            180                 185                 190

Gln
```

<210> SEQ ID NO 48
<211> LENGTH: 8999
<212> TYPE: DNA
<213> ORGANISM: Artificial Sequence
<220> FEATURE:
<223> OTHER INFORMATION: Description of Artificial Sequence:
      p(PZ)-Bac-EYFP sequence

<400> SEQUENCE: 48

```
accgaagtat acacttaaat tcagtgcacg tttgcttgtt gagaggaaag gttgtgtgcg     60
gacgaatttt ttttttgaaaa cattaaccct tacgtggaat aaaaaaaaat gaaatattgc   120 aaatttgct gcaaagctgt gactggagta aaattaattc acgtgccgaa gtgtgctatt    180
```

```
aagagaaaat tgtgggagca gagccttggg tgcagccttg gtgaaaactc ccaaatttgt    240
gatacccact ttaatgattc gcagtggaag gctgcacctg caaaaggtca gacatttaaa    300
aggaggcgac tcaacgcaga tgccgtacct agtaaagtga tagagcctga accagaaaag    360
ataaaagaag gctataccag tgggagtaca caaacagagt aagtttgaat agtaaaaaaa    420
atcatttatg taaacaataa cgtgactgtg cgttaggtcc tgttcattgt ttaatgaaaa    480
taagagcttg agggaaaaaa ttcgtacttt ggagtacgaa atgcgtcgtt tagagcagca    540
gccgaattca ctggccgtcg ttttacaacg tcgtgactgg gaaaaccctg gcgttaccca    600
acttaatcgc cttgcagcac atccccctt cgccagctgg cgtaatagcg aagaggcccg    660
caccgatcgc ccttcccaac agttgcgcag cctgaatggc gaatggcgct ttgcctggtt    720
tccggcacca gaagcggtgc cggaaagctg gctggagtgc gatcttcctg aggccgatac    780
tgtcgtcgtc ccctcaaact ggcagatgca cggttacgat gcgcccatct acaccaacgt    840
aacctatccc attacggtca atccgccgtt tgttcccacg gagaatccga cgggttgtta    900
ctcgctcaca tttaatgttg atgaaagctg gctacaggaa ggccagacgc gaattatttt    960
tgatggcgtt aactcggcgt ttcatctgtg gtgcaacggg cgctgggtcg gttacggcca    1020
ggacagtcgt ttgccgtctg aatttgacct gagcgcattt ttacgcgccg gagaaaaccg    1080
cctcgcggtg atggtgctgc gttggagtga cggcagttat ctggaagatc aggatatgtg    1140
gcggatgagc ggcattttcc gtgacgtctc gttgctgcat aaaccgacta cacaaatcag    1200
cgatttccat gttgccactc gctttaatga tgatttcagc cgcgctgtac tggaggctga    1260
agttcagatg tgcggcgagt tgcgtgacta cctacgggta acagtttctt tatggcaggg    1320
tgaaacgcag gtcgccagcg gcaccgcgcc tttcggcggt gaaattatcg atgagcgtgg    1380
tggttatgcc gatcgcgtca cactacgtct gaacgtcgaa acccgaaac tgtggagcgc    1440 cgaaatcccg aatctctatc gtgcggtggt tgaactgcac accgccgacg gcacgctgat    1500
tgaagcagaa gcctgcgatg tcggtttccg cgaggtgcgg attgaaaatg gtctgctgct    1560
gctgaacggc aagccgttgc tgattcgagg cgttaaccgt cacgagcatc atcctctgca    1620
tggtcaggtc atggatgagc agacgatggt gcaggatatc ctgctgatga gcagaacaa    1680 ctttaacgcc gtgcgctgtt cgcattatcc gaaccatccg ctgtggtaca cgctgtgcga    1740
ccgctacggc ctgtatgtgg tggatgaagc caatattgaa acccacgca tggtgccaat    1800 gaatcgtctg accgatgatc cgcgctggct accggcgatg agcgaacgcg taacgcgaat    1860
ggtgcagcgc gatcgtaatc acccgagtgt gatcatctgg tcgctgggga atgaatcagg    1920
ccacggcgct aatcacgacg cgctgtatcg ctggatcaaa tctgtcgatc cttcccgccc    1980
ggtgcagtat gaaggcggcg gagccgacac cacggccacc gatattattt gcccgatgta    2040
cgcgcgcgtg gatgaagacc agcccttccc ggctgtgccg aaatggtcca tcaaaaatg    2100 gctttcgcta cctggagaga cgcgcccgct gatcctttgc gaatacgccc acgcgatggg    2160
taacagtctt ggcggtttcg ctaaatactg gcaggcgttt cgtcagtatc ccgtttaca    2220 gggcggcttc gtctgggact gggtggatca gtcgctgatt aaatatgatg aaaacggcaa    2280
cccgtggtcg gcttacggcg gtgattttgg cgatacgccg aacgatcgcc agttctgtat    2340
gaacggtctg gtctttgccg accgcacgcc gcatccagcg ctgacggaag caaaacacca    2400
gcagcagttt ttccagttcc gtttatccgg gcaaaccatc gaagtgacca gcgaatacct    2460
gttccgtcat agcgataacg agctcctgca ctggatggtg gcgctggatg gtaagccgct    2520
ggcaagcggt gaagtgcctc tggatgtcgc tccacaaggt aaacagttga ttgaactgcc    2580
```

-continued

```
tgaactaccg cagccggaga gcgccgggca actctggctc acagtacgcg tagtgcaacc    2640
gaacgcgacc gcatggtcag aagccgggca catcagcgcc tggcagcagt ggcgtctggc    2700
ggaaaacctc agtgtgacgc tccccgccgc gtcccacgcc atcccgcatc tgaccaccag    2760
cgaaatggat ttttgcatcg agctgggtaa taagcgttgg caatttaacc gccagtcagg    2820 cttttctttca cagatgtgga ttggcgataa aaacaactg ctgacgccgc tgcgcgatca    2880
gttcacccgt gcaccgctgg ataacgacat tggcgtaagt gaagcgaccc gcattgaccc    2940
taacgcctgg gtcgaacgct ggaaggcggc gggccattac caggccgaag cagcgttgtt    3000
gcagtgcacg gcagatacac ttgctgatgc ggtgctgatt acgaccgctc acgcgtggca    3060
gcatcagggg aaaaccttat ttatcagccg aaaacctac cggattgatg gtagtggtca    3120
aatggcgatt accgttgatg ttgaagtggc gagcgataca ccgcatccgg cgcggattgg    3180
cctgaactgc cagctggcgc aggtagcaga gcggtaaac tggctcggat tagggccgca    3240
agaaaactat cccgaccgcc ttactgccgc ctgttttgac cgctgggatc tgccattgtc    3300
agacatgtat accccgtacg tcttcccgag cgaaaacggt ctgcgctgcg ggacgcgcga    3360
attgaattat ggcccacacc agtggcgcgg cgacttccag ttcaacatca gccgctacag    3420
tcaacagcaa ctgatggaaa ccagccatcg ccatctgctg cacgcggaag aaggcacatg    3480
gctgaatatc gacggtttcc atatggggat tggtggcgac gactcctgga gcccgtcagt    3540
atcggcggaa ttccagctga gcgccggtcg ctaccattac cagttggtct ggtgtcgggg    3600
atccgtcgac taaggccaaa gagtctaatt tttgttcatc aatgggttat aacatatggg    3660
ttatattata gtttgtttt aagtttttga gactgataag aatgtttcga tcgaatattc    3720
catagaacaa caatagtatt acctaattac caagtcttaa tttagcaaaa atgttattgc    3780
ttatagaaaa aataaattat ttatttgaaa tttaaagtca acttgtcatt taatgtcttg    3840 tagactttg aaagtcttac gatacaatta gtatctaata tacatgggtt cattctacat    3900
tctatattag tgatgatttc tttagctagt aatacatttt aattatattc ggctttgatg    3960
attttctgat ttttttccgaa cggatttttcg tagacccttt cgatctcata atggctcatt    4020
ttattgcgat ggacggtcag gagagctcca ctttgaatt tctgttcgca gacaccgcat    4080
ttgtagcaca tagccgggac atccggttttg gggagatttt ccagtctctg ttgcaattgg    4140
ttttcgggaa tgcgttgcag gcgcatacgc tctatatcct ccgaacggcg ctggttgacc    4200
ctagcattta cataaggatc agcagcaaaa tttgcctctg cttcattgcc cggaatcaca    4260
gcaatcagat gtcccttttcg gttacgatgg atattcaggt gcgaaccgca cacaaagctc    4320
tcgccgcaca ctccacactg atatggtcgc tcgccctgtg gcgccgcata tggatcttaa    4380
ggtcgttgga ctgcacaaag ctcttgctgc acattttgca ggagtacggc ctttgacccg    4440
tgtgcaatcg catgtgtcgc gccagcttgt tctgcgaaat aaacttcttg gagcagatgc    4500
ggccgcccgg ggtgggcgaa gaactccagc atgagatccc cgcgctggag gatcatccag    4560
ccggcgtccc ggaaaacgat tccgaagccc aacctttcat agaaggcggc ggtggaatcg    4620
aaatctcgtg atggcaggtt gggcgtcgct tggtcggtca tttcgaaccc cagagtcccg    4680
ctcagaagaa ctcgtcaaga aggcgataga aggcgatgcg ctgcgaatcg ggagcggcga    4740
taccgtaaag cacgaggaag cggtcagccc attcgccgcc aagctcttca gcaatatcac    4800
gggtagccaa cgctatgtcc tgatagcggt ccgccacacc cagccggcca cagtcgatga    4860
atccagaaaa gcggccattt tccaccatga tattcggcaa gcaggcatcg ccatgggtca    4920
```

```
cgacgagatc ctcgccgtcg ggcatgcgcg ccttgagcct ggcgaacagt tcggctggcg      4980
cgagcccctg atgctcttcg tccagatcat cctgatcgac aagaccggct tccatccgag      5040
tacgtgctcg ctcgatgcga tgtttcgctt ggtggtcgaa tgggcaggta gccggatcaa      5100
gcgtatgcag ccgccgcatt gcatcagcca tgatggatac tttctcggca ggagcaaggt      5160
gagatgacag gagatcctgc cccggcactt cgcccaatag cagccagtcc cttcccgctt      5220
cagtgacaac gtcgagcaca gctgcgcaag gaacgcccgt cgtggccagc cacgatagcc      5280
gcgctgcctc gtcctgcagt tcattcaggg caccggacag gtcggtcttg acaaaaagaa      5340
ccgggcgccc ctgcgctgac agccggaaca cggcggcatc agagcagccg attgtctgtt      5400
gtgcccagtc atagccgaat agcctctcca cccaagcggc cggagaacct gcgtgcaatc      5460
catcttgttc aatcatgcga aacgatcctc atcctgtctc ttgatcagat cttgatcccc      5520
tgcgccatca gatccttggc ggcaagaaag ccatccagtt tactttgcag ggcttcccaa      5580
ccttaccaga gggcgcccca gctggcaatt ccggttcgct tgctgtccat aaaaccgccc      5640
agtctagcta tcgccatgta agcccactgc aagctacctg ctttctcttt gcgcttgcgt      5700
tttcccttgt ccagatagcc cagtagctga cattcatccg gggtcagcac cgtttctgcg      5760
gactggcttt ctacgtgttc cgcttccttt agcagccctt gcgccctgag tgcttgcggc      5820
agcgtgaagc taattcatgg ttataaattt ttgttaaatc agctcatttt ttaaccaata      5880
ggccgaaatc ggcaaaatcc cttataaatc aaaagaatag cccgagatag ggttgagtgt      5940
tgttccagtt tggaacaaga gtccactatt aagaacgtg gactccaacg tcaaagggcg      6000
aaaaaccgtc tatcagggcg atggccggat cagcttatgc ggtgtgaaat accgcacaga      6060
tgcgtaagga gaaataccg catcaggcgc tcttccgctt cctcgctcac tgactcgctg      6120
cgctcggtcg ttcggctgcg gcgagcggta tcagctcact caaaggcggt aatacggtta      6180
tccacagaat caggggataa cgcaggaaag aacatgtgag caaaaggcca gcaaaaggcc      6240
aggaaccgta aaaaggccgc gttgctggcg ttttttccata ggctccgccc ccctgacgag      6300
catcacaaaa atcgacgctc aagtcagagg tggcgaaacc cgacaggact ataaagatac      6360
caggcgtttc ccccctggaag ctccctcgtg cgctctcctg ttccgaccct gccgcttacc      6420
ggatacctgt ccgcctttct cccttcggga agcgtggcgc tttctcatag ctcacgctgt      6480
aggtatctca gttcggtgta ggtcgttcgc tccaagctgg gctgtgtgca cgaaccccc      6540 gttcagcccg accgctgcgc cttatccggt aactatcgtc ttgagtccaa cccggtaaga      6600
cacgacttat cgccactggc agcagccact ggtaacagga ttagcagagc gaggtatgta      6660
ggcggtgcta cagagttctt gaagtggtgg cctaactacg gctacactag aaggacagta      6720
tttggtatct gcgctctgct gaagccagtt accttcggaa aaagagttgg tagctcttga      6780
tccggcaaac aaaccaccgc tggtagcggc ggttttttgt ttgcaagcag cagattacgc      6840
gcagaaaaaa aggatctcaa gaagatcctt tgatctttc ttactgaacg gtgatcccca      6900
ccggaattgc ggccgcggaa ttctcatgtt tgacagctta tcatcgataa gctggccgct      6960
ctagaactag tgttcccaca atggttaatt cgagctcgcc cggggatcta attcaattag      7020
agactaattc aattagagct aattcaatta ggatccaagc ttatcgattt cgaaccctcg      7080
accgccggag tataaataga ggcgcttcgt ctacggagcg acaattcaat tcaaacaagc      7140
aaagtgaaca cgtcgctaag cgaaagctaa gcaaataaac aagcgcagct gaacaagcta      7200
aacaatcggg gtaccgctag agtcgacggt acgatccacc ggtcgccacc atggtgagca      7260
agggcgagga gctgttcacc ggggtggtgc ccatcctggt cgagctggac ggcgacgtaa      7320
```

```
acggccacaa gttcagcgtg tccggcgagg gcgagggcga tgccacctac ggcaagctga      7380
ccctgaagtt catctgcacc accggcaagc tgcccgtgcc ctggcccacc ctcgtgacca      7440
ccttcggcta cggcctgcag tgcttcgccc gctaccccga ccacatgaag cagcacgact      7500
tcttcaagtc cgccatgccc gaaggctacg tccaggagcg caccatcttc ttcaaggacg      7560
acggcaacta caagacccgc gccgaggtga agttcgaggg cgacaccctg gtgaaccgca      7620
tcgagctgaa gggcatcgac ttcaaggagg acggcaacat cctggggcac aagctggagt      7680
acaactacaa cagccacaac gtctatatca tggccgacaa gcagaagaac ggcatcaagg      7740
tgaacttcaa gatccgccac aacatcgagg acggcagcgt gcagctcgcc gaccactacc      7800
agcagaacac ccccatcggc gacggccccg tgctgctgcc cgacaaccac tacctgagct      7860
accagtccgc cctgagcaaa gaccccaacg agaagcgcga tcacatggtc ctgctggagt      7920
tcgtgaccgc cgccgggatc actctcggca tggacgagct gtacaagtaa agcggccgcg      7980
actctagatc ataatcagcc ataccacatt tgtagaggtt ttacttgctt taaaaaacct      8040
cccacacctc cccctgaacc tgaaacataa aatgaatgca attgttgttg ttaacttgtt      8100
tattgcagct tataatggtt acaaataaag caatagcatc acaaatttca caaataaagc      8160 attttttttca ctgcattcta gttgtggttt gtccaaactc atcaatgtat cttaaagctt      8220
atcgatacgc gtacggcact agtggatccc atgcgtcaat tttacgcatg attatcttta      8280
acgtacgtca caatatgatt atctttctag ggttaatcta gctgcgtgtt ctgcagcgtg      8340
tcgagcatct tcatctgctc catcacgctg taaaacacat ttgcaccgcg agtctgcccg      8400
tcctccacgg gttcaaaaac gtgaatgaac gaggcgcgcc cgccgggtaa ctcacggggt      8460
atccatgtcc atttctgcgg catccagcca ggatacccgt cctcgctgac gtaatatccc      8520
agcgccgcac cgctgtcatt aatctgcaca ccggcacggc agttccggct gtcgccggta      8580
ttgttcgggt tgctgatgcg cttcgggctg accatccgga actgtgtccg gaaaagccgc      8640
gacgaactgg tatcccaggt ggcctgaacg aacagttcac cgttaaaggc gtgcatggcc      8700
acaccttccc gaatcatcat ggtaaacgtg cgttttcgct caacgtcaat gcagcagcag      8760
tcatcctcgg caaactcttt ccatgccgct tcaacctcgc gggaaaaggc acgggcttct      8820
tcctccccga tgcccagata cgcgcagctt ggcgcgatgc tgagccggaa aaaagacccg      8880
acgatatgat cctgatgcag ctagattaac cctagaaaga tagtctgcgt aaaattgacg      8940
catgggatcc cccgggctgc aggaattcga tatcaagctt atcgataccg tcgaagctt       8999
```

<210> SEQ ID NO 49
<211> LENGTH: 9012
<212> TYPE: DNA
<213> ORGANISM: Artificial Sequence
<220> FEATURE:
<223> OTHER INFORMATION: Description of Artificial Sequence:
      p(PZ)-Bac-ECFP sequence

<400> SEQUENCE: 49

```
accgaagtat acacttaaat tcagtgcacg tttgcttgtt gagaggaaag gttgtgtgcg        60
gacgaatttt ttttttgaaaa cattaaccct tacgtggaat aaaaaaaaat gaaatattgc       120
aaattttgct gcaaagctgt gactggagta aaattaattc acgtgccgaa gtgtgctatt       180
aagagaaaat tgtgggagca gagccttggg tgcagccttg gtgaaaactc ccaaatttgt       240
gatacccact ttaatgattc gcagtggaag gctgcacctg caaaaggtca gacatttaaa       300
aggaggcgac tcaacgcaga tgccgtacct agtaaagtga tagagcctga accagaaaag       360
```

-continued

```
ataaaagaag gctataccag tgggagtaca caaacagagt aagtttgaat agtaaaaaaa      420
atcatttatg taaacaataa cgtgactgtg cgttaggtcc tgttcattgt ttaatgaaaa      480
taagagcttg agggaaaaaa ttcgtacttt ggagtacgaa atgcgtcgtt tagagcagca      540
gccgaattca ctggccgtcg ttttacaacg tcgtgactgg gaaaaccctg gcgttaccca      600
acttaatcgc cttgcagcac atccccgttt cgccagctgg cgtaatagcg aagaggcccg      660
caccgatcgc ccttcccaac agttgcgcag cctgaatggc gaatggcgct ttgcctggtt      720
tccggcacca gaagcggtgc cggaaagctg gctggagtgc gatcttcctg aggccgatac      780
tgtcgtcgtc ccctcaaact ggcagatgca cggttacgat gcgcccatct acaccaacgt      840
aacctatccc attacggtca atccgccgtt tgttcccacg gagaatccga cgggttgtta      900
ctcgctcaca tttaatgttg atgaaagctg gctacaggaa ggccagacgc gaattatttt      960
tgatggcgtt aactcggcgt ttcatctgtg gtgcaacggg cgctgggtcg ttacggccca     1020
ggacagtcgt ttgccgtctg aatttgacct gagcgcattt ttacgcgccg gagaaaaccg     1080
cctcgcggtg atggtgctgc gttggagtga cggcagttat ctggaagatc aggatatgtg     1140
gcggatgagc ggcattttcc gtgacgtctc gttgctgcat aaaccgacta cacaaatcag     1200
cgatttccat gttgccactc gctttaatga tgatttcagc cgcgctgtac tggaggctga     1260
agttcagatg tgcggcgagt tgcgtgacta cctacgggta acagtttctt tatggcaggg     1320
tgaaacgcag gtcgccagcg gcaccgcgcc tttcggcggt gaaattatcg atgagcgtgg     1380
tggttatgcc gatcgcgtca cactacgtct gaacgtcgaa acccgaaac tgtggagcgc     1440 cgaaatcccg aatctctatc gtgcggtggt tgaactgcac accgccgacg gcacgctgat     1500
tgaagcagaa gcctgcgatg tcggtttccg cgaggtgcgg attgaaaatg gtctgctgct     1560
gctgaacggc aagccgttgc tgattcgagg cgttaaccgt cacgagcatc atcctctgca     1620
tggtcaggtc atggatgagc agacgatggt gcaggatatc ctgctgatga agcagaacaa     1680
ctttaacgcc gtgcgctgtt cgcattatcc gaaccatccg ctgtggtaca cgctgtgcga     1740
ccgctacggc ctgtatgtgg tggatgaagc caatattgaa acccacggca tggtgccaat     1800
gaatcgtctg accgatgatc cgcgctggct accggcgatg agcgaacgcg taacgcgaat     1860
ggtgcagcgc gatcgtaatc acccgagtgt gatcatctgg tcgctgggga atgaatcagg     1920
ccacggcgct aatcacgacg cgctgtatcg ctggatcaaa tctgtcgatc cttcccgccc     1980
ggtgcagtat gaaggcggcg gagccgacac cacggccacc gatattattt gcccgatgta     2040
cgcgcgcgtg gatgaagacc agcccttccc ggctgtgccg aaatggtcca tcaaaaaatg     2100
gctttcgcta cctggagaga cgcgcccgct gatcctttgc gaatacgccc acgcgatggg     2160
taacagtctt ggcggtttcg ctaaatactg gcaggcgttt cgtcagtatc ccgtttaca     2220 gggcggcttc gtctgggact gggtggatca gtcgctgatt aaatatgatg aaaacggcaa     2280
cccgtggtcg gcttacggcg gtgattttgg cgatacgccg aacgatcgcc agttctgtat     2340
gaacggtctg gtctttgccg accgcacgcc gcatccagcg ctgacggaag caaaacacca     2400
gcagcagttt ttccagttcc gtttatccgg gcaaaccatc gaagtgacca gcgaatacct     2460
gttccgtcat agcgataacg agctcctgca ctggatggtg gcgctggatg gtaagccgct     2520
ggcaagcggt gaagtgcctc tggatgtcgc tccacaaggt aaacagttga ttgaactgcc     2580
tgaactaccg cagccggaga gcgccgggca actctggctc acagtacgcg tagtgcaacc     2640
gaacgcgacc gcatggtcag aagccgggca catcagcgcc tggcagcagt ggcgtctggc     2700
```

```
ggaaaacctc agtgtgacgc tccccgccgc gtcccacgcc atcccgcatc tgaccaccag   2760
cgaaatggat ttttgcatcg agctgggtaa taagcgttgg caatttaacc gccagtcagg   2820
cttctcttca cagatgtgga ttggcgataa aaacaactg ctgacgccgc tgcgcgatca    2880
gttcacccgt gcaccgctgg ataacgacat tggcgtaagt gaagcgaccc gcattgaccc   2940
taacgcctgg gtcgaacgct ggaaggcggg gggccattac caggccgaag cagcgttgtt   3000
gcagtgcacg gcagatacac ttgctgatgc ggtgctgatt acgaccgctc acgcgtggca   3060
gcatcagggg aaaaccttat ttatcagccg gaaaacctac cggattgatg gtagtggtca   3120
aatggcgatt accgttgatg ttgaagtggc gagcgataca ccgcatccgg cgcggattgg   3180
cctgaactgc cagctggcgc aggtagcaga gcgggtaaac tggctcggat tagggccgca   3240
agaaaactat cccgaccgcc ttactgccgc ctgttttgac cgctgggatc tgccattgtc   3300
agacatgtat accccgtacg tcttcccgag cgaaaacggt ctgcgctgcg gacgcgcga    3360 attgaattat ggcccacacc agtggcgcgg cgacttccag ttcaacatca gccgctacag   3420
tcaacagcaa ctgatggaaa ccagccatcg ccatctgctg cacgcggaag aaggcacatg   3480
gctgaatatc gacggtttcc atatggggat tggtggcgac gactcctgga gcccgtcagt   3540
atcggcggaa ttccagctga gcgccggtcg ctaccattac cagttggtct ggtgtcgggg   3600
atccgtcgac taaggccaaa gagtctaatt tttgttcatc aatgggttat aacatatggg   3660
ttatattata agtttgtttt aagtttttga gactgataag aatgtttcga tcgaatattc   3720
catagaacaa caatagtatt acctaattac caagtcttaa tttagcaaaa atgttattgc   3780
ttatagaaaa aataaattat ttatttgaaa tttaaagtca acttgtcatt taatgtcttg   3840
tagacttttg aaagtcttac gatacaatta gtatctaata tacatgggtt cattctacat   3900
tctatattag tgatgatttc tttagctagt aatacatttt aattatattc ggctttgatg   3960
attttctgat tttttccgaa cggatttttcg tagacccttt cgatctcata atggctcatt   4020
ttattgcgat ggacggtcag gagagctcca cttttgaatt tctgttcgca gacaccgcat   4080
ttgtagcaca tagccgggac atccggtttg gggagatttt ccagtctctg ttgcaattgg   4140
ttttcgggaa tgcgttgcag gcgcatacgc tctatatcct ccgaacggcg ctggttgacc   4200
ctagcattta cataaggatc agcagcaaaa tttgcctctg cttcattgcc cggaatcaca   4260
gcaatcagat gtccctttcg gttacgatgg atattcaggt gcgaaccgca cacaaagctc   4320
tcgccgcaca ctccacactg atatggtcgc tcgccctgtg gcgccgcata tggatcttaa   4380
ggtcgttgga ctgcacaaag ctcttgctgc acattttgca ggagtacggc cttgacccg    4440 tgtgcaatcg catgtgtcgc gccagcttgt tctgcgaaat aaacttcttg gagcagatgc   4500
ggccgcccgg ggtgggcgaa gaactccagc atgagatccc cgcgctggag gatcatccag   4560
ccggcgtccc ggaaaacgat tccgaagccc aacctttcat agaaggcggc ggtggaatcg   4620
aaatctcgtg atggcaggtt gggcgtcgct tggtcgtca tttcgaaccc cagagtcccg     4680
ctcagaagaa ctcgtcaaga aggcgataga aggcgatgcg ctgcgaatcg ggagcggcga   4740
taccgtaaag cacgaggaag cggtcagccc attcgccgcc aagctcttca gcaatatcac   4800
gggtagccaa cgctatgtcc tgatagcggt ccgccacacc cagccggcca cagtcgatga   4860
atcgagaaaa gcgccatttt ccaccatga tattcggcaa gcaggcatcg ccatgggtca   4920
cgacgagatc ctcgccgtcg gcatgcgcg ccttgagcct ggcgaacagt tcggctggcg   4980 cgagccctg atgctcttcg tccagatcat cctgatcgac aagaccggct tccatccgag   5040
tacgtgctcg ctcgatgcga tgtttcgctt ggtggtcgaa tgggcaggta gccggatcaa   5100
```

-continued

```
gcgtatgcag ccgccgcatt gcatcagcca tgatggatac tttctcggca ggagcaaggt      5160
gagatgacag gagatcctgc cccggcactt cgcccaatag cagccagtcc cttcccgctt      5220
cagtgacaac gtcgagcaca gctgcgcaag gaacgcccgt cgtggccagc cacgatagcc      5280
gcgctgcctc gtcctgcagt tcattcaggg caccggacag gtcggtcttg acaaaaagaa      5340
ccgggcgccc ctgcgctgac agccggaaca cggcggcatc agagcagccg attgtctgtt      5400
gtgcccagtc atagccgaat agcctctcca cccaagcggc cggagaacct gcgtgcaatc      5460
catcttgttc aatcatgcga aacgatcctc atcctgtctc ttgatcagat cttgatcccc      5520
tgcgccatca gatccttggc ggcaagaaag ccatccagtt tactttgcag ggcttcccaa      5580
ccttaccaga gggcgcccca gctggcaatt ccggttcgct tgctgtccat aaaaccgccc      5640
agtctagcta tcgccatgta agcccactgc aagctacctg ctttctcttt gcgcttgcgt      5700
tttcccttgt ccagatagcc cagtagctga cattcatccg gggtcagcac cgtttctgcg      5760
gactggcttt ctacgtgttc cgcttccttt agcagcccct gcgccctgag tgcttgcggc      5820
agcgtgaagc taattcatgg ttataaattt ttgttaaatc agctcatttt ttaaccaata      5880
ggccgaaatc ggcaaaatcc cttataaatc aaaagaatag cccgagatag ggttgagtgt      5940
tgttccagtt tggaacaaga gtccactatt aaagaacgtg gactccaacg tcaaagggcg      6000
aaaaaccgtc tatcagggcg atggccggat cagcttatgc ggtgtgaaat accgcacaga      6060
tgcgtaagga gaaataccg catcaggcgc tcttccgctt cctcgctcac tgactcgctg      6120
cgctcggtcg ttcggctgcg gcgagcggta tcagctcact caaaggcggt aatacggtta      6180
tccacagaat caggggataa cgcaggaaag aacatgtgag caaaaggcca gcaaaaggcc      6240
aggaaccgta aaaaggccgc gttgctggcg ttttttccata ggctccgccc ccctgacgag      6300
catcacaaaa atcgacgctc aagtcagagg tggcgaaacc cgacaggact ataaagatac      6360
caggcgtttc cccctggaag ctccctcgtg cgctctcctg ttccgaccct gccgcttacc      6420
ggatacctgt ccgcctttct cccttcggga agcgtggcgc tttctcatag ctcacgctgt      6480
aggtatctca gttcggtgta ggtcgttcgc tccaagctgg gctgtgtgca cgaacccccc      6540
gttcagcccg accgctgcgc cttatccggt aactatcgtc ttgagtccaa cccggtaaga      6600
cacgacttat cgccactggc agcagccact ggtaacagga ttagcagagc gaggtatgta      6660
ggcggtgcta cagagttctt gaagtggtgg cctaactacg gctacactag aaggacagta      6720
tttggtatct gcgctctgct gaagccagtt accttcggaa aaagagttgg tagctcttga      6780
tccggcaaac aaaccaccgc tggtagcggc ggttttttgt ttgcaagcag cagattacgc      6840
gcagaaaaaa aggatctcaa gaagatcctt tgatcttttc ttactgaacg gtgatcccca      6900
ccggaattgc ggccgcggaa ttctcatgtt tgacagctta tcatcgataa gctggccgct      6960
ctagaactag tgttcccaca atggttaatt cgagctcgcc cggggatcta attcaattag      7020
agactaattc aattagagct aattcaatta ggatccaagc ttatcgattt cgaaccctcg      7080
accgccggag tataaataga ggcgcttcgt ctacggagcg acaattcaat tcaaacaagc      7140
aaagtgaaca cgtcgctaag cgaaagctaa gcaaataaac aagcgcagct gaacaagcta      7200
aacaatcggg gtaccgctag agtcgacggt acgatccacc ggtcgccacc atggtgagca      7260
agggcgagga gctgttcacc ggggtggtgc ccatcctggt cgagctggac ggcgacgtaa      7320
acggccacaa gttcagcgtg tccggcgagg gcgagggcga tgccacctac ggcaagctga      7380 cccctgaagtt catctgcacc accggcaagc tgcccgtgcc ctggcccacc ctcgtgacca      7440
```

-continued

```
ccctgacctg gggcgtgcag tgcttcagcc gctaccccga ccacatgaag cagcacgact      7500
tcttcaagtc cgccatgccc gaaggctacg tccaggagcg caccatcttc ttcaaggacg      7560
acggcaacta caagacccgc gccgaggtga agttcgaggg cgacaccctg gtgaaccgca      7620
tcgagctgaa gggcatcgac ttcaaggagg acggcaacat cctggggcac aagctggagt      7680
acaactagat cagccacaac gtctatatca ccgccgacaa gcagaagaac ggcatcaagg      7740
ccaacttcaa gatccgccac aacatcgagg acggcagcgt gcagctcgcc gaccactacc      7800
agcagaacac ccccatcggc gacggccccg tgctgctgcc cgacaaccac tacctgagca      7860
cccagtccgc cctgagcaaa gaccccaacg agaagcgcga tcacatggtc ctgctggagt      7920
tcgtgaccgc cgccgggatc actctcggca tggacgagct gtacaagtaa agcggccgcg      7980
actctagatc ataatcagcc ataccacatt tgtagaggtt ttacttgctt taaaaaacct      8040
cccacacctc cccctgaacc tgaaacataa aatgaatgca attgttgttg ttaacttgtt      8100
tattgcagct tataatggtt acaaataaag caatagcatc acaaatttca caaataaagc      8160
atttttttca ctgcattcta gttgtggttt gtccaaactc atcaatgtat cttaaagctt      8220
atcgatacgc gtacggcgcg cctaggccgg ccgattggat cccatgcgtc aattttacgc      8280
atgattatct ttaacgtacg tcacaatatg attatctttc tagggttaat ctagctgcgt      8340
gttctgcagc gtgtcgagca tcttcatctg ctccatcacg ctgtaaaaca catttgcacc      8400
gcgagtctgc ccgtcctcca cgggttcaaa acgtgaatg aacgaggcgc gcccgccggg      8460
taactcacgg ggtatccatg tccatttctg cggcatccag ccaggatacc cgtcctcgct      8520
gacgtaatat cccagcgccg caccgctgtc attaatctgc acaccggcac ggcagttccg      8580
gctgtcgccg gtattgttcg ggttgctgat gcgcttcggg ctgaccatcc ggaactgtgt      8640
ccggaaaagc cgcgacgaac tggtatccca ggtggcctga cgaacagtt caccgttaaa      8700 ggcgtgcatg gccacacctt cccgaatcat catggtaaac gtgcgttttc gctcaacgtc      8760
aatgcagcag cagtcatcct cggcaaactc tttccatgcc gcttcaacct cgcgggaaaa      8820
ggcacgggct tcttcctccc cgatgccag atagcgccag cttgggcgat gactgagccg      8880
gaaaaaagac ccgacgatat gatcctgatg cagctagatt aaccctagaa agatagtctg      8940
cgtaaaattg acgcatggga tcccccgggc tgcaggaatt cgatatcaag cttatcgata      9000
ccgtcgaagc tt                                                         9012
```

<210> SEQ ID NO 50
<211> LENGTH: 9013
<212> TYPE: DNA
<213> ORGANISM: Artificial Sequence
<220> FEATURE:
<223> OTHER INFORMATION: Description of Artificial Sequence:
     p(PZ)-Bac-EGFP sequence

<400> SEQUENCE: 50

```
accgaagtat acacttaaat tcagtgcacg tttgcttgtt gagaggaaag gttgtgtgcg       60
gacgaatttt tttttgaaaa cattaacccc tacgtggaat aaaaaaaaat gaaatattgc      120 aaatttgct gcaaagctgt gactggagta aaattaattc acgtgccgaa gtgtgctatt      180
aagagaaaat tgtgggagca gagccttggg tgcagccttg gtgaaaactc ccaaatttgt      240
gatacccact ttaatgattc gcagtggaag gctgcacctg caaaaggtca gacatttaaa      300
aggaggcgac tcaacgcaga tgccgtacct agtaaagtga tagagcctga accagaaaag      360
ataaaagaag gctataccag tgggagtaca caaacagagt aagtttgaat agtaaaaaaa      420
```

-continued

| | |
|---|---|
| atcatttatg taaacaataa cgtgactgtg cgttaggtcc tgttcattgt taatgaaaa | 480 |
| taagagcttg agggaaaaaa ttcgtacttt ggagtacgaa atgcgtcgtt tagagcagca | 540 |
| gccgaattca ctggccgtcg ttttacaacg tcgtgactgg gaaaaccctg gcgttaccca | 600 |
| acttaatcgc cttgcagcac atccccttt cgccagctgc cgtaatagcg aagaggcccg | 660 |
| caccgatcgc ccttcccaac agttgcgcag cctgaatggc gaatggcgct ttgcctggtt | 720 |
| tccggcacca gaagcggtgc cggaaagctg gctggagtgc gatcttcctg aggccgatac | 780 |
| tgtcgtcgtc ccctcaaact ggcagatgca cggttacgat gcgcccatct acaccaacgt | 840 |
| aacctatccc attacggtca atccgccgtt tgttcccacg gagaatccga cgggttgtta | 900 |
| ctcgctcaca tttaatgttg atgaaagctg gctacaggaa ggccagacgc gaattatttt | 960 |
| tgatggcgtt aactcggcgt ttcatctgtg gtgcaacggg cgctgggtcg gttacggcca | 1020 |
| ggacagtcgt ttgccgtctg aatttgacct gagcgcattt ttacgcgccg gagaaaaccg | 1080 |
| cctcgcggtg atggtgctgc gttggagtga cggcagttat ctggaagatc aggatatgtg | 1140 |
| gcggatgagc ggcatttcc gtgacgtctc gttgctgcat aaaccgacta cacaaatcag | 1200 |
| cgatttccat gttgccactc gctttaatga tgatttcagc cgcgctgtac tggaggctga | 1260 |
| agttcagatg tgcggcgagt tgcgtgacta cctacgggta acagtttctt tatggcaggg | 1320 |
| tgaaacgcag gtcgccagcg gcaccgcgcc tttcggcggt gaaattatcg atgagcgtgg | 1380 |
| tggttatgcc gatcgcgtca cactacgtct gaacgtcgaa aacccgaaac tgtggagcgc | 1440 |
| cgaaatcccg aatctctatc gtgcggtggt tgaactgcac accgccgacg gcacgctgat | 1500 |
| tgaagcagaa gcctgcgatg tcggtttccg cgaggtgcgg attgaaaatg gtctgctgct | 1560 |
| gctgaacggc aagccgttgc tgattcgagg cgttaaccgt cacgagcatc atcctctgca | 1620 |
| tggtcaggtc atggatgagc agacgatggt gcaggatatc ctgctgatga agcagaacaa | 1680 |
| cttaacgcc gtgcgctgtt cgcattatcc gaaccatccg ctgtggtaca cgctgtgcga | 1740 |
| ccgctacggc ctgtatgtgg tggatgaagc caatattgaa acccacggca tggtgccaat | 1800 |
| gaatcgtctg accgatgatc cgcgctggct accggcgatg agcgaacgcg taacgcgaat | 1860 |
| ggtgcagcgc gatcgtaatc acccgagtgt gatcatctgg tcgctgggga atgaatcagg | 1920 |
| ccacggcgct aatcacgacg cgctgtatcg ctggatcaaa tctgtcgatc cttcccgccc | 1980 |
| ggtgcagtat gaaggcggcg gagccgacac cacggccacc gatattattt gcccgatgta | 2040 |
| cgcgcgcgtg gatgaagacc agcccttccc ggctgtgccg aaatggtcca tcaaaaaatg | 2100 |
| gctttcgcta cctggagaga cgcgcccgct gatcctttgc gaatacgccc acgcgatggg | 2160 |
| taacagtctt ggcggtttcg ctaaatactg gcaggcgttt cgtcagtatc cccgtttaca | 2220 |
| gggcggcttc gtctgggact gggtggatca gtcgctgatt aaatatgatg aaaacggcaa | 2280 |
| cccgtggtcg gcttacggcg gtgattttgg cgatacgccg aacgatcgcc agttctgtat | 2340 |
| gaacggtctg gtctttgccg accgcacgcc gcatccagcg ctgacggaag caaaacacca | 2400 |
| gcagcagttt ttccagttcc gtttatccgg gcaaaccatc gaagtgacca gcgaatacct | 2460 |
| gttccgtcat agcgataacg agctcctgca ctggatggtg gcgctggatg gtaagccgct | 2520 |
| ggcaagcggt gaagtgcctc tggatgtcgc tccacaaggt aaacagttga ttgaactgcc | 2580 |
| tgaactaccg cagccggaga gcgccgggca actctggctc acagtacgcg tagtgcaacc | 2640 |
| gaacgcgacc gcatggtcag aagccgggca catcagcgcc tggcagcagt ggcgtctggc | 2700 |
| ggaaaacctc agtgtgacgc tccccgccgc gtcccacgcc atcccgcatc tgaccaccag | 2760 |
| cgaaatggat ttttgcatcg agctgggtaa taagcgttgg caatttaacc gccagtcagg | 2820 |

```
ctttctttca cagatgtgga ttggcgataa aaacaactg ctgacgccgc tgcgcgatca      2880
gttcacccgt gcaccgctgg ataacgacat tggcgtaagt gaagcgaccc gcattgaccc      2940
taacgcctgg gtcgaacgct ggaaggcggc gggccattac caggccgaag cagcgttgtt      3000
gcagtgcacg gcagatacac ttgctgatgc ggtgctgatt acgaccgctc acgcgtggca      3060
gcatcagggg aaaaccttat ttatcagccg aaaacctac cggattgatg gtagtggtca      3120
aatggcgatt accgttgatg ttgaagtggc gagcgataca ccgcatccgg cgcggattgg      3180
cctgaactgc cagctggcgc aggtagcaga gcgggtaaac tggctcggat tagggccgca      3240
agaaaactat cccgaccgcc ttactgccgc ctgttttgac cgctgggatc tgccattgtc      3300
agacatgtat accccgtacg tcttcccgag cgaaaacggt ctgcgctgcg ggacgcgcga      3360
attgaattat ggcccacacc agtggcgcgg cgacttccag ttcaacatca gccgctacag      3420
tcaacagcaa ctgatggaaa ccagccatcg ccatctgctg cacgcggaag aaggcacatg      3480
gctgaatatc gacggtttcc atatggggat tggtggcgac gactcctgga gcccgtcagt      3540
atcggcggaa ttccagctga cgccggtcg ctaccattac cagttggtct ggtgtcgggg      3600
atccgtcgac taaggccaaa gagtctaatt tttgttcatc aatgggttat aacatatggg      3660
ttatattata agtttgtttt aagtttttga gactgataag aatgtttcga tcgaatattc      3720
catagaacaa caatagtatt acctaattac caagtcttaa tttagcaaaa atgtaattgc      3780
ttatagaaaa aataaattat ttatttgaaa tttaaagtca acttgtcatt taatgtcttg      3840
tagacttttg aaagtcttac gatacaatta gtatctaata tacatgggtt cattctacat      3900
tctatattag tgatgatttc tttagctagt aatacatttt aattatattc ggctttgatg      3960
attttctgat tttttccgaa cggatttccg tagacccttt cgatctcata atggctcatt      4020
ttattgcgat ggacggtcag gagagctcca cttttgaatt tctgttcgca gacaccgcat      4080
ttgtagcaca tagccgggac atccggtttg gggagatttt ccagtctctg ttgcaattgg      4140
ttttcgggaa tgcgttgcag gcgcatacgc tctatatcct ccgaacggcg ctggttgacc      4200
ctagcattta cataaggatc agcagcaaaa tttgcctctg cttcattgcc cggaatcaca      4260
gcaatcagat gtccctttcg gttacgatgg atattcaggt gcgaaccgca cacaaagctc      4320
tcgccgcaca ctccacactg atatggtcgc tcgccctgtg cgccgcata tggatcttaa      4380 ggtcgttgga ctgcacaaag ctcttgctgc acattttgca ggagtacggc ctttgacccg      4440
tgtgcaatcg catgtgtcgc gccagcttgt tctgcgaaat aaacttcttg gagcagatgc      4500
ggccgcccgg ggtgggcgaa gaactccagc atgagatccc cgcgctggag gatcatccag      4560
ccggcgtccc ggaaaacgat tccgaagccc aacctttcat agaaggcggc ggtggaatcg      4620
aaatctcgtg atggcaggtt gggcgtcgct tggtcggtca tttcgaaccc cagagtcccg      4680
ctcagaagaa ctcgtcaaga aggcgataga aggcgatgcg ctgcgaatcg ggagcggcga      4740
taccgtaaag cacgaggaag cggtcagccc attcgccgcc aagctcttca gcaatatcac      4800
gggtagccaa cgctatgtcc tgatagcggt ccgccacacc cagccggcca cagtcgatga      4860
atccagaaaa gcggccattt tccaccatga tattcggcaa gcaggcatcg ccatgggtca      4920
cgacgagatc ctcgccgtcg gcatgcgcgc ccttgagcct ggcgaacagt tcggctggcg      4980
cgagcccctg atgctcttcg tccagatcat cctgatcgac aagaccggct tccatccgag      5040
tacgtgctcg ctcgatgcga tgtttcgctt ggtggtcgaa tgggcaggta gccggatcaa      5100
gcgtatgcag ccgccgcatt gcatcagcca tgatggatac tttctcggca ggagcaaggt      5160
```

```
gagatgacag gagatcctgc cccggcactt cgcccaatag cagccagtcc cttcccgctt    5220
cagtgacaac gtcgagcaca gctgcgcaag gaacgcccgt cgtggccagc cacgatagcc    5280
gcgctgcctc gtcctgcagt tcattcaggg caccggacag gtcggtcttg acaaaaagaa    5340
ccgggcgccc ctgcgctgac agccggaaca cggcggcatc agagcagccg attgtctgtt    5400
gtgcccagtc atagccgaat agcctctcca cccaagcggc cggagaacct gcgtgcaatc    5460
catcttgttc aatcatgcga aacgatcctc atcctgtctc ttgatcagat cttgatcccc    5520
tgcgccatca gatccttggc ggcaagaaag ccatccagtt actttgcag ggcttcccaa     5580 ccttaccaga gggcgcccca gctggcaatt ccggttcgct tgctgtccat aaaaccgccc    5640
agtctagcta tcgccatgta agcccactgc aagctacctg ctttctcttt gcgcttgcgt    5700
tttcccttgt ccagatagcc cagtagctga cattcatccg gggtcagcac cgtttctgcg    5760
gactggcttt ctacgtgttc cgcttccttt agcagccctt gcgccctgag tgcttgcggc    5820
agcgtgaagc taattcatgg ttataaattt ttgttaaatc agctcatttt ttaaccaata    5880
ggccgaaatc ggcaaaatcc cttataaatc aaagaatag cccgagatag ggttgagtgt     5940
tgttccagtt tggaacaaga gtccactatt aagaacgtg gactccaacg tcaaagggcg      6000
aaaaaccgtc tatcagggcg atggccggat cagcttatgc ggtgtgaaat accgcacaga    6060
tgcgtaagga gaaataccg catcaggcgc tcttccgctt cctcgctcac tgactcgctg      6120
cgctcggtcg ttcggctgcg gcgagcggta tcagctcact caaaggcggt aatacggtta    6180
tccacagaat caggggataa cgcaggaaag aacatgtgag caaaaggcca gcaaaaggcc    6240
aggaaccgta aaaaggccgc gttgctggcg ttttttccata ggctccgccc cctgacgag     6300 catcacaaaa atcgacgctc aagtcagagg tggcgaaacc cgacaggact ataaagatac    6360
caggcgtttc cccctggaag ctccctcgtg cgctctcctg ttccgaccct gccgcttacc    6420
ggatacctgt ccgcctttct cccttcggga agcgtggcgc tttctcatag ctcacgctgt    6480
aggtatctca gttcggtgta ggtcgttcgc tccaagctgg gctgtgtgca cgaaccccc    6540 gttcagcccg accgctgcgc cttatccggt aactatcgtc ttgagtccaa cccggtaaga    6600
cacgacttat cgccactggc agcagccact ggtaacagga ttagcagagc gaggtatgta    6660
ggcggtgcta cagagttctt gaagtggtgg cctaactacg gctacactag aaggacagta    6720
tttggtatct gcgctctgct gaagccagtt accttcggaa aaagagttgg tagctcttga    6780
tccggcaaac aaaccaccgc tggtagcggc ggtttttgt ttgcaagcag cagattacgc       6840
gcagaaaaaa aggatctcaa gaagatcctt tgatctttc ttactgaacg gtgatcccca      6900
ccggaattgc ggccgcggaa ttctcatgtt tgacagctta tcatcgataa gctggccgct    6960
ctagaactag tgttcccaca atggttaatt cgagctcgcc cggggatcta attcaattag    7020
agactaattc aattagagct aattcaatta ggatccaagc ttatcgattt cgaaccctcg    7080
accgccggag tataaataga ggcgcttcgt ctacggagcg acaattcaat tcaaacaagc    7140
aaagtgaaca cgtcgctaag cgaaagctaa gcaaataaac aagcgcagct gaacaagcta    7200
aacaatcggg gtaccgctag agtcgacggt accgcgggcc cgggatccac cggtcgccac    7260
catggtgagc aagggcgagg agctgttcac cggggtggtg cccatcctgg tcgagctgga    7320
cggcgacgta aacggccaca agttcagcgt gtccggcgag ggcgagggcg atgccaccta    7380
cggcaagctg accctgaagt tcatctgcac caccggcaag ctgcccgtgc cctggcccac    7440
cctcgtgacc accctgacct acggcgtgca gtgcttcagc cgctacccg accacatgaa      7500 gcagcacgac ttcttcaagt ccgccatgcc cgaaggctac gtccaggagc gcaccatctt    7560
```

```
cttcaaggac gacggcaact acaagacccg cgccgaggtg aagttcgagg gcgacaccct    7620
ggtgaaccgc atcgagctga agggcatcga cttcaaggag gacggcaaca tcctggggca    7680
caagctggag tacaactaca acagccacaa cgtctatatc atggccgaca gcagaagaa     7740 cggcatcaag gtgaacttca agatccgcca caacatcgag gacggcagcg tgcagctcgc    7800
cgaccactac cagcagaaca cccccatcgg cgacggcccc gtgctgctgc ccgacaacca    7860
ctacctgagc acccagtccg ccctgagcaa agaccccaac gagaagcgcg atcacatggt    7920
cctgctggag ttcgtgaccg ccgccgggat cactctcggc atggacgagc tgtacaagta    7980
aagcggccgc gactctagat cataatcagc cataccacat ttgtagaggt tttacttgct    8040
ttaaaaaacc tcccacacct cccctgaac ctgaaacata aaatgaatgc aattgttgtt     8100
gttaacttgt ttattgcagc ttataatggt tacaaataaa gcaatagcat cacaaatttc    8160
acaaataaag catttttttc actgcattct agttgtggtt tgtccaaact catcaatgta    8220
tcttaaagct tatcgatacg cgtacggcgc gcctagtgga tcccatgcgt caatttacg     8280 catgattatc tttaacgtac gtcacaatat gattatcttt ctagggttaa tctagctgcg    8340
tgttctgcag cgtgtcgagc atcttcatct gctccatcac gctgtaaaac acatttgcac    8400
cgcgagtctg cccgtcctcc acgggttcaa aaacgtgaat gaacgaggcg cgcccgccgg    8460
gtaactcacg gggtatccat gtccatttct gcggcatcca gccaggatac ccgtcctcgc    8520
tgacgtaata tcccagcgcc gcaccgctgt cattaatctg cacaccggca cggcagttcc    8580
ggctgtcgcc ggtattgttc gggttgctga tgcgcttcgg gctgaccatc cggaactgtg    8640
tccggaaaag ccgcgacgaa ctggtatccc aggtggcctg aacgaacagt tcaccgttaa    8700
aggcgtgcat ggccacacct tcccgaatca tcatggtaaa cgtgcgtttt cgctcaacgt    8760
caatgcagca gcagtcatcc tcggcaaact cttttccatgc cgcttcaacc tcgcgggaaa    8820
aggcacgggc ttcttcctcc ccgatgccca gatagcgcca gcttgggcga tgactgagcc    8880
ggaaaaaaga cccgacgata tgatcctgat gcagctagat taaccctaga aagatagtct    8940
gcgtaaaatt gacgcatggg atccccgggg ctgcaggaat tcgatatcaa gcttatcgat    9000
accgtcgaag ctt                                                      9013
```

<210> SEQ ID NO 51
<211> LENGTH: 4951
<212> TYPE: DNA
<213> ORGANISM: Artificial Sequence
<220> FEATURE:
<223> OTHER INFORMATION: Description of Artificial Sequence:
    pXL-Bac-EYFP sequence

<400> SEQUENCE: 51

```
ctaaattgta agcgttaata ttttgttaaa attcgcgtta aatttttgtt aaatcagctc      60
attttttaac caataggccg aaatcggcaa aatcccttat aaatcaaaag aatagaccga    120
gatagggttg agtgttgttc cagtttggaa caagagtcca ctattaaaga acgtggactc    180
caacgtcaaa gggcgaaaaa ccgtctatca gggcgatggc ccactacgtg aaccatcacc    240
ctaatcaagt tttttggggt cgaggtgccg taaagcacta atcggaacc ctaaagggag     300 cccccgattt agagcttgac ggggaaagcc ggcgaacgtg gcgagaaagg aagggaagaa    360
agcgaaagga gcgggcgcta gggcgctggc aagtgtagcg gtcacgctgc gcgtaaccac    420
cacacccgcc gcgcttaatg cgccgctaca gggcgcgtcc cattcgccat tcaggctgcg    480
caactgttgg gaagggcgat cggtgcgggc ctcttcgcta ttacgccagc tggcgaaagg    540
```

-continued

```
gggatgtgct gcaaggcgat taagttgggt aacgccaggg ttttcccagt cacgacgttg     600
taaaacgacg gccagtgagc gcgcccgccg ggtaactcac ggggtatcca tgtccatttc     660
tgcggcatcc agccaggata cccgtcctcg ctgacgtaat atcccagcgc cgcaccgctg     720
tcattaatct gcacaccggc acggcagttc cggctgtcgc cggtattgtt cgggttgctg     780
atgcgcttcg ggctgaccat ccggaactgt gtccggaaaa gccgcgacga actggtatcc     840
caggtggcct gaacgaacag ttcaccgtta aaggcgtgca tggccacacc ttcccgaatc     900
atcatggtaa acgtgcgttt tcgctcaacg tcaatgcagc agcagtcatc ctcggcaaac     960
tctttccatg ccgcttcaac ctcgcgggaa aaggcacggg cttcttcctc cccgatgccc    1020
agatagcgcc agcttgggcg atgactgagc cggaaaaaag acccgacgat atgatcctga    1080
tgcagctaga ttaaccctag aaagatagtc tgcgtaaaat tgacgcatga tctaattaac    1140
cctcactaaa gggaacaaaa gctggagctc caccgcggtg gcggccgctc tagaactagt    1200
gttcccacaa tggttaattc gagctcgccc gggatctaa ttcaattaga gactaattca     1260
attagagcta attcaattag gatccaagct tatcgatttc gaaccctcga ccgccggagt    1320
ataaatagag gcgcttcgtc tacggagcga caattcaatt caaacaagca aagtgaacac    1380
gtcgctaagc gaaagctaag caaataaaca agcgcagctg aacaagctaa acaatcgggg    1440
taccgctaga gtcgacggta cgatccaccg gtcgccacca tggtgagcaa gggcgaggag    1500
ctgttcaccg gggtggtgcc catcctggtc gagctggacg gcgacgtaaa cggccacaag    1560
ttcagcgtgt ccggcgaggg cgagggcgat gccacctacg gcaagctgac cctgaagttc    1620
atctgcacca ccggcaagct gcccgtgccc tggcccaccc tcgtgaccac cttcggctac    1680
ggcctgcagt gcttcgcccg ctaccccgac cacatgaagc agcacgactt cttcaagtcc    1740
gccatgcccg aaggctacgt ccaggagcgc accatcttct tcaaggacga cggcaactac    1800
aagacccgcg ccgaggtgaa gttcgagggc gacaccctgg tgaaccgcat cgagctgaag    1860
ggcatcgact tcaaggagga cggcaacatc ctggggcaca agctggagta caactacaac    1920
agccacaacg tctatatcat ggccgacaag cagaagaacg gcatcaaggt gaacttcaag    1980
atccgccaca acatcgagga cggcagcgtg cagctcgccg accactacca gcagaacacc    2040
cccatcggcg acggccccgt gctgctgccc gacaaccact acctgagcta ccagtccgcc    2100
ctgagcaaag accccaacga gaagcgcgat cacatggtcc tgctggagtt cgtgaccgcc    2160
gccgggatca ctctcggcat ggacgagctg tacaagtaaa gcggccgcga ctctagatca    2220
taatcagcca taccacattt gtagaggttt tacttgcttt aaaaaacctc ccacacctcc    2280
ccctgaacct gaaacataaa atgaatgcaa ttgttgttgt taacttgttt attgcagctt    2340
ataatggtta caaataaagc aatagcatca caaatttcac aaataaagca ttttttttcac    2400 tgcattctag ttgtggtttg tccaaactca tcaatgtatc ttaaagctta tcgatacgcg    2460
tacggcgcgc ctaggcacta gtggatcccc cgggctgcag gaattcgata tcaagcttat    2520
cgataccgtc gacctcgagg gggggcccgg tacccaattc gccctatagt gagtcgtatt    2580
aagatcacgc gtagatccat gcgtcaattt tacgcatgat tatctttaac gtacgtcaca    2640
atatgattat ctttctaggg ttaatctagc tgcgtgttct gcagcgtgtc gagcatcttc    2700
atctgctcca tcacgctgta aaacacattt gcaccgcgag tctgcccgtc ctccacgggt    2760
tcaaaaacgt gaatgaacga ggcgcgcttg gcgtaatcat ggtcatagct gtttcctgtg    2820
tgaaattgtt atccgctcac aattccacac aacatacgag ccggaagcat aaagtgtaaa    2880
```

```
gcctggggtg cctaatgagt gagctaactc acattaattg cgttgcgctc actgcccgct      2940
ttccagtcgg gaaacctgtc gtgccagctg cattaatgaa tcggccaacg cgcggggaga      3000
ggcggtttgc gtattgggcg ctcttccgct tcctcgctca ctgactcgct gcgctcggtc      3060
gttcggctgc ggcgagcggt atcagctcac tcaaaggcgg taatacggtt atccacagaa      3120
tcagggata cgcaggaaa gaacatgtga gcaaaaggcc agcaaaaggc caggaaccgt        3180
aaaaaggccg cgttgctggc gttttccat aggctccgcc cccctgacga gcatcacaaa       3240
aatcgacgct caagtcagag gtggcgaaac ccgacaggac tataaagata ccaggcgttt      3300
ccccctggaa gctccctcgt gcgctctcct gttccgaccc tgccgcttac cggatacctg      3360
tccgcctttc tcccttcggg aagcgtggcg ctttctcata gctcacgctg taggtatctc      3420
agttcggtgt aggtcgttcg ctccaagctg ggctgtgtgc acgaaccccc cgttcagccc      3480
gaccgctgcg ccttatccgg taactatcgt cttgagtcca acccggtaag acacgactta      3540
tcgccactgg cagcagccac tggtaacagg attagcagag cgaggtatgt aggcggtgct      3600
acagagttct tgaagtggtg gcctaactac ggctacacta aaggacagt atttggtatc       3660
tgcgctctgc tgaagccagt taccttcgga aaaagagttg gtagctcttg atccggcaaa      3720
caaaccaccg ctggtagcgg tggtttttttt gtttgcaagc agcagattac gcgcagaaaa     3780
aaaggatctc aagaagatcc tttgatcttt tctacgggt ctgacgctca gtggaacgaa       3840
aactcacgtt aagggatttt ggtcatgaga ttatcaaaaa ggatcttcac ctagatcctt      3900
ttaaattaaa aatgaagttt taaatcaatc taaagtatat atgagtaaac ttggtctgac      3960
agttaccaat gcttaatcag tgaggcacct atctcagcga tctgtctatt tcgttcatcc      4020
atagttgcct gactccccgt cgtgtagata actacgatac gggagggctt accatctggc      4080
cccagtgctg caatgatacc gcgagaccca cgctcaccgg ctccagattt atcagcaata      4140
aaccagccag ccggaagggc cgagcgcaga agtggtcctg caactttatc cgcctccatc      4200
cagtctatta attgttgccg ggaagctaga gtaagtagtt cgccagttaa tagtttgcgc      4260
aacgttgttg ccattgctac aggcatcgtg gtgtcacgct cgtcgtttgg tatggcttca      4320
ttcagctccg gttcccaacg atcaaggcga gttacatgat ccccccatgtt gtgcaaaaaa    4380
gcggttagct ccttcggtcc tccgatcgtt gtcagaagta agttggccgc agtgttatca     4440
ctcatggtta tggcagcact gcataattct cttactgtca tgccatccgt aagatgcttt     4500
tctgtgactg gtgagtactc aaccaagtca ttctgagaat agtgtatgcg gcgaccgagt    4560
tgctcttgcc cggcgtcaat acgggataat accgcgccac atagcagaac tttaaaagtg   4620
ctcatcattg gaaaacgttc ttcggggcga aaactctcaa ggatcttacc gctgttgaga   4680
tccagttcga tgtaacccac tcgtgcaccc aactgatctt cagcatcttt tactttcacc    4740
agcgtttctg ggtgagcaaa aacaggaagg caaaatgccg caaaaaaggg aataagggcg   4800
acacggaaat gttgaatact catactcttc ctttttcaat attattgaag catttatcag   4860
ggttattgtc tcatgagcgg atacatattt gaatgtattt agaaaaataa acaaataggg   4920
gttccgcgca catttccccg aaaagtgcca c                                    4951
```

<210> SEQ ID NO 52  
<211> LENGTH: 4952  
<212> TYPE: DNA  
<213> ORGANISM: Artificial Sequence  
<220> FEATURE:  
<223> OTHER INFORMATION: Description of Artificial Sequence: pXL-Bac-EGFP sequence

```
<400> SEQUENCE: 52
ctaaattgta agcgttaata ttttgttaaa attcgcgtta aatttttgtt aaatcagctc      60 atttttaac caataggccg aaatcggcaa aatcccttat aaatcaaaag aatagaccga     120 gataggttg agtgttgttc cagtttggaa caagagtcca ctattaaaga acgtggactc     180
caacgtcaaa gggcgaaaaa ccgtctatca gggcgatggc ccactacgtg aaccatcacc     240
ctaatcaagt tttttggggt cgaggtgccg taaagcacta atcggaacc ctaaagggag     300 cccccgattt agagcttgac ggggaaagcc ggcgaacgtg gcgagaaagg aagggaagaa     360
agcgaaagga gcgggcgcta gggcgctggc aagtgtagcg gtcacgctgc gcgtaaccac     420
cacacccgcc gcgcttaatg cgccgctaca gggcgcgtcc cattcgccat tcaggctgcg     480
caactgttgg gaaggcgat cggtgcgggc ctcttcgcta ttacgccagc tggcgaaagg     540
gggatgtgct gcaaggcgat taagttgggt aacgccaggg ttttcccagt cacgacgttg     600
taaaacgacg gccagtgagc gcgcccgccg ggtaactcac ggggtatcca tgtccatttc     660
tgcggcatcc agccaggata cccgtcctcg ctgacgtaat atcccagcgc cgcaccgctg     720
tcattaatct gcacaccggc acggcagttc ggctgtcgc cggtattgtt cgggttgctg     780
atgcgcttcg ggctgaccat ccggaactgt gtccggaaaa gccgcgacga actggtatcc     840
caggtggcct gaacgaacag ttcaccgtta aaggcgtgca tggccacacc ttcccgaatc     900
atcatggtaa acgtgcgttt cgctcaacg tcaatgcagc agcagtcatc ctcggcaaac     960
tctttccatg ccgcttcaac ctcgcgggaa aaggcacggg cttcttcctc cccgatgccc    1020
agatagcgcc agcttgggcg atgactgagc cggaaaaaag acccgacgat atgatcctga    1080
tgcagctaga ttaaccctag aaagatagtc tgcgtaaaat tgacgcatga tctaattaac    1140
cctcactaaa gggaacaaaa gctggagctc caccgcggtg gcggccgctc tagaactagt    1200
gccgtacgcg tatcgataag ctttaagata cattgatgag tttggacaaa ccacaactag    1260
aatgcagtga aaaaaatgct ttatttgtga aatttgtgat gctattgctt tatttgtaac    1320
cattataagc tgcaataaac aagttaacaa caacaattgc attcatttta tgtttcaggt    1380
tcagggggag gtgtgggagg ttttttaaag caagtaaaac ctctacaaat gtggtatggc    1440
tgattatgat ctagagtcgc ggccgcttta cttgtacagc tcgtccatgc cgagagtgat    1500
cccggcggcg gtcacgaact ccagcaggac catgtgatcg cgcttctcgt tggggtcttt    1560
gctcagggcg gactgggtgc tcaggtagtg gttgtcgggc agcagcacgg ggccgtcgcc    1620
gatgggggtg ttctgctggt agtggtcggc gagctgcacg ctgccgtcct cgatgttgtg    1680
gcggatcttg aagttcacct tgatgccgtt cttctgcttg tcggccatga tatagacgtt    1740
gtggctgttg tagttgtact ccagcttgtg ccccaggatg ttgccgtcct ccttgaagtc    1800
gatgcccttc agctcgatgc ggttcaccag ggtgtcgccc tcgaacttca cctcggcgcg    1860
ggtcttgtag ttgccgtcgt ccttgaagaa gatggtgcgc tcctggacgt agccttcggg    1920
catggcggac ttgaagaagt cgtgctgctt catgtggtcg gggtagcggc tgaagcactg    1980
cacgccgtag gtcagggtgg tcacgagggt gggccaggggc acgggcagct tgccggtggt    2040
gcagatgaac ttcagggtca gcttgccgta ggtggcatcg ccctcgccct cgccggacac    2100
gctgaacttg tggccgtttta cgtcgccgtc cagctcgacc aggatgggca ccaccccggt    2160
gaacagctcc tcgcccttgc tcaccatggt ggcgaccggt ggatcccggg cccgcggtac    2220
cgtcgactct agcggtaccc cgattgttta gcttgttcag ctgcgcttgt ttatttgctt    2280
agctttcgct tagcgacgtg ttcactttgc ttgtttgaat tgaattgtcg ctccgtagac    2340
```

-continued

```
gaagcgcctc tatttatact ccggcggtcg agggttcgaa atcgataagc ttggatccta    2400
attgaattag ctctaattga attagtctct aattgaatta gatccccggg cgagctcgaa    2460
ttaaccattg tgggaacact agtggatccc ccgggctgca ggaattcgat atcaagctta    2520
tcgataccgt cgacctcgag ggggggcccg gtacccaatt cgccctatag tgagtcgtat    2580
taagatcacg cgtagatcca tgcgtcaatt ttacgcatga ttatctttaa cgtacgtcac    2640
aatatgatta tctttctagg gttaatctag ctgcgtgttc tgcagcgtgt cgagcatctt    2700
catctgctcc atcacgctgt aaaacacatt gcaccgcga gtctgcccgt cctccacggg    2760
ttcaaaaacg tgaatgaacg aggcgcgctt ggcgtaatca tggtcatagc tgtttcctgt    2820
gtgaaattgt tatccgctca caattccaca acatacga gccggaagca taaagtgtaa     2880
agcctgggt gcctaatgag tgagctaact cacattaatt gcgttgcgct cactgcccgc     2940
tttccagtcg ggaaacctgt cgtgccagct gcattaatga atcggccaac gcgcggggag    3000
aggcggtttg cgtattggc gctcttccgc ttcctcgctc actgactcgc tgcgctcggt     3060
cgttcggctg cggcgagcgg tatcagctca ctcaaaggcg gtaatacggt tatccacaga    3120
atcaggggat aacgcaggaa agaacatgtg agcaaaaggc cagcaaaagg ccaggaaccg    3180
taaaaaggcc gcgttgctgg cgttttttcca taggctccgc ccccctgacg agcatcacaa    3240
aaatcgacgc tcaagtcaga ggtggcgaaa cccgacagga ctataaagat accaggcgtt    3300
tcccctgga agctccctcg tgcgctctcc tgttccgacc ctgccgctta ccggatacct     3360
gtccgccttt ctcccttcgg gaagcgtggc gctttctcat agctcacgct gtaggtatct    3420
cagttcggtg taggtcgttc gctccaagct gggctgtgtg cacgaacccc ccgttcagcc    3480
cgaccgctgc gccttatccg gtaactatcg tcttgagtcc aacccggtaa gacacgactt    3540
atcgccactg gcagcagcca ctggtaacag gattagcaga gcgaggtatg taggcggtgc    3600
tacagagttc ttgaagtggt ggcctaacta cggctacact agaaggacag tatttggtat    3660
ctgcgctctg ctgaagccag ttaccttcgg aaaaagagtt ggtagctctt gatccggcaa    3720
acaaaccacc gctggtagcg gtggtttttt tgtttgcaag cagcagatta cgcgcagaaa    3780
aaaaggatct caagaagatc ctttgatctt ttctacgggg tctgacgctc agtggaacga    3840
aaactcacgt taagggattt tggtcatgag attatcaaaa aggatcttca cctagatcct    3900
tttaaattaa aaatgaagtt ttaaatcaat ctaaagtata tatgagtaaa cttggtctga    3960
cagttaccaa tgcttaatca gtgaggcacc tatctcagcg atctgtctat ttcgttcatc    4020
catagttgcc tgactccccg tcgtgtagat aactacgata cgggagggct taccatctgg    4080
ccccagtgct gcaatgatac cgcgagaccc acgctcaccg gctccagatt tatcagcaat    4140
aaaccagcca gccggaaggg ccgagcgcag aagtggtcct gcaactttat ccgcctccat    4200
ccagtctatt aattgttgcc gggaagctag agtaagtagt tcgccagtta atagtttgcg    4260
caacgttgtt gccattgcta caggcatcgt ggtgtcacgc tcgtcgtttg gtatggcttc    4320
attcagctcc ggttcccaac gatcaaggcg agttacatga tcccccatgt tgtgcaaaaa    4380
agcggttagc tccttcggtc ctccgatcgt tgtcagaagt aagttggccg cagtgttatc    4440
actcatggtt atggcagcac tgcataattc tcttactgtc atgccatccg taagatgctt    4500
ttctgtgact ggtgagtact caaccaagtc attctgagaa tagtgtatgc ggcgaccgag    4560
ttgctcttgc ccggcgtcaa tacgggataa taccgcgcca catagcagaa ctttaaaagt    4620
gctcatcatt ggaaaacgtt cttcggggcg aaaactctca aggatcttac cgctgttgag    4680
```

| | |
|---|---:|
| atccagttcg atgtaaccca ctcgtgcacc caactgatct tcagcatctt ttactttcac | 4740 |
| cagcgtttct gggtgagcaa aaacaggaag gcaaaatgcc gcaaaaaagg gaataagggc | 4800 |
| gacacggaaa tgttgaatac tcatactctt cctttttcaa tattattgaa gcatttatca | 4860 |
| gggttattgt ctcatgagcg gatacatatt tgaatgtatt tagaaaaata aacaaatagg | 4920 |
| ggttccgcgc acatttcccc gaaaagtgcc ac | 4952 |

```
<210> SEQ ID NO 53
<211> LENGTH: 4941
<212> TYPE: DNA
<213> ORGANISM: Artificial Sequence
<220> FEATURE:
<223> OTHER INFORMATION: Description of Artificial Sequence:
      pXL-Bac-ECFP sequence

<400> SEQUENCE: 53
```

| | |
|---|---:|
| ctaaattgta agcgttaata ttttgttaaa attcgcgtta aattttttgtt aaatcagctc | 60 |
| attttttaac caataggccg aaatcggcaa aatcccttat aaatcaaaag aatagaccga | 120 |
| gatagggttg agtgttgttc cagtttggaa caagagtcca ctattaaaga acgtggactc | 180 |
| caacgtcaaa gggcgaaaaa ccgtctatca gggcgatggc ccactacgtg aaccatcacc | 240 |
| ctaatcaagt tttttggggt cgaggtgccg taaagcacta aatcggaacc ctaaagggag | 300 |
| cccccgattt agagcttgac ggggaaagcc ggcgaacgtg gcgagaaagg aagggaagaa | 360 |
| agcgaaagga gcgggcgcta gggcgctggc aagtgtagcg gtcacgctgc gcgtaaccac | 420 |
| cacacccgcc gcgcttaatg cgccgctaca gggcgcgtcc cattcgccat tcaggctgcg | 480 |
| caactgttgg gaagggcgat cggtgcgggc ctcttcgcta ttacgccagc tggcgaaagg | 540 |
| gggatgtgct gcaaggcgat taagttgggt aacgccaggg ttttcccagt cacgacgttg | 600 |
| taaaacgacg gccagtgagc gcgccgccg ggtaactcac ggggtatcca tgtccatttc | 660 |
| tgcggcatcc agccaggata cccgtcctcg ctgacgtaat atcccagcgc cgcaccgctg | 720 |
| tcattaatct gcacaccggc acggcagttc cggctgtcgc cggtattgtt cgggttgctg | 780 |
| atgcgcttcg ggctgaccat ccggaactgt gtccggaaaa gccgcgacga actggtatcc | 840 |
| caggtggcct gaacgaacag ttcaccgtta aaggcgtgca tggccacacc ttcccgaatc | 900 |
| atcatggtaa acgtgcgttt cgctcaacg tcaatgcagc agcagtcatc ctcggcaaac | 960 |
| tctttccatg ccgcttcaac ctcgcgggaa aaggcacggg cttcttcctc cccgatgccc | 1020 |
| agatagcgcc agcttgggcg atgactgagc cggaaaaaag acccgacgat atgatcctga | 1080 |
| tgcagctaga ttaaccctag aaagatagtc tgcgtaaaat tgacgcatga tctaattaac | 1140 |
| cctcactaaa gggaacaaaa gctggagctc caccgcggtg gcgccgcctc tagaactagt | 1200 |
| gttcccacaa tggttaattc gagctcgccc gggatctaa ttcaattaga gactaattca | 1260 |
| attagagcta attcaattag gatccaagct tatcgatttc gaaccctcga ccgccggagt | 1320 |
| ataaatagag gcgcttcgtc tacggagcga caattcaatt caaacaagca aagtgaacac | 1380 |
| gtcgctaagc gaaagctaag caaataaaca agcgcagctg aacaagctaa acaatcgggg | 1440 |
| taccgctaga gtcgacggta cgatccaccg gtcgccacca tggtgagcaa gggcgaggag | 1500 |
| ctgttcaccg gggtggtgcc catcctggtc gagctggacg gcgacgtaaa cggccacaag | 1560 |
| ttcagcgtgt ccggcgaggg cgagggcgat gccacctacg gcaagctgac cctgaagttc | 1620 |
| atctgcacca ccggcaagct gcccgtgccc tggcccaccc tcgtgaccac cctgacctgg | 1680 |
| ggcgtgcagt gcttcagccg ctaccccgac cacatgaagc agcacgactt cttcaagtcc | 1740 |

-continued

```
gccatgcccg aaggctacgt ccaggagcgc accatcttct tcaaggacga cggcaactac    1800
aagacccgcg ccgaggtgaa gttcgagggc gacaccctgg tgaaccgcat cgagctgaag    1860
ggcatcgact tcaaggagga cggcaacatc ctggggcaca agctggagta caactacatc    1920
agccacaacg tctatatcac cgccgacaag cagaagaacg gcatcaaggc caacttcaag    1980
atccgccaca acatcgagga cggcagcgtg cagctcgccg accactacca gcagaacacc    2040
cccatcggcg acggccccgt gctgctgccc gacaaccact acctgagcac ccagtccgcc    2100
ctgagcaaag accccaacga gaagcgcgat cacatggtcc tgctggagtt cgtgaccgcc    2160
gccgggatca ctctcggcat ggacgagctg tacaagtaaa gcggccgcga ctctagatca    2220
taatcagcca taccacattt gtagaggttt tacttgcttt aaaaaacctc ccacacctcc    2280
ccctgaacct gaaacataaa atgaatgcaa ttgttgttgt taacttgttt attgcagctt    2340
ataatggtta caaataaagc aatagcatca caaatttcac aaataaagca ttttttttcac    2400 tgcattctag ttgtggtttg tccaaactca tcaatgtatc ttaaagctta tcgatacgcg    2460
tacggcacta gtggatcccc cgggctgcag gaattcgata tcaagcttat cgataccgtc    2520
gacctcgagg ggggcccgg tacccaattc gccctatagt gagtcgtatt aagatcacgc    2580
gtagatccat gcgtcaattt tacgcatgat tatctttaac gtacgtcaca atatgattat    2640
ctttctaggg ttaatctagc tgcgtgttct gcagcgtgtc gagcatcttc atctgctcca    2700
tcacgctgta aaacacattt gcaccgcgag tctgcccgtc ctccacgggt tcaaaaacgt    2760
gaatgaacga ggcgcgcttg gcgtaatcat ggtcatagct gtttcctgtg tgaaattgtt    2820
atccgctcac aattccacac aacatacgag ccggaagcat aaagtgtaaa gcctggggtg    2880
cctaatgagt gagctaactc acattaattg cgttgcgctc actgcccgct ttccagtcgg    2940
gaaacctgtc gtgccagctg cattaatgaa tcggccaacg cgcggggaga ggcggtttgc    3000
gtattgggcg ctcttccgct tcctcgctca ctgactcgct gcgctcggtc gttcggctgc    3060
ggcgagcggt atcagctcac tcaaaggcgg taatacggtt atccacagaa tcaggggata    3120
acgcaggaaa gaacatgtga gcaaaaggcc agcaaaaggc caggaaccgt aaaaaggccg    3180
cgttgctggc gtttttccat aggctccgcc cccctgacga gcatcacaaa aatcgacgct    3240
caagtcagag gtggcgaaac ccgacaggac tataaagata ccaggcgttt ccccctggaa    3300
gctccctcgt gcgctctcct gttccgaccc tgccgcttac cggatacctg tccgcctttc    3360
tcccttcggg aagcgtggcg ctttctcata gctcacgctg taggtatctc agttcggtgt    3420
aggtcgttcg ctccaagctg ggctgtgtgc acgaaccccc cgttcagccc gaccgctgcg    3480
ccttatccgg taactatcgt cttgagtcca acccggtaag acacgactta tcgccactgg    3540
cagcagccac tggtaacagg attagcagag cgaggtatgt aggcggtgct acagagttct    3600
tgaagtggtg gcctaactac ggctacacta aaggacagt atttggtatc tgcgctctgc    3660
tgaagccagt taccttcgga aaagagttg gtagctcttg atccggcaaa caaaccaccg    3720
ctggtagcgg tggttttttt gtttgcaagc agcagattac gcgcagaaaa aaggatctc    3780 aagaagatcc tttgatcttt tctacggggt ctgacgctca gtggaacgaa aactcacgtt    3840
aagggatttt ggtcatgaga ttatcaaaaa ggatcttcac ctagatcctt ttaaattaaa    3900
aatgaagttt taaatcaatc taagtatat atgagtaaac ttggtctgac agttaccaat    3960
gcttaatcag tgaggcacct atctcagcga tctgtctatt tcgttcatcc atagttgcct    4020
gactccccgt cgtgtagata actacgatac ggggggcttt accatctggc cccagtgctg    4080
caatgatacc gcgagaccca cgctcaccgg ctccagattt atcagcaata aaccagccag    4140
```

```
ccggaagggc cgagcgcaga agtggtcctg caactttatc cgcctccatc cagtctatta    4200
attgttgccg ggaagctaga gtaagtagtt cgccagttaa tagtttgcgc aacgttgttg    4260
ccattgctac aggcatcgtg gtgtcacgct cgtcgtttgg tatggcttca ttcagctccg    4320
gttcccaacg atcaaggcga gttacatgat cccccatgtt gtgcaaaaaa gcggttagct    4380
ccttcggtcc tccgatcgtt gtcagaagta agttggccgc agtgttatca ctcatggtta    4440
tggcagcact gcataattct cttactgtca tgccatccgt aagatgcttt tctgtgactg    4500
gtgagtactc aaccaagtca ttctgagaat agtgtatgcg gcgaccgagt tgctcttgcc    4560
cggcgtcaat acgggataat accgcgccac atagcagaac tttaaaagtg ctcatcattg    4620
gaaaacgttc ttcggggcga aaactctcaa ggatcttacc gctgttgaga tccagttcga    4680
tgtaacccac tcgtgcaccc aactgatctt cagcatcttt tactttcacc agcgtttctg    4740
ggtgagcaaa aacaggaagg caaaatgccg caaaaaaggg aataagggcg acacggaaat    4800
gttgaatact catactcttc ctttttcaat attattgaag catttatcag ggttattgtc    4860
tcatgagcgg atacatattt gaatgtattt agaaaaataa acaaataggg gttccgcgca    4920
catttccccg aaaagtgcca c                                              4941
```

<210> SEQ ID NO 54
<211> LENGTH: 4943
<212> TYPE: DNA
<213> ORGANISM: Artificial Sequence
<220> FEATURE:
<223> OTHER INFORMATION: Description of Artificial Sequence:
    PBS-ITR-ECFP sequence

<400> SEQUENCE: 54

```
cacctgacgc gccctgtagc ggcgcattaa gcgcggcggg tgtggtggtt acgcgcagcg      60
tgaccgctac acttgccagc gccctagcgc ccgctccttt cgctttcttc ccttcctttc     120
tcgccacgtt cgccggcttt ccccgtcaag ctctaaatcg ggggctccct ttagggttcc     180
gatttagtgc tttacggcac ctcgacccca aaaaacttga ttagggtgat ggttcacgta     240
gtgggccatc gccctgatag acggtttttc gccctttgac gttggagtcc acgttcttta     300
atagtggact cttgttccaa actggaacaa cactcaaccc tatctcggtc tattcttttg     360
atttataagg gattttgccg atttcggcct attggttaaa aaatgagctg atttaacaaa     420
aatttaacgc gaattttaac aaaatattaa cgcttacaat ttccattcgc cattcaggct     480
gcgcaactgt tgggaagggc gatcggtgcg ggcctcttcg ctattacgcc agctggcgaa     540
agggggatgt gctgcaaggc gattaagttg ggtaacgcca gggttttccc agtcacgacg     600
ttgtaaaacg acgccagtg aattgtaata cgactcacta tagggcgaat tgggtaccgg     660
gccccccctc gaggtcgacg gtatcgataa gcttgatatc gaattcctgc agcccggggg     720
atcccatgcg tcaattttac gcagactatc tttctagggt taatctagct gcatcaggat     780
catatcgtcg ggtcttttt ccggctcagt catcgcccaa gctggcgcta tctgggcatc     840
ggggaggaag aagcccgtgc cttttcccgc gaggttgaag cggcatggaa agagtttgcc     900
gaggatgact gctgctgcat tgacgttgag cgaaaacgca cgtttaccat gatgattcgg     960
gaaggtgtgg ccatgcacgc ctttaacggt gaactgttcg ttcaggccac ctgggatacc    1020
agttcgtcgc ggcttttccg gacacagttc cggatggtca gcccgaagcg catcagcaac    1080
ccgaacaata ccggcgacag ccggaactgc cgtgccggtg tgcagattaa tgacagcggt    1140
gcggcgctgg gatattacgt cagcgaggac gggtatcctg gctggatgcc gcagaaatgg    1200
```

-continued

```
acatggatac cccgtgagtt acccggcggc tcgttcattc acgtttttga acccgtggag    1260
gacgggcaga ctcgcggtgc aaatgtgttt tacagcgtga tggagcagat gaagatgctc    1320
gacacgctgc agaacacgca gctagattaa ccctagaaag ataatcatat tgtgacgtac    1380
gttaaagata atcatgcgta aaattgacgc atgggatcca ctagtgttcc cacaatggtt    1440
aattcgagct cgcccgggga tctaattcaa ttagagacta attcaattag agctaattca    1500
attaggatcc aagcttatcg atttcgaacc ctcgaccgcc ggagtataaa tagaggcgct    1560
tcgtctacgg agcgacaatt caattcaaac aagcaaagtg aacacgtcgc taagcgaaag    1620
ctaagcaaat aaacaagcgc agctgaacaa gctaaacaat cggggtaccg ctagagtcga    1680
cggtacgatc caccggtcgc caccatggtg agcaagggcg aggagctgtt caccggggtg    1740
gtgcccatcc tggtcgagct ggacggcgac gtaaacggcc acaagttcag cgtgtccggc    1800
gagggcgagg gcgatgccac ctacggcaag ctgaccctga agttcatctg caccaccggc    1860
aagctgcccg tgccctggcc caccctcgtg accaccctga cctgggcgt gcagtgcttc     1920
agccgctacc ccgaccacat gaagcagcac gacttcttca gtccgccat gcccgaaggc     1980
tacgtccagg agcgcaccat cttcttcaag gacgacggca actacaagac ccgcgccgag    2040
gtgaagttcg agggcgacac cctggtgaac cgcatcgagc tgaagggcat cgacttcaag    2100
gaggacggca acatcctggg gcacaagctg gagtacaact acatcagcca caacgtctat    2160
atcaccgccg acaagcagaa gaacggcatc aaggccaact tcaagatccg ccacaacatc    2220
gaggacggca gcgtgcagct cgccgaccac taccagcaga cacccccat cggcgacggc     2280
cccgtgctgc tgcccgacaa ccactacctg agcacccagt ccgccctgag caaagacccc    2340
aacgagaagc gcgatcacat ggtcctgctg gagttcgtga ccgccgccgg gatcactctc    2400
ggcatggacg agctgtacaa gtaaagcggc cgcgactcta gatcataatc agccatacca    2460
catttgtaga ggttttactt gctttaaaaa acctcccaca cctcccctg aacctgaaac     2520
ataaaatgaa tgcaattgtt gttgttaact tgtttattgc agcttataat ggttacaaat    2580
aaagcaatag catcacaaat ttcacaaata agcatttttt tcactgcat tctagttgtg     2640
gtttgtccaa actcatcaat gtatcttaaa gcttatcgat acgcgtacgg cgcgcctagg    2700
ccggccgata ctagttctag agcggccgcc accgcggtgg agctccagct tttgttccct    2760
ttagtgaggg ttaatttcga gcttggcgta atcatggtca tagctgtttc ctgtgtgaaa    2820
ttgttatccg ctcacaattc cacacaacat acgagccgga agcataaagt gtaaagcctg    2880
gggtgcctaa tgagtgagct aactcacatt aattgcgttg cgctcactgc ccgctttcca    2940
gtcgggaaac ctgtcgtgcc agctgcatta atgaatcggc caacgcgcgg ggagaggcgg    3000
tttgcgtatt gggcgctctt ccgcttcctc gctcactgac tcgctgcgct cggtcgttcg    3060
gctgcggcga gcggtatcag ctcactcaaa ggcggtaata cggttatcca cagaatcagg    3120
ggataacgca ggaaagaaca tgtgagcaaa aggccagcaa aaggccagga accgtaaaaa    3180
ggccgcgttg ctggcgtttt tccataggct ccgcccccct gacgagcatc acaaaaatcg    3240
acgctcaagt cagaggtggc gaaacccgac aggactataa agataccagg cgtttccccc    3300
tggaagctcc ctcgtgcgct ctcctgttcc gaccctgccg cttaccggat acctgtccgc    3360
ctttctccct tcgggaagcg tggcgctttc tcatagctca cgctgtaggt atctcagttc    3420
ggtgtaggtc gttcgctcca agctgggctg tgtgcacgaa ccccccgttc agcccgaccg    3480
ctgcgcctta tccggtaact atcgtcttga gtccaacccg gtaagacacg acttatcgcc    3540
```

```
actggcagca gccactggta acaggattag cagagcgagg tatgtaggcg gtgctacaga      3600
gttcttgaag tggtggccta actacggcta cactagaagg acagtatttg gtatctgcgc      3660
tctgctgaag ccagttacct tcggaaaaag agttggtagc tcttgatccg gcaaacaaac      3720
caccgctggt agcggtggtt ttttgtttg caagcagcag attacgcgca gaaaaaaagg      3780
atctcaagaa gatcctttga tcttttctac ggggtctgac gctcagtgga acgaaaactc      3840
acgttaaggg attttggtca tgagattatc aaaaaggatc ttcacctaga tcctttaaaa      3900
ttaaaaatga agttttaaat caatctaaag tatatatgag taaacttggt ctgacagtta      3960
ccaatgctta atcagtgagg cacctatctc agcgatctgt ctatttcgtt catccatagt      4020
tgcctgactc cccgtcgtgt agataactac gatacgggag ggcttaccat ctggccccag      4080
tgctgcaatg ataccgcgag acccacgctc accggctcca gatttatcag caataaacca      4140
gccagccgga agggccgagc gcagaagtgg tcctgcaact ttatccgcct ccatccagtc      4200
tattaattgt tgccgggaag ctagagtaag tagttcgcca gttaatagtt tgcgcaacgt      4260
tgttgccatt gctacaggca tcgtggtgtc acgctcgtcg tttggtatgg cttcattcag      4320
ctccggttcc caacgatcaa ggcgagttac atgatccccc atgttgtgca aaaaagcggt      4380
tagctccttc ggtcctccga tcgttgtcag aagtaagttg gccgcagtgt tatcactcat      4440
ggttatggca gcactgcata attctcttac tgtcatgcca tccgtaagat gcttttctgt      4500
gactggtgag tactcaacca agtcattctg agaatagtgt atgcggcgac cgagttgctc      4560
ttgcccggcg tcaatacggg ataataccgc gccacatagc agaactttaa aagtgctcat      4620
cattggaaaa cgttcttcgg ggcgaaaact ctcaaggatc ttaccgctgt tgagatccag      4680
ttcgatgtaa cccactcgtg cacccaactg atcttcagca tcttttactt tcaccagcgt      4740
ttctgggtga gcaaaaacag gaaggcaaaa tgccgcaaaa aagggaataa gggcgacacg      4800
gaaatgttga atactcatac tcttcctttt tcaatattat tgaagcattt atcagggtta      4860
ttgtctcatg agcggataca tatttgaatg tatttagaaa aataaacaaa tagggggttcc      4920 gcgcacattt ccccgaaaag tgc                                              4943
```

<210> SEQ ID NO 55
<211> LENGTH: 4944
<212> TYPE: DNA
<213> ORGANISM: Artificial Sequence
<220> FEATURE:
<223> OTHER INFORMATION: Description of Artificial Sequence:
      PBS-ITR-EGFP sequence

<400> SEQUENCE: 55

```
cacctgacgc gccctgtagc ggcgcattaa gcgcggcggg tgtggtggtt acgcgcagcg       60
tgaccgctac acttgccagc gccctagcgc ccgctccttt cgctttcttc ccttcctttc      120
tcgccacgtt cgccggcttt ccccgtcaag ctctaaatcg gggctccct ttagggttcc       180 gatttagtgc tttacggcac ctcgacccca aaaaacttga ttagggtgat ggttcacgta      240
gtgggccatc gccctgatag acggttttc gccctttgac gttggagtcc acgttcttta      300
atagtggact cttgttccaa actggaacaa cactcaaccc tatctcggtc tattcttttg      360
atttataagg gattttgccg atttcggcct attggttaaa aaatgagctg atttaacaaa      420
aatttaacgc gaattttaac aaaatattaa cgcttacaat ttccattcgc cattcaggct      480
gcgcaactgt tgggaagggc gatcggtgcg ggcctcttcg ctattacgcc agctggcgaa      540
agggggatgt gctgcaaggc gattaagttg ggtaacgcca gggttttccc agtcacgacg      600
```

-continued

```
ttgtaaaacg acggccagtg aattgtaata cgactcacta tagggcgaat tgggtaccgg       660
gccccccctc gaggtcgacg gtatcgataa gcttgatatc gaattcctgc agcccggggg       720
atcccatgcg tcaattttac gcagactatc tttctagggt taatctagct gcatcaggat       780
catatcgtcg ggtcttttt ccggctcagt catcgcccaa gctggcgcta tctgggcatc        840
ggggaggaag aagcccgtgc cttttcccgc gaggttgaag cggcatggaa agagtttgcc       900
gaggatgact gctgctgcat tgacgttgag cgaaaacgca cgtttaccat gatgattcgg       960
gaaggtgtgg ccatgcacgc ctttaacggt gaactgttcg ttcaggccac ctgggatacc      1020
agttcgtcgc ggcttttccg gacacagttc cggatggtca gcccgaagcg catcagcaac      1080
ccgaacaata ccggcgacag ccggaactgc cgtgccggtg tgcagattaa tgacagcggt      1140
gcggcgctgg gatattacgt cagcgaggac gggtatcctg gctggatgcc gcagaaatgg      1200
acatggatac cccgtgagtt acccggcggc tcgttcattc acgttttga acccgtggag       1260
gacgggcaga ctcgcggtgc aaatgtgttt tacagcgtga tggagcagat gaagatgctc      1320
gacacgctgc agaacacgca gctagattaa ccctagaaag ataatcatat tgtgacgtac      1380
gttaaagata atcatgcgta aaattgacgc atgggatcca ctagtgttcc cacaatggtt      1440
aattcgagct cgcccgggga tctaattcaa ttagagacta attcaattag agctaattca      1500
attaggatcc aagcttatcg atttcgaacc ctcgaccgcc ggagtataaa tagaggcgct      1560
tcgtctacgg agcgacaatt caattcaaac aagcaaagtg aacacgtcgc taagcgaaag      1620
ctaagcaaat aaacaagcgc agctgaacaa gctaaacaat cggggtaccg ctagagtcga      1680
cggtaccgcg ggcccgggat ccaccggtcg ccaccatggt gagcaagggc gaggagctgt      1740
tcaccggggt ggtgcccatc ctggtcgagc tggacggcga cgtaaacggc cacaagttca      1800
gcgtgtccgg cgagggcgag ggcgatgcca cctacggcaa gctgaccctg aagttcatct      1860
gcaccaccgg caagctgccc gtgccctggc ccaccctcgt gaccaccctg acctacggcg      1920
tgcagtgctt cagccgctac cccgaccaca tgaagcagca cgacttcttc aagtccgcca      1980
tgcccgaagg ctacgtccag gagcgcacca tcttcttcaa ggacgacggc aactacaaga      2040
cccgcgccga ggtgaagttc gagggcgaca ccctggtgaa ccgcatcgag ctgaagggca      2100
tcgacttcaa ggaggacggc aacatcctgg ggcacaagct ggagtacaac tacaacagcc      2160
acaacgtcta tatcatggcc gacaagcaga agaacggcat caaggtgaac ttcaagatcc      2220
gccacaacat cgaggacggc agcgtgcagc tcgccgacca ctaccagcag aacacccccca     2280
tcggcgacgg ccccgtgctg ctgcccgaca accactacct gagcacccag tccgccctga      2340
gcaaagaccc caacgagaag cgcgatcaca tggtcctgct ggagttcgtg accgccgccg      2400
ggatcactct cggcatggac gagctgtaca agtaaagcgg ccgcgactct agatcataat      2460
cagccatacc acatttgtag aggttttact tgctttaaaa aacctcccac acctcccct       2520
gaacctgaaa cataaaatga atgcaattgt tgttgttaac ttgtttattg cagcttataa      2580
tggttacaaa taaagcaata gcatcacaaa tttcacaaat aaagcatttt tttcactgca      2640
ttctagttgt ggtttgtcca aactcatcaa tgtatcttaa agcttatcga tacgcgtacg      2700
gcgcgcctag actagttcta gagcggccgc caccgcggtg gagctccagc ttttgttccc      2760
tttagtgagg gttaatttcg agcttggcgt aatcatggtc atagctgttt cctgtgtgaa      2820
attgttatcc gctcacaatt ccacacaaca tacgagccgg aagcataaag tgtaaagcct      2880
ggggtgccta atgagtgagc taactcacat taattgcgtt gcgctcactg cccgctttcc      2940
agtcgggaaa cctgtcgtgc cagctgcatt aatgaatcgg ccaacgcgcg gggagaggcg      3000
```

```
gtttgcgtat tgggcgctct tccgcttcct cgctcactga ctcgctgcgc tcggtcgttc    3060
ggctgcggcg agcggtatca gctcactcaa aggcggtaat acggttatcc acagaatcag    3120
gggataacgc aggaaagaac atgtgagcaa aaggccagca aaaggccagg aaccgtaaaa    3180
aggccgcgtt gctggcgttt ttccataggc tccgccccc  tgacgagcat cacaaaaatc    3240
gacgctcaag tcagaggtgg cgaaacccga caggactata aagataccag gcgtttcccc    3300
ctggaagctc cctcgtgcgc tctcctgttc cgaccctgcc gcttaccgga tacctgtccg    3360
cctttctccc ttcgggaagc gtggcgcttt ctcatagctc acgctgtagg tatctcagtt    3420
cggtgtaggt cgttcgctcc aagctgggct gtgtgcacga accccccgtt cagcccgacc    3480
gctgcgcctt atccggtaac tatcgtcttg agtccaaccc ggtaagacac gacttatcgc    3540
cactggcagc agccactggt aacaggatta gcagagcgag gtatgtaggc ggtgctacag    3600
agttcttgaa gtggtggcct aactacggct acactagaag gacagtattt ggtatctgcg    3660
ctctgctgaa gccagttacc ttcggaaaaa gagttggtag ctcttgatcc ggcaaacaaa    3720
ccaccgctgg tagcggtggt ttttttgttt gcaagcagca gattacgcgc agaaaaaaag    3780
gatctcaaga agatccttg  atcttttcta cggggtctga cgctcagtgg aacgaaaact    3840
cacgttaagg gattttggtc atgagattat caaaaaggat cttcacctag atccttttaa    3900
attaaaaatg aagttttaaa tcaatctaaa gtatatatga gtaaacttgg tctgacagtt    3960
accaatgctt aatcagtgag gcacctatct cagggatctg tctatttcgt tcatccatag    4020
ttgcctgact ccccgtcgtg tagataacta cgatacggga gggcttacca tctggcccca    4080
gtgctgcaat gataccgcga gacccacgct caccggctcc agatttatca gcaataaacc    4140
agccagccgg aagggccgag cgcagaagtg gtcctgcaac tttatccgcc tccatccagt    4200
ctattaattg ttgccgggaa gctagagtaa gtagttcgcc agttaatagt ttgcgcaacg    4260
ttgttgccat tgctacaggc atcgtggtgt cacgctcgtc gtttggtatg gcttcattca    4320
gctccggttc ccaacgatca aggcgagtta catgatcccc catgttgtgc aaaaaagcgg    4380
ttagctcctt cggtcctccg atcgttgtca gaagtaagtt ggccgcagtg ttatcactca    4440
tggttatggc agcactgcat aattctctta ctgtcatgcc atccgtaaga tgcttttctg    4500
tgactggtga gtactcaacc aagtcattct gagaatagtg tatgcggcga ccgagttgct    4560
cttgcccggc gtcaatacgg gataataccg cgccacatag cagaacttta aaagtgctca    4620
tcattggaaa acgttcttcg gggcgaaaac tctcaaggat cttaccgctg ttgagatcca    4680
gttcgatgta acccactcgt gcacccaact gatcttcagc atcttttact ttcaccagcg    4740
tttctgggtg agcaaaaaca ggaaggcaaa atgccgcaaa aaagggaata agggcgacac    4800
ggaaatgttg aatactcata ctcttccttt ttcaatatta ttgaagcatt tatcagggtt    4860
attgtctcat gagcggatac atatttgaat gtatttagaa aaataaacaa ataggggttc    4920
cgcgcacatt tccccgaaaa gtgc                                          4944
```

<210> SEQ ID NO 56
<211> LENGTH: 4944
<212> TYPE: DNA
<213> ORGANISM: Artificial Sequence
<220> FEATURE:
<223> OTHER INFORMATION: Description of Artificial Sequence:
    pBS-ITR-EYFP sequence

<400> SEQUENCE: 56

```
cacctgacgc gccctgtagc ggcgcattaa gcgcggcggg tgtggtggtt acgcgcagcg      60
```

-continued

```
tgaccgctac acttgccagc gccctagcgc ccgctccttt cgctttcttc ccttcctttc    120
tcgccacgtt cgccggcttt ccccgtcaag ctctaaatcg ggggctccct ttagggttcc    180
gatttagtgc tttacggcac ctcgaccccc aaaaacttga ttagggtgat ggttcacgta    240
gtgggccatc gccctgatag acggttttcc gcccttcgac gttggagtcc acgttcttta    300
atagtggact cttgttccaa actgaacaa cactcaaccc tatctcggtc tattcttttg    360
atttataagg gattttgccg atttcggcct attggttaaa aaatgagctg atttaacaaa    420
aatttaacgc gaattttaac aaaatattaa cgcttacaat ttccattcgc cattcaggct    480
gcgcaactgt tgggaagggc gatcggtgcg ggcctcttcg ctattacgcc agctggcgaa    540 aggggggatgt gctgcaaggc gattaagttg ggtaacgcca gggttttccc agtcacgacg    600
ttgtaaaacg acggccagtg aattgtaata cgactcacta tagggcgaat tgggtaccgg    660
gccccccctc gaggtcgacg gtatcgataa gcttgatatc gaattcctgc agcccggggg    720
atcccatgcg tcaattttac gcagactatc tttctagggt taatctagct gcatcaggat    780
catatcgtcg ggtcttttttt ccggctcagt catcgcccaa gctggcgcta tctgggcatc    840
ggggaggaag aagcccgtgc cttttcccgc gaggttgaag cggcatggaa agagtttgcc    900
gaggatgact gctgctgcat tgacgttgag cgaaaacgca cgtttaccat gatgattcgg    960
gaaggtgtgg ccatgcacgc ctttaacggt gaactgttcg ttcaggccac ctgggatacc   1020
agttcgtcgc ggcttttccg gacacagttc cggatggtca gcccgaagcg catcagcaac   1080
ccgaacaata ccgcgacag ccggaactgc cgtgccggtg tgcagattaa tgacagcggt   1140
gcggcgctgg gatattacgt cagcgaggac gggtatcctg gctggatgcc gcagaaatgg   1200
acatggatac cccgtgagtt accggcggc tcgttcattc acgttttga acccgtggag   1260 gacgggcaga ctcgcggtgc aaatgtgttt tacagcgtga tggagcagat gaagatgctc   1320
gacacgctgc agaacacgca gctagattaa ccctagaaag ataatcatat tgtgacgtac   1380
gttaaagata atcatgcgta aaattgacgc atgggatcca ctagtgttcc cacaatggtt   1440
aattcgagct cgcccgggga tctaattcaa ttagagacta attcaattag agctaattca   1500
attaggatcc aagcttatcg atttcgaacc ctcgaccgcc ggagtataaa tagaggcgct   1560
tcgtctacgg agcgacaatt caattcaaac aagcaaagtg aacacgtcgc taagcgaaag   1620
ctaagcaaat aaacaagcgc agctgaacaa gctaaacaat cggggtaccg ctagagtcga   1680
cggtacgatc caccggtcgc caccatggtg agcaagggcg aggagctgtt caccggggtg   1740
gtgcccatcc tggtcgagct ggacggcgac gtaaacggcc acaagttcag cgtgtccggc   1800
gagggcgagg gcgatgccac ctacggcaag ctgaccctga agttcatctg caccaccggc   1860
aagctgcccg tgccctggcc caccctcgtg accaccttcg gctacggcct gcagtgcttc   1920
gcccgctacc ccgaccacat gaagcagcac gacttcttca gtccgccat gcccgaaggc   1980 tacgtccagg agcgcaccat cttcttcaag gacgacggca actacaagac ccgcgccgag   2040
gtgaagttcg agggcgacac cctggtgaac cgcatcgagc tgaagggcat cgacttcaag   2100
gaggacggca acatcctggg gcacaagctg gagtacaact acaacagcca caacgtctat   2160 atcatgccg acaagcagaa gaacggcatc aaggtgaact tcaagatccg ccacaacatc   2220
gaggacggca gcgtgcagct cgccgaccac taccagcaga cacccccat cggcgacggc   2280 cccgtgctgc tgcccgacaa ccactacctg agctaccagt ccgccctgag caaagacccc   2340
aacgagaagc gcgatcacat ggtcctgctg gagttcgtga ccgccgccgg gatcactctc   2400
```

-continued

```
ggcatggacg agctgtacaa gtaaagcggc cgcgactcta gatcataatc agccatacca    2460
catttgtaga ggttttactt gctttaaaaa acctcccaca cctcccctg aacctgaaac     2520
ataaaatgaa tgcaattgtt gttgttaact tgtttattgc agcttataat ggttacaaat    2580
aaagcaatag catcacaaat ttcacaaata agcattttt ttcactgcat tctagttgtg     2640
gtttgtccaa actcatcaat gtatcttaaa gcttatcgat acgcgtacgg cgcgcctagg    2700
ccggccgatc actagttcta gagcggccgc caccgcggtg gagctccagc ttttgttccc    2760
tttagtgagg gttaatttcg agcttggcgt aatcatggtc atagctgttt cctgtgtgaa    2820
attgttatcc gctcacaatt ccacacaaca tacgagccgg aagcataaag tgtaaagcct    2880
ggggtgccta atgagtgagc taactcacat taattgcgtt gcgctcactg cccgctttcc    2940
agtcgggaaa cctgtcgtgc cagctgcatt aatgaatcgg ccaacgcgcg gggagaggcg    3000
gtttgcgtat tgggcgctct tccgcttcct cgctcactga ctcgctgcgc tcggtcgttc    3060
ggctgcggcg agcggtatca gctcactcaa aggcggtaat acggttatcc acagaatcag    3120
gggataacgc aggaaagaac atgtgagcaa aaggccagca aaaggccagg aaccgtaaaa    3180
aggccgcgtt gctggcgttt ttccataggc tccgccccc tgacgagcat cacaaaaatc      3240
gacgctcaag tcagaggtgg cgaaacccga caggactata agataccag gcgtttcccc     3300
ctggaagctc cctcgtgcgc tctcctgttc cgaccctgcc gcttaccgga tacctgtccg    3360
cctttctccc ttcgggaagc gtggcgcttt ctcatagctc acgctgtagg tatctcagtt    3420
cggtgtaggt cgttcgctcc aagctgggct gtgtgcacga acccccgtt cagcccgacc     3480
gctgcgcctt atccggtaac tatcgtcttg agtccaaccc ggtaagacac gacttatcgc    3540
cactggcagc agccactggt aacaggatta gcagagcgag gtatgtaggc ggtgctacag    3600
agttcttgaa gtggtggcct aactacggct acactagaag gacagtattt ggtatctgcg    3660
ctctgctgaa gccagttacc ttcggaaaaa gagttggtag ctcttgatcc ggcaaacaaa    3720
ccaccgctgg tagcggtggt ttttttgttt gcaagcagca gattacgcgc agaaaaaaag    3780
gatctcaaga agatcctttg atcttttcta cggggtctga cgctcagtgg aacgaaaact    3840
cacgttaagg gattttggtc atgagattat caaaaaggat cttcacctag atcctttaa     3900
attaaaaatg aagttttaaa tcaatctaaa gtatatatga gtaaacttgg tctgacagtt    3960
accaatgctt aatcagtgag gcacctatct cagcgatctg tctatttcgt tcatccatag    4020
ttgcctgact ccccgtcgtg tagataacta cgatacggga gggcttacca tctggcccca    4080
gtgctgcaat gataccgcga gacccacgct caccggctcc agatttatca gcaataaacc    4140
agccagccgg aagggccgag cgcagaagtg gtcctgcaac tttatccgcc tccatccagt    4200
ctattaattg ttgccgggaa gctagagtaa gtagttcgcc agttaatagt ttgcgcaacg    4260
ttgttgccat tgctacaggc atcgtggtgt cacgctcgtc gtttggtatg gcttcattca    4320
gctccggttc ccaacgatca aggcgagtta catgatcccc catgttgtgc aaaaaagcgg    4380
ttagctcctt cggtcctccg atcgttgtca gaagtaagtt ggccgcagtg ttatcactca    4440
tggttatggc agcactgcat aattctctta ctgtcatgcc atccgtaaga tgcttttctg    4500
tgactggtga gtactcaacc aagtcattct gagaatagtg tatgcggcga ccgagttgct    4560
cttgcccggc gtcaatacgg gataataccg cgccacatag cagaacttta aaagtgctca    4620
tcattggaaa acgttcttcg ggcgaaaac tctcaaggat cttaccgctg ttgagatcca      4680
gttcgatgta acccactcgt gcacccaact gatcttcagc atcttttact ttcaccagcg    4740
tttctgggtg agcaaaaaca ggaaggcaaa atgccgcaaa aaagggaata agggcgacac    4800
```

-continued

```
ggaaatgttg aatactcata ctcttccttt ttcaatatta ttgaagcatt tatcagggtt    4860
attgtctcat gagcggatac atatttgaat gtatttagaa aaataaacaa ataggggttc    4920
cgcgcacatt tccccgaaaa gtgc                                           4944
```

```
<210> SEQ ID NO 57
<211> LENGTH: 7670
<212> TYPE: DNA
<213> ORGANISM: Artificial Sequence
<220> FEATURE:
<223> OTHER INFORMATION: Description of Artificial Sequence:
      pIAO-pL DNA sequence

<400> SEQUENCE: 57
```

```
aacgcgcggg gagaggcggt ttgcgtattg ggcgctcttc cgcttcctcg ctcactgact      60
cgctgcgctc ggtcgttcgg ctgcggcgag cggtatcagc tcactcaaag gcggtaatac     120
ggttatccac agaatcaggg gataacgcag gaaagaacat gtgagcaaaa ggccagcaaa     180
aggccaggaa ccgtaaaaag gccgcgttgc tggcgttttt ccataggctc cgcccccctg     240
acgagcatca caaaaatcga cgctcaagtc agaggtggcg aaacccgaca ggactataaa     300
gataccaggc gtttccccct ggaagctccc tcgtgcgctc tcctgttccg accctgccgc     360
ttaccggata cctgtccgcc tttctccctt cgggaagcgt ggcgctttct caatgctcac     420
gctgtaggta tctcagttcg gtgtaggtcg ttcgctccaa gctgggctgt gtgcacgaac     480 ccccgttca gcccgaccgc tgcgccttat ccggtaacta tcgtcttgag tccaacccgg      540
taagacacga cttatcgcca ctggcagcag ccactggtaa caggattagc agagcgaggt     600
atgtaggcgg tgctacagag ttcttgaagt ggtggcctaa ctacggctac actagaagga     660
cagtatttgg tatctgcgct ctgctgaagc cagttacctt cggaaaaaga gttggtagct     720
cttgatccgg caaacaaacc accgctggta gcggtggttt ttttgtttgc aagcagcaga     780
ttacgcgcag aaaaaaagga tctcaagaag atcctttgat cttttctacg ggtctgacg      840 ctcagtggaa cgaaaactca cgttaaggga ttttggtcat gagattatca aaaaggatct     900
tcacctagat ccttttaaat taaaaatgaa gttttaaatc aatctaaagt atatatgagt     960
aaacttggtc tgacagttac caatgcttaa tcagtgaggc acctatctca gcgatctgtc    1020
tatttcgttc atccatagtt gcctgactcc ccgtcgtgta gataactacg atacgggagg    1080
gcttaccatc tggccccagt gctgcaatga taccgcgaga cccacgctca ccggctccag    1140
atttatcagc aataaaccag ccagccggaa gggccgagcg cagaagtggt cctgcaactt    1200
tatccgcctc catccagtct attaattgtt gccgggaagc tagagtaagt agttcgccag    1260
ttaatagttt gcgcaacgtt gttgccattg ctacaggcat cgtggtgtca cgctcgtcgt    1320
ttggtatggc ttcattcagc tccggttccc aacgatcaag gcgagttaca tgatccccca    1380
tgttgtgcaa aaaagcggtt agctccttcg gtcctccgat cgttgtcaga agtaagttgg    1440
ccgcagtgtt atcactcatg gttatggcag cactgcataa ttctcttact gtcatgccat    1500
ccgtaagatg cttttctgtg actggtgagt actcaaccaa gtcattctga atagtgta     1560 tgcggcgacc gagttgctct tgcccggcgt caatacggga taataccgcg ccacatagca    1620
gaactttaaa agtgctcatc attggaaaac gttcttcggg gcgaaaactc tcaaggatct    1680
taccgctgtt gagatccagt tcgatgtaac ccactcgtgc acccaactga tcttcagcat    1740
cttttacttt caccagcgtt tctgggtgag caaaaacagg aaggcaaaat gccgcaaaaa    1800
agggaataag ggcgacacgg aaatgttgaa tactcatact cttccttttt caatattatt    1860
```

-continued

```
gaagcattta tcagggttat tgtctcatga gcggatacat atttgaatgt atttagaaaa   1920
ataaacaaat aggggttccg cgcacatttc cccgaaaagt gccacctgac gtctaagaaa   1980
ccattattat catgacatta acctataaaa ataggcgtat cacggggccc tgaggtgaac   2040
caattgtcac acgtaatatt acgacaacta ccgtgcacag gctttgataa ctccttcacg   2100
tagtattcac cgagtggtac tccgttggtc tgtgttcctc ttcccaaata aggcattcca   2160
tttatcatat acttcgtacc actgtcacac atcatgagga tttttattcc atacttactt   2220
ggcttgtttg ggatatacat cctaaacgga caccgtcctc taaaaccaag taactgttca   2280
tctatggtca aatgagcccc tggagtgtaa ttttgtatgc actgatggat aaagagatcc   2340
catatttttc taacaggagt aaatacatcg ttttctcgaa gtgtgggccg tatacttttg   2400
tcatccattc taagacatcg tatcaaaaaa tccaaaacga tccacagact cattacagag   2460
acgtacacat tgacaaagat cgatccaaag aggtcatctg tggacatgtg gttatctttt   2520
ctcactgctg tcattaccag aataccaaag aaagcataga tttcatcttc attcgtgtca   2580
cgaaatgtag cacctgtcat agattcccga cgtttcaatg atatctcagc atttgtccat   2640
tttacaattt gcgaaattat ctcatcagta aaaaatagtt tgaagcataa aagtgggtca   2700
tatatattgc ggcacatacg cgtcggacct ctttgagatc tgacaatgtt cagtgcagag   2760
actcggctac cgctcgtgga ctttgaagtt aaattcagat ataaagacgc tgaaaatcat   2820
ttgattttcg ctctaacata ccaccctaaa gattataaat ttaatgaatt attaaaatac   2880
gtacaacaat tgtctgtaaa tcaacaacgc acagaatcta gcgcttaata aatgtactaa   2940
taacaatgta tcgtgtttta atacgccgga ccagtgaaca gaggtgcgtc tggtgcaaac   3000
tcctttactt tgaacaccag ggaaacttca aggagaattt cctcctcttc agcagagtcg   3060
gtaccggtca cccggggatc ccccctgccc ggttattatt attttttgaca ccagaccaac   3120
tggtaatggt agcgaccggc gctcagctgg aattccgccg atactgacgg gctccaggag   3180
tcgtcgccac caatcccccat atggaaaccg tcgatattca gccatgtgcc ttcttccgcg   3240
tgcagcagat ggcgatggct ggtttccatc agttgctgtt gactgtagcg gctgatgttg   3300
aactggaagt cgccgcgcca ctggtgtggg ccataattca attcgcgcgt cccgcagcgc   3360
agaccgtttt cgctcgggaa gacgtacggg gtatacatgt ctgacaatgg cagatcccag   3420
cggtcaaaac aggcggcagt aaggcggtcg ggatagtttt cttgcggccc taatccgagc   3480
cagtttaccc gctctgctac ctgcgccagc tggcagttca ggccaatccg cgccggatgc   3540
ggtgtatcgc tcgccacttc aacatcaacg gtaatcgcca tttgaccact accatcaatc   3600
cggtaggttt tccggctgat aaataaggtt ttcccctgat gctgccacgc gtgagcggtc   3660
gtaatcagca ccgcatcagc aagtgtatct gccgtgcact gcaacaacgc tgcttcggcc   3720
tggtaatggc ccgccgcctt ccagcgttcg acccaggcgt tagggtcaat gcgggtcgct   3780
tcacttacgc caatgtcgtt atccagcggt gcacgggtga actgatcgcg cagcggcgtc   3840
agcagttgtt ttttatcgcc aatccacatc tgtgaaagaa agcctgactg gcggttaaat   3900
tgccaacgct tattacccag ctcgatgcaa aaatccattt cgctggtggt cagatgcggg   3960
atggcgtggg acgcgcgggg gagcgtcaca ctgaggtttt ccgccagacg ccactgctgc   4020
caggcgctga tgtgcccggc ttctgaccat gcggtcgcgt tcggttgcac tacgcgtact   4080
gtgagccaga gttgcccggc gctctccggc tgcggtagtt caggcagttc aatcaactgt   4140
ttaccttgtg gagcgacatc cagaggcact tcaccgcttg ccagcggctt accatccagc   4200
```

-continued

```
gccaccatcc agtgcaggag ctcgttatcg ctatgacgga acaggtattc gctggtcact    4260
tcgatggttt gcccggataa acggaactgg aaaaactgct gctggtgttt tgcttccgtc    4320
agcgctggat gcggcgtgcg gtcggcaaag accagaccgt tcatacagaa ctggcgatcg    4380
ttcggcgtat cgccaaaatc accgccgtaa gccgaccacg ggttgccgtt ttcatcatat    4440
ttaatcagcg actgatccac ccagtcccag acgaagccgc cctgtaaacg gggatactga    4500
cgaaacgcct gccagtattt agcgaaaccg ccaagactgt tacccatcgc gtgggcgtat    4560
tcgcaaagga tcagcgggcg cgtctctcca ggtagcgaaa gccattttt gatggaccat    4620 ttcggcacag ccgggaaggg ctggtcttca tccacgcgcg cgtacatcgg gcaaataata    4680
tcggtggccg tggtgtcggc tccgccgcct tcatactgca ccgggcggga aggatcgaca    4740
gatttgatcc agcgatacag cgcgtcgtga ttagcgccgg ggcctgattc attccccagc    4800
gaccagatga tcacactcgg gtgattacga tcgcgctgca ccattcgcgt tacgcgttcg    4860
ctcatcgccg gtagccagcg cggatcatcg gtcagacgat tcattggcac catgccgtgg    4920
gtttcaatat tggcttcatc caccacatac aggccgtagc ggtcgcacag cgtgtaccac    4980
agcggatggt tcgataatg cgaacagcgc acggcgttaa agttgttctg cttcatcagc    5040
aggatatcct gcaccatcgt ctgctcatcc atgacctgac catgcagagg atgatgctcg    5100
tgacggttaa cgcctcgaat cagcaacggc ttgccgttca gcagcagcag accattttca    5160
atccgcacct cgcggaaacc gacatcgcag gcttctgctt caatcagcgt gccgtcggcg    5220
gtgtgcagtt caaccaccgc acgatagaga ttcgggattt cggcgctcca cagtttcggg    5280
ttttcgacgt tcagacgtag tgtgacgcga tcggcataac caccacgctc atcgataatt    5340
tcaccgccga aaggcgcggt gccgctggcg acctgcgttt caccctgcca taaagaaact    5400
gttacccgta ggtagtcacg caactcgccg cacatctgaa cttcagcctc cagtacagcg    5460
cggctgaaat catcattaaa gcgagtggca acatggaaat cgctgatttg tgtagtcggt    5520
ttatgcagca acgagacgtc acggaaaatg ccgctcatcc gccacatatc ctgatcttcc    5580
agataactgc cgtcactcca acgcagcacc atcaccgcga ggcggttttc tccggcgcgt    5640
aaaaatgcgc tcaggtcaaa ttcagacggc aaacgactgt cctggccgta accgacccag    5700
cgcccgttgc accacagatg aaacgccgag ttaacgccat caaaaataat tcgcgtctgg    5760
ccttcctgta gccagctttc atcaacatta aatgtgagcg agtaacaacc cgtcggattc    5820
tccgtgggaa caaacggcgg attgaccgta atgggatagg ttacgttggt gtagatgggc    5880
gcatcgtaac cgtgcatctg ccagtttgag gggacgacga cgggatccgt ttttttatta    5940
caaaactgtt acgaaaacag taaaatactt atttattcgg accaacaatg tttattctta    6000
cctctaatag tcctctgtgg caaggtcaag attctgttag aagccaatga agaacctggt    6060
tgttcaataa cattttgttc gtctaatatt tcactacgct tgacgttggc tgacacttca    6120
tgtacctcat ctataaacgc ttcttctgta tcgctctgga cgtcttcact tacgtgatct    6180
gatatttcac tgtcagaatc ctcaccaaca agctcgtcat cgccttgcag aagagcagag    6240
aggatatgct catcgtctaa agaacatccc attttattat atattagtca cgatatctat    6300
aacaagaaaa tatatatata ataagttatc acgtaagtag aacatgaaat aacaatatta    6360
attatcgtat gagttaaatc ttaaaagtca cgtaaaagat aatcatgcgt catttttgact    6420 cacgcggtcg ttatagttca aaatcagtga cacttaccgc attgacaagc acgcctcagc    6480
cgagctccaa gcggcgactg agatgtccta aattgcaaac agcgacggat tcgcgctatt    6540
tagaaagaga gagcaatatt tcaagaatgc atgcgtcaat tttacgcaga ctatctttct    6600
```

```
agggttaatc tagaggatcc tctagattaa ccctagaaag ataatcatat tgtgacgtac      6660
gttaaagata atcatgcgta aaattgacgc atgtgttttt atcggtctgt atatcgaggt      6720
ttatttatta atttgaatag atattaagtt ttattatatt tacacttaca tactaataat      6780
aaattcaaca aacaatttat ttatgtttat ttatttatta aaaaaaaaca aaaactcaaa      6840
atttcttcta aagtaacaaa acttttaaac attctctctt ttacaaaaat aaacttattt      6900
tgtactttaa aaacagtcat gttgtattat aaaataagta attagcttaa cttatacata      6960
atagaaacaa attatactta ttagtcagtc cagaaacaac tttggcacat atcaatatta      7020
tgctctcgac aaataacttt tttgcatttt ttgcacgatg catttgcctt tcgccttatt      7080
ttagaggggc agtaagtaca gtaagtacgt tttttcatta ctggctcttc agtactgtca      7140
tctgatgtac caggcacttc atttggcaaa atattagaga tattatcgcg caaatatctc      7200
ttcaaagtag gagcttctaa acggttacgc ataaacgatg acgtcaggct catgtaaagg      7260
tttctcataa atttttttgcg actttgaacc ttttctccct tgctactgac attatggctg      7320
tatataataa aagaatttat gcaggcaatg tttatcattc cgtacaataa tgccataggc      7380
cacctattcg tcttcctact gcaggtcatc acagaacaca tttggtctag cgtgtccact      7440
ccgcctttag tttgattata atacataacc atttgcggtt taccggtact ttcgttgata      7500
gaagcatcct catcacaaga tgataataag tataccatct tagctggctt cggtttatat      7560
gagacgagag taagggggtcc gtcaaaacaa acatcgatg ttcccactgg cctggagcga      7620
ctgtttttca gtacttccgg tatctcgcgt ttgtttgatc gcacggtacc                 7670
```

<210> SEQ ID NO 58
<211> LENGTH: 286
<212> TYPE: PRT
<213> ORGANISM: Artificial Sequence
<220> FEATURE:
<223> OTHER INFORMATION: Description of Artificial Sequence: pIAO-pL
      amino acid sequence

<400> SEQUENCE: 58

```
Trp His Lys Ile Leu Ser Ala Gly Ile Glu Ala Ile Gln Arg Asn Arg
 1               5                  10                  15

Glu Asp Met Thr Ala Gln Ser Gly Thr Thr Tyr Ile Val Val Ile Arg
            20                  25                  30

Ser Pro Lys Gly Asp Pro Gly Leu Ala Ala Ile Ile Gly Arg Ser Gly
        35                  40                  45

Arg Glu Gly Ala Gly Ser Lys Asp Ala Ile Phe Trp Gly Ala Pro Leu
    50                  55                  60

Ala Ser Arg Leu Leu Pro Gly Ala Val Lys Asp Ala Glu Met Trp Asp
65                  70                  75                  80

Ile Leu Gln Gln Arg Ser Ala Leu Thr Leu Leu Glu Gly Thr Leu Leu
                85                  90                  95

Lys Arg Leu Thr Thr Ala Met Ala Val Pro Met Thr Thr Asp Arg Glu
            100                 105                 110

Asp Asn Pro Ile Ala Glu Asn Leu Glu Pro Glu Trp Arg Asp Leu Arg
        115                 120                 125

Thr Val His Asp Gly Met Asn His Leu Phe Ala Thr Leu Glu Lys Pro
    130                 135                 140

Gly Gly Ile Thr Thr Leu Leu Leu Asn Ala Ala Thr Asn Asp Ser Met
145                 150                 155                 160

Thr Ile Ala Ala Ser Cys Leu Glu Arg Val Thr Met Gly Asp Thr Leu
```

-continued

```
                165                 170                 175
His Lys Glu Thr Val Pro Ser Tyr Glu Val Leu Asp Asn Gln Ser Tyr
            180                 185                 190

His Ile Arg Arg Gly Leu Gln Glu Gln Gly Ala Asp Ile Arg Ser Leu
            195                 200                 205

Val Ala Gly Cys Leu Leu Val Lys Phe Thr Ser Met Met Pro Phe Arg
            210                 215                 220

Glu Glu Pro Arg Phe Ser Glu Leu Ile Lys Gly Ser Asn Leu Asp Leu
225                 230                 235                 240

Glu Ile Tyr Gly Val Arg Ala Gly Leu Gln Asp Glu Ala Asp Lys Val
            245                 250                 255

Lys Val Leu Thr Glu Pro His Ala Phe Val Pro Leu Cys Phe Ala Ala
            260                 265                 270

Phe Phe Pro Ile Leu Ala Val Arg Phe His Gln Ile Ser Met
            275                 280                 285

<210> SEQ ID NO 59
<211> LENGTH: 240
<212> TYPE: PRT
<213> ORGANISM: Artificial Sequence
<220> FEATURE:
<223> OTHER INFORMATION: Description of Artificial Sequence: pIAO-pL
      amino acid sequence

<400> SEQUENCE: 59

Arg Tyr Phe Tyr Ala Tyr Pro Ala Arg Leu His Val Leu Gln Val Tyr
1               5                  10                  15

Tyr Ser Leu Arg Ala Cys Ala Lys Ile Val Gly Glu Arg Leu Ile Arg
            20                  25                  30

Thr Thr Ser Arg Gln Asp Thr Asn Arg Lys Gly Phe Leu Ala Asn Trp
        35                  40                  45

Lys Asp Tyr Val Glu Tyr Trp Gln Val Asp His Pro Asn Lys Asn Trp
    50                  55                  60

Val Lys Ala Gln Lys Pro Tyr Val Asp Val Ser Val Thr Arg Phe Trp
65                  70                  75                  80

Thr Val Thr Arg His Asp Phe Ser Gly Arg Ser His Leu Lys Thr His
            85                  90                  95

Val Ser Pro Tyr Leu Ser Gly Met Asn Lys Cys Ser Tyr Ile Cys Arg
            100                 105                 110

Lys Arg Ser Thr His Ala Thr Tyr Lys Gln Gly Asn Ser Met Thr Asp
            115                 120                 125

Phe Phe Gly Phe Arg Asp Val Ser Glu Asn Cys Leu Arg Val Cys Gln
            130                 135                 140

Cys Leu Asp Ile Trp Leu Pro Arg His Val His Pro Arg Lys Glu Ser
145                 150                 155                 160

Ser Asp Asn Gly Ser Tyr Trp Leu Phe Cys Leu Asn Arg Glu His Ser
            165                 170                 175

Ile Tyr Cys Arg Asp Tyr Ile Gly Ser Thr Glu Ile Ile Asp Cys Lys
            180                 185                 190

Asp Met Lys Cys Asn Ala Phe Asn Asp Tyr Phe Ile Thr Gln Leu Met
            195                 200                 205

Phe Thr Pro Ile Tyr Gln Pro Val Tyr Ala Asp Ser Arg Lys Ser Ile
            210                 215                 220

Gln Cys His Glu Thr Cys Leu Ser Pro Arg Glu His Val Lys Phe Asn
225                 230                 235                 240
```

-continued

```
<210> SEQ ID NO 60
<211> LENGTH: 933
<212> TYPE: PRT
<213> ORGANISM: Artificial Sequence
<220> FEATURE:
<223> OTHER INFORMATION: Description of Artificial Sequence: pIAO-pL
      amino acid sequence

<400> SEQUENCE: 60

Lys Gln Cys Trp Val Leu Gln Tyr His Tyr Arg Gly Ala Ser Leu Gln
 1               5                  10                  15

Phe Glu Ala Ser Val Ser Pro Ser Trp Ser Asp Asp Gly Gly Ile Gly
                20                  25                  30

Met His Phe Gly Asp Ile Asn Leu Trp Thr Gly Glu Glu Ala His Leu
            35                  40                  45

Leu His Arg His Ser Thr Glu Met Leu Gln Gln Ser Tyr Arg Ser
        50                  55                  60

Ile Asn Phe Gln Phe Asp Gly Arg Trp Gln His Pro Gly Tyr Asn Leu
 65                  70                  75                  80

Glu Arg Thr Gly Cys Arg Leu Gly Asn Glu Ser Pro Phe Val Tyr Pro
                85                  90                  95

Thr Tyr Met Asp Ser Leu Pro Leu Asp Trp Arg Asp Phe Cys Ala Ala
               100                 105                 110

Thr Leu Arg Asp Pro Tyr Asn Glu Gln Pro Gly Leu Gly Leu Trp Asn
           115                 120                 125

Val Arg Glu Ala Val Gln Ala Leu Gln Cys Asn Leu Gly Ile Arg Ala
130                 135                 140

Pro His Pro Thr Asp Ser Ala Val Glu Val Asp Val Thr Ile Ala Met
145                 150                 155                 160

Gln Gly Ser Gly Asp Ile Arg Tyr Thr Lys Arg Ser Ile Phe Leu Thr
                165                 170                 175

Lys Gly Gln His Gln Trp Ala His Thr Thr Ile Leu Val Ala Asp
            180                 185                 190

Ala Leu Thr Asp Ala Thr Cys Gln Leu Leu Ala Ala Glu Ala Gln Tyr
        195                 200                 205

His Gly Ala Ala Lys Trp Arg Glu Val Trp Ala Asn Pro Asp Ile Arg
    210                 215                 220

Thr Ala Glu Ser Val Gly Ile Asp Asn Asp Leu Pro Ala Arg Thr Phe
225                 230                 235                 240

Gln Asp Arg Leu Pro Thr Leu Leu Gln Lys Lys Asp Gly Ile Trp Met
                245                 250                 255

Gln Ser Leu Phe Gly Ser Gln Arg Asn Phe Gln Trp Arg Lys Asn Gly
            260                 265                 270

Leu Glu Ile Cys Phe Asp Met Glu Ser Thr Thr Leu His Pro Ile Ala
        275                 280                 285

His Ser Ala Ala Pro Leu Thr Val Ser Leu Asn Glu Ala Leu Arg Trp
    290                 295                 300

Gln Gln Trp Ala Ser Ile His Gly Ala Glu Ser Trp Ala Thr Ala Asn
305                 310                 315                 320

Pro Gln Val Val Arg Val Thr Leu Trp Leu Gln Gly Ala Ser Glu Pro
                325                 330                 335

Gln Pro Leu Glu Pro Leu Glu Ile Leu Gln Lys Gly Gln Pro Ala Val
            340                 345                 350

Asp Leu Pro Val Glu Gly Ser Ala Leu Pro Lys Gly Asp Leu Ala Val
        355                 360                 365
```

-continued

```
Met Trp His Leu Leu Glu Asn Asp Ser His Arg Phe Leu Tyr Glu Ser
        370                 375                 380

Thr Val Glu Ile Thr Gln Gly Ser Leu Arg Phe Gln Phe Phe Gln Gln
385                 390                 395                 400

Gln His Lys Ala Glu Thr Leu Ala Pro His Pro Thr Arg Asp Ala Phe
                405                 410                 415

Val Leu Gly Asn Met Cys Phe Gln Arg Asp Asn Pro Thr Asp Gly Phe
                420                 425                 430

Asp Gly Gly Tyr Ala Ser Trp Pro Asn Gly Asn Glu Asp Tyr Lys Ile
            435                 440                 445

Leu Ser Gln Asp Val Trp Asp Trp Val Phe Gly Gly Gln Leu Arg Pro
450                 455                 460

Tyr Gln Arg Phe Ala Gln Trp Tyr Lys Ala Phe Gly Leu Ser Asn
465                 470                 475                 480

Gly Met Ala His Ala Tyr Glu Cys Leu Ile Leu Pro Arg Thr Glu Gly
                485                 490                 495

Pro Leu Ser Leu Trp Lys Lys Ile Ser Trp Lys Pro Val Ala Pro Phe
                500                 505                 510

Pro Gln Asp Glu Asp Val Arg Ala Tyr Met Pro Cys Ile Ile Asp Thr
            515                 520                 525

Ala Thr Thr Asp Ala Gly Gly Glu Tyr Gln Val Pro Arg Ser Pro
        530                 535                 540

Asp Val Ser Lys Ile Trp Arg Tyr Leu Ala Asp His Asn Ala Gly His
545                 550                 555                 560

Gly Ser Glu Asn Gly Leu Ser Trp Ile Ile Val Ser Pro His Asn Arg
                565                 570                 575

Asp Arg Gln Val Met Arg Thr Val Arg Glu Ser Met Ala Pro Leu Trp
                580                 585                 590

Arg Pro Asp Asp Thr Leu Arg Asn Met Pro Val Met Gly His Thr Glu
            595                 600                 605

Ile Asn Ala Glu Asp Val Val Tyr Leu Gly Tyr Arg Asp Cys Leu Thr
610                 615                 620

Tyr Trp Leu Pro His Asn Pro Tyr His Ser Cys Arg Val Ala Asn Phe
625                 630                 635                 640

Asn Asn Gln Lys Met Leu Leu Ile Asp Gln Val Met Thr Gln Glu Asp
                645                 650                 655

Met Val Gln Gly His Leu Pro His His Glu His Arg Asn Val Gly Arg
                660                 665                 670

Ile Leu Leu Pro Lys Gly Asn Leu Leu Leu Gly Asn Glu Ile Arg
            675                 680                 685

Val Glu Arg Phe Gly Val Asp Cys Ala Glu Ala Glu Ile Leu Thr Gly
        690                 695                 700

Asp Ala Thr His Leu Glu Val Val Ala Arg Tyr Leu Asn Pro Ile Glu
705                 710                 715                 720

Ala Ser Trp Leu Lys Pro Asn Glu Val Asn Leu Arg Leu Thr Val Arg
                725                 730                 735

Asp Ala Tyr Gly Gly Arg Glu Asp Ile Ile Glu Gly Gly Phe Pro Ala
                740                 745                 750

Thr Gly Ser Ala Val Gln Thr Glu Gly Gln Trp Leu Ser Val Thr Val
        755                 760                 765

Arg Leu Tyr Asp Arg Leu Glu Gly Cys Met Gln Val Glu Ala Glu Leu
770                 775                 780
```

-continued

```
Val Ala Arg Ser Phe Asp Asp Asn Phe Arg Thr Ala Val His Phe Asp
785                 790                 795                 800

Ser Ile Gln Thr Thr Pro Lys His Leu Leu Ser Val Asp Arg Phe Ile
                805                 810                 815

Gly Ser Met Arg Trp Met Asp Gln Asp Glu Leu Tyr Ser Gly Asp Ser
            820                 825                 830

Trp Arg Leu Val Met Val Ala Leu Arg Asn Glu Gly Ala Arg Leu Phe
        835                 840                 845

Ala Ser Leu Asp Phe Glu Ser Pro Leu Arg Ser Asp Gln Gly Tyr Gly
    850                 855                 860

Val Trp Arg Gly Asn Cys Trp Leu His Phe Ala Ser Asn Val Gly Asp
865                 870                 875                 880

Phe Ile Ile Arg Thr Gln Gly Glu Gln Leu Trp Ser Glu Asp Val Asn
                885                 890                 895

Phe Thr Leu Ser Tyr Cys Gly Thr Pro Asn Glu Thr Pro Val Phe Pro
            900                 905                 910

Pro Asn Val Thr Ile Pro Tyr Thr Val Asn Thr Tyr Ile Pro Ala Asp
        915                 920                 925

Tyr Gly His Met Gln
        930

<210> SEQ ID NO 61
<211> LENGTH: 110
<212> TYPE: PRT
<213> ORGANISM: Artificial Sequence
<220> FEATURE:
<223> OTHER INFORMATION: Description of Artificial Sequence: pIAO-pL
      amino acid sequence
<220> FEATURE:
<221> NAME/KEY: MOD_RES
<222> LOCATION: (110)
<223> OTHER INFORMATION: Any amino acid

<400> SEQUENCE: 61

Val Leu Leu Thr Glu Trp Asn Ser Pro Val Val Pro Asp Thr Lys
  1               5                  10                  15

Lys Asn Cys Phe Gln Ser Phe Leu Leu Ile Ser Ile Glu Ser Trp Cys
                 20                  25                  30

Arg Tyr Asp Glu Thr Ala Leu Asp Leu Asn Gln Phe Gly Ile Phe Phe
             35                  40                  45

Arg Thr Thr Tyr Cys Lys Thr Arg Arg Ile Asn Ala Gln Arg Gln Ser
         50                  55                  60

Val Ser Thr Gly Arg Tyr Val Ser Arg Arg Tyr Arg Glu Pro Arg Arg
 65                  70                  75                  80

Lys Arg Ser Arg Ile Asn Gln Phe Gly Trp Cys Ala Arg Arg Arg Ala
                 85                  90                  95

Ser Ser Cys Leu Pro Tyr Ala Arg Arg Phe Phe Met Gly Xaa
                100                 105                 110

<210> SEQ ID NO 62
<211> LENGTH: 229
<212> TYPE: PRT
<213> ORGANISM: Artificial Sequence
<220> FEATURE:
<223> OTHER INFORMATION: Description of Artificial Sequence: pIAO-pL
      amino acid sequence

<400> SEQUENCE: 62

Asp Thr Trp Phe Cys Ser Gln Cys Met Asp Ile Asn His Glu Arg Cys
  1               5                  10                  15
```

```
Ile Val Lys Lys Cys Lys Lys Cys Ser Ala Asn Ala Lys Arg Arg Ile
            20                  25                  30

Lys Ser Pro Cys Tyr Thr Cys Tyr Thr Arg Lys Lys Met Val Pro Glu
        35                  40                  45

Glu Thr Ser Asp Asp Ser Thr Gly Pro Val Glu Asn Pro Leu Ile Asn
    50                  55                  60

Ser Ile Asn Asp Arg Leu Tyr Arg Lys Leu Thr Pro Ala Glu Leu Arg
65                  70                  75                  80

Asn Arg Met Phe Ser Ser Thr Leu Ser Met Tyr Leu Asn Arg Met Phe
                85                  90                  95

Lys Lys Arg Ser Gln Val Lys Glu Gly Lys Ser Ser Val Asn His Ser
            100                 105                 110

Tyr Ile Ile Phe Ser Asn Ile Cys Ala Ile Asn Ile Met Gly Tyr Leu
            115                 120                 125

Leu Ala Met Pro Trp Arg Asn Thr Lys Arg Ser Cys Thr Met Val Ser
130                 135                 140

Cys Met Gln Asp Leu Thr Asp Val Gly Gly Lys Thr Gln Asn Tyr Tyr
145                 150                 155                 160

Met Val Met Gln Pro Lys Gly Thr Ser Glu Asn Ile Ser Ala Asp Glu
                165                 170                 175

Asp Cys Ser Ser Leu Leu Tyr Val Met Lys Ala Pro Lys Pro Lys Tyr
            180                 185                 190

Ser Val Leu Thr Leu Pro Gly Asp Phe Cys Phe Met Ser Thr Gly Val
            195                 200                 205

Pro Arg Ser Arg Ser Asn Lys Leu Val Glu Pro Ile Glu Arg Lys Asn
    210                 215                 220

Ser Arg Val Thr Gly
225

<210> SEQ ID NO 63
<211> LENGTH: 9984
<212> TYPE: DNA
<213> ORGANISM: Artificial Sequence
<220> FEATURE:
<223> OTHER INFORMATION: Description of Artificial Sequence:
      pIAO-p/L-Lambda-2.2kb sequence

<400> SEQUENCE: 63
aacgcgcggg gagaggcggt ttgcgtattg ggcgctcttc cgcttcctcg ctcactgact      60
cgctgcgctc ggtcgttcgg ctgcggcgag cggtatcagc tcactcaaag gcggtaatac     120
ggttatccac agaatcaggg gataacgcag gaaagaacat gtgagcaaaa ggccagcaaa     180
aggccaggaa ccgtaaaaag gccgcgttgc tggcgttttt ccataggctc cgcccccctg     240
acgagcatca caaaaatcga cgctcaagtc agaggtggcg aaacccgaca ggactataaa     300
gataccaggc gtttccccct ggaagctccc tcgtgcgctc tcctgttccg accctgccgc     360
ttaccggata cctgtccgcc tttctccctt cgggaagcgt ggcgctttct caatgctcac     420
gctgtaggta tctcagttcg gtgtaggtcg ttcgctccaa gctgggctgt gtgcacgaac     480
cccccgttca gcccgaccgc tgcgccttat ccggtaacta tcgtcttgag tccaacccgg     540
taagacacga cttatcgcca ctggcagcag ccactggtaa caggattagc agagcgaggt     600
atgtaggcgg tgctacagag ttcttgaagt ggtggcctaa ctacggctac actagaagga     660
cagtatttgg tatctgcgct ctgctgaagc cagttacctt cggaaaaaga gttggtagct     720
cttgatccgg caaacaaacc accgctggta gcggtggttt ttttgtttgc aagcagcaga     780
```

-continued

| | |
|---|---|
| ttacgcgcag aaaaaaagga tctcaagaag atcctttgat cttttctacg gggtctgacg | 840 |
| ctcagtggaa cgaaaactca cgttaaggga ttttggtcat gagattatca aaaggatct | 900 |
| tcacctagat cctttaaat taaaaatgaa gttttaaatc aatctaaagt atatatgagt | 960 |
| aaacttggtc tgacagttac caatgcttaa tcagtgaggc acctatctca gcgatctgtc | 1020 |
| tatttcgttc atccatagtt gcctgactcc ccgtcgtgta gataactacg atacgggagg | 1080 |
| gcttaccatc tggccccagt gctgcaatga taccgcgaga cccacgctca ccggctccag | 1140 |
| atttatcagc aataaaccag ccagccgaa gggccgagcg cagaagtggt cctgcaactt | 1200 |
| tatccgcctc catccagtct attaattgtt gccgggaagc tagagtaagt agttcgccag | 1260 |
| ttaatagttt cgcaacgtt gttgccattg ctacaggcat cgtggtgtca cgctcgtcgt | 1320 |
| ttggtatggc ttcattcagc tccggttccc aacgatcaag gcgagttaca tgatccccca | 1380 |
| tgttgtgcaa aaaagcggtt agctccttcg gtcctccgat cgttgtcaga agtaagttgg | 1440 |
| ccgcagtgtt atcactcatg gttatggcag cactgcataa ttctcttact gtcatgccat | 1500 |
| ccgtaagatg cttttctgtg actggtgagt actcaaccaa gtcattctga aatagtgta | 1560 |
| tgcggcgacc gagttgctct tgcccggcgt caatacggga taataccgcg ccacatagca | 1620 |
| gaactttaaa agtgctcatc attggaaaac gttcttcggg gcgaaaactc tcaaggatct | 1680 |
| taccgctgtt gagatccagt tcgatgtaac ccactcgtgc acccaactga tcttcagcat | 1740 |
| cttttacttt caccagcgtt tctgggtgag caaaaacagg aaggcaaaat gccgcaaaaa | 1800 |
| agggaataag ggcgacacgg aaatgttgaa tactcatact cttccttttt caatattatt | 1860 |
| gaagcattta tcaggttat tgtctcatga gcggatacat atttgaatgt atttagaaaa | 1920 |
| ataaacaaat aggggttccg cgcacatttc cccgaaaagt gccacctgac gtctaagaaa | 1980 |
| ccattattat catgacatta acctataaaa ataggcgtat cacggggccc tgagtgaac | 2040 |
| caattgtcac acgtaatatt acgacaacta ccgtgcacag gctttgataa ctccttcacg | 2100 |
| tagtattcac cgagtggtac tccgttggtc tgtgttcctc ttcccaaata aggcattcca | 2160 |
| tttatcatat acttcgtacc actgtcacac atcatgagga ttttttattcc atacttactt | 2220 |
| ggcttgtttg ggatatacat cctaaacgga caccgtcctc taaaaccaag taactgttca | 2280 |
| tctatggtca aatgagcccc tggagtgtaa ttttgtatgc actgatggat aaagagatcc | 2340 |
| catattttc taacaggagt aaatacatcg ttttctcgaa gtgtgggccg tatacttttg | 2400 |
| tcatccattc taagacatcg tatcaaaaaa tccaaaacga tccacagact cattacagag | 2460 |
| acgtacacat tgacaaagat cgatccaaag aggtcatctg tggacatgtg gttatctttt | 2520 |
| ctcactgctg tcattaccag aataccaaag aaagcataga tttcatcttc attcgtgtca | 2580 |
| cgaaatgtag cacctgtcat agattcccga cgtttcaatg atatctcagc atttgtccat | 2640 |
| tttacaattt gcgaaattat ctcatcagta aaaaatagtt tgaagcataa aagtgggtca | 2700 |
| tatatattgc ggcacatacg cgtcggacct ctttgagatc tgacaatgtt cagtgcagag | 2760 |
| actcggctac cgctcgtgga ctttgaagtt aaattcagat ataaagacgc tgaaaatcat | 2820 |
| ttgattttcg ctctaacata ccaccctaaa gattataaat ttaatgaatt attaaaatac | 2880 |
| gtacaacaat tgtctgtaaa tcaacaacgc acagaatcta gcgcttaata aatgtactaa | 2940 |
| taacaatgta tcgtgtttta atacgccgga ccagtgaaca gaggtcgtc tggtgcaaac | 3000 |
| tcctttactt tgaacaccag ggaaacttca aggagaattt cctcctcttc agcagagtcg | 3060 |
| gtaccggtca cccggggatc cccctgccc ggttattatt atttttgaca ccagaccaac | 3120 |

```
tggtaatggt agcgaccggc gctcagctgg aattccgccg atactgacgg gctccaggag    3180
tcgtcgccac caatccccat atggaaaccg tcgatattca gccatgtgcc ttcttccgcg    3240
tgcagcagat ggcgatggct ggtttccatc agttgctgtt gactgtagcg gctgatgttg    3300
aactggaagt cgccgcgcca ctggtgtggg ccataattca attcgcgcgt cccgcagcgc    3360
agaccgtttt cgctcgggaa gacgtacggg gtatacatgt ctgacaatgg cagatcccag    3420
cggtcaaaac aggcggcagt aaggcggtcg ggatagtttt cttgcggccc taatccgagc    3480
cagtttaccc gctctgctac ctgcgccagc tggcagttca ggccaatccg cgccggatgc    3540
ggtgtatcgc tcgccacttc aacatcaacg gtaatcgcca tttgaccact accatcaatc    3600
cggtaggttt tccggctgat aaataaggtt ttcccctgat gctgccacgc gtgagcggtc    3660
gtaatcagca ccgcatcagc aagtgtatct gccgtgcact gcaacaacgc tgcttcggcc    3720
tggtaatggc ccgccgcctt ccagcgttcg acccaggcgt tagggtcaat gcgggtcgct    3780
tcacttacgc caatgtcgtt atccagcggt gcacgggtga actgatcgcg cagcggcgtc    3840
agcagttgtt ttttatcgcc aatccacatc tgtgaaagaa agcctgactg gcggttaaat    3900
tgccaacgct tattacccag ctcgatgcaa aaatccattt cgctggtggt cagatgcggg    3960
atggcgtggg acgcggcggg gagcgtcaca ctgaggtttt ccgccagacg ccactgctgc    4020
caggcgctga tgtgccccgc ttctgaccat gcggtcgcgt tcggttgcac tacgcgtact    4080
gtgagccaga gttgcccggc gctctccggc tgcggtagtt caggcagttc aatcaactgt    4140
ttaccttgtg gagcgacatc cagaggcact tcaccgcttg ccagcggctt accatccagc    4200
gccaccatcc agtgcaggag ctcgttatcg ctatgacgga acaggtattc gctggtcact    4260
tcgatggttt gcccggataa acggaactgg aaaaactgct gctggtgttt tgcttccgtc    4320
agcgctggat gcggcgtgcg gtcggcaaag accagaccgt tcatacagaa ctggcgatcg    4380
ttcggcgtat cgccaaaatc accgccgtaa gccgaccacg ggttgccgtt ttcatcatat    4440
ttaatcagcg actgatccac ccagtcccag acgaagccgc cctgtaaacg gggatactga    4500
cgaaacgcct gccagtattt agcgaaaccg ccaagactgt tacccatcgc gtgggcgtat    4560
tcgcaaagga tcagcgggcg cgtctctcca ggtagcgaaa gccatttttt gatggaccat    4620
ttcggcacag ccgggaaggg ctggtcttca tccacgcgcg cgtacatcgg gcaaataata    4680
tcggtggccg tggtgtcggc tccgccgcct tcatactgca ccgggcggga aggatcgaca    4740
gatttgatcc agcgatacag cgcgtcgtga ttagcgccgt ggcctgattc attccccagc    4800
gaccagatga tcacactcgg gtgattacga tcgcgctgca ccattcgcgt tacgcgttcg    4860
ctcatcgccg gtagccagcg cggatcatcg gtcagacgat tcattggcac catgccgtgg    4920
gtttcaatat tggcttcatc caccacatac aggccgtagc ggtcgcacag cgtgtaccac    4980
agcggatggt tcgataatg cgaacagcgc acggcgttaa agttgttctg cttcatcagc    5040
aggatatcct gcaccatcgt ctgctcatcc atgacctgac catgcagagg atgatgctcg    5100
tgacggttaa cgcctcgaat cagcaacggc ttgccgttca gcagcagcag accattttca    5160
atccgcacct cgcggaaacc gacatcgcag gcttctgctt caatcagcgt gccgtcggcg    5220
gtgtgcagtt caaccaccgc acgatagaga ttcgggattt cggcgctcca cagtttcggg    5280
ttttcgacgt tcagacgtag tgtgacgcga tcggcataac caccacgctc atcgataatt    5340
tcaccgccga aaggcgcggt gccgctggcg acctgcgttt caccctgcca taaagaaact    5400
gttacccgta ggtagtcacg caactcgccg cacatctgaa cttcagcctc cagtacagcg    5460
cggctgaaat catcattaaa gcgagtggca acatggaaat cgctgatttg tgtagtcggt    5520
```

```
ttatgcagca acgagacgtc acggaaaatg ccgctcatcc gccacatatc ctgatcttcc    5580
agataactgc cgtcactcca acgcagcacc atcaccgcga ggcggttttc tccggcgcgt    5640
aaaaatgcgc tcaggtcaaa ttcagacggc aaacgactgt cctggccgta accgacccag    5700
cgcccgttgc accacagatg aaacgccgag ttaacgccat caaaaataat tcgcgtctgg    5760
ccttcctgta gccagctttc atcaacatta aatgtgagcg agtaacaacc cgtcggattc    5820
tccgtgggaa caaacggcgg attgaccgta atgggatagg ttacgttggt gtagatgggc    5880
gcatcgtaac cgtgcatctg ccagtttgag gggacgacga cgggatccgt tttttattta    5940
caaaactgtt acgaaaacag taaaatactt atttattcgg accaacaatg tttattctta    6000
cctctaatag tcctctgtgg caaggtcaag attctgttag aagccaatga agaacctggt    6060
tgttcaataa cattttgttc gtctaatatt tcactacgct tgacgttggc tgacacttca    6120
tgtacctcat ctataaacgc ttcttctgta tcgctctgga cgtcttcact tacgtgatct    6180
gatatttcac tgtcagaatc ctcaccaaca agctcgtcat cgccttgcag aagagcagag    6240
aggatatgct catcgtctaa agaacatccc attttattat atattagtca cgatatctat    6300
aacaagaaaa tatatatata ataagttatc acgtaagtag aacatgaaat aacaatatta    6360
attatcgtat gagttaaatc ttaaaagtca cgtaaaagat aatcatgcgt cattttgact    6420
cacgcggtcg ttatagttca aaatcagtga cacttaccgc attgacaagc acgcctcagc    6480
cgagctccaa gcggcgactg agatgtccta aattgcaaac agcgacggat tcgcgctatt    6540
tagaaagaga gagcaatatt tcaagaatgc atgcgtcaat tttacgcaga ctatctttct    6600
agggttaatc tagcttttct aatttaacct ttgtcaggtt accaactact aaggttgtag    6660
gctcaagagg gtgtgtcctg tcgtaggtaa ataactgacc tgtcgagctt aatattctat    6720
attgttgttc tttctgcaaa aaagtgggga agtgagtaat gaaattattt ctaacattta    6780
tctgcatcat accttccgag catttattaa gcatttcgct ataagttctc gctggaagag    6840
gtagtttttt cattgtactt taccttcatc tctgttcatt atcatcgctt ttaaaacggt    6900
tcgaccttct aatcctatct gaccattata atttttttaga atggtttcat aagaaagctc    6960
tgaatcaacg gactgcgata ataagtggtg gtatccagaa tttgtcactt caagtaaaaa    7020
cacctcacga gttaaaacac ctaagttctc accgaatgtc tcaatatccg gacggataat    7080
atttattgct tctcttgacc gtaggacttt ccacatgcag gattttggaa cctcttgcag    7140
tactactggg gaatgagttg caattattgc tacaccattg cgtgcatcga gtaagtcgct    7200
taatgttcgt aaaaaagcag agagcaaagg tggatgcaga tgaacctctg gttcatcgaa    7260
taaaactaat gacttttcgc caacgacatc tactaatctt gtgatagtaa ataaaacaat    7320
tgcatgtcca gagctcattc gaagcagata tttctggata ttgtcataaa acaatttagt    7380
gaatttatca tcgtccactt gaatctgtgg ttcattacgt cttaactctt catatttaga    7440
aatgaggctg atgagttcca tatttgaaaa gttttcatca ctacttagtt ttttgatagc    7500
ttcaagccag agttgtcttt ttctatctac tctcatacaa ccaataaatg ctgaaatgaa    7560
ttctaagcgg agatcgccta gtgattttaa actattgctg gcagcattct tgagtccaat    7620
ataaagtat tgtgtacctt tgctgggtc aggttgttct ttaggaggag taaaaggatc    7680
aaatgcacta acgaaactg aaacaagcga tcgaaaatat ccctttggga ttcttgactc    7740
gataagtcta ttattttcag agaaaaaata ttcattgttt tctggggttgg tgattgcacc    7800
aatcattcca ttcaaaattg ttgttttacc acacccattc cgcccgataa aagcatgaat    7860
```

```
gttcgtgctg ggcatagaat taaccgtcac ctcaaaaggt atagttaaat cactgaatcc    7920
gggagcactt tttctattaa atgaaaagtg gaaatctgac aattctggca aaccatttaa    7980
cacacgtgcg aactgtccat gaatttctga agagttacc cctctaagta atgaggtgtt    8040
aaggacgctt tcattttcaa tgtcggctaa tcgatttggc catactacta aatcctgaat    8100
agctttaaga aggttatgtt taaaaccatc gcttaatttg ctgagattaa catagtagtc    8160
aatgctttca cctaaggaaa aaaacatttc agggagttga ctgaattttt tatctattaa    8220
tgaataagtg cttacttctt cttttttgacc tacaaaacca attttaacat ttccgatatc    8280 gcattttca ccatgctcat caaagacagt aagataaaac attgtaacaa aggaatagtc    8340
attccaacca tctgctcgta ggaatgcctt atttttttct actgcaggaa tatacccgcc    8400
tctttcaata acactaaact ccaacatata gtaacccta attttattaa aataaccgca    8460
atttatttgg cggcaacaca ggatctctct tttaagttac tctctattac atacgttttc    8520
catctaaaaa ttagtagtat tgaacttaac ggggcatcgt attgtagttt tccatattta    8580
gctttctgct tccttttgga taacccactg ttattcatgt tgcatggtgc actgtttata    8640
ccaacgatat agtctattaa tgcatatata gtatcgccga acgattagct cttcaggctt    8700
ctgaagaagc gtttcaagta ctaataagcc gatagatagc cacggacttc gtagccattt    8760
ttcataagtg ttaacttccg ctcctcgctc ataacagaca ttcactacag ttatggcgga    8820
aaggtatgca tgctgggtgt ggggaagtcg tgaaagaaaa gaagtcagct gcgtcgtttg    8880
acatcactgc tatcttctta ctggttatgc aggtcgtagt gggtggcaca caaagctaga    8940
ttaaccctag aaagataatc atattgtgac gtacgttaaa gataatcatg cgtaaaattg    9000
acgcatgtgt ttttatcggt ctgtatatcg aggtttattt attaatttga atagatatta    9060
agttttatta tatttacact tacatactaa taataaattc aacaaacaat ttatttatgt    9120
ttatttattt attaaaaaaa aacaaaaact caaaatttct tctaaagtaa caaaactttt    9180
aaacattctc tcttttacaa aaataaactt attttgtact ttaaaaacag tcatgttgta    9240
ttataaaata agtaattagc ttaacttata cataatagaa acaaattata cttattagtc    9300
agtccagaaa caactttggc acatatcaat attatgctct cgacaaataa cttttttgca    9360
ttttttgcac gatgcatttg cctttcgcct tattttagag gggcagtaag tacagtaagt    9420
acgttttttc attactggct cttcagtact gtcatctgat gtaccaggca cttcatttgg    9480
caaaatatta gagatattat cgcgcaaata tctcttcaaa gtaggagctt ctaaacggtt    9540
acgcataaac gatgacgtca ggctcatgta aaggtttctc ataaattttt tgcgactttg    9600
aacctttctt cccttgctac tgacattatg gctgtatata ataaagaat ttatgcaggc    9660 aatgtttatc attccgtaca ataatgccat aggccaccta ttcgtcttcc tactgcaggt    9720
catcacagaa cacatttggt ctagcgtgtc cactccgcct ttagtttgat tataatacat    9780
aaccatttgc ggtttaccgg tactttcgtt gatagaagca tcctcatcac aagatgataa    9840
taagtatacc atcttagctg gcttcggttt atatgagacg agagtaaggg gtccgtcaaa    9900
acaaaacatc gatgttccca ctggcctgga gcgactgttt ttcagtactt ccggtatctc    9960
gcgtttgttt gatcgcacgg tacc                                          9984
```

<210> SEQ ID NO 64
<211> LENGTH: 60
<212> TYPE: PRT
<213> ORGANISM: Artificial Sequence
<220> FEATURE:
<223> OTHER INFORMATION: Description of Artificial Sequence:

pIAO-p/L-Lambda-2.2kb amino acid sequence

<400> SEQUENCE: 64

Lys Arg Ile Gly Lys Asp Pro Trp Ser Ser Leu Asn Tyr Ala Ser Pro
1               5                   10                  15

Thr Asp Gln Arg Leu Tyr Ile Val Ser Arg Asp Leu Lys Ile Asn Ile
            20                  25                  30

Thr Thr Arg Glu Ala Phe Phe His Pro Leu Ser Tyr His Phe Lys Cys
        35                  40                  45

Lys Asp Ala Asp Tyr Arg Gly Leu Met Ala Asn Arg
    50                  55                  60

<210> SEQ ID NO 65
<211> LENGTH: 470
<212> TYPE: PRT
<213> ORGANISM: Artificial Sequence
<220> FEATURE:
<223> OTHER INFORMATION: Description of Artificial Sequence:
      pIAO-p/L-Lambda-2.2kb amino acid sequence

<400> SEQUENCE: 65

Ser Tyr Thr Arg Ala Pro Leu Pro Leu Lys Lys Met Thr Ser Arg Arg
1               5                   10                  15

Gln Glu Asn Asp Asp Ser Lys Phe Arg Asn Ser Arg Arg Ile Arg Asp
            20                  25                  30

Ser Trp Leu Lys Lys Ser His Asn Leu Phe Ala Arg Phe Arg Val Ala
        35                  40                  45

Ile Ile Leu Pro Pro Ile Trp Phe Lys Asp Ser Thr Phe Val Gly Ser
    50                  55                  60

Asn Phe Cys Arg Leu Glu Arg Ile Asp Tyr Gly Ser Pro Tyr Tyr Lys
65                  70                  75                  80

Asn Ser Arg Lys Val Thr Pro Ser Glu Val His Leu Ile Lys Ser Gly
            85                  90                  95

Arg Ala Thr Ser Ser Pro Phe Ser Asn Cys Asn Asn Ser Cys Trp Gln
        100                 105                 110

Thr Cys Arg Thr Leu Arg Lys Ile Asn Thr Phe Phe Cys Leu Ala Phe
    115                 120                 125

Thr Ser Ala Ser Ser Gly Arg Thr Arg Ile Phe Ser Ile Val Lys Arg
    130                 135                 140

Trp Arg Cys Arg Ser Ile Lys His Tyr Tyr Ile Phe Cys Asn Cys Thr
145                 150                 155                 160

Trp Leu Glu Asn Ser Ala Ser Ile Glu Pro Tyr Gln Leu Val Ile His
            165                 170                 175

Ile Arg Gly Ser Ser Asp Thr Thr Thr Lys Val Arg Ile Phe His Pro
        180                 185                 190

Gln His Thr Gly Tyr Lys Phe Leu Lys Lys Thr Lys Gln Tyr Ser Ala
    195                 200                 205

Leu Thr Thr Lys Lys Arg Ser Glu Tyr Leu Trp Tyr Ile Ser Phe His
    210                 215                 220

Ile Arg Leu Pro Ser Arg Arg Thr Ile Lys Phe Gln Gln Cys Cys Glu
225                 230                 235                 240

Gln Thr Trp Tyr Leu Leu Ile Tyr Arg Lys Ser Pro Thr Arg
            245                 250                 255

Ser Ser Tyr Phe Ser Ile Cys Val Phe Ser Phe Cys Ala Ile Ser Phe
            260                 265                 270

Ile Gly Lys Pro Asn Lys Val Arg Tyr Thr Lys Leu Phe Phe Ile Gln

-continued

```
                275                 280                 285
Lys Arg Pro Gln His Asn Cys Trp Asp Asn Trp Glu Phe Asn Asn Asn
        290                 295                 300

Trp Val Trp Glu Ala Arg Tyr Phe Cys Ser His Glu His Gln Ala Tyr
305                 310                 315                 320

Phe Gly Asp Gly Phe Thr Tyr Asn Phe Gln Ile Arg Ser Cys Lys Lys
                325                 330                 335

Ile Phe Leu Pro Phe Arg Val Ile Arg Ala Phe Trp Lys Val Cys Thr
                340                 345                 350

Arg Val Thr Trp Ser Asn Arg Phe Ser Asn Gly Arg Thr Ile Leu His
            355                 360                 365

Pro Arg Lys Lys His Arg Ser Ile Ser Lys Ala Met Ser Ser Phe Gly
    370                 375                 380

Ser Tyr Ser Ser Pro Thr Phe Trp Arg Lys Ile Gln Gln Ser Cys Leu
385                 390                 395                 400

Leu His Lys Arg Leu Phe Phe Val Asn Pro Thr Ser Gln Ile Lys Arg
                405                 410                 415

Asn Ile Phe Leu His Lys Ser Arg Arg Lys Ser Arg Cys Phe Trp Asn
                420                 425                 430

Cys Lys Arg Tyr Arg Met Lys Trp Ala Leu Cys Tyr Ser Leu Val Asn
            435                 440                 445

Tyr Cys Leu Phe Leu Glu Leu Trp Arg Ser Thr Pro Ile Gly Lys Lys
    450                 455                 460

Arg Ser Cys Ser Tyr Val
465                 470

<210> SEQ ID NO 66
<211> LENGTH: 229
<212> TYPE: PRT
<213> ORGANISM: Artificial Sequence
<220> FEATURE:
<223> OTHER INFORMATION: Description of Artificial Sequence:
      pIAO-P/L-Lambda-2.2kb amino acid sequence

<400> SEQUENCE: 66

Asp Thr Trp Phe Cys Ser Gln Cys Met Asp Ile Asn His Glu Arg Cys
1               5                   10                  15

Ile Val Lys Lys Cys Lys Lys Cys Ser Ala Asn Ala Lys Arg Arg Ile
            20                  25                  30

Lys Ser Pro Cys Tyr Thr Cys Tyr Thr Arg Lys Lys Met Val Pro Glu
        35                  40                  45

Glu Thr Ser Asp Asp Ser Thr Gly Pro Val Glu Asn Pro Leu Ile Asn
    50                  55                  60

Ser Ile Asn Asp Arg Leu Tyr Arg Lys Leu Thr Pro Ala Glu Leu Arg
65                  70                  75                  80

Asn Arg Met Phe Ser Ser Thr Leu Ser Met Tyr Leu Asn Arg Met Phe
                85                  90                  95

Lys Lys Arg Ser Gln Val Lys Glu Gly Lys Ser Ser Val Asn His Ser
            100                 105                 110

Tyr Ile Ile Phe Ser Asn Ile Cys Ala Ile Asn Ile Met Gly Tyr Leu
        115                 120                 125

Leu Ala Met Pro Trp Arg Asn Thr Lys Arg Ser Cys Thr Met Val Ser
    130                 135                 140

Cys Met Gln Asp Leu Thr Asp Val Gly Gly Lys Thr Gln Asn Tyr Tyr
145                 150                 155                 160
```

-continued

```
Met Val Met Gln Pro Lys Gly Thr Ser Glu Asn Ile Ser Ala Asp Glu
            165                 170                 175

Asp Cys Ser Ser Leu Leu Tyr Val Met Lys Ala Pro Lys Pro Lys Tyr
            180                 185                 190

Ser Val Leu Thr Leu Pro Gly Asp Phe Cys Phe Met Ser Thr Gly Val
            195                 200                 205

Pro Arg Ser Arg Ser Asn Lys Leu Val Glu Pro Ile Glu Arg Lys Asn
            210                 215                 220

Ser Arg Val Thr Gly
225

<210> SEQ ID NO 67
<211> LENGTH: 7411
<212> TYPE: DNA
<213> ORGANISM: Artificial Sequence
<220> FEATURE:
<223> OTHER INFORMATION: Description of Artificial Sequence:
      pBSII-Act5c-orf sequence

<400> SEQUENCE: 67
ctaaattgta agcgttaata tttttgttaaa attcgcgtta aatttttgtt aaatcagctc      60 atttttaac caataggccg aaatcggcaa atcccttat aaatcaaaag aatagaccga      120 gataggttg agtgttgttc cagtttggaa caagagtcca ctattaaaga acgtggactc      180
caacgtcaaa gggcgaaaaa ccgtctatca gggcgatggc ccactacgtg aaccatcacc      240
ctaatcaagt ttttttgggt cgaggtgccg taaagcacta aatcggaacc ctaaagggag      300
cccccgattt agagcttgac ggggaaagcc ggcgaacgtg gcgagaaagg aagggaagaa      360
agcgaaagga gcgggcgcta gggcgctggc aagtgtagcg gtcacgctgc gcgtaaccac      420
cacacccgcc gcgcttaatg cgccgctaca gggcgcgtcc cattcgccat tcaggctgcg      480
caactgttgg gaagggcgat cggtgcgggc ctcttcgcta ttacgccagc tggcgaaagg      540
gggatgtgct gcaaggcgat taagttgggt aacgccaggg ttttcccagt cacgacgttg      600
taaaacgacg gccagtgagc gcgcgtaata cgactcacta gggcgaat tgggtaccgg      660 gccccccctc gaggtcgacg gtatcgataa gcttgatatc gaattctaaa aaaaatcatg      720
aatggcatca actctgaatc aaatctttgc agatgcacct acttctcatt tccactgtca      780 catcatttt ccagatctcg ctgcctgtta tgtgggccac aaaaccaagac acgttttatg      840 gccattaaag ctggctgatc gtcgccaaac accaaataca tatcaatatg tacattcgag      900
aaagaagcga tcaaagaagc gtcttcgggc gagtaggaga atgcggagga aaggagaac      960 gagctgatct agtatctctc cacaatccaa tgccaactga ccaactgcc atattcggag      1020 caatttgaag ccaatttcca tcgcctggcg atcgctccat tcttggctat atgttttca      1080 ccgttcccgg ggccatttc aaagactcgt cggtaagata agattgtgtc actcgctgtc      1140
tctcttcatt tgtcgaagaa tgctgaggaa tttcgcgatg acgtcggcga gtatttgaa      1200 gaatgagaat aatttgtatt tatacgaaaa tcagttagtg gaattttcta caaaaacatg      1260
ttatctatag ataattttgt tgcaaaatat gttgactatg acaaagattg tatgtatata      1320
cctttaatgt attctcatt tcttatgtat ttataatggc aatgatgata ctgatgatat      1380
tttaagatga tgccagacca caggctgatt tctgcgtctt ttgccgaacg cagtgcatgt      1440
gcggttgttg tttttttggaa tagtttcaat tttcggactg tccgctttga tttcagtttc      1500
ttggcttatt caaaaagcaa agtaaagcca aaaagcgag atggcaatac caatgcggc      1560 aaaacggtag tggaaggaaa ggggtgcggg gcagcggaag gaagggtggg gcgggcgtg      1620
```

-continued

```
gcggggtctg tggctgggcg cgacgtcacc gacgttggag ccactccttt gaccatgtgt    1680
gcgtgtgtgt attattcgtg tctcgccact cgccggttgt ttttttcttt ttatctcgct    1740
ctctctagcg ccatctcgta cgcatgctca acgcaccgca tgttgccgtg tcctttatgc    1800
gtcattttgg ctcgaaatag gcaattattt aaacaaagat tagtcaacga aaacgctaaa    1860
ataaataagt ctacaatatg gttacttatt gccatgtgtg tgcagccaac gatagcaaca    1920
aaagcaacaa cacagtggct ttccctcttt cacttttttgt ttgcaagcgc gtgcgagcaa    1980
gacggcacga ccggcaaacg caattacgct gacaaagagc agacgaagtt ttggccgaaa    2040
aacatcaagg cgcctgatac gaatgcattt gcaataacaa ttgcgatatt taatattgtt    2100
tatgaagctg tttgacttca aaacacacaa aaaaaaaaat aaaacaaatt atttgaaaga    2160
gaattaggaa tcggacagct tatcgttacg ggctaacagc acaccgagac gaaatagctt    2220
acctgacgtc acagcctctg gaagaactgc cgccaagcag acgatgcaga ggacgacaca    2280
tagagtagcg gagtaggcca cgtagtacg catgtgcttg tgtgtgaggc gtctctctct    2340
tcgtctcctg tttgcgcaaa cgcatagact gcactgagaa aatcgattac ctatttttta    2400
tgaatgaata tttgcactat tactattcaa aactattaag atagcaatca cattcaatag    2460
ccaaatacta taccacctga gcgatgcaac gaaatgatca atttgagcaa aaatgctgca    2520
tatttaggac ggcatcatta tagaaatgct tcttgctgtg tacttttctc tcgtctggca    2580
gctgtttcgc cgttattgtt aaaaccggct taagttaggt gtgttttcta cgactagtga    2640
tgcccctact agaagatgtg tgttgcacaa atgtccctga ataaccaatt tgaagtgcag    2700
atagcagtaa acgtaagcta atatgaatat tatttaactg taatgtttta atatcgctgg    2760
acattactaa taaacccact ataaacacat gtacatatgt atgttttggc atacaatgag    2820
tagttgggga aaaaatgtgt aaaagcaccg tgaccatcac agcataaaga taaccagctg    2880
aagtatcgaa tatgagtaac ccccaaattg aatcacatgc cgcaactgat aggacccatg    2940
gaagtacact cttcatggcg atatacaaga cacacacaag cacgaacacc cagttgcgga    3000
ggaaattctc cgtaaatgaa aacccaatcg gcgaacaatt catacccata tatggtaaaa    3060
gttttgaacg cgacttgaga gcggagagca ttgcggctga taaggtttta gcgctaagcg    3120
ggctttataa aacgggctgc gggaccagtt ttcatatcgg atcctatata ataaaatggg    3180
tagttcttta gacgatgagc atatcctctc tgctcttctg caaagcgatg acgagcttgt    3240
tggtgaggat tctgacagtg aaatatcaga tcacgtaagt gaagatgacg tccagagcga    3300
tacagaagaa gcgtttatag atgaggtaca tgaagtgcag ccaacgtcaa gcggtagtga    3360
aatattagac gaacaaaatg ttattgaaca accaggttct tcattggctt ctaacagaat    3420
cttgaccttg ccacagagga ctattagagg taagaataaa cattgttggt caacttcaaa    3480
gtccacgagg cgtagccgag tctctgcact gaacattgtc agatctcaaa gaggtccgac    3540
gcgtatgtgc cgcaatatat atgacccact tttatgcttc aaactatttt ttactgatga    3600
gataatttcg gaaattgtaa aatggacaaa tgctgagata tcattgaaac gtcgggaatc    3660
tatgacaggt gctacatttc gtgacacgaa tgaagatgaa atctatgctt tctttggtat    3720
tctggtaatg acagcagtga gaaaagataa ccacatgtcc acagatgacc tctttgatcg    3780
atctttgtca atggtgtacg tctctgtaat gagtcgtgat cgttttgatt ttttgatacg    3840
atgtcttaga atggatgaca aaagtatacg gcccacactt cgagaaaacg atgtatttac    3900
tcctgttaga aaaatatggg atctcttat ccatcagtgc atacaaaatt acactccagg    3960
```

```
ggctcatttg accatagatg aacagttact tggttttaga ggacggtgtc cgtttaggat    4020
gtatatccca aacaagccaa gtaagtatgg aataaaaatc ctcatgatgt gtgacagtgg    4080
tacgaagtat atgataaatg gaatgcctta tttgggaaga ggaacacaga ccaacggagt    4140
accactcggt gaatactacg tgaaggagtt atcaaagcct gtgcacggta gttgtcgtaa    4200
tattacgtgt gacaattggt tcacctcaat ccctttggca aaaaacttac tacaagaacc    4260
gtataagtta accattgtgg gaaccgtgcg atcaaacaaa cgcgagatac cggaagtact    4320
gaaaaacagt cgctccaggc cagtgggaac atcgatgttt tgttttgacg gaccccttac    4380
tctcgtctca tataaaccga agccagctaa gatggtatac ttattatcat cttgtgatga    4440
ggatgcttct atcaacgaaa gtaccggtaa accgcaaatg gttatgtatt ataatcaaac    4500
taaaggcgga gtggacacgc tagaccaaat gtgttctgtg atgacctgca gtaggaagac    4560
gaataggtgg cctatggcat tattgtacgg aatgataaac attgcctgca taaattcttt    4620
tattatatac agccataatg tcagtagcaa gggagaaaag gttcaaagtc gcaaaaaatt    4680
tatgagaaac ctttacatga gcctgacgtc atcgtttatg cgtaagcgtt tagaagctcc    4740
tactttgaag agatatttgc gcgataatat ctctaatatt ttgccaaatg aagtgcctgg    4800
tacatcagat gacagtactg aagagccagt aatgaaaaaa cgtacttact gtacttactg    4860
cccctctaaa ataaggcgaa aggcaaatgc atcgtgcaaa aaatgcaaaa aagttatttg    4920
tcgagagcat aatattgata tgtgccaaag ttgtttctga ctgactaata agtataattt    4980
gtttctatta tgtataagtt aagctaatta cttatttat aatacaacat gactgttttt    5040
aaagtacaaa ataagtttat ttttgtaaaa gagagaatgt ttaaaagttt tgttactta    5100 gaagaaattt tgagtttttg ttttttttta ataaataaat aaacataaat aaattgtttg    5160
ttgaatttgg atccactagt tctagagcgg ccgccaccgc ggtggagctc cagcttttgt    5220
tccctttagt gagggttaat tgcgcgcttg gcgtaatcat ggtcatagct gtttcctgtg    5280
tgaaattgtt atccgctcac aattccacac aacatacgag ccggaagcat aaagtgtaaa    5340
gcctggggtg cctaatgagt gagctaactc acattaattg cgttgcgctc actgcccgct    5400
ttccagtcgg gaaacctgtc gtgccagctg cattaatgaa tcggccaacg cgcggggaga    5460
ggcggtttgc gtattgggcg ctcttccgct tcctcgctca ctgactcgct gcgctcggtc    5520
gttcggctgc ggcgagcggt atcagctcac tcaaaggcgg taatacggtt atccacagaa    5580 tcagggata acgcaggaaa gaacatgtga gcaaaaggcc agcaaaaggc caggaaccgt    5640
aaaaaggccg cgttgctggc gttttccat aggctccgcc cccctgacga gcatcacaaa    5700
aatcgacgct caagtcagag gtggcgaaac ccgacaggac tataaagata ccaggcgttt    5760
ccccctggaa gctccctcgt gcgctctcct gttccgaccc tgccgcttac cggatacctg    5820
tccgcctttc tcccttcggg aagcgtggcg ctttctcata gctcacgctg taggtatctc    5880
agttcggtgt aggtcgttcg ctccaagctg ggctgtgtgc acgaaccccc cgttcagccc    5940
gaccgctgcg ccttatccgg taactatcgt cttgagtcca acccggtaag acacgactta    6000
tcgccactgg cagcagccac tggtaacagg attagcagag cgaggtatgt aggcggtgct    6060
acagagttct tgaagtggtg gcctaactac ggctacacta aggacagt atttggtatc    6120 tgcgctctgc tgaagccagt taccttcgga aaagagttg gtagctcttg atccggcaaa    6180
caaaccaccg ctggtagcgg tggttttttt gtttgcaagc agcagattac gcgcagaaaa    6240
aaaggatctc aagaagatcc tttgatcttt tctacgggt ctgacgctca gtggaacgaa    6300
aactcacgtt aagggatttt ggtcatgaga ttatcaaaaa ggatcttcac ctagatcctt    6360
```

-continued

```
ttaaattaaa aatgaagttt taaatcaatc taaagtatat atgagtaaac ttggtctgac      6420
agttaccaat gcttaatcag tgaggcacct atctcagcga tctgtctatt tcgttcatcc      6480
atagttgcct gactccccgt cgtgtagata actacgatac gggagggctt accatctggc      6540
cccagtgctg caatgatacc gcgagaccca cgctcaccgg ctccagattt atcagcaata      6600
aaccagccag ccggaagggc cgagcgcaga agtggtcctg caactttatc cgcctccatc      6660
cagtctatta attgttgccg ggaagctaga gtaagtagtt cgccagttaa tagtttgcgc      6720
aacgttgttg ccattgctac aggcatcgtg gtgtcacgct cgtcgtttgg tatggcttca      6780
ttcagctccg gttcccaacg atcaaggcga gttacatgat cccccatgtt gtgcaaaaaa      6840
gcggttagct ccttcggtcc tccgatcgtt gtcagaagta agttggccgc agtgttatca      6900
ctcatggtta tggcagcact gcataattct cttactgtca tgccatccgt aagatgcttt      6960
tctgtgactg gtgagtactc aaccaagtca ttctgagaat agtgtatgcg gcgaccgagt      7020
tgctcttgcc cggcgtcaat acgggataat accgcgccac atagcagaac tttaaaagtg      7080
ctcatcattg gaaaacgttc ttcggggcga aaactctcaa ggatcttacc gctgttgaga      7140
tccagttcga tgtaacccac tcgtgcaccc aactgatctt cagcatcttt tactttcacc      7200
agcgtttctg ggtgagcaaa aacaggaagg caaaatgccg caaaaaaggg aataagggcg      7260
acacggaaat gttgaatact catactcttc cttttttcaat attattgaag catttatcag      7320
ggttattgtc tcatgagcgg atacatattt gaatgtattt agaaaaataa acaaataggg      7380
gttccgcgca catttccccg aaaagtgcca c                                    7411
```

<210> SEQ ID NO 68
<211> LENGTH: 10330
<212> TYPE: DNA
<213> ORGANISM: Artificial Sequence
<220> FEATURE:
<223> OTHER INFORMATION: Description of Artificial Sequence:
      pCaSpeR-hs-pBac sequence

<400> SEQUENCE: 68

```
aagcttgggc tgcaggtcga cggatccaaa ttcaacaaac aatttatttta tgtttattta      60 tttattaaaa aaaacaaaa actcaaaatt tcttctaaag taacaaaact tttaaacatt      120
ctctctttta caaaaataaa cttattttgt actttaaaaa cagtcatgtt gtattataaa      180
ataagtaatt agcttaactt atacataata gaaacaaatt atacttatta gtcagtcaga      240
aacaactttg gcacatatca atattatgct ctcgacaaat aactttttg catttttgc       300 acgatgcatt tgccttttcgc cttattttag aggggcagta agtacagtaa gtacgttttt      360
tcattactgg ctcttcagta ctgtcatctg atgtaccagg cacttcattt ggcaaaatat      420
tagagatatt atcgcgcaaa tatctcttca agtaggagc ttctaaacgc ttacgcataa       480
acgatgacgt caggctcatg taaaggtttc tcataaattt tttgcgactt tgaacctttt      540
ctcccttgct actgacatta tggctgtata taataaaga atttatgcag gcaatgttta      600
tcattccgta caataatgcc ataggccacc tattcgtctt cctactgcag gtcatcacag      660
aacacatttg gtctagcgtg tccactccgc ctttagtttg attataatac ataaccattt      720 gcggttacc ggtactttcg ttgatagaag catcctcatc acaagatgat aataagtata      780
ccatcttagc tggcttcggt ttatatgaga cgagagtaag gggtccgtca aaacaaaaca      840
tcgatgttcc cactggcctg gagcgactgt ttttcagtac ttccggtatc tcgcgtttgt      900
ttgatcgcac ggttcccaca atggttaact tatacggttc ttgtagtaag ttttttgcca      960
```

```
aagggattga ggtgaaccaa ttgtcacacg taatattacg acaactaccg tgcacaggct    1020
ttgataactc cttcacgtag tattcaccga gtggtactcc gttggtctgt gttcctcttc    1080
ccaaataagg cattccattt atcatatact tcgtaccact gtcacacatc atgaggattt    1140
ttattccata cttacttggc ttgtttggga tatacatcct aaacggacac cgtcctctaa    1200
aaccaagtaa ctgttcatct atggtcaaat gagcccctgg agtgtaattt tgtatgcact    1260
gatggataaa gagatcccat attttctaa caggagtaaa tacatcgttt tctcgaagtg     1320
tgggccgtat acttttgtca tccattctaa gacatcgtat caaaaaatca aaacgatcac    1380
gactcattac agagacgtac accattgaca aagatcgatc aaagaggtca tctgtggaca    1440
tgtggttatc ttttctcact gctgtcatta ccagaatacc aaagaaagca tagatttcat    1500
cttcattcgt gtcacgaaat gtagcacctg tcatagattc ccgacgtttc aatgatatct    1560
cagcatttgt ccattttaca atttccgaaa ttatctcatc agtaaaaaat agtttgaagc    1620
ataaaagtgg gtcatatata ttgcggcaca tacgcgtcgg acctctttga gatctgacaa    1680
tgttcagtgc agagactcgg ctacgcctcg tggactttga agttgaccaa caatgtttat    1740
tcttacctct aatagtcctc tgtggcaagg tcaagattct gttagaagcc aatgaagaac    1800
ctggttgttc aataacattt tgttcgtcta atatttcact accgcttgac gttggctgca    1860
cttcatgtac ctcatctata aacgcttctt ctgtatcgct ctggacgtca tcttcactta    1920
cgtgatctga tatttcactg tcagaatcct caccaacaag ctcgtcatcg ctttgcagaa    1980
gagcagagag gatatgctca tcgtctaaag aactacccat tttattatat aggatccccg    2040
acaccagacc aactggtaat ggtagcgacc ggcgctcagc tggaattagg ccttctagac    2100
cgcggccgca gatctgttaa cgaattccca attccctatt cagagttctc ttcttgtatt    2160
caataattac ttcttggcag atttcagtag ttgcagttga tttacttggt tgctggttac    2220
ttttaattga ttcactttaa cttgcacttt actgcagatt gtttagcttg ttcagctgcg    2280
cttgtttatt tgcttagctt tcgcttagcg acgtgttcac ttgcttgttt gaattgaatt    2340
gtcgctccgt agacgaagcg ctctatttat actccgcgc tcttttcgcg aacattcgag     2400
gcgcgctctc tcgaaccaac gagagcagta tgccgtttac tgtgtgacag agtgagagag    2460
cattagtgca gagagggaga cccaaaaaga aagagagaa taacgaataa cggccagaga     2520
aatttctcga gttttcttct gccaaacaaa tgacctacca caataaccag tttgtttggg    2580
gattctaggg ggatcgggga tcaattctag tatgtatgta agttaataaa accctttttt    2640
ggagaatgta gatttaaaaa aacatatttt ttttttattt tttactgcac tggatatcat    2700
tgaacttatc tgatcagttt taaatttact tcgatccaag ggtatttgaa gtaccaggtt    2760 cttttcgatta cctctcactc aaaatgacat tccactcaaa gtcagcgctg tttgcctcct   2820
tctctgtcca cagaaatatc gccgtctctt tcgccgctgc gtccgctatc tcttcgcca    2880 ccgtttgtag cgttacctag cgtcaatgtc cgccttcagt tgcactttgt cagcggtttc    2940
gtgacgaagc tccaagcggt ttacgccatc aattaaacac aaagtgctgt gccaaaactc    3000
ctctcgcttc ttattttgt ttgttttttg agtgattggg gtggtgattg gttttgggtg     3060
ggtaagcagg ggaaagtgtg aaaaatcccg gcaatgggcc aagaggatca ggagctatta    3120
attcgcggag gcagcaaaca cccatctgcc gagcatctga acaatgtgag tagtacatgt    3180
gcatacatct taagttcact tgatctatag gaactgcgat tgcaacatca aattgtctgc    3240
ggcgtgagaa ctgcgaccca caaaaatccc aaaccgcaat cgcacaaaca aatagtgaca    3300
```

-continued

```
cgaaacagat tattctggta gctgtgctcg ctatataaga caattttaa gatcatatca    3360
tgatcaagac atctaaaggc attcattttc gactacattc tttttacaa aaatataac    3420
aaccagatat tttaagctga tcctagatgc acaaaaata aataaaagta taaacctact   3480
tcgtaggata cttcgttttg ttcggggtta gatgagcata acgcttgtag ttgatatttg   3540
agatcccta tcattgcagg gtgacagcgg agcggcttcg cagagctgca ttaaccaggg    3600
cttcgggcag gccaaaaact acggcacgct cctgccaccc agtccgccgg aggactccgg   3660
ttcagggagc ggccaactag ccgagaacct cacctatgcc tggcacaata tggacatctt   3720
tggggcggtc aatcagccgg gctccggatg gcggcagctg gtcaaccgga cacgcggact   3780
attctgcaac gagcgacaca taccggcgcc caggaaacat ttgctcaaga acggtgagtt   3840
tctattcgca gtcggctgat ctgtgtgaaa tcttaataaa gggtccaatt accaatttga   3900
aactcagttt gcggcgtggc ctatccgggc gaacttttgg ccgtgatggg cagttccggt   3960
gccgaaaga cgaccctgct gaatgccctt gcctttcgat cgccgcaggg catccaagta   4020
tcgccatccg ggatgcgact gctcaatggc caacctgtgg acgccaagga gatgcaggcc   4080
aggtgcgcct atgtccagca ggatgacctc tttatcggct ccctaacggc cagggaacac   4140
ctgatttttcc aggccatggt gcggatgcca cgacatctga cctatcggca gcgagtggcc   4200
cgcgtggatc aggtgatcca ggagcttttcg ctcagcaaat gtcagcacac gatcatcggt   4260
gtgcccggca gggtgaaagg tctgtccggc ggagaaagga agcgtctggc attcgcctcc   4320
gaggcactaa ccgatccgcc gcttctgatc tgcgatgagc ccacctccgg actggactca   4380
tttaccgccc acagcgtcgt ccaggtgctg aagaagctgt cgcagaaggg caagaccgtc   4440
atcctgacca ttcatcagcc gtcttccgag ctgtttgagc tctttgacaa gatccttctg   4500
atggccgagg gcagggtagc tttcttgggc actcccagcg aagccgtcga cttcttttcc   4560
tagtgagttc gatgtgttta ttaagggtat ctagcattac attacatctc aactcctatc   4620
cagcgtgggt gcccagtgtc ctaccaacta caatccggcg gacttttacg tacaggtgtt   4680
ggccgttgtg cccggacggg agatcgagtc ccgtgatcgg atcgccaaga tatgcgacaa   4740
ttttgctatt agcaaagtag cccgggatat ggagcagttg ttggccacca aaaatttgga   4800
gaagccactg gagcagccgg agaatgggta cacctacaag gccacctggt tcatgcagtt   4860
ccggcggtc ctgtggcgat cctggctgtc ggtgctcaag gaaccactcc tcgtaaaagt   4920
gcgacttatt cagacaacgg tgagtggttc cagtggaaac aaatgatata acgcttacaa   4980
ttcttggaaa caaattcgct agattttagt tagaattgcc tgattccaca cccttcttag   5040
ttttttcaa tgagatgtat agtttatagt tttgcagaaa ataaataaat ttcatttaac   5100
tcgcgaacat gttgaagata tgaatattaa tgagatgcga gtaacattt aatttgcaga   5160
tggttgccat cttgattggc ctcatctttt tgggccaaca actcacgcaa gtgggcgtga   5220
tgaatatcaa cggagccatc ttcctcttcc tgaccaacat gacctttcaa aacgtctttg   5280
ccacgataaa tgtaagtctt gtttagaata catttgcata ttaataattt actaactttc   5340
taatgaatcg attcgattta ggtgttcacc tcagagctgc cagttttat gagggaggcc   5400
cgaagtcgac tttatcgctg tgacacatac tttctgggca aaacgattgc cgaattaccg   5460
cttttctca cagtgccact ggtcttcacg gcgattgcct atccgatgat cggactgcgg   5520
gccggagtgc tgcacttctt caactgcctg gcgctggtca ctctggtggc caatgtgtca   5580
acgtccttcg gatatctaat atcctgcgcc agctcctcga cctcgatggc gctgtctgtg   5640
ggtccgccgg ttatcatacc attcctgctc tttggcggct tcttcttgaa ctcgggctcg   5700
```

```
gtgccagtat acctcaaatg gttgtcgtac ctctcatggt tccgttacgc caacgagggt    5760
ctgctgatta accaatgggc ggacgtggag ccgggcgaaa ttagctgcac atcgtcgaac    5820
accacgtgcc ccagttcggg caaggtcatc ctggagacgc ttaacttctc cgccgccgat    5880
ctgccgctgg actacgtggg tctggccatt ctcatcgtga gcttccgggt gctcgcatat    5940
ctggctctaa gacttcgggc ccgacgcaag gagtagccga catatatccg aaataactgc    6000
ttgttttttt ttttaccatt attaccatcg tgtttactgt ttattgcccc ctcaaaaagc    6060
taatgtaatt atatttgtgc caataaaaac aagatatgac ctatagaata caagtatttc    6120
cccttcgaac atccccacaa gtagactttg gatttgtctt ctaaccaaaa gacttacaca    6180
cctgcatacc ttacatcaaa aactcgttta tcgctacata aaacaccggg atatatttt     6240 tatatacata cttttcaaat cgcgcgccct cttcataatt cacctccacc acaccacgtt    6300
tcgtagttgc tctttcgctg tctcccaccc gctctccgca acacattcac cttttgttcg    6360
acgaccttgg agcgactgtc gttagttccg cgcgattcgg ttcgctcaaa tggttccgag    6420
tggttcattt cgtctcaata gaaattagta ataaatattt gtatgtacaa tttatttgct    6480
ccaatatatt tgtatatatt tccctcacag ctatatttat tctaatttaa tattatgact    6540
ttttaaggta atttttgtg acctgttcgg agtgattagc gttacaattt gaactgaaag     6600
tgacatccag tgtttgttcc ttgtgtagat gcatctcaaa aaaatggtgg gcataatagt    6660
gttgtttata tatatcaaaa ataagaacta taataataag aatacattta atttagaaaa    6720
tgcttggatt tcactggaac tagaattaat tcggctgctg ctctaaacga cgcatttcgt    6780
actccaaagt acgaattttt tccctcaagc tcttattttc attaaacaat gaacaggacc    6840
taacgcacag tcacgttatt gtttacataa atgattttt ttactattca aacttactct     6900
gtttgtgtac tcccactggt atagccttct tttatctttt ctggttcagg ctctatcact    6960
ttactaggta cggcatctgc gttgagtcgc ctccttttaa atgtctgacc ttttgcaggt    7020
gcagccttcc actgcgaatc tttaaagtgg gtatcacaaa tttgggagtt ttcaccaagg    7080
ctgcacccaa ggctctgctc ccacaatttt ctcttaatag cacacttcgg cacgtgaatt    7140
aattttactc cagtcacagc ttgcagcaaa atttgcaata tttcattttt ttttattcca    7200
cgtaagggtt aatgttttca aaaaaaatt cgtccgcaca caacctttcc tctcaacaag     7260
caaacgtgca ctgaatttaa gtgtatactt cggtaagctt cggctatcga cgggaccacc    7320
ttatgttatt tcatcatggg ccagacccac gtagtccagc ggcagatcgg cggcggagaa    7380
gttaagcgtc tccaggatga ccttgcccga actggggcac gtggtgttcg acgatgtgca    7440
gctaatttcg cccggctcca cgtccgccca ttggttaatc agcagaccct cgttggcgta    7500
acggaaccat gagaggtacg acaaccattt gaggtatact ggcaccgagc ccgagttcaa    7560
gaagaaggcg ttttccata ggctccgccc ccctgacgag catcacaaaa atcgacgctc     7620
aagtcagagg tggcgaaacc cgacaggact ataaagatac caggcgtttc ccctggaag    7680 ctccctcgtg cgctctcctg ttccgaccct gccgcttacc ggatacctgt ccgcctttct    7740
cccttcggga agcgtggcgc tttctcaatg ctcacgctgt aggtatctca gttcggtgta    7800
ggtcgttcgc tccaagctgg gctgtgtgca cgaaccccc gttcagcccg accgctgcgc     7860
cttatccggt aactatcgtc ttgagtccaa cccggtaaga cacgacttat cgccactggc    7920
agcagccact ggtaacagga ttagcagagc gaggtatgta ggcggtgcta cagagttctt    7980
gaagtggtgg cctaactacg gctacactag aaggacagta tttggtatct gcgctctgct    8040
```

```
gaagccagtt accttcggaa aaagagttgg tagctcttga tccggcaaac aaaccaccgc   8100
tggtagcggt ggttttttg  tttgcaagca gcagattacg cgcagaaaaa aaggatctca   8160
agaagatcct ttgatctttt ctacggggtc tgacgctcag tggaacgaaa actcacgtta   8220
agggattttg gtcatgagat tatcaaaaag gatcttcacc tagatccttt taaattaaaa   8280
atgaagtttt aaatcaatct aaagtatata tgagtaaact tggtctgaca gttaccaatg   8340
cttaatcagt gaggcaccta tctcagcgat ctgtctattt cgttcatcca tagttgcctg   8400
actccccgtc gtgtagataa ctacgatacg ggagggctta ccatctggcc ccagtgctgc   8460
aatgataccg cgagacccac gctcaccggc tccagattta tcagcaataa accagccagc   8520
cggaagggcc gagcgcagaa gtggtcctgc aactttatcc gcctccatcc agtctattaa   8580
ttgttgccgg gaagctgagt aagtagttcg ccagttaata gtttgcgcaa cgttgttgcc   8640
attgctacag gcatcgtggt gtcacgctcg tcgtttggta tggcttcatt cagctccggt   8700
tcccaacgat caaggcgagt tacatgatcc cccatgttgt gcaaaaaagc ggttagctcc   8760
ttcggtcctc cgatcgttgt cagaagtaag ttggccgcag tgttatcact catggttatg   8820
gcagcactgc ataattctct tactgtcatg ccatccgtaa gatgcttttc tgtgactggt   8880
gagtactcaa ccaagtcatt ctgagaatag tgtatgcggc gaccgagttg ctcttgcccg   8940
gcgtcaatac gggataatac cgcgccacat agcagaactt taaaagtgct catcattgga   9000
aaacgttctt cggggcgaaa actctcaagg atcttaccgc tgttgagatc cagttcgatg   9060
taacccactc gtgcacccaa ctgatcttca gcatctttta ctttcaccag cgtttctggg   9120
tgagcaaaaa caggaaggca aaatgccgca aaaagggaa taagggcgac acggaaatgt   9180
tgaatactca tactcttcct ttttcaatat tattgaagca tttatcaggg ttattgtctc   9240
atgagcggat acatatttga atgtatttag aaaaataaac aaataggggt tccgcgcaca   9300
tttccccgaa aagtgccacc tgacgtctaa gaaaccatta ttatcatgac attaacctat   9360
aaaaataggc gtatcacgag gccctttcgt ctcgcgcgtt tcggtgatga cggtgaaaac   9420
ctctgacaca tgcagctccc ggagacggtc acagcttgtc tgtaagcgga tgccgggagc   9480
agacaagccc gtcagggcgc gtcagcgggt gttggcgggt gtcggggctg gcttaactat   9540
gcggcatcag agcagattgt actgagagtg caccatatgc ggtgtgaaat accgcaccga   9600
atcgcgcgga actaacgaca gtcgctccaa ggtcgtcgaa caaaaggtga atgtgttgcg   9660
gagagcgggt gggagacagc gaaagagcaa ctacgaaacg tggtgtggtg gaggtgaatt   9720
atgaagaggg cgcgcgattt gaaaagtatg tatataaaaa atatatcccg gtgttttatg   9780
tagcgataaa cgagttttt  atgtaaggta tgcaggtgtg taagtctttt ggttagaaga   9840
caaatccaaa gtctacttgt ggggatgttc gaagggaaa tacttgtatt ctataggtca   9900
tatcttgttt ttattggcac aaatataatt acattagctt tttgagggg  caataaacag   9960
taaacacgat ggtaataatg gtaaaaaaa  aaacaagcag ttatttcgga tatatgtcgg  10020
ctactccttg cgtcgggccc gaagtcttag agccagatat gcgagcaccc ggaagctcac  10080
gatgagaatg gccagaccat gatgaaataa cataaggtgg tcccgtcggc aagagacatc  10140
cacttaacgt atgcttgcaa taagtgcgag tgaaaggaat agtattctga gtgtcgtatt  10200
gagtctgagt gagacagcga tatgattgtt gattaaccct tagcatgtcc gtggggtttg  10260
aattaactca taatattaat tagacgaaat tatttttaaa gttttatttt taataatttg  10320
cgagtacgca                                                         10330
```

<210> SEQ ID NO 69
<211> LENGTH: 1785
<212> TYPE: DNA
<213> ORGANISM: Unknown Organism
<220> FEATURE:
<223> OTHER INFORMATION: Description of Unknown Organism: Natural piggyBac orf sequence

<400> SEQUENCE: 69

| | | | | | |
|---|---|---|---|---|---|
| atgggtagtt | ctttagacga | tgagcatatc | ctctctgctc | ttctgcaaag | cgatgacgag | 60 |
| cttgttggtg | aggattctga | cagtgaaata | tcagatcacg | taagtgaaga | tgacgtccag | 120 |
| agcgatacag | aagaagcgtt | tatagatgag | gtacatgaag | tgcagccaac | gtcaagcggt | 180 |
| agtgaaatat | tagacgaaca | aaatgttatt | gaacaaccag | gttcttcatt | ggcttctaac | 240 |
| agaatcttga | ccttgccaca | gaggactatt | agaggtaaga | ataaacattg | ttggtcaact | 300 |
| tcaaagtcca | cgaggcgtag | ccgagtctct | gcactgaaca | ttgtcagatc | tcaaagaggt | 360 |
| ccgacgcgta | tgtgccgcaa | tatatatgac | ccactttat | gcttcaaact | attttttact | 420 |
| gatgagataa | tttcggaaat | tgtaaaatgg | acaaatgctg | agatatcatt | gaaacgtcgg | 480 |
| gaatctatga | caggtgctac | atttcgtgac | acgaatgaag | atgaaatcta | tgctttcttt | 540 |
| ggtattctgg | taatgacagc | agtgagaaaa | gataaccaca | tgtccacaga | tgacctcttt | 600 |
| gatcgatctt | tgtcaatggt | gtacgtctct | gtaatgagtc | gtgatcgttt | tgatttttg | 660 |
| atacgatgtc | ttagaatgga | tgcaaaagt | atacggccca | cacttcgaga | aaacgatgta | 720 |
| tttactcctg | ttagaaaaat | atgggatctc | tttatccatc | agtgcataca | aaattacact | 780 |
| ccagggctc | atttgaccat | agatgaacag | ttacttggtt | ttagaggacg | gtgtccgttt | 840 |
| aggatgtata | tcccaaacaa | gccaagtaag | tatggaataa | aaatcctcat | gatgtgtgac | 900 |
| agtggtacga | agtatatgat | aaatggaatg | ccttatttgg | gaagaggaac | acagaccaac | 960 |
| ggagtaccac | tcggtgaata | ctacgtgaag | gagttatcaa | agcctgtgca | cggtagttgt | 1020 |
| cgtaatatta | cgtgtgacaa | ttggttcacc | tcaatccctt | tggcaaaaaa | cttactacaa | 1080 |
| gaaccgtata | agttaaccat | tgtgggaacc | gtgcgatcaa | acaaacgcga | gataccggaa | 1140 |
| gtactgaaaa | acagtcgctc | caggccagtg | ggaacatcga | tgttttgttt | tgacggaccc | 1200 |
| cttactctcg | tctcatataa | accgaagcca | gctaagatgg | tatacttatt | atcatcttgt | 1260 |
| gatgaggatg | cttctatcaa | cgaaagtacc | ggtaaaccgc | aaatggttat | gtattataat | 1320 |
| caaactaaag | gcggagtgga | cacgctagac | caaatgtgtt | ctgtgatgac | ctgcagtagg | 1380 |
| aagacgaata | ggtggcctat | ggcattattg | tacggaatga | taaacattgc | ctgcataaat | 1440 |
| tcttttatta | tatacagcca | taatgtcagt | agcaagggag | aaaaggttca | aagtcgcaaa | 1500 |
| aaatttatga | gaacccttta | catgagcctg | acgtcatcgt | ttatgcgtaa | gcgtttagaa | 1560 |
| gctcctactt | tgaagagata | tttgcgcgat | aatatctcta | atattttgcc | aaatgaagtg | 1620 |
| cctggtacat | cagatgacag | tactgaagag | ccagtaatga | aaaacgtac | ttactgtact | 1680 |
| tactgcccct | ctaaaataag | gcgaaaggca | aatgcatcgt | gcaaaaaatg | caaaaaagtt | 1740 |
| atttgtcgag | agcataatat | tgatatgtgc | caaagttgtt | tctga | | 1785 |

<210> SEQ ID NO 70
<211> LENGTH: 1785
<212> TYPE: DNA
<213> ORGANISM: Unknown Organism
<220> FEATURE:
<223> OTHER INFORMATION: Description of Unknown Organism: Optimized piggyBac orf sequence

```
<400> SEQUENCE: 70
atgggtagca gcctggatga tgaacatatc ctgagcgcgc tgctgcagag cgacgacgaa      60
ctggttggtg aagatagcga cagcgaaatc agcgatcacg tgagcgaaga cgacgttcag     120
agcgataccg aagaagcgtt catcgacgaa gttcacgaag tgcagccgac cagcagcggt     180
agcgaaatcc tggatgaaca gaacgttatc gaacagccgg gtagcagcct ggcgagcaac     240
cgtatcctga ccctgccgca gcgcaccatc cgtggtaaaa acaaacactg ttggagcacc     300
agcaaaagca cccgccgtag ccgtgttagc gcgctgaaca ttgttcgtag ccagcgtggt     360
ccgacccgta tgtgccgcaa catctacgat ccgctgctgt gcttcaaact gttcttcacc     420
gatgaaatca tcagcgaaat cgtgaaatgg accaacgccg aaatcagcct gaaacgtcgc     480
gaaagcatga ccggcgcgac cttccgcgat accaacgaag atgaaatcta cgccttcttc     540
ggtatcctgg tgatgaccgc ggtgcgtaaa gataaccaca tgagcaccga tgatctgttt     600
gatcgtagcc tgagcatggt ttacgttagc gttatgagcc gtgaccgttt cgatttcctg     660
atccgttgtc tgcgtatgga tgataaaagc atccgcccga ccctgcgcga aaacgatgtg     720
ttcaccccgg ttcgcaaaat ctgggatctg ttcatccacc agtgcatcca gaactacacc     780
ccgggcgcgc acctgaccat cgatgaacag ctgctgggtt ttcgtggtcg ctgtccgttt     840
cgtatgtaca tcccgaacaa accgagcaaa tacggtatca aaatcctgat gatgtgtgac     900
agcggtacca agtacatgat caacggtatg ccgtatctgg gtcgtggtac ccagaccaac     960
ggtgtgccgc tgggtgaata ctacgtgaaa gaactgagca aaccggtgca cggtagctgt    1020
cgtaacatca cctgtgacaa ctggttcacc agcatcccgc tggcgaaaaa cctgctgcag    1080
gaaccgtata aactgaccat cgtgggtacc gttcgtagca caaacgtga aatcccggaa     1140
gtgctgaaaa acagccgtag ccgtccggtg ggcaccagca tgttctgttt cgatggtccg    1200
ctgaccctgg ttagctacaa accgaaaccg gcgaaaatgg tgtacctgct gagcagctgc    1260
gacgaagacg cgagcatcaa cgaaagcacc ggtaaaccgc agatggttat gtactacaac    1320
cagaccaaag gcggtgtgga caccctggat cagatgtgca gcgttatgac ctgcagccgc    1380
aaaaccaacc gctggccgat ggcgctgctg tacggtatga tcaacatcgc ctgcatcaac    1440
agctttatca tctacagcca taacgttagc agcaaaggtg aaaaagttca gagccgcaaa    1500
aaatttatgc gtaacctgta catgagcctg accagcagct tcatgcgtaa acgtctggaa    1560
gccccgaccc tgaaacgtta tctgcgcgat aacatcagca acatcctgcc gaacgaagtg    1620
ccgggtacca gcgatgatag caccgaagaa ccggtgatga aaaaacgtac ctactgtacc    1680
tactgcccga gcaaaatccg ccgtaaagcg aacgcgagct gcaaaaaatg caaaaaagtt    1740
atctgtcgtg aacataacat cgatatgtgc cagagctgtt tctga                    1785
```

METHODS AND COMPOSITIONS FOR TRANSPOSITION USING MINIMAL SEGMENTS OF THE EUKARYOTIC TRANSFORMATION VECTOR PIGGYBAC

This application claims priority to co-pending U.S. Provisional Application No. 60/244,984 filed on Nov. 1, 2000 and U.S. Provisional Application No. 60/244,667 filed on Oct. 31, 2000.

The U.S. government may have rights to this invention based on partial support under USDA/NRI Grant 96-35302-3796 and NIH/NIAID 1RO1AI40960, NIH/NIAID 1RO1AI48561.

BACKGROUND

The present invention identifies the specific sequences in a mobile genetic element, the transposon piggyBac, and sequence configurations outside of piggyBac, that are minimally required for full functionality of the sequence as a transposon. Inserting DNA molecules into cells is enhanced using the methods and compositions of the present invention.

Transposable elements (transposons) can move around a genome of a cell and are useful for inserting genes for the production of transgenic organisms. The Lepidopteran transposon piggyBac is capable of moving within the genomes of a wide variety of species, and is gaining prominence as a useful gene transduction vector. The transposon structure includes a complex repeat configuration consisting of an internal repeat (IR), a spacer, and a terminal repeat (TR) at both ends, and a single open reading frame encoding a transposase.

The Lepidopteran transposable element piggyBac was originally isolated from the TN-368 *Trichoplusia ni* cell culture as a gene disrupting insertion within spontaneous baculovirus plaque morphology mutants. piggyBac is a 2475 bp short inverted repeat element that has an asymmetric terminal repeat structure with a 3-bp spacer between the 5' 13-bp TR (terminal repeat) and the 19-bp IR (internal repeat), and a 31-bp spacer between the 3' TR and IR. The single 2.1 kb open reading frame encodes a functional transposase (Cary et al., 1989; Fraser et al., 1983, 1995; Elick et al., 1996a; Lobo et al., 1999; Handler et al., 1998).

piggyBac transposes via a unique cut-and-paste mechanism, inserting exclusively at 5' TTAA 3' target sites that are duplicated upon insertion, and excising precisely, leaving no footprint (Elick et al., 1996b; Fraser et al., 1996; Wang and Fraser 1993).

Transient excision and interplasmid transposition assays have verified movement of this element in the SF21 AE *Spodoptera frugiperda* cell line, and embryos of the Lepidopteran *Pectinophora glossypiella*, *Bombyx mori*, and *T.ni*, as well as the Dipteran species *Drosophila melanogaster*, *Aedes aegypti*, *Aedes triseriatus* and *Aedes albopictus*, and *Anopheles gambiae*. There is also evidence of transposition in the mouse Cos-7 vertebrate cell line, and embryos of the zebra fish, Danio rerio (Fraser et al., 1995; Elick et al., 1996b; Fraser et al., 1996; Elick et al., 1997; Thibault et al., 1999; Tamura et al., 2000; Lobo et al., 1999).

The piggyBac element has been used successfully as a helper-dependent gene transfer vector in a wide variety of insect species, including the Mediterranean fruit fly, *C. capitata*, *D. melanogaster*, *Bombyx mori* , *P. glossypiella*, *Tribollium casteneum*, and *Ae. aegypti* (Handler et al., 1998, 1999; Tamura et al., 2000; Berghammer et al., 1999).

Excision assays using both wildtype and mutagenized piggyBac terminal sequences demonstrated that the element does not discriminate between proximal or distal duplicated ends, and suggest that the transposase does not first recognize an internal binding site and then scan towards the ends. In addition, mutagenesis of the terminal trinucleotides or the terminal-proximate three bases of the TTAA target sequence eliminates excision at the altered terminus (Elick et al., 1996b).

Although the reported piggyBac vector is useful, length of genes that could be transferred is limited by the size of the other components of the vector. Minimizing the length of the vector to allow more room for the genetic material to be transferred, would improve the versatility of the system and reduce costs of preparing synthetic vectors. Previously, the gene to be expressed or transduced was inserted into the middle of the piggyBac transposon in the plasmid p3E1.2. The final construct included the entire length of the piggyBac transposon (2475 bases) and flanking sequences derived from the baculovirus 25K gene region of approximately 813 bases, as well as the plasmid pUC backbone of 2686 bp, and an overall size of approximately 5962 bp. (In cloning sequences into the pUC vector, 12 bp of multiple cloning site DNA was lost). This size limited the effective size of genes that may be inserted, because plasmids larger than 10 KB are generally more difficult to construct, maintain, and transduce into host genomes.

Another problem was that previous cloning regimens involved the excision of a gene, the promoter controlling the gene, and polyadenylation signals, from one plasmid followed by insertion into the piggyBac transfer vector. This procedure was often complicated by the lack of suitable restriction enzyme sites for these manipulations.

SUMMARY

The present invention solves problems in use of the piggyBac vector for gene transfer caused by lack of suitable restriction sites to cut the components needed for gene transfer, and limitations on the sizes (lengths) of genes transferred by use of this vector. Methods and compositions of the present invention enlarge the size of the gene that can be transferred in two ways. First, a minimal sequence cartridge, designated ITR, can be easily amplified using primers containing desired restriction endonuclease sites, and the cartridge is inserted into any plasmid containing the gene with its attendant promoter and polyadenylation signals intact, converting that plasmid into a piggyBac transposon. Second, a multiple cloning site is inserted into the minimal plasmid vector pXL-Bac, facilitating the insertion of genes in this more traditional plasmid vector. The vectors are both used for applications including producing transgenic organisms, both plants and animals. The present invention has been successful in transpositions using the mouse cos-1 vertebrate cell line and embryos of the zebra fish, *Danto rerio*.

Methods and compositions are disclosed herein for transferring genes using the minimum internal and external sequences of the transformation vector piggyBac. In an embodiment of the invention, all non-essential sequences are removed, including the bulk of the piggyBac internal domain and the flanking baculovirus sequences. By means of the minimal piggyBac cartridge, a DNA molecule is transferred from a plasmid into a host cell.

An embodiment of the invention includes a DNA molecule comprising at least 163 consecutive nucleotide base pairs of the 3' terminal region beginning at the 3' terminal base pair, and at least 125 consecutive nucleotide base pairs of the 5' terminal region beginning at the 5' terminal base pair, of the piggyBac molecule, said region extending from the restriction site SacI to the end of the piggyBac molecule. The DNA molecule has a configuration of an internal repeat (IR), a spacer, and a terminal repeat (TR). The spacer of the molecule is further defined as having at least 55 base pairs.

The invention also relates a vector designated pXL-Bac as shown in FIGS. 3(A–C), and a cartridge comprising the minimal piggyBac 5' terminal regions and intervening sequences. An embodiment of a cartridge is IR/31BP/TR/ TTAA . . . 589 . . . TTAA/TR/IR. The DNA molecule to be transferred is flanked by the piggyBac sequences.

Another aspect of the invention is a kit for the construction of piggyBac transformation vectors from existing plasmids. The kit may include the vectors designated A, B, p3E1.2, and a helper construct expressing the transposase. Embodiments of these are disclosed herein.

A method of constructing a transposition piggyBac vector IR/31BP/TR/TTAA . . . 589 . . . TTAA/TR/IR is also within the scope of the invention. The method includes having a helper plasmid expressing a transposase in the trans position.

A method of constructing a mobilized and operational transposable piggyBac vector includes the following steps:
(a) inserting a DNA molecule that contains the sequences essential for piggyBac mobility into a recipient plasmid; and
(b) converting the recipient plasmid into an operational transposable sequence by means of a transposase gene or protein.

A transposase gene product interacts with transposon inverted repeat sequences to induce transposition of the DNA molecule of interest. The gene encoding the transposase can either be physically liked to the transposition vector or introduced into a host (recipient) cell separately.

A method of transferring a segment of a DNA molecule into an embryo or host cell, includes:
(a) obtaining a transposon vector that contains the minimal piggyBac elements;
(b) transferring the vector into the embryo or host cell;
(c) co-injecting a helper plasmid expressing a transposase specific for the elements of the piggyBac vector into the host embryo or cell; and
(d) removing the segment of DNA and inserting it into the host cell or embryo genome, and excising some piggyBac elements.

A DNA construct for transforming a cell, in particular a eukaryotic cell, includes a DNA molecule of interest to be transferred and generally its regulatory elements allowing the DNA to be expressed in a host cell or embryo. Restriction endonuclease digestion of genomic DNA can be done with any enzyme that cuts at locations in the DNA molecule to yield the DNA of interest. Various promoters including inducible promoters such as the well known heat shock promoter hsp70, are suitable. Other DNA molecules such as selectable markers may also be included in the construct. Selectable markers include those for antibiotic resistance, e.g. kanomycin resistance (FIG. 10).

A gene ligated into a cartridge of the present invention may be transferred into bacteria by means of the cartridge.

To produce a multicellular transgenic organism, a transposition construct with a DNA molecule to be transferred is inserted into an egg of the organism, followed by excision of the transposon from the construct (plasmid) and insertion of the DNA molecule into the genome of the egg. Selection and breeding methods known to those of skill in the art, will then produce transgenic organisms in which the DNA molecule transferred is present in all cells of the organism. This process enables production of plants and animals with new, beneficial traits.

BRIEF DESCRIPTION OF THE DRAWINGS

FIG. 22 is the nucleotide sequence (SEQ ID NO: 68) of pCaSpeR-hs-pBac.

FIG. 23 is a comparison of natural and optimized piggyBac nucleotide sequences (SEQ ID NOS 69 & 70) wherein "optimizing" means using cordons specific for insects.

DESCRIPTION OF THE INVENTION

Figure 1:
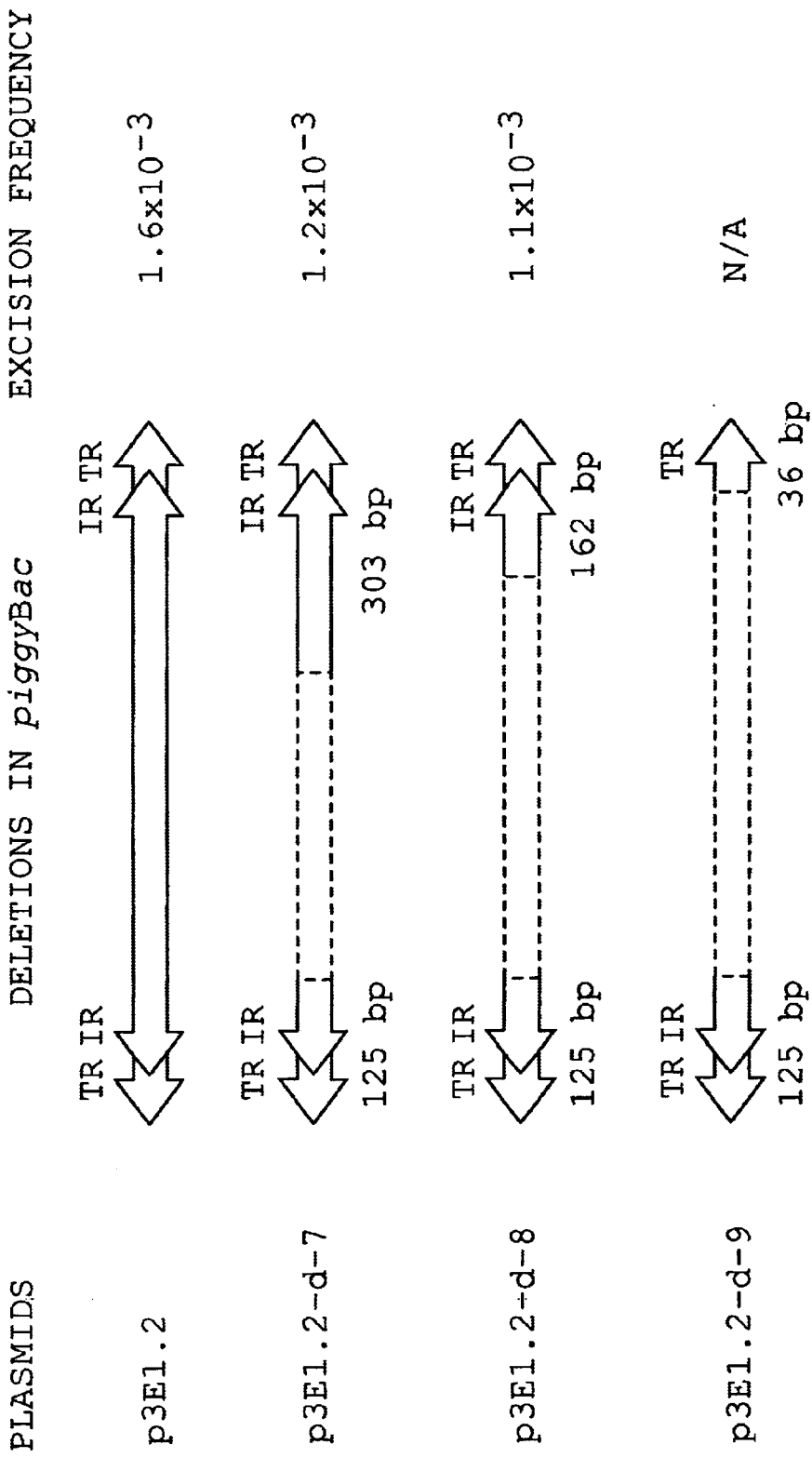
FIG. 1 shows a p3E1.2 deletion series of plasmids and excision assay results; the p3E1.2 plasmid was used to make progressive deletions using the restriction endonuclease ExoIII; three of the maximum deletion plasmids, p3E1.2-d-7, p3E1.2-d-8 and p3E1.2-d-9, were used to perform excision assays in T.ni embryos; p3E1.2d-7 and p3E1.2-d-8 plasmids retained the complete 3' terminal repeat configurations and were characterized by a similar excision frequency as the intact p3E1.2 plasmid; however, p3E1.2-d-9 did not have any excision events recovered, and sequencing results show that its 3'N IR and part of the spacer sequence are deleted.

The minimal sequence cartridges of the present invention facilitate transposition of DNA molecules of interest into cells, and production of transgenic organisms that include the transferred DNA molecule in all their cells. A DNA molecule(s) is excised from a genetic (transformation) construct, and is transferred to a cell where it is inserted into the cell's genome. The DNA molecule is accompanied by regulatory elements sufficient to allow its expression in the host cell. "Cell" as used herein includes eukaryotic and prokaryotic cells. The genetic transposition construct includes a DNA molecule to be transferred flanked by a pair of transposon terminal inverted repeat nucleotide sequences from the piggyBac transposon. The DNA molecule to be transferred may be any molecule capable of being expressed in a host cell and/or transgenic organism. The method would also transfer cells not able to be expressed, but that is not generally useful.

In the present invention, excision (Elick et al., 1996b) and interplasmid transposition assays (Lobo et al., 1999) were used to determine the relative importance of sequences internal to, or external to, the terminal repeat (TR) and internal repeat (IR) sequence configurations for movement of the piggyBac element.

It was found that progressive deletions within the internal sequence of the element have no noticeable effect on either excision or transposition capabilities. In contrast, deletion of the 3' IR eliminated excision of the element. Construction of vectors having only intact 5' and 3' repeat domains regenerates mobility of the plasmids when supplied with a helper vector expressing a transposase. These features permitted construction of a set of minimal vectors for use in transformation experiments.

The length of the intervening sequence between piggyBac termini in the donor plasmid also affects the piggyBac transposition frequency. A minimal distance of 55 nucleotide base pairs (bp) seems to be necessary between target sites and termini to allow optimal movement of the element. This suggests that the piggyBac transposase binds the termini simultaneously before any cleavage can occur, and/or that the formation of the transposition complex requires DNA bending between the two termini.

An aspect of this invention is that it allows the design of minimally sized genetic vectors that are functional for efficient insertion of genes into host genomes, in particular animal, plant and insect genomes.

Two of the useful plasmids created are:

A) A transposition piggyBac ITR cartridge Plasmid: PCR amplifications and restriction endonuclease cleavage and ligation allowed insertion of a 702 bp fragment containing the sequences essential for piggyBac mobility into any given plasmid of choice, converting the recipient plasmid into an operational transposable sequence capable of being mobilized into an animal genome using the piggyBac transposase gene or purified protein. The PCR II (Invitrogen) plasmid re-amplification using specified primers allows this ITR cartridge to be inserted into any plasmid.

B) Operational Transposable Vector (pXO): Standard restriction endonuclease cleavage and ligation allows insertion of any gene of choice between the minimally required sequences of the piggyBac transposon necessary for transposition into the genome of an animal.

The total size of the resulting plasmid is preferably not larger than 10 kb.

The invention relates that the inverted repeat configuration indicated as [TTAA/TR/IR . . . IR/31 bp/TR/TTAA] is minimally required for full functionality of a piggyBac transposon. This observation was arrived at through structured deletion mutagenesis within the piggyBac transposon sequence and examining the properties of both excision and interplasmid transposition of the deleted product.

Additionally, it was discovered through deletion of external sequences, that the minimal size for a spacer between the target site on a plasmid having the terminal repeat configuration [IR/31 bp/TR/TTAA . . . spacer . . . TTAA/TR/IR] is 55 bp for optimal mobility.

For ease of manipulation, a cartridge having the configuration [IR/31 bp/TRTTAA . . . 589 . . . TTAA/TR/IR] which can be inserted within any plasmid, converting that plasmid into a functional piggyBac transposon, was constructed. The cartridge was cloned into the plasmid pCRII (Invitrogen). A cartridge is defined herein as a nucleic acid molecule of a specified construction (plasmid) that can be inserted into a vector.

A cartridge was derived from circularization of the construct A and cutting the construct A with BssHII to cleave at a unique BssHII site within the 589 bp spacer. This yielded a fragment BssHII . . . TTAA/TR/31 bp/IR/BamHI/IR/TR/TTAA . . . BssHII. Construct B was derived from a pBSII (Stratagene) plasmid by BssHII deletion of the multiple cloning site (MCS). The linearized fragment was then inserted into the pBSII BssHII backbone. An MCS primer was synthesized and inserted in the BamHI site.

Construct A allows ease of construction of genetic vectors through use of a simple 702 bp cartridge that may be inserted into any existing plasmid to convert it immediately into a functional transposon.

Construct B allows ease of insertion of any genetic sequence into a plasmid having the minimal terminal sequence requirement for piggyBac mobility. The advantage of this construct is it provides a minimal backbone cloning vector for piggyBac transposon construction.

A kit is contemplated that would contain the two vector constructs along with the original p3E1.2, and/or a helper construct allowing constitutive production of piggyBac transposase in virtually any animal system. Promoter driven expression of the piggyBac transposase using either RSV LTR sequences, CMV early promoter, AcMNPV/IE-1 promoter of poly-ubiquitin promoter, among others, is also contemplated.

Excision assays of plasmids containing progressive deletions of the piggyBac internal sequence revealed that the 5' and 3' IR, spacer, and TR configurations are sufficient for piggyBac movement when provided with a transposase in the trans position. Interplasmid transposition assays of plasmids having different lengths of sequence between the target sites demonstrated a minimum of 55 bp of intervening sequence is required for optimal piggyBac transposition, whereas lengths less than 40 bp result in dramatic decreases in frequency of transpositions. These results suggest that the piggyBac transposase binds the termini simultaneously before cleavage, and/or that the formation of the transposition complex requires DNA bending between the two termini. Based on these results, a 702 bp cartridge having a minimum piggyBac 5' and 3' terminal region configuration and intervening sequence was constructed. The ability of this region to convert any existing plasmid into a non-autonomous piggyBac transposon was verified. A minimal piggyBac vector, pXL-Bac, that contains an internal multiple cloning site sequence between the terminal regions, was also constructed. These vectors facilitate manipulations of the piggyBac transposon for use in a wide variety of hosts.

The excision assay provides a rapid way to characterize essential sequences involved in piggyBac transposition. The p3E1.2-d-7 and p3E1.2-d-8 plasmids, which retain the entire 3' and 5' IR, spacer and TR sequences, exhibit precise excision. In contrast, the p3E1.2-d-9 plasmid that retains the entire 5' terminal region and only 36 bp of the 3' terminal domain, including the TR and a portion of the 31 bp spacer, does not excise at a detectable frequency. The requirement for an internal 3' IR sequence in the excision process suggests that the IR region might play an essential role in transposase recognition or cleavage of the target site.

An alternative explanation is that simply shortening the internal sequence may hinder the formation of a transposition complex, or the binding of transposase to two termini simultaneously. A similar result is observed with the IS50 elements for which the lengthening of Tn5 internal sequences increases the transposition frequency (Goryshin et al., 1994). However, insertion of a KOα fragment into the p3E1.2-d-9 at the SphI site did not improve the frequency of precise excision events recovered in the excision assay, suggesting that the length of the internal domain is less important than the presence of an intact IR sequence in excision of the piggyBac element.

The interplasmid transposition assays of pIAO-P/L series plasmids demonstrate that when the external sequence separating the terminal repeats is at least 55 bp, the transposition frequency is over $10^{-4}$, while reducing the length to less than 40 bp depresses the frequency of transposition. The inhibition of piggyBac transposition as terminal sequences are brought closer together, suggests that formation of a transposition complex likely precedes DNA cleavage or nicking, and the shorter distances between these termini do not allow proper bending of the sequences to permit formation of the complex, or result in steric hindrance of transposase binding at the termini.

These results also imply a necessity for transposase binding of both termini simultaneously before any cleavage (or nicking) can occur. If the simultaneous binding were not necessary, then the transposase could bind one terminal repeat, cleave it, and then bind the second to cleave, and transposition should occur with equivalent frequencies even with smaller intervening sequences.

Figure 10A:
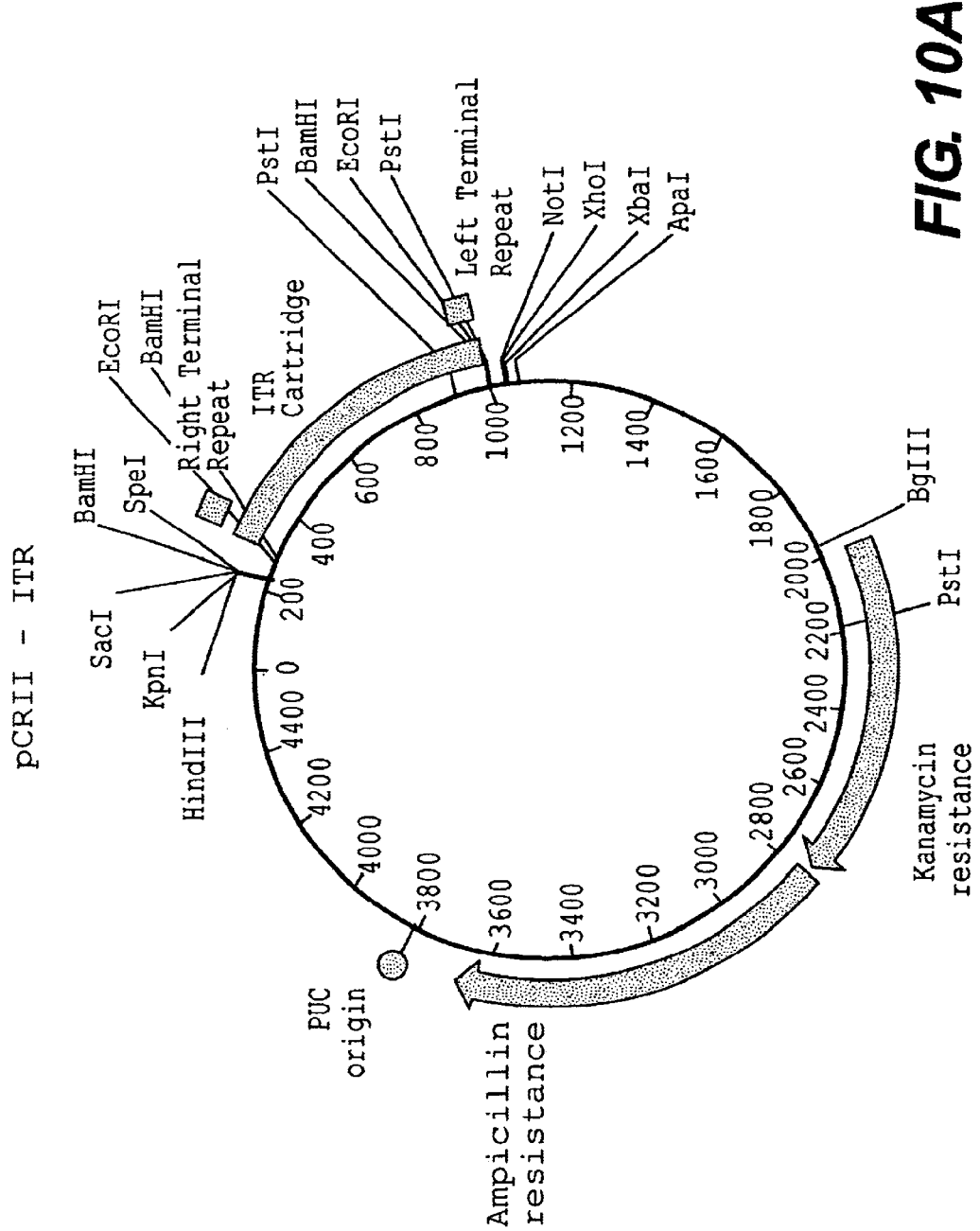
FIG. 10(A) is a plasmid map showing the ITR cartridge was PCR amplified as a BamH I fragment using a piggyBac internal repeat specific primer (5'-GGATCCCATGCGTCAATTTTACGCA-3') (SEQ ID NO: 1) and pIAO-P/L-589 bp plasmid as a template, and cloned into the pCRII plasmid (Invitrogen) to form the pCRII-ITR plasmid; (B) is the nucleotide sequence of pCRII-ITR (SEQ ID NO: 46) and the amino acid sequence (SEQ ID NO: 47).

Interplasmid transposition assays using pCRII-ITR (FIG. 10) verify that the terminal configuration IR, spacer, TR are the minimum sequence requirements for efficient piggyBac transposition. The rest of the piggyBac internal sequence is not required if transposase is provided in trans configuration. With the ITR fragment, a minimum piggyBac vector can easily be constructed from any plasmid which reduces vector size and leaves maximum space for desired foreign genes.

Figure 11:
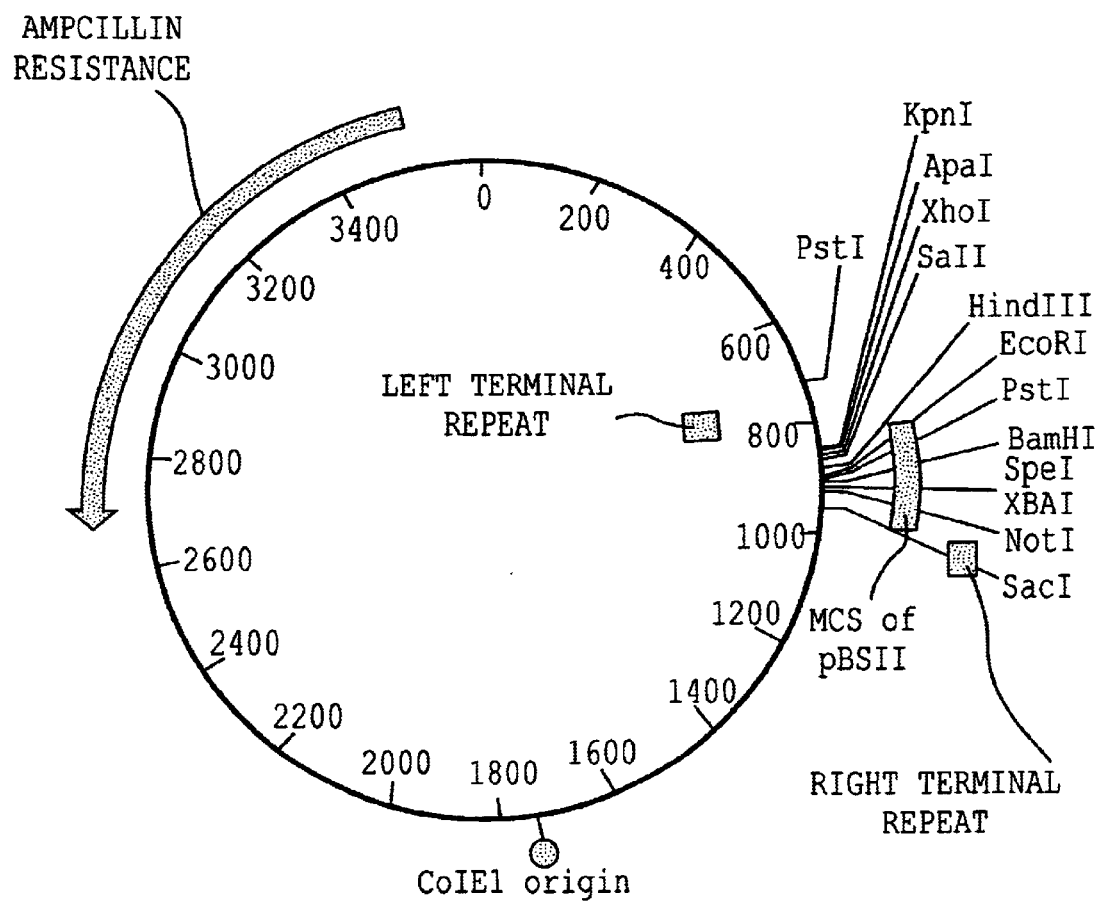
FIG. 11 is a plasmid map showing the ITR BamH I cartridge was recovered from the PCRII-ITR plasmid and religated, then cut with BssH II and cloned into the BssH II sites of the pBSII plasmid (Stratagene) to form pBS-ITR (rev) plasmid. The Multiple Cloning Sites were PCR amplified as a Bgl II fragment from the pBSII plasmid and were cloned into the BamH I site to from the pXL-Bac plasmid.

Inserting the ITR fragment into pBlueScript, converts the plasmid into a transposable element that moves with a frequency similar to the intact piggyBac element. This ITR cartridge facilitates the construction of piggyBac transformation vectors from existing plasmids. In addition, the co-integration of the Amp/ori sequences from the donor plasmid into the genome provides an easy way to locate the insertion site because these insertions may be recovered by restriction enzyme digestion, religation, and transformation. The pXL-Bac (FIG. 11) minimum piggyBac vector replaces the internal sequence of the piggyBac transposon with a multiple cloning site. This plasmid allows any desired foreign genes or sequences to be easily inserted between piggyBac termini for movement in the presence of a helper plasmid. These constructs provide useful tools for the examination and use of piggyBac as a gene transfer vector in a wide variety of organisms.

EXAMPLES

Example 1

Excision Assay of p3E1.2 Internal Deletion Series in *T. ni*

The analysis was begun using three plasmids having the most extensive internal deletions, p3E1.2-d-9, p3E1.2-d-8 and p3E1.2-d-7. Sequencing of these three plasmids revealed that p3E1.2-d-8 and p3E1.2-d-7 retained 163 bp and 303 bp of the 3' terminal region, respectively, including the IR, 31 bp spacer, and TR sequence. The p3E1.2-d-9 deletion plasmid retained only 36 bp of the 3' terminal domain, including the TR and a portion of the 31 bp spacer, but lacked the 3' IR sequence.

Embryos of *T. ni* were injected with combinations of each of the p3E1.2 deletion plasmids and the phspBac helper plasmid. Loss of piggyBac sequences from the deletion series plasmids renders the plasmids resistant to BsiWI and SphI digestion. Transformation of Hirt extract DNAs digested with BsiWI and SphI were compared with transformations employing equal amounts of uncut DNA as a control to determine the frequency of excision. Precise excision events were initially identified by a quick size screen for the characteristic 3.5 kb plasmid in recovered colonies, and these plasmids were then sequenced to confirm the precise excision events.

A quick size screen method is used to quickly identify the plasmids with changed size directly from colonies (Sekar, 1987). Colonies at least 1 mm in diameter are picked up with pipette tips and resuspended in 10 ml protoplasting buffer (30 mM Tris-HCl pH 8.0, 50 mM NaCl, 20% Sucrose, 5 mM EDTA, 100 mg/ml RNase, 100 mg/ml Lysozyme) in the Lux 60 well mini culture plate. A 0.9% agarose gel containing ethidium bromide is preloaded with 4.5 ml lysis solution (80 mM Tris, 5% Sucrose, 0.04% Bromophenol Blue, 2% SDS, 2.5 mM EDTA) per well. The bacterial suspension is then loaded into the wells and the gel electrophoresed. Two kind of markers are needed to distinguished the plasmids with changed size. One is the colony from the control plate or the original plasmid, another is a molecular weight marker. The plasmids with a difference of 500 bp or greater in size are easily distinguished.

Both the p3E1.2-d-8 and p3E1.2-d-7 yielded precise excision events at about the same relative frequency, while no excision events were recovered with the maximum deletion plasmid p3E1.2-d-9 (FIG. 1).

Example 2

Figure 4A:
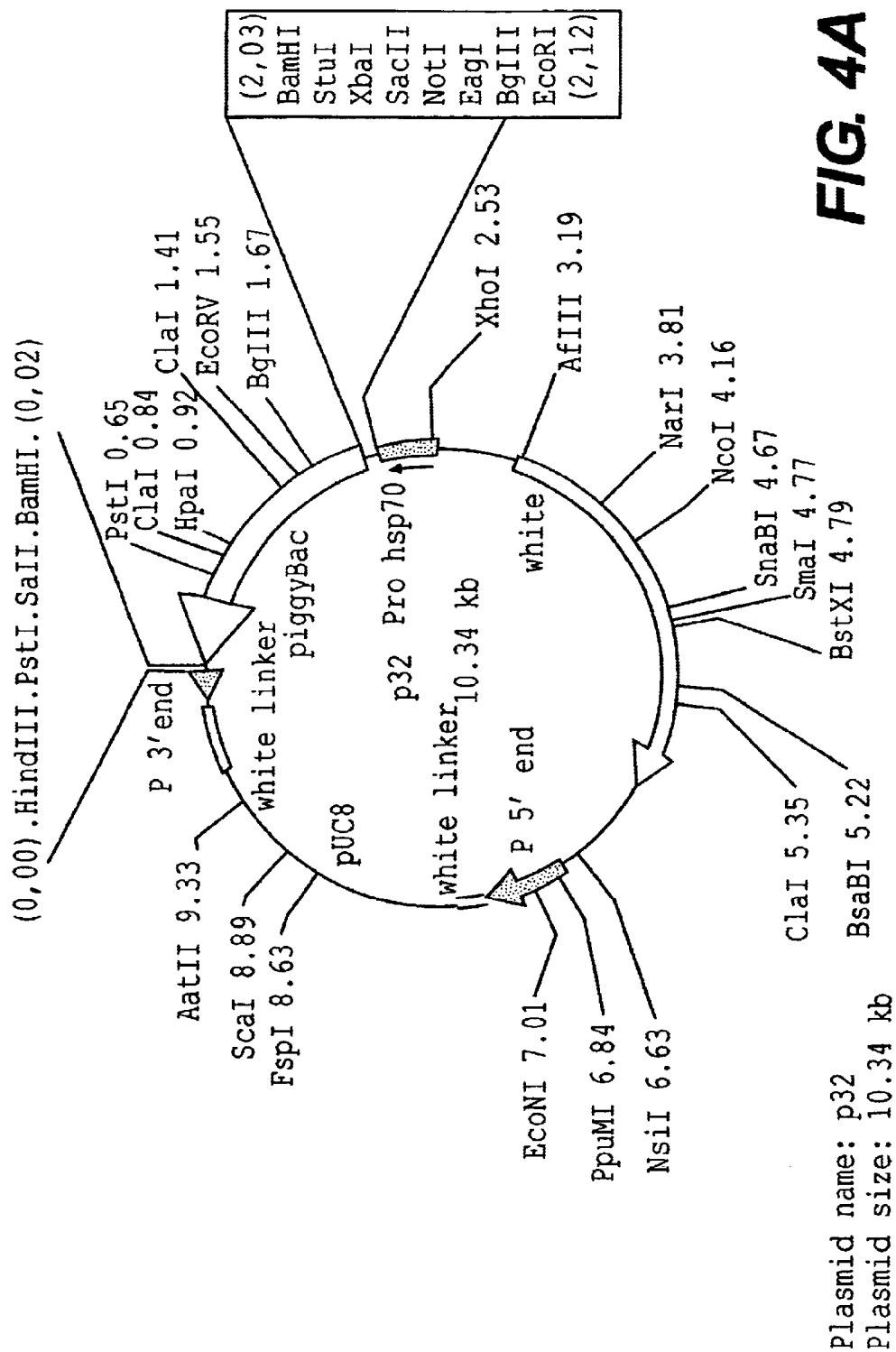
FIG. 4 is a restriction map of plasmid pCasper-hs-orf (p32), containing a 2016 bp PCR BamHI fragment containing piggyBac transposase and its terminator, cloned into BamHI sites of pCaSpeR-hs.
Figure 5A:
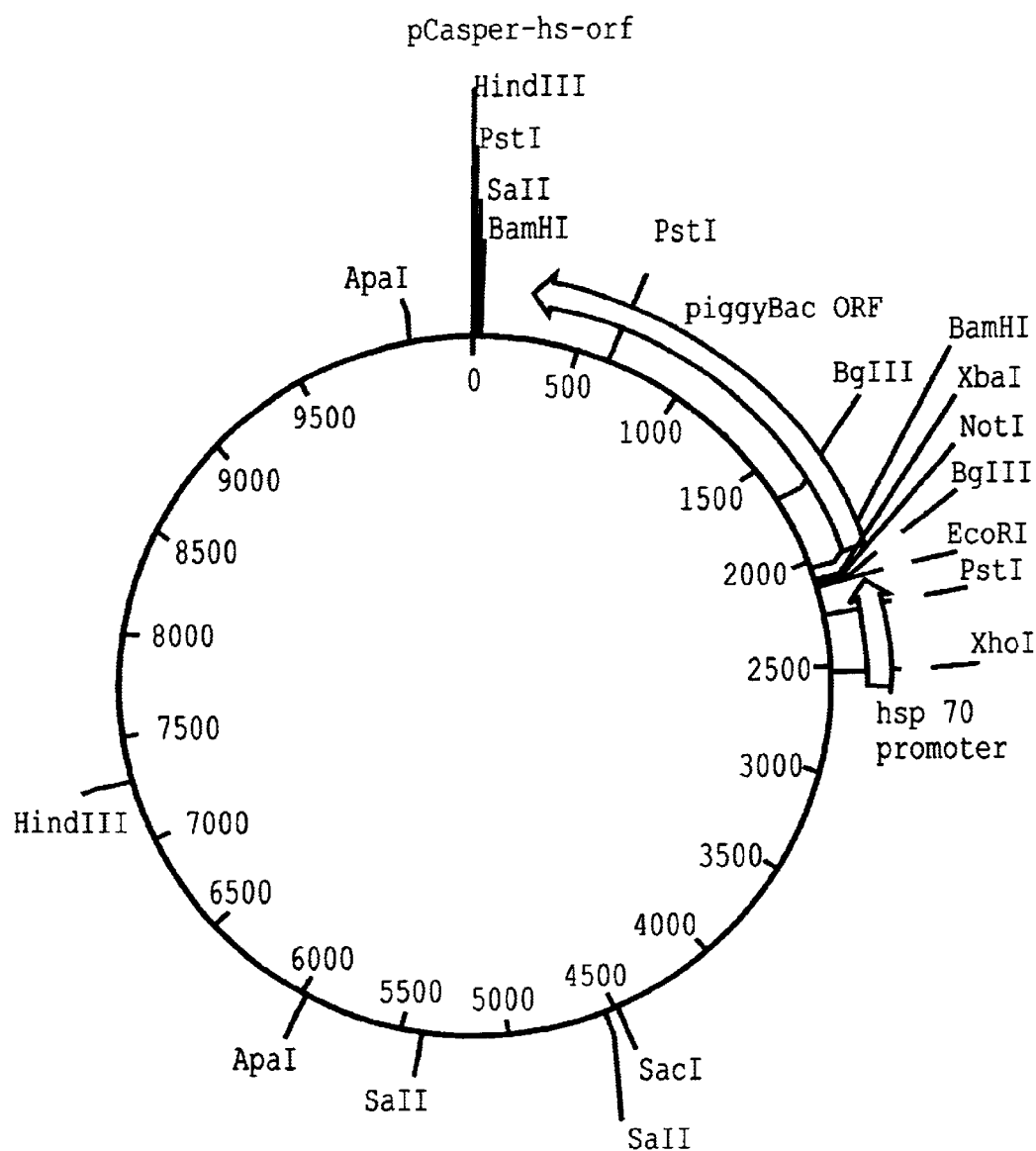
FIG. 5(A) is a plasmid map showing the piggyBac ORF was amplified as a BamH I cartridge from the p3E1.2 plasmid and cloned into pCaSpeR-hs plasmid, positioning it for transcriptional control of the hsp70 promoter; (B) is the nucleotide sequence (SEQ ID NO: 42) of pBSII-hs-orf.

Minimal Distance Required Between Termini for Movement of a piggyBac Transposon Construct The interplasmid transposition assay was carried out essentially as previously described by Lobo et al. (1999), Thibault et al. (1999) and Sarkar et al. (1997). Embryos were injected with a combination of 3 plasmids. The donor plasmid, pB(KOα), carried a piggyBac element marked with the kanamycin resistance gene, ColE1 origin of replication, and the lac-Z gene. The transposase providing helper plasmid, pCaSpeR-pB-orf, expressed the full length of the piggyBac ORF under the control of the *D. melanogaster* hsp70 promoter. The target *B. subtilis* plasmid, pGDV1, is incapable of replication in *E. coli*, and contains the chloramphenicol resistance gene. Upon transposition of the genetically tagged piggyBac element from pB(KOα) into the target plasmid pGDV1 with the help of the transposase provided by the helper pCaSpeR-pB-orf that expresses the piggyBac transposase protein from a minimal hsp70 promoter (see FIG. 4) only the interplasmid transposition product would be able to replicate in *E. coli* and produce blue colonies on LB/kan/cam/X-gal plates. Embryos were injected with a mixture of the transposase-providing helper plasmid, phspBac, one of the pIAO-P/L series plasmids as the donor, and the pGDV1 target plasmid. Transposition of the tagged piggyBac element from any of the pIAO-P/L plasmids into the target plasmid pGDV1 allows the recipient pGDV1 to replicate in *E. coli* and produces blue colonies on LB/Amp/Cam/X-gal plates.

A total of 10 blue colonies were randomly picked from each transformation and prepared for sequencing analysis.

Initial sequence analysis of terminal repeat junction showed that all of the sequenced clones had the distinctive duplication of a TTAA tetranucleotide target site, a characteristic feature of piggyBac transposition. A random set of those clones for which the 5' terminus had been sequenced were also examined at their 3' terminus to confirm the duplication of the TTAA site at both ends. The accumulated results confirmed transposon insertion at 12 of the 21 possible TTAA target sites in the pGDV1 plasmid, all of which were previously identified as insertion sites in Lepidopteran assays by Lobo et al. (1999) and Thibault et al. (1999).

Figure 2B:
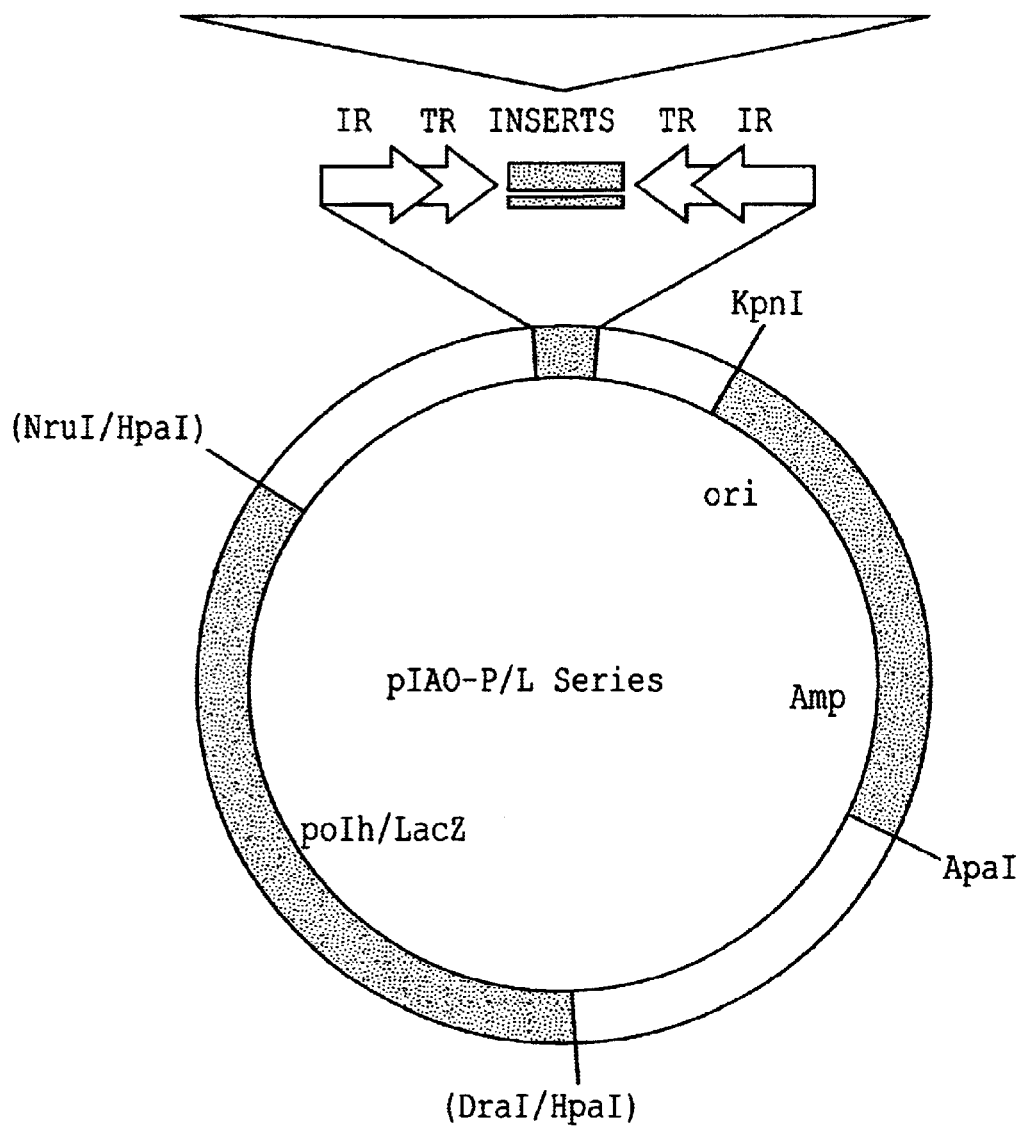
FIG. 2 shows pIAO-P/L insertion series of plasmids and presents interplasmid transposition assay results: (A) lists the pIAO-P/L series of plasmids' insertion sequences (SEQ ID NOS 35–39) and their interplasmid transposition assay (IPTA) frequencies are shown; all the pIAO-P/L insertion plasmids were co-injected with piggyBac helper plasmid, phspBac, and the target plasmid, pGDV1, into T.ni embryos to perform an interplasmid transposition assay; the results show that when the insertion sequence is less than 40 bp, the transposition drops dramatically; (B) is a schematic representation of the pIAO-P/L series plasmids; the piggyBac sequence was PCR amplified from a p3E1.2B/X plasmid, polh/lacZ is from a pD2/-gal DraI/NruI fragment and AMP/ ori was PCR amplified from a pUC18 plasmid; and (C1) is the nucleotide sequence of pIAO-pL (SEQ ID NO: 57) and the amino acid sequences (SEQ ID NOS 58–62) (C2) is the nucleotide sequence of pIAO-p/L-Lambda (2.2 kb) (SEQ ID NO: 63) and the amino acid sequences (SEQ ID NOS: 58–61 & 64–66).
Figure 2(C1):
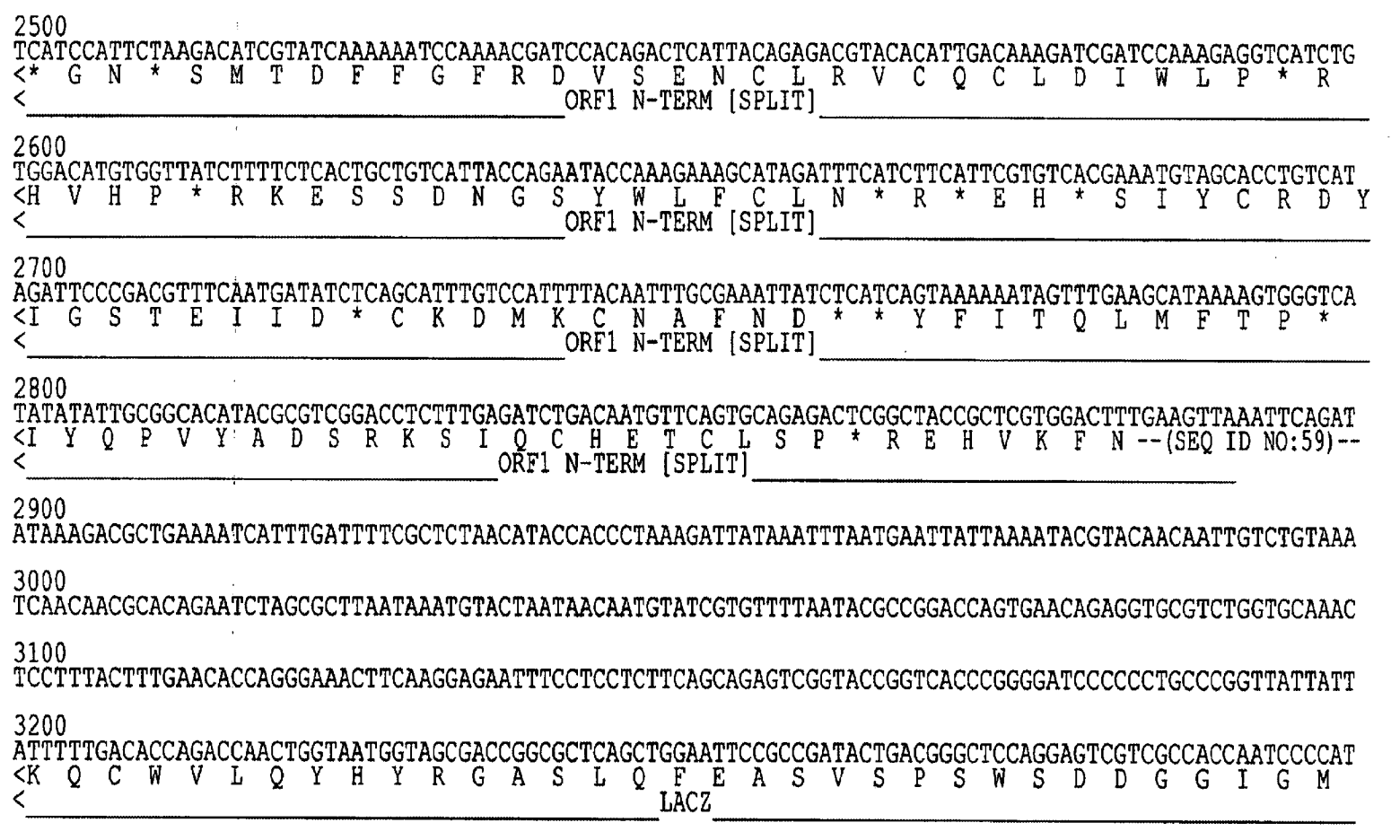
Figure 2(C1):
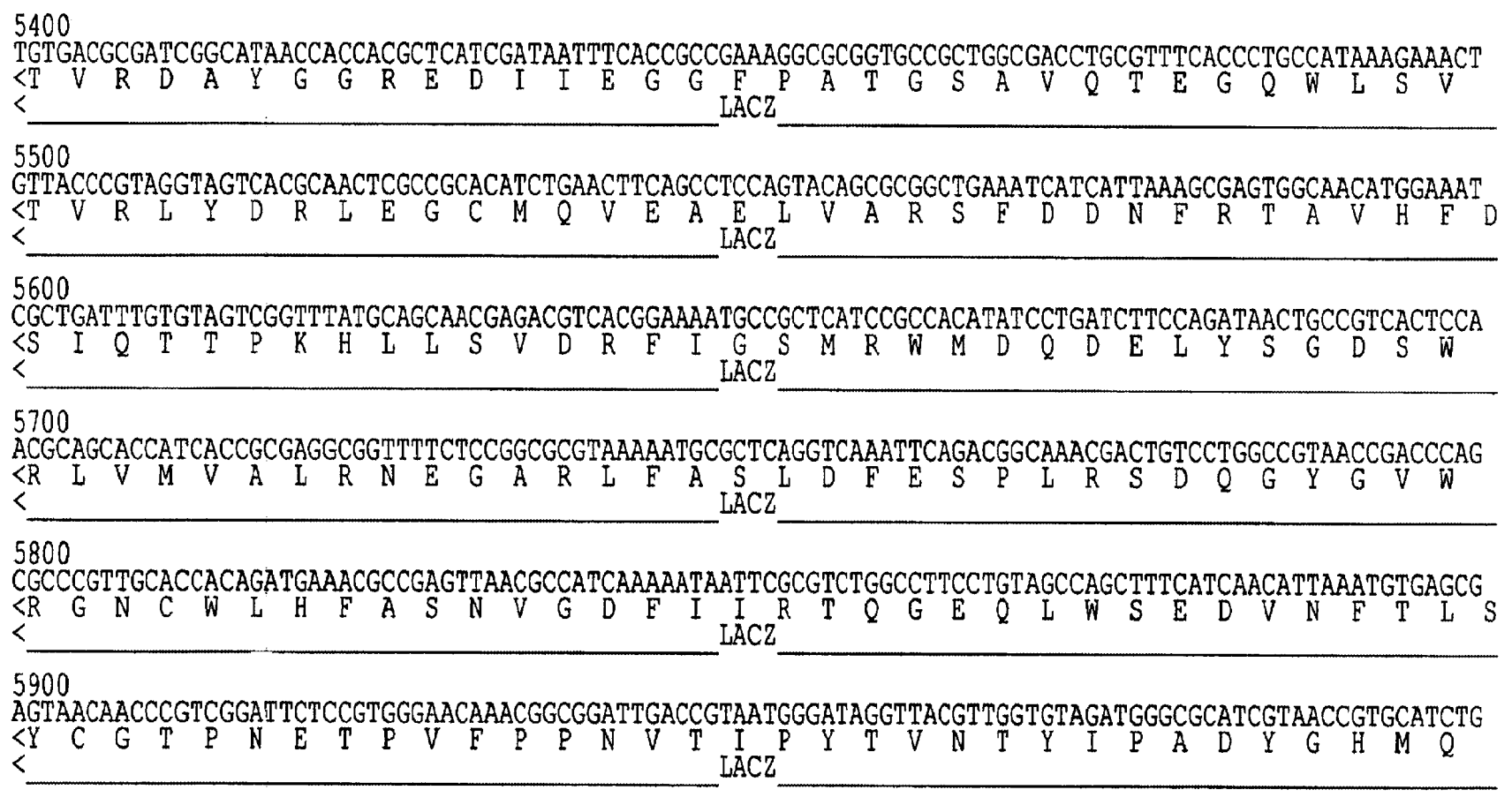
Figure 2(C2):
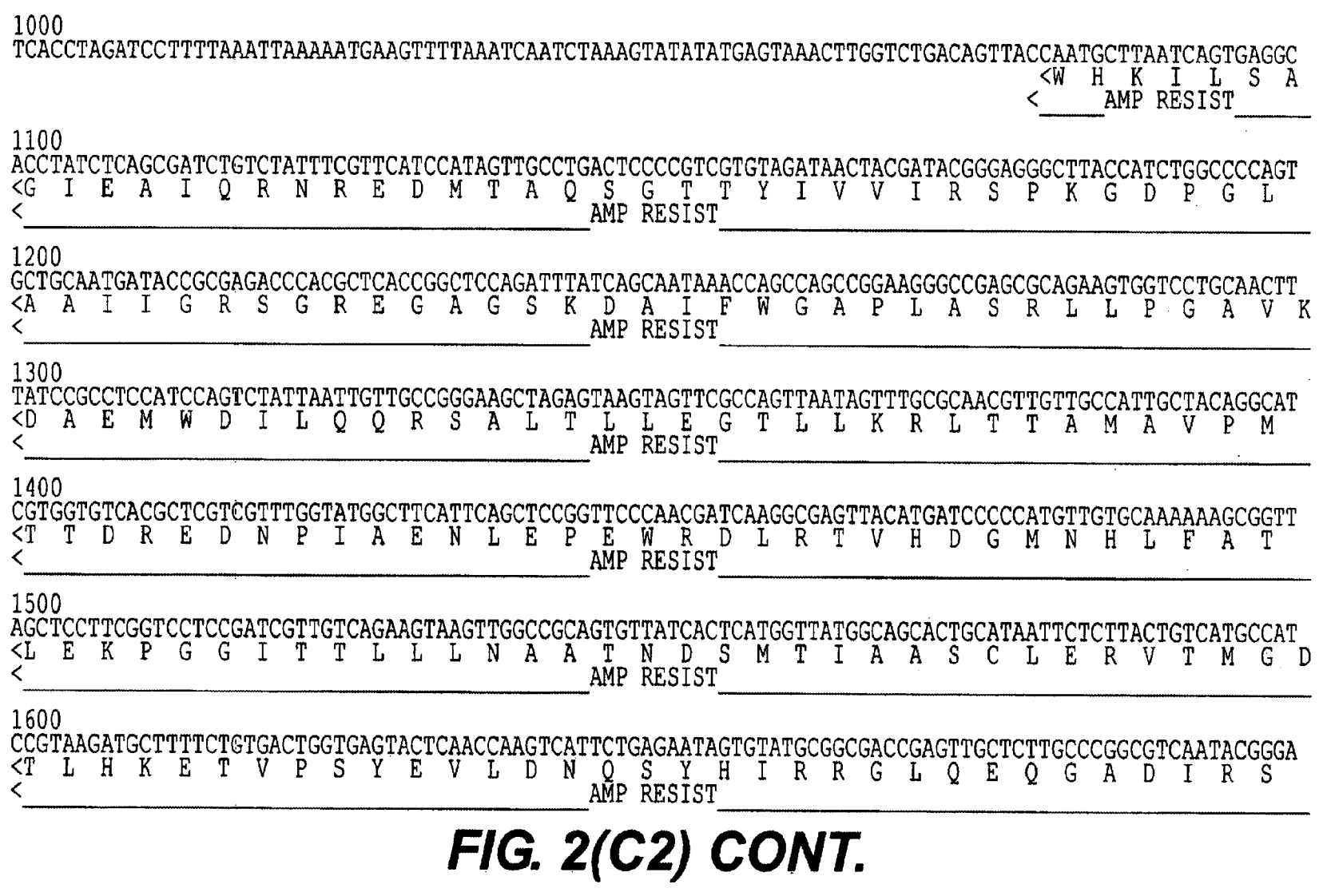
Figure 2(C2):
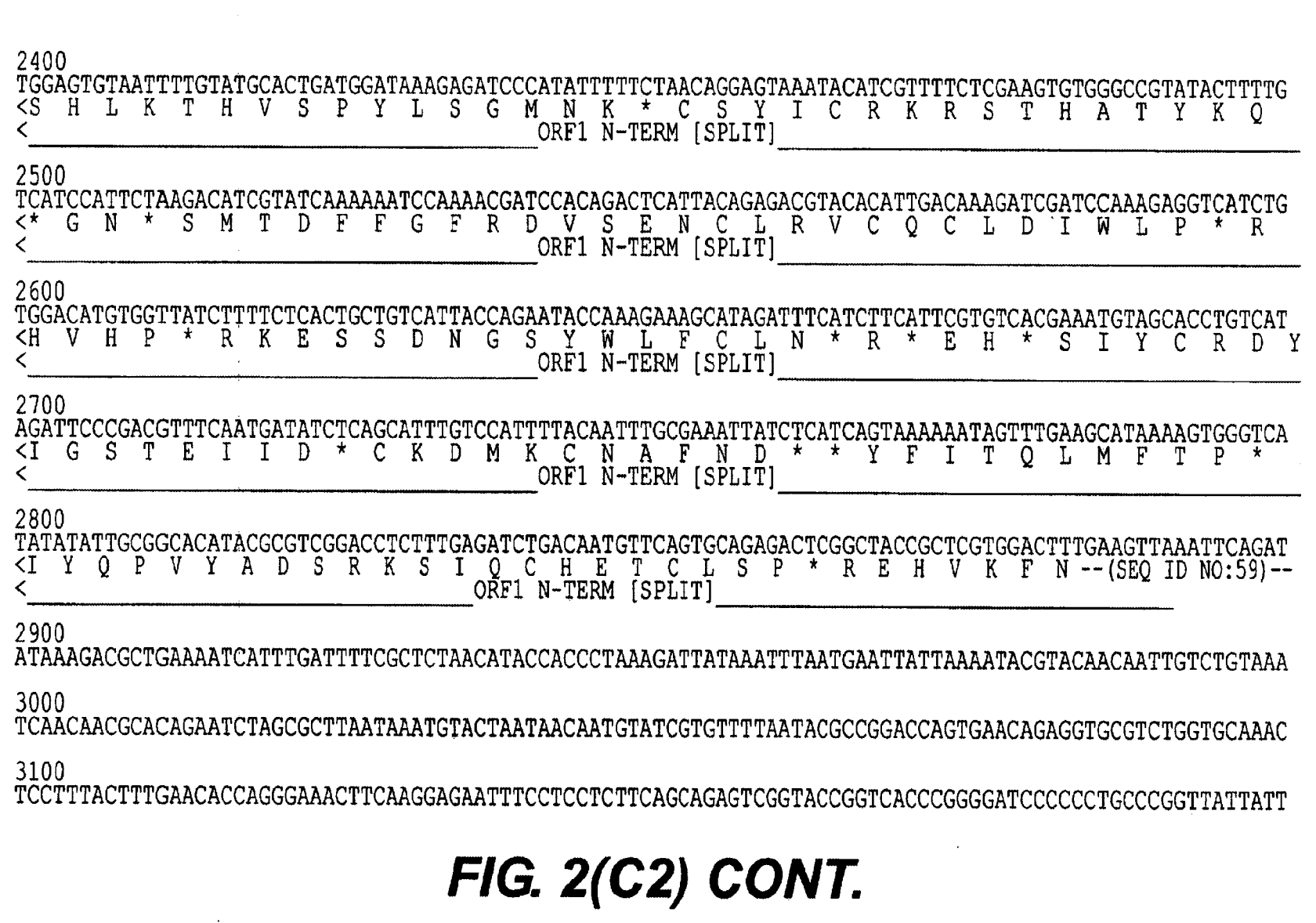
Figure 2(C2):
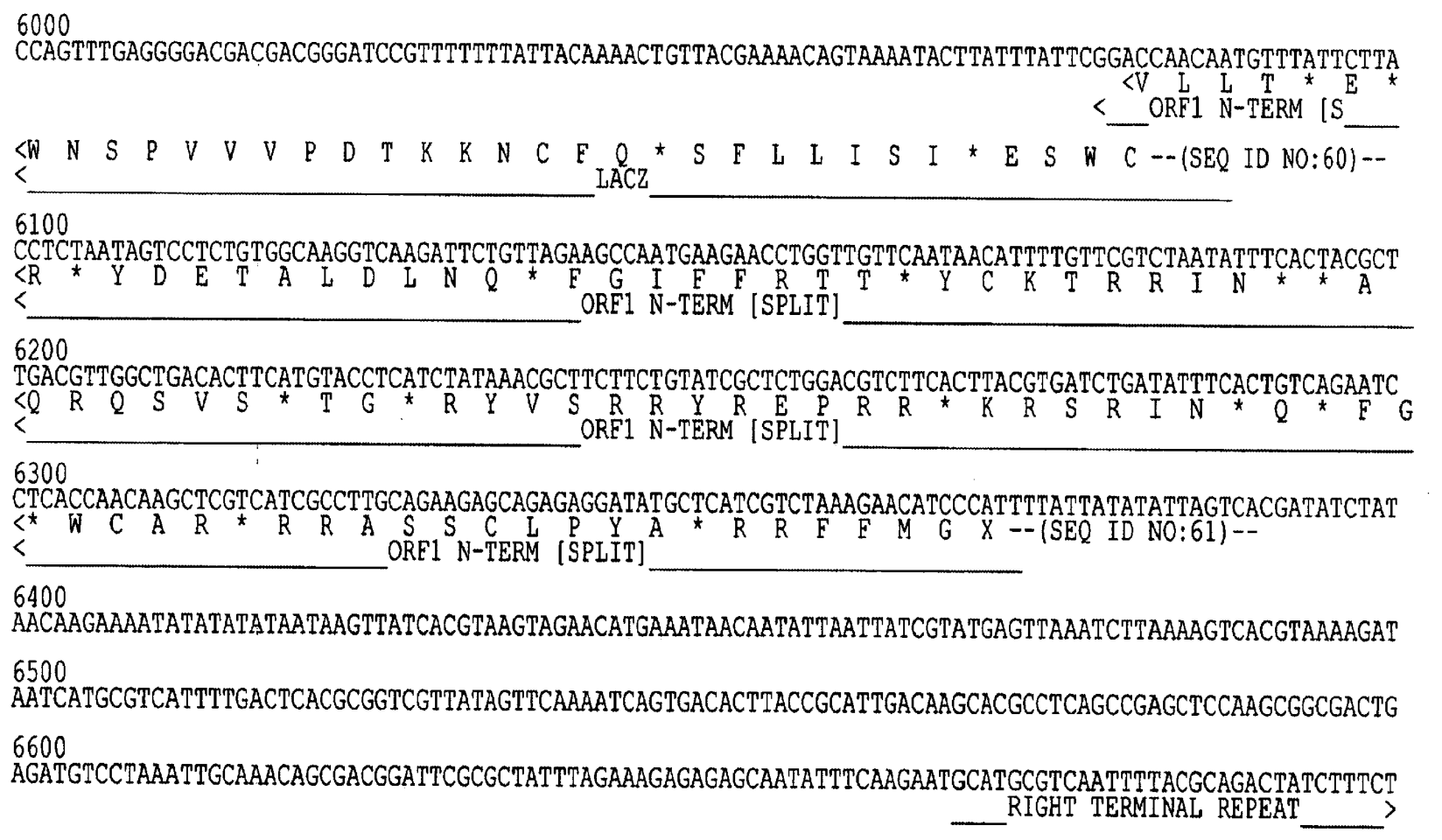
Figure 2(C2):
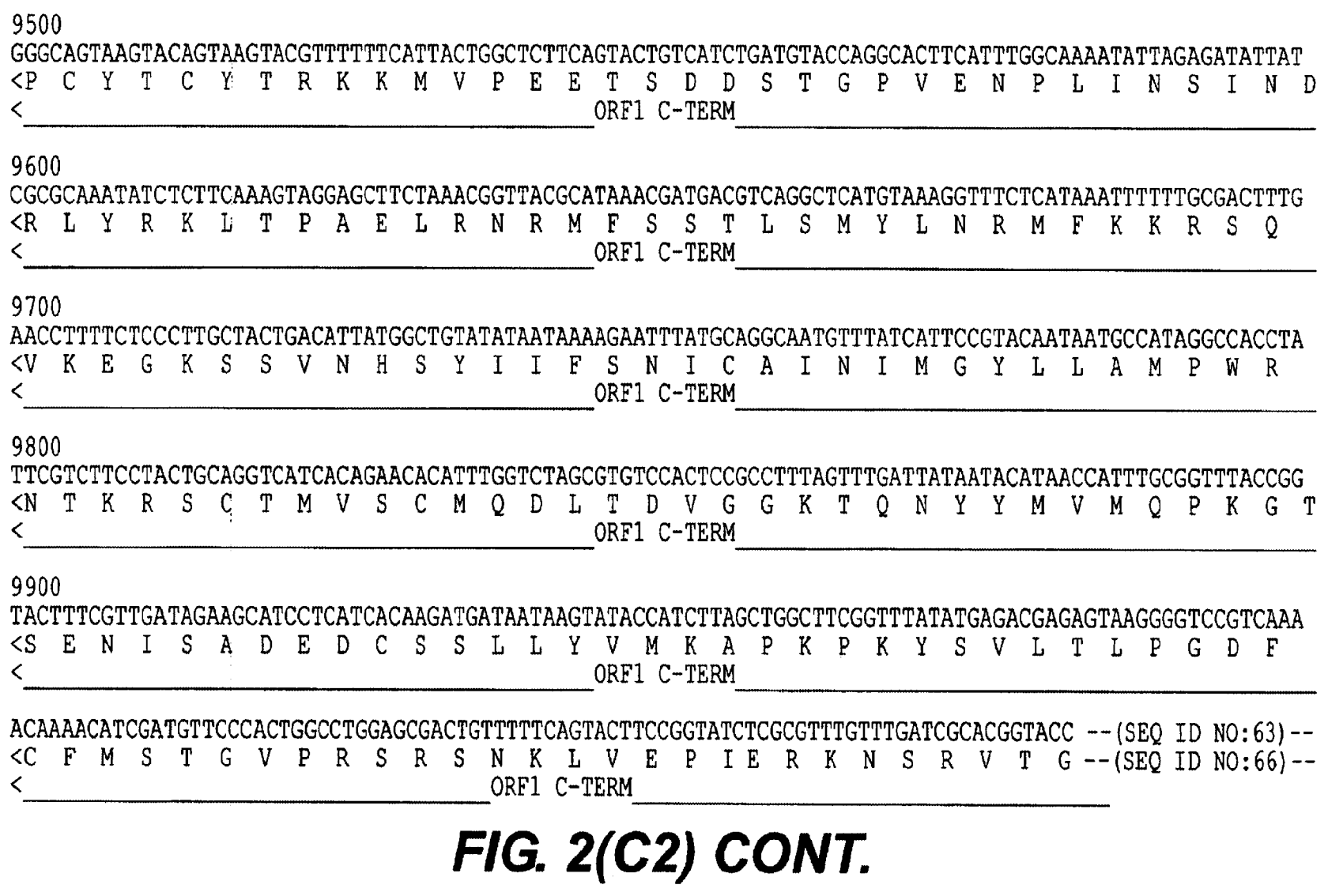

The relative frequency at which a given pIAO-P/L series plasmid was able to undergo transposition into the target plasmid correlated with the sizes of the intervening sequence between the termini. With intervening sequences greater than 55 bp, the transposition frequency was over $1.2 \times 10^{-4}$, which is consistent with the frequency obtained in previous assays with the p3E1.2 derived vectors by Lobo et al. (1999). If the length of the intervening sequence was reduced to 40 bp or less, the frequency of transposition began to decrease dramatically (FIG. 2).

Example 3

Interplasmid Transposition Assay of pCRII-ITR and pBS-ITR Plasmids

The excision assay described herein demonstrated that a minimum of 163 bp of the 3' terminal region and 125 bp of the 5' terminal region (from the restriction site SacI to the end of the element) are sufficient for excision, while the pIAO-P/L constructs showed that a minimal distance of 55 bp between termini was necessary for optimal movement. These data suggested that the inclusion of only intact left and right terminal and internal repeats and spacer domains would be sufficient for transposition.

The pCRII-ITR plasmid was constructed following PCR of the terminal domains from pIAO-P/L-589 using a single IR specific primer because of uncertainty that repeat proximal sequences were also not required. A second construct pCRII-IF03/04 was also prepared using two primers that annealed to the piggyBac internal domain respectively, in case repeat proximate sequences were required.

The interplasmid transposition assay was performed in *T. ni* embryos and the plasmids were recovered using LB/Kan/Cam plates (Sambrook et al., 1989) with the controls plated on LB/Amp plates. A total of 10 randomly picked colonies were sequenced, and all were confirmed as resulting from transposition events, having the characteristic tetranucleotide TTAA duplication at the insertion sites. These insertion sites in pGDV1 were among the same previously (Lobo et al., 1999 and Thibault et al., 1999). The sequencing results also confirmed that all 10 transposition events retained the expected terminal domain configurations. The frequency of transposition events was estimated at $2 \times 10^{-4}$, a similar frequency to that obtained with non-mutagenized constructs for this species (Lobo et al., 1999).

Figure 3A:
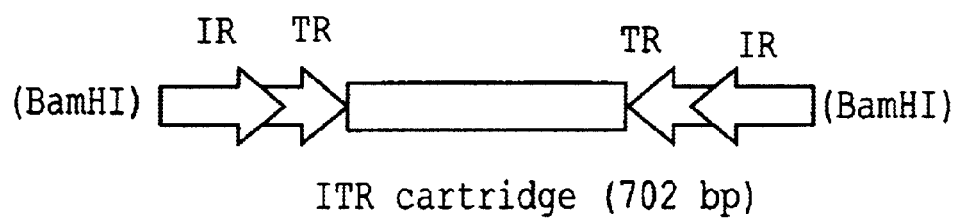
FIG. 3 is a schematic representation of an ITR cartridge and pXL-Bac minimum piggyBac vectors; (A) the ITR cartridge may be amplified from the PIAO-P/L-589 bp plasmid using an IR-specific primer; the amplified ITR can convert any existing plasmid into a piggyBac transposon, which can be mobilized if provided with a transposase; (B) is a map of the pXL-Bac plasmid. (MCS=multiple cloning site, BamHI or BasHII are restriction sites); (C1) the ITR cartridge nucleotide sequence (SEQ ID NO: 40); and (C2) is the nucicotide sequence (SEQ ID NO: 41) of pXL-Bac.
Figure 3B:
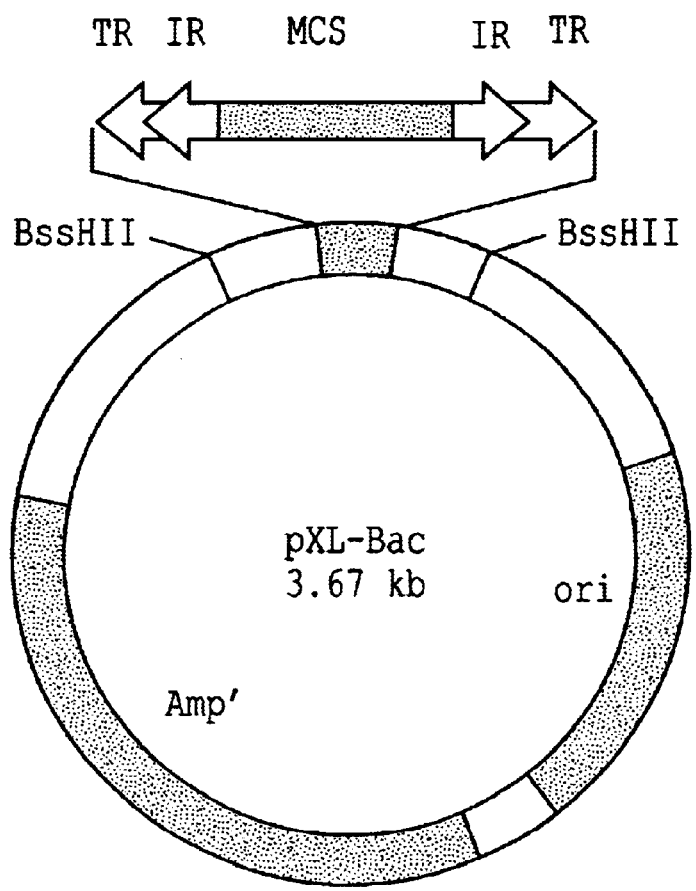

Independent verification that the 702 bp PCR cloned fragment (ITR cartridge, FIG. 3(C1)) could be used as a cartridge to generate transpositionally competent plasmids by excising the BamHI fragment from pCRII-ITR, and ligating it into the pBlueScript (Stratagene) plasmid to construct Pbs-ITR. Frequencies similar to those for the pCRII-ITR construct in the interplasmid transposition assay, were obtained.

Example 4

Construction of Minimum pigygBac Vectors—pXL-Bac

A new piggyBac minimum vector pXL-Bac (FIG. 3(C2)) was also constructed by combining the 702 bp BamHI ITR fragment with the pBlueScript II BamHI fragment and inserting a PCR amplified pBSII multiple cloning site (MCS) between the terminal repeats. The pXL-Bac vector was tested by inserting an XbaI fragment from pKOa (obtained from A. Sarkar, University of Notre Dame), containing the Kanamycin resistance gene, *E. coli* replication origin, and Lac a-peptide, into the MCS of pXL-Bac to form pXL-Bac-KOa. Interplasmid transposition assays yielded a frequency of over $10^{-4}$ for transposition of the modified ITR sequence, a similar level as observed for the intact piggyBac element.

Example 5

Derivative Vectors of PXL-Bac

Figure 15A:
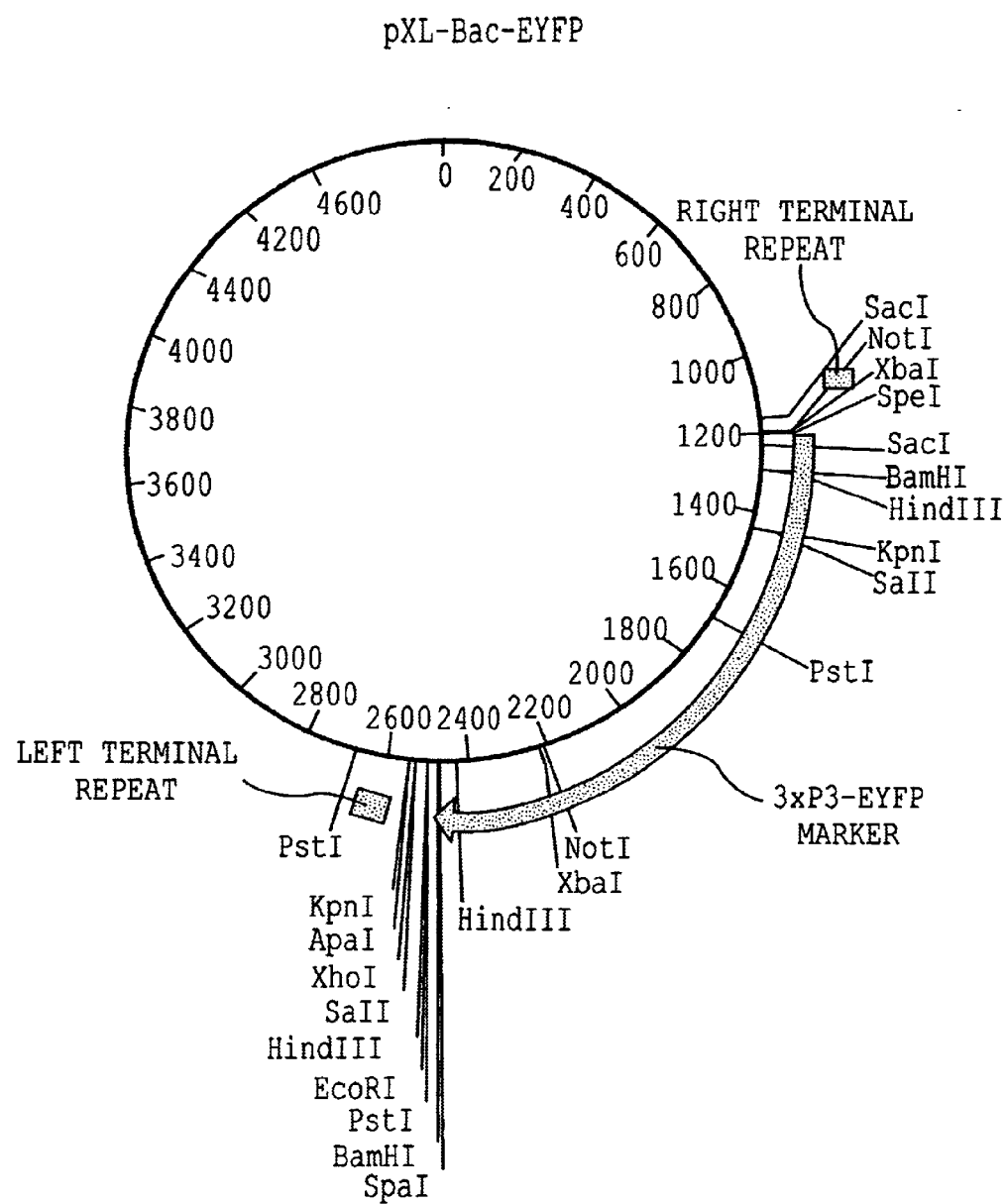
FIG. 15(A) is a plasmid map showing the 3xP3-EYFP gene was PCR amplified as an Spe I fragment from pBac [3xP3-EYFPafm] (Horn and Wimmer, 2000) and cloned into the Spe I site of the pXL-Bac plasmid to form the pXL-Bac-EYFP plasmid; (B) is the nucleotide sequence (SEQ ID NO: 51) of pXL-Bac-EYFP.
Figure 16A:
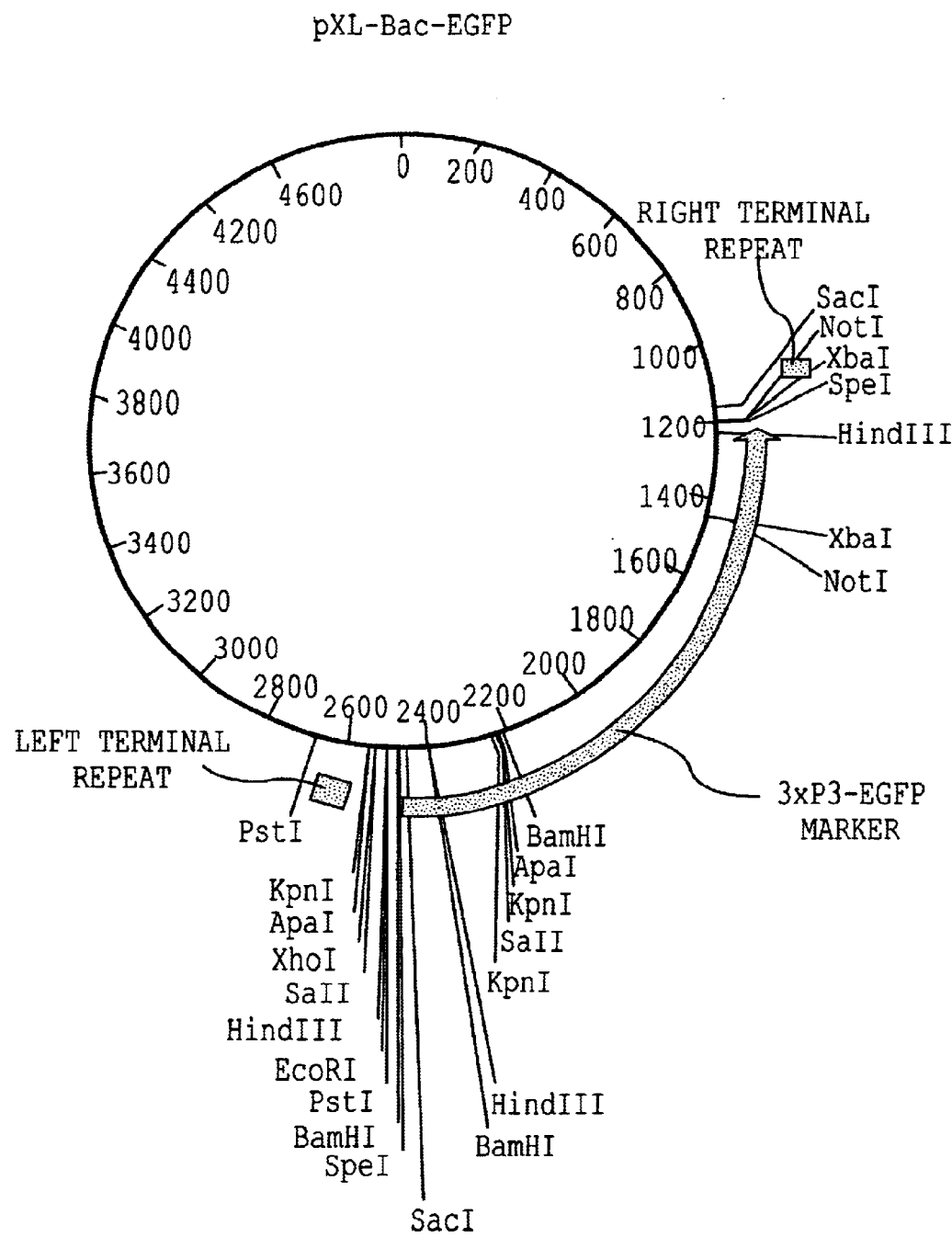
FIG. 16(A) is a plasmid map showing the 3xP3-EGFP gene was PCR amplified as an Spe I fragment from pBac [3xP3-EGFPafm] (Horn and Wimmer, 2000) and cloned into the Spe I site of the pXL-Bac plasmid to form the pXL-Bac-EGFP plasmid; (B) is the nucleotide sequence (SEQ ID NO: 52) of pXL-Bac-EGFP.
Figure 17A:
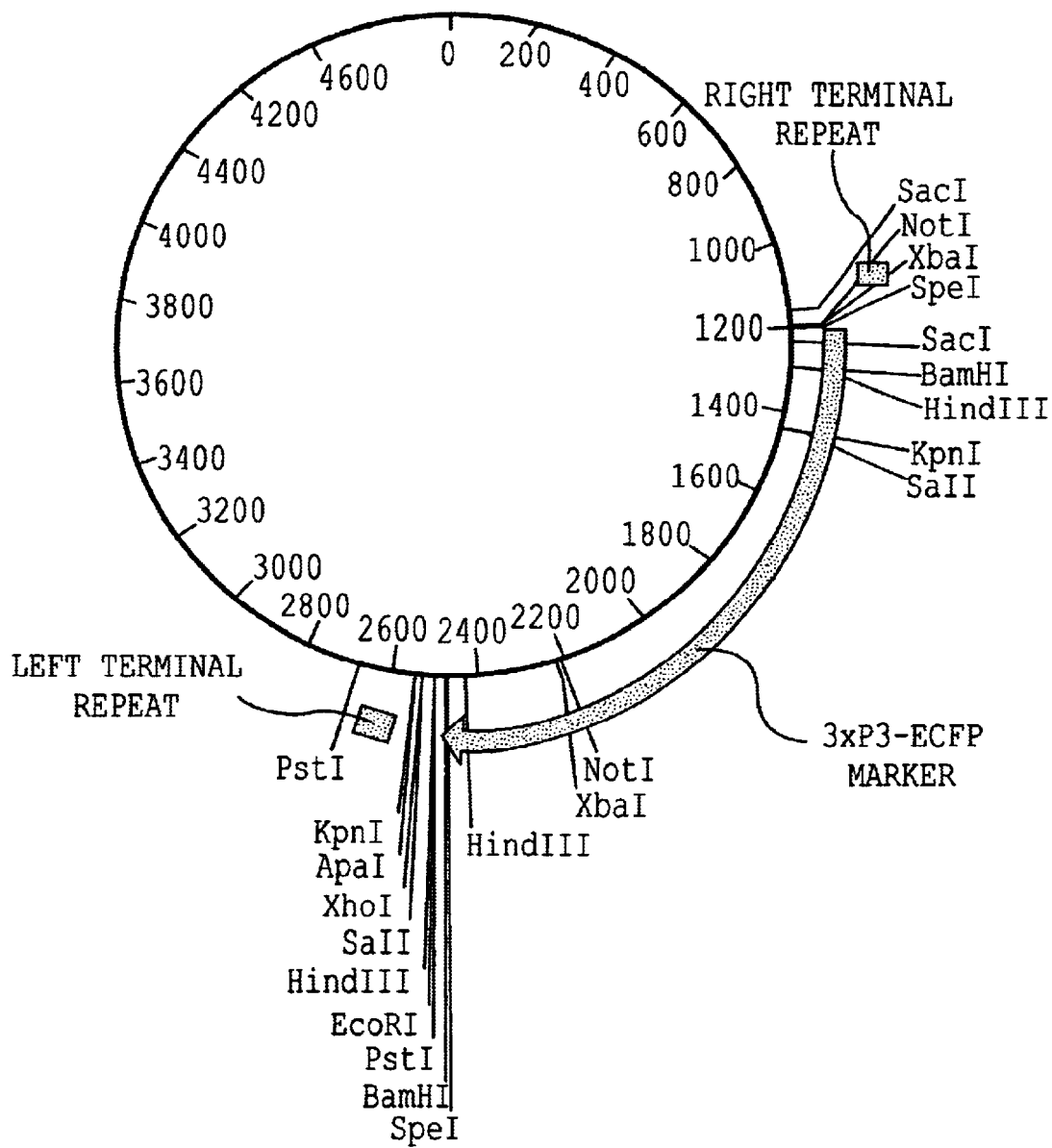
FIG. 17(A) is a plasmid map showing the 3xP3-ECFP gene was PCR amplified as an Spe I fragment from pBac [3xP3-ECFPafm] (Horn and Wimmer, 2000) and cloned into the Spe I site of the pXL-Bac plasmid to form the pXL-Bac-ECFP plasmid; (B) is the nucleotide sequence (SEQ ID NO: 53) of pXL-Bac-ECFP.

Using the pXL-Bac minimal vector, several derivative vectors can be constructed containing marker genes for detection of successful transformations. In one example, the vectors pXL-Bac-EYFP, pXL-Bac-EGFP, and pXL-Bac-ECFP (FIGS. 15–17) were assembled to contain the 3XP3 promoter driven flourescent protein genes of Horn and Wimrnmer (2000) by PCR amplifying these sequences from their respective piggyBac vectors using the primers E*FP-for (5' ACGACTAGTGTTCCCACAATGGTTAATTCG 3') (SEQ ID NO: 2) and E*FP-rev (5' ACGACTAGTGCCG-TACGCGTATCGATAAGC 3') (SEQ ID NO: 3) each terminating in an SpeI restriction endonuclease site, and inserting these fragments into the SpeI digested pXL-Bac vector at the unique SpeI site of the multiple cloning site. Vectors constructed in this fashion allow detection of successful transformation by the pXL-Bac vector, and can be further modified to include a separate gene of choice and suitable promoter adjacent to the marker gene in the multiple cloning site.

Example 6

Derivative Vectors of pCII-ITR or pBS-ITR

Figure 18A:
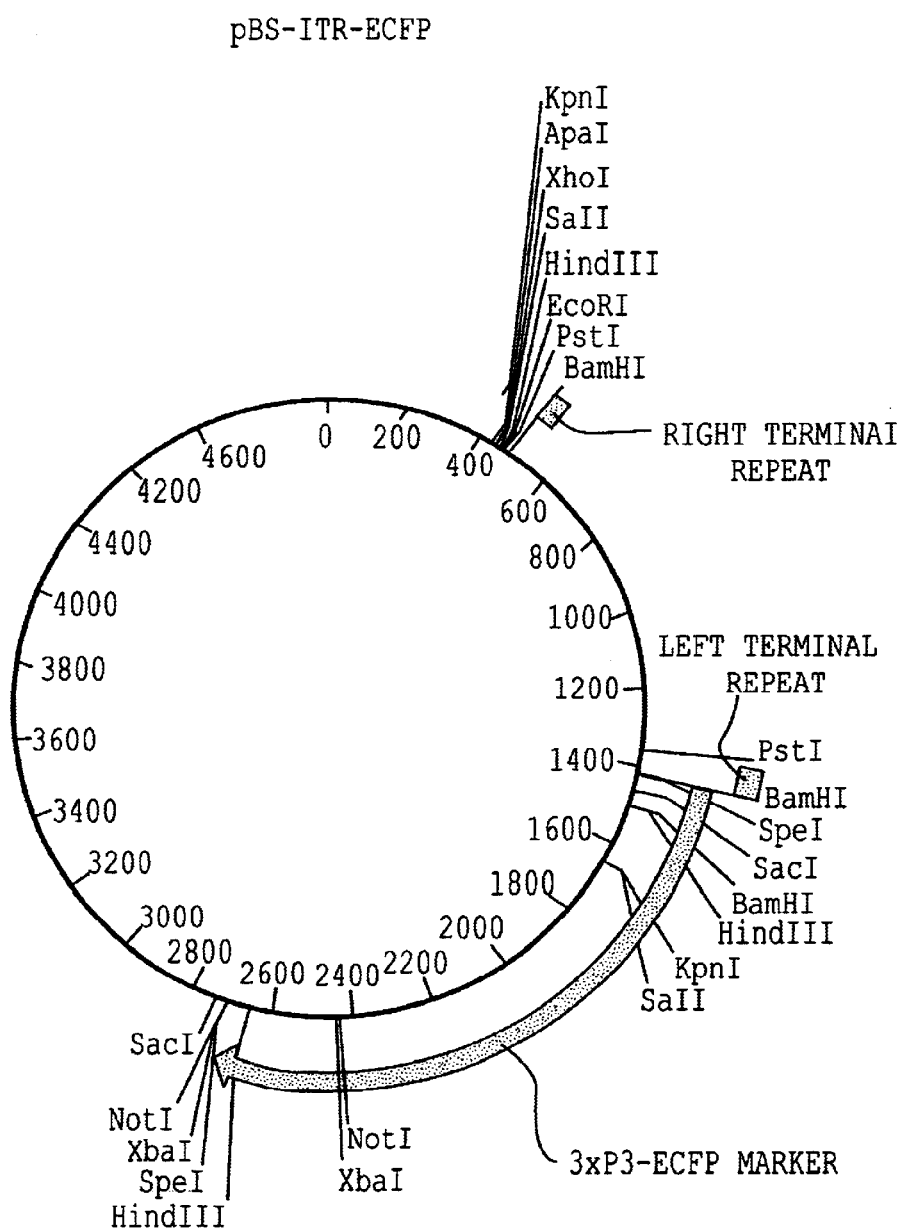
FIG. 18(A) is a plasmid map showing the 3xP3-ECFP was PCR amplified as an Spe I fragment from pBac[3xP3-ECFPafm] (Horn and Wimmer, 2000) and cloned into the Spe I site of the pBS-ITR plasmid to form the pBS-ITR-ECFP plasmid; (B) is the nucleotide sequence (SEQ ID NO: 54) of pBS-ITR-ECFP.
Figure 19A:
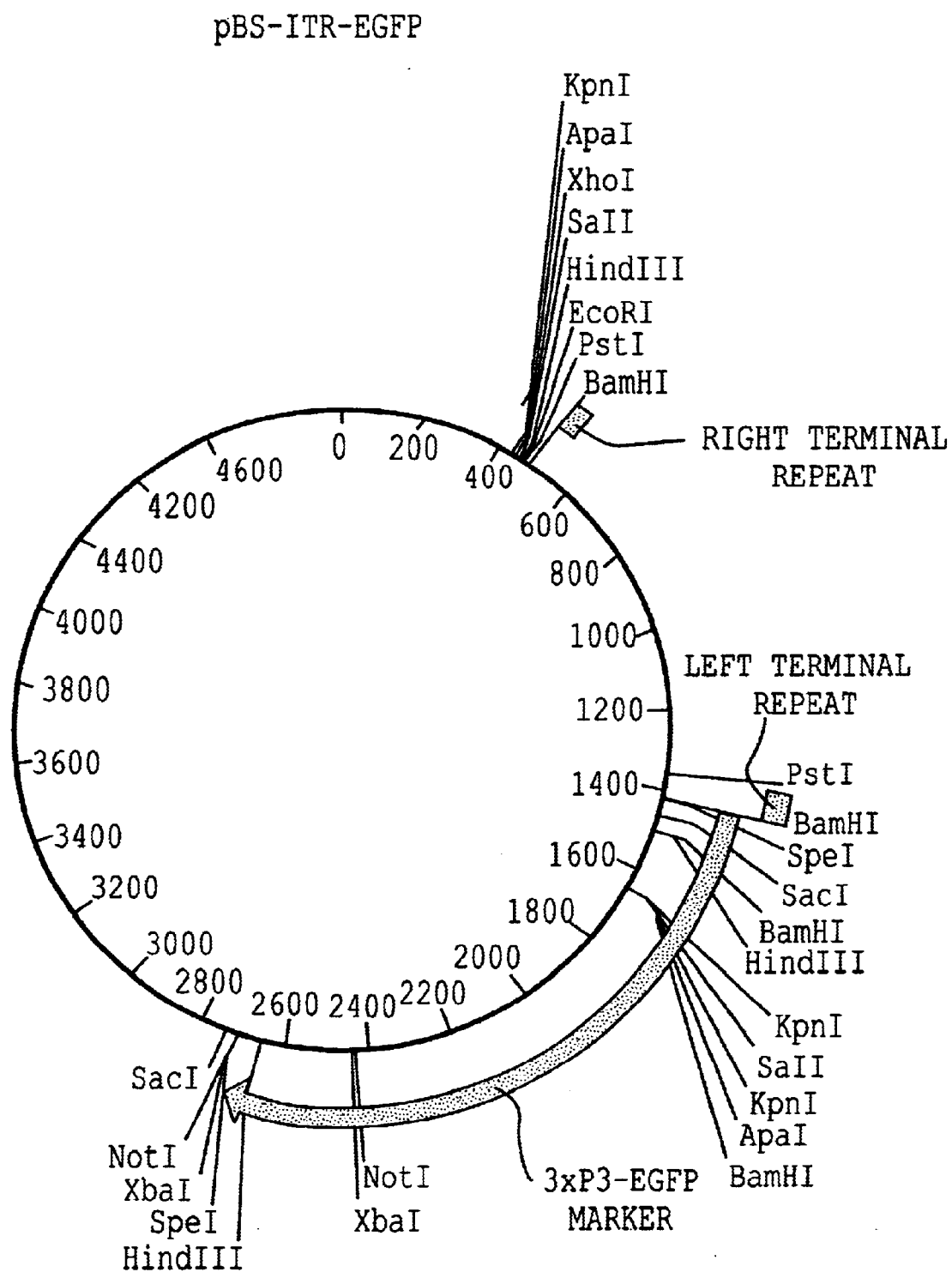
FIG. 19(A) is a plasmid map showing the 3xP3-EGFP was PCR amplified as an Spe I fragment from pBac[3xP3-EGFPafm] (Horn and Wimmer, 2000) and cloned into the Spe I site of the pBS-ITR plasmid to form the pBS-ITR-EGFP plasmid; (B) is the nucleotide sequence (SEQ ID NO: 55) of pBS-ITR-EGFP.
Figure 20A:
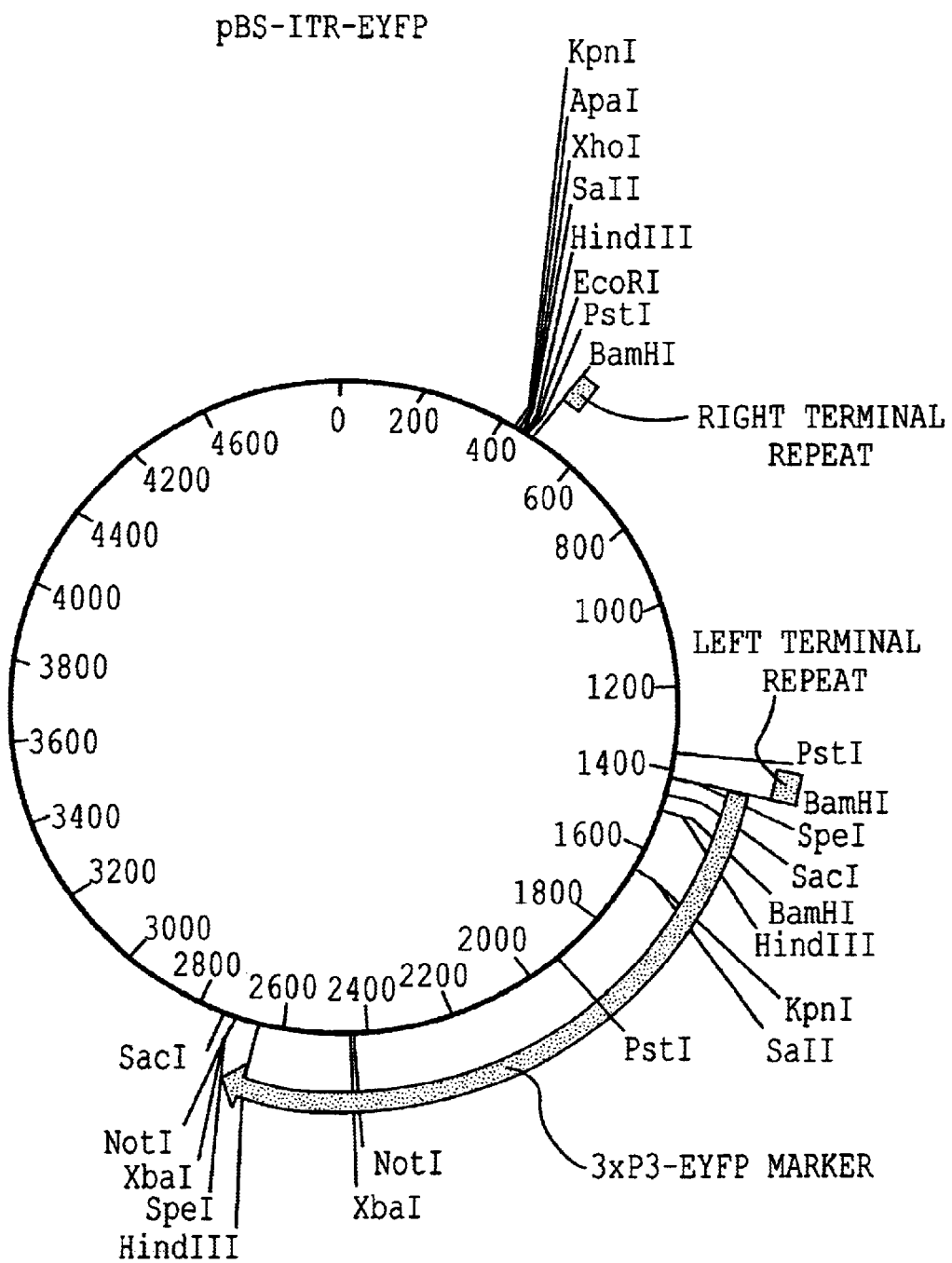
FIG. 20(A) is a plasmid map showing the 3xP3-EYFP was PCR amplified as an Spe I fragment from pBac[3xP3-EYFPafm] (Horn and Wimmer, 2000) and cloned into the Spe I site of the pBS-ITR plasmid to form the pBS-ITR-EYFP plasmid; (B) is the nucleotide sequence (SEQ ID NO: 56) of pBS-ITR-EYFP.

Similar modifications can be made to either the pCRII-ITR or the companion vector, pBS-ITR, by inserting a marker gene into the plasmid adjacent to the ITR cartridge of these plasmids. In one example, the plasmids pBS-ITR-ECFP, pBS-ITR-EGFP, and pBS-ITR-EYFP (FIGS. 18–20) were constructed using the strategy described in Example 5 to PRC amplify an SpeI fragment containing the marker genes from the Horn and Wimmer (2000) piggyBac vectors and insert them into the unique SpeI site of the pBS-ITR plasmid.

Example 7

Facilitating Expression of the Transposase

Expression of the transposase is essential in gaining movement of any of the vectors described here. To facilitate expression of the transposase, a BamHI cartridge containing only the piggyBac open reading frame sequences was PCR amplified from the piggyBac transposon clone p3E1.2 using the primers BamHI E-for1 (5' GCTTGATAAGAAGAG 3') (SEQ ID NO: 4) and BamHI E-rev1 (5' GCATGTTGCLT-GCTATT 3') (SEQ ID NO: 5). This cartridge was then cloned into the pCaSpeR-hs vector at a unique BamHI site downstream of the Drosophila heat shock promoter (pCaSpeR-hs-orf) to effect heat shock induced expression of the piggyBac transposase following co-injection with any piggyBac vector.

Example 8

In Vitro Expression of mRNA of piggyBac Transposase

Figure 6A:
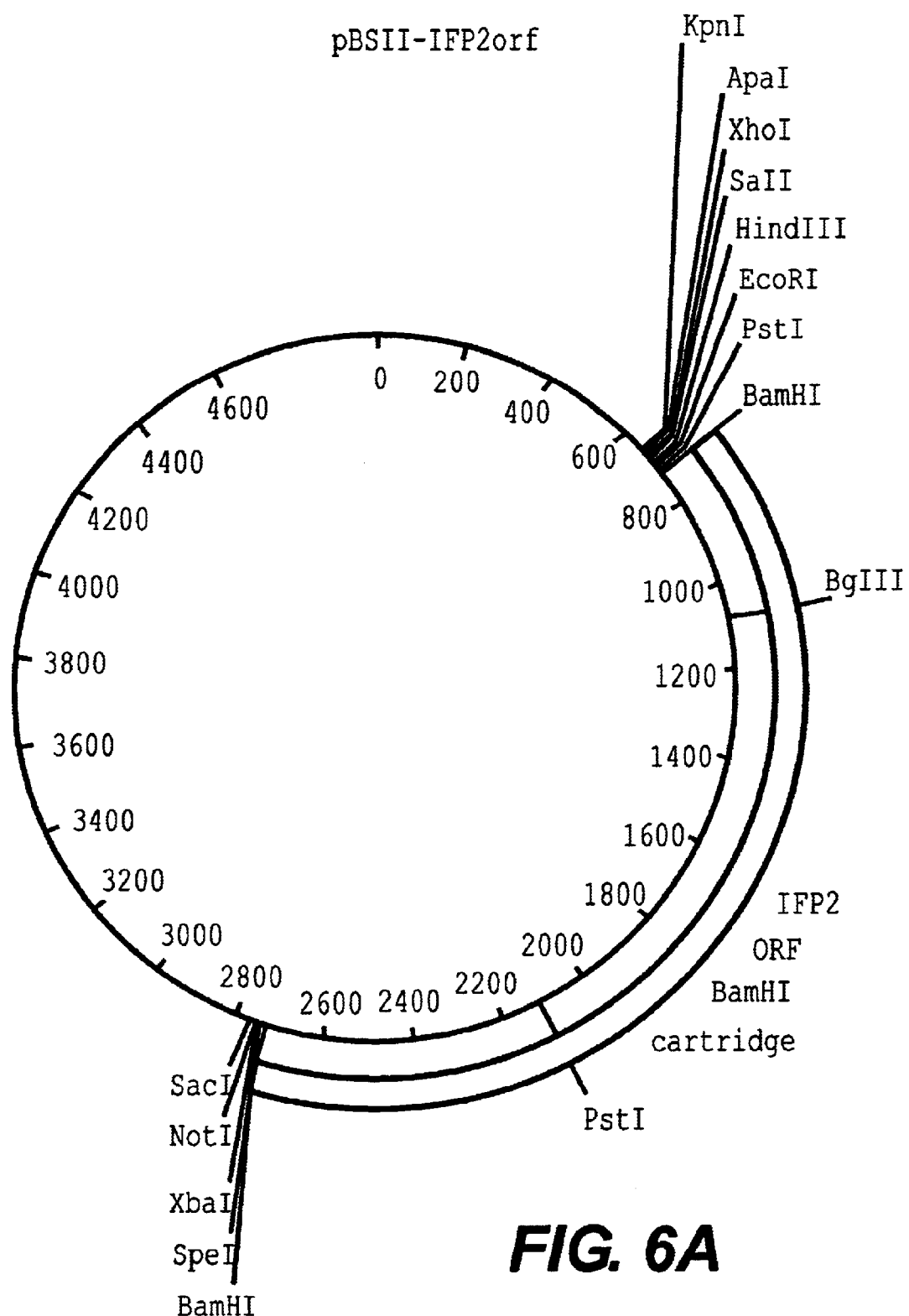
FIG. 6(A) is a plasmid map showing the piggyBac ORF BamH I cartridge from pCaSpeR-hs-orf was cloned into the pBSII (Stratagene) positioning it for transcription under control of the T7 promoter to form pBSII-IFP2orf; (B) is the nucleotide sequence (SEQ ID NO: 43) of pBSII-IFP2-orf.

In some eukaryotic systems, the heat shock promoter may not function to express the transposase protein. An additional plasmid was constructed to allow in vitro expression of the messenger RNA sequence of the piggyBac transposase. Co-injection of this mRNA into embryos along with the piggyBac vectors would allow translation of the piggy-Bac transposase without having to rely on the expression of the mRNA from a promoter which may or may not be active in the desired system. In addition, this strategy provides much more transposase protein in the embryos, leading to a greater mobility of the piggyBac vectors. The BamHI cartridge was excised from the plasmid pCaSpeR-hs-orf by restriction digestion with BamHI and ligated into a BamHI digested commercially available vector, pBSII (Stratagene) to make pBSII-IFP2orf (FIG. 6), allowing in vitro transcription of the piggyBac transposase mRNA under control of the bacteriophage T7 promoter.

Example 9

Alternative Promoters for the piggyBac Transposase Gene

Figure 7:
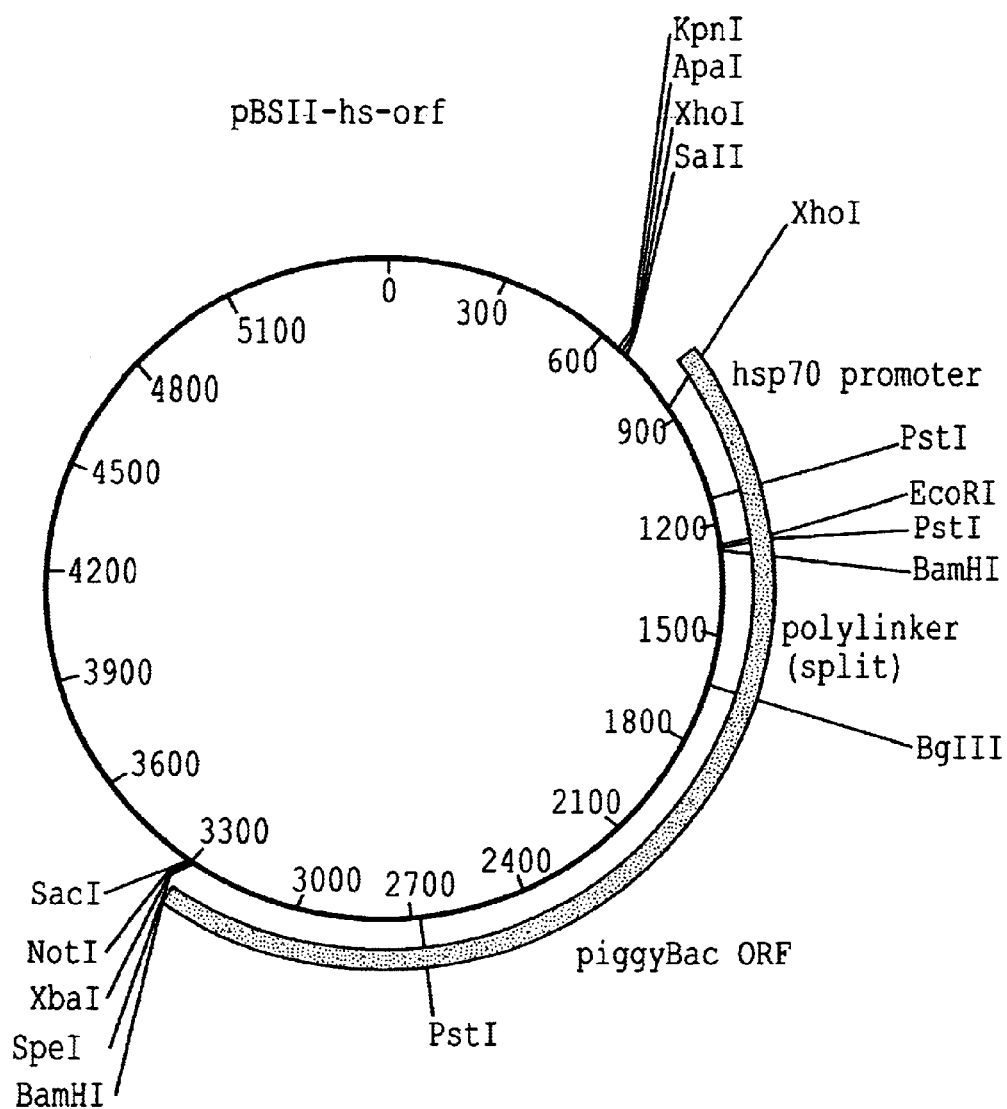
FIG. 7 is a plasmid map showing the hsp70 promoter was excised from the pCaSpeR-hs plasmid by EcoR I and EcoR V digestion, followed by blunt ending cloning in pBSII-IFP2orf at the EcoR I and Hind III (blunt ended) sites to form pBSII-hs-orf (SEQ ID NO: 43).
Figure 8A:
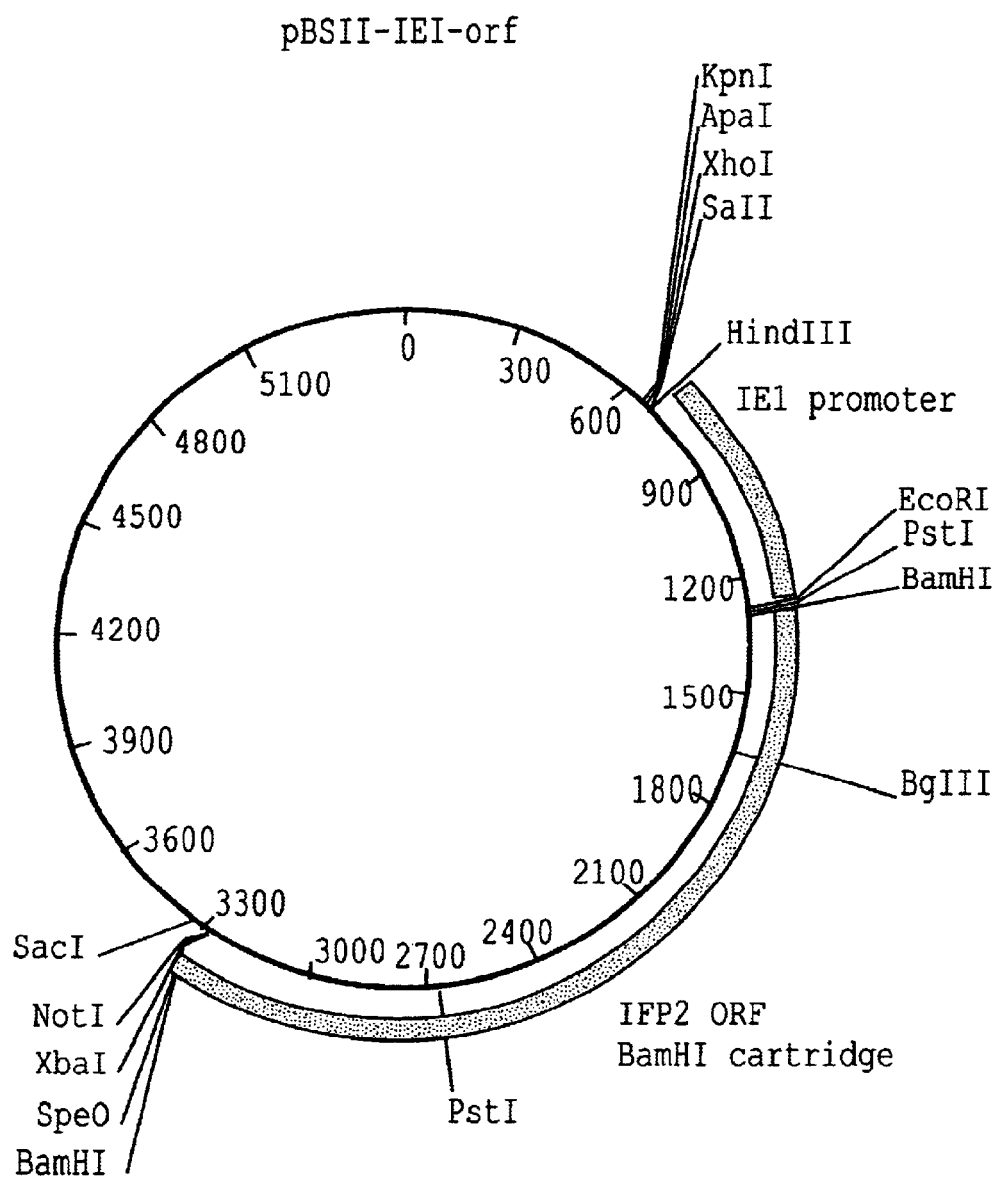
FIG. 8(A) is a plasmid map showing the IE1 promoter was PCR amplified from the pIE1FB plasmiid (Jarvis et al., 1990) and cloned into the pBSII-IFP2orf plasmid to from pBSII-IE1-orf; (B) is the nucleotide sequence (SEQ ID NO: 44) of pBSII-IE1-orf.
Figure 21A:
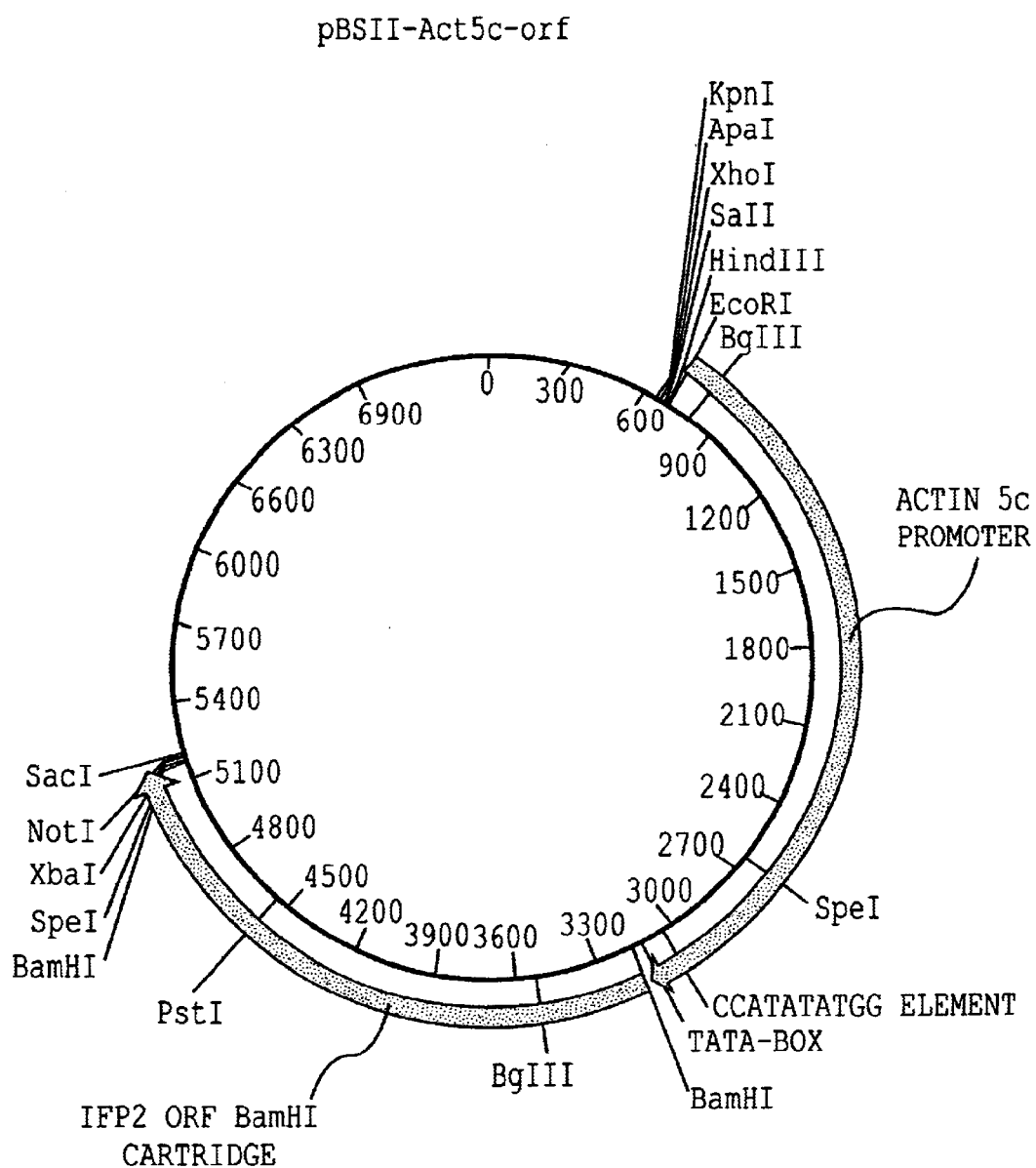
FIG. 21(A) is a plasmid map showing the Actin 5c promoter was cloned as a BamH I and Eco I fragment (bases 3046 to 3055 of SEQ ID NO: 67) from the pHAct5cEFGP plasmid (from Dr. Atkinson, UC Riverside) into the BamH I and EcoR I sites of the pBSII plasmid (Stratagene) to form the pBSII-Act5c plasmid. The piggyBac ORF BamH I cartridge from pCaSpeR-hs-orf was then cloned into pBSII-Act5c plasmid under control of the Act5c promoter; (B) is the nucleotide sequence (SEQ ID NO: 67) of pBSII-Act5c-orf.

Further modification of pBSII-IFP2orf can be effected to introduce alternative promoters that would drive expression of the piggyBac transposase gene. Three examples are provided. PBSII-hs-orf (FIG. 7) was constructed by excising the heat shock promoter region from pCaSpeR-hs using EcoRI and EcoRV digestion followed by blunt end polishing of the EcoRI terminus, and ligating the fragment to the blunt end polished EcoRI/HindIII digested pBSII-IFP2orf plasmid. The plasmid pBSII-E1-orf was prepared by PCR amplification of the IE1 promoter from the plasmid pIE1 FB using the primers IE1-Ac-for (5' ACGTAAGCTTCGATGTCT-TRGTGATGCGCC 3') (SEQ ID NO: 6) and IE1-Ac-rev (5' ACGGAATTCACTTGCAACTGAAACAATATCC 3') (SEQ ID NO: 7) to generate an EcoRI/HindIII tailed fragment that was then inserted into EcoRI and HindIII digested pBSII-IFP2orf. This plasmid allows constitutive expression of the piggyBac tuansposase in a diversity of eukaryotic systems. A final demonstration was prepared by digesting the plasmid pHAct5cEGFP (Pinkerton et al., 2000) with BamHI and EcoRI to recover the Actin 5c promoter which was then inserted into pBSII digested with EcoRI and BamHI. The BamHI cartridge from pCaSpeR-hs-orf was excised by digestion with BamHI and cloned downstream of the Actin 5c promoter at the unique BamHI site to form the plasmid pBSII-Act5c-orf (FIG. 21). This allows high level expression of the piggyBac transposase in embryos of insects.

Example 10

Transposase Exgression in Vertebrate Systems

Figure 9A:
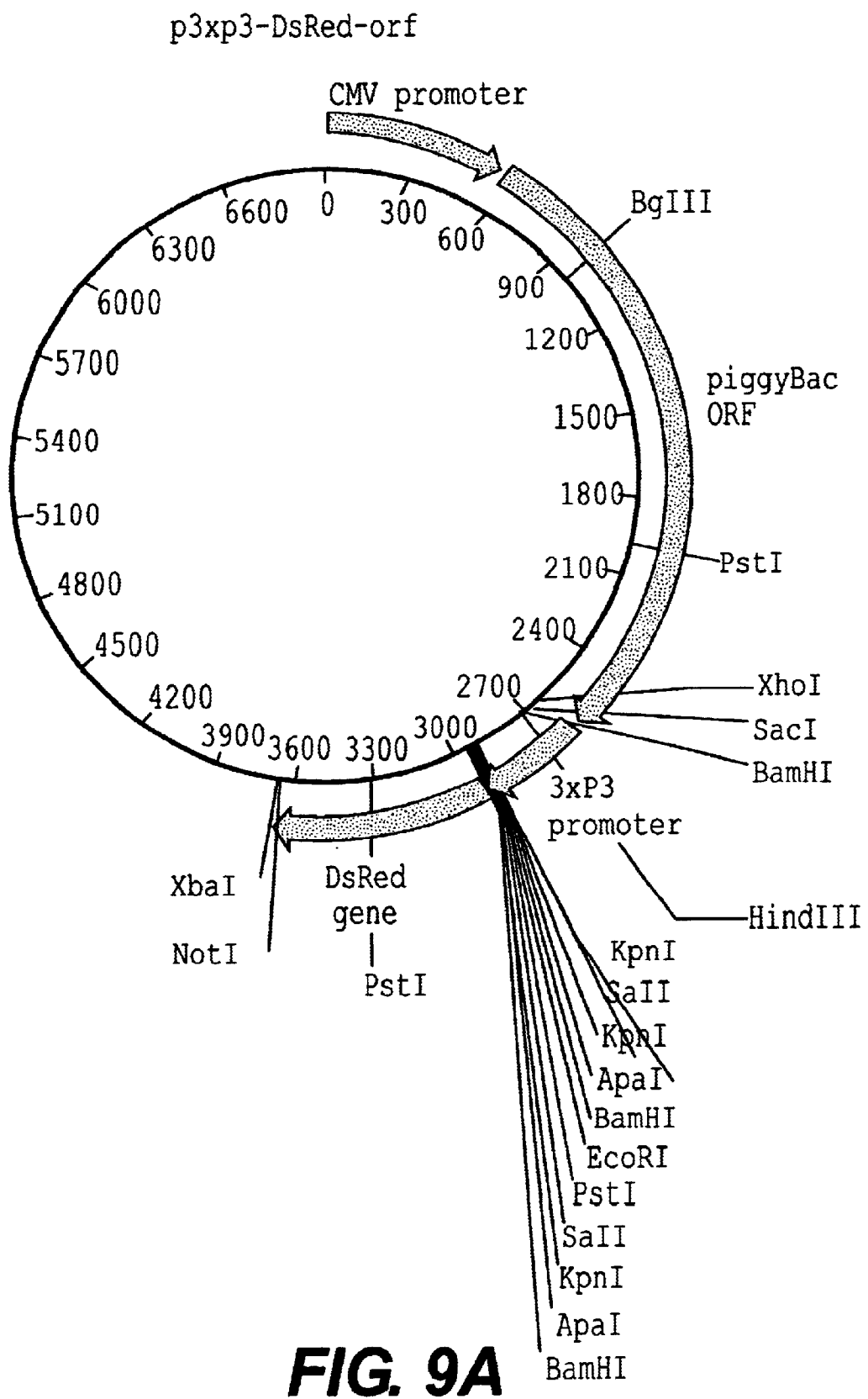
FIG. 9(A) is a plasmid map showing the base plasmid is pDsRed1-N1 (Clontech). The 3xP3 promoter was PCR amplified from pBac [3xP3-EYFPafm] (Horn and Wimmer, 2000) and cloned into the Xho I and EcoR I sites of pDsRed1-N1 to form the p3xP3-DsRed plasmid. The piggyBac ORF BamH I cartridge from pCaSpeR-hs-orf was then cloned into the Bgl II site of p3xP3 DsRed positioning it under control of the CMV (cytomegalovirus) promoter to form p3xP3-DsRed-orf; (B) is the nucleotide sequence (SEQ ID NO: 45) of p3xP3-DsRed-orf. DsRed is a marker from Invitrogen. pxP3 is a promoter specific for eyes of insects.

While all of the constructs in Example 9 permit expression of the transposase in insect systems, they may not permit optimal expression of the transposase in vertebrate systems. Using the commercially available pDsRed1-N1 plasmid (Clonetech) the BamHI cartridge was cloned from pBSII-IFP2orf into the BamHI site adjacent to the CMV promoter to effect efficient expression of the piggyBac transposase in vertebrate systems. This plasmid was fer modified by adding the 3XP3 promoter through PCR amplification of this promoter from the plasmid pBac[3XP3-EYFPafm] (Horn and Wimmer, 2000) using the primers 3XP3-for (5' ACTCTCGAGGTTCCCACAATGGITAAT-TCG 3') (SEQ ID NO: 8) and 3XP3-rev (5' ACTGAAT-TCATGGTGGCGACCGGTGGATCG 3') (SEQ ID NO: 9) to generate a XhoI/EcoRI tailed cartridge that was then cloned into the XhoI and EcoRI digested pDsRed1-N1 backbone to generate the plasmid p3XP3-DsRed-orf (FIG. 9).

Example 11

Optimizing piggyBac

In some cases it may be preferable to inject transposase protein to permit movement of the piggyBac transposon. The natural piggyBac transposase sequence is not efficiently expressed in prokaryotic systems due to a preponderance of eukaryotic codons. To achieve better expression of the piggyBac transposase in bacterial systems for purification and functional utility a sequence called optimized piggyBac orf (FIG. 23), substituting prokaryotic codon biases wherever possible. This sequence generated the same protein sequence, but represents an artificial gene expressing the piggyBac transposase.

Materials and Methods

Plasmids p3E1.2 deletion series: The p3E1.2 plasmid (Fraser et al., 1995) was first linearized using the restriction sites BamHI and EcoRI, blunt ended with the klenow fragment, then religated to construct the p3E1.2(DMCS) eliminating the MCS of the pUC18 sequence. Internal deletions were made using the Erase-A-Base System (Promega). p3E1.2(DMCS) was cut at the unique SacI site within the piggyBac element, generating an ExoIII resistant end, and then cut at the BglII site to generate an ExoIII sensitive end. Fractions of the ExoII deletion reaction from the BglII site toward the 3' terminus were stopped every 30 seconds, and were blunt ended by S1 nuclease, recircularized, and transformed into DH5a cells. Recovered plasmids were size analyzed using a quick screen method (Sekar, 1987). The presence of intact 3' termini was confirmed using a BsiWI digestion, and then sequencing. Nine consecutive plasmids in the size range of approximately 100–200 bp deletions were recovered and named p3E1.2-d-1 to p3E1.2-d-9, with p3E1.2-d-9 having the maximum deletion (FIG. 1).

pIAO-P/L series: The p3E1.2 B/X plasmid was constructed as a pCR II TA clone (Invitrogen) of the entire piggyBac transposon and flanking TTAA targets sites following PCR from the plasmid p3E1.2 using the BamHI/XbaI-tailed primer MF34 (5'-GGATCCTCTAGATTAACCCTAGAAAGATA-3') (SEQ ID NO: 10). The element and flanking TTAA sites were then excised using the enzyme BamHI and ligated to form a circular molecule. Two outward facing internal piggyBac primers, one with a terminal ApaI site (5'-GAAA GGGCCCGTGATACGCCTATTTTATAGGTT-3') (SEQ ID NO: 11) and the other with a terminaI KpnI site (5'-AATC GGTACCAACGCGCGGGGAGAGGCGGTTTGCG-3') (SEQ ID NO: 12), were used to generate a linear ApaI/KpnI-tailed fragment. This fragment was ligated to a PCR fragment containing the beta-lactamase gene and E. coli replication origin amplified from pUC18 using an ApaI-tailed primer (5'-CCAA GGGCCCTGAACCATTGTCACACGT-3') (SEQ ID NO: 13) and a KpnI tailed (5'-TGTGG GTACCGTCGATCAAACAAACGCGAGATACCG-3') (SEQ ID NO: 14) primer pair. The resulting pIAO plasmid contains the circularized piggyBac transposon with ends separated by an 18 bp fragment of DNA having the restriction sites configuration XbaI/BamHI/XbaI, with a beta-lactamase gene and the E. coli origin of replication. The lacZ gene under the control of the polyhedron promoter was excised from pD-2/B-gal (Fraser et al., 1996) using restriction enzymes NruI and DraI, and cloned into the unique HpaI site within the piggyBac element of pIAO to form pIAO-polh/lacZ (pIAO-P/L) plasmid.

The pIAO-P/L-TTAA1 plasmid was constructed by digesting pIAO-polh/lacZ with SphI and BsiWI, and the fragment containing the internal piggybac sequence was isolated. Two complementing oligonucleotides, SphI (5'-CGTCAATTTTACGCAGACTATCTTTCTAGGG-3') (SEQ ID NO: 15) and TTAA-SphI (5'-TTAACCCTAGAAAGATAGTCTGCG-TAAAATTGACGCATG -3') (SEQ ID NO: 16), were annealed to form a SphI site on one end and a TTAA overhang on the other end. A second pair of oligonucleotides, BsiWI (5'-GTACGTCACAATATGATTATCTTTCTAGGG-3') (SEQ ID NO: 17) and TTAA-BsiWI (5'-TTAACCCTAGAAAGATAATCATATTGTGAC-3') (SEQ ID NO: 18) were annealed to form a BsiWI site on one end and a TTAA overhang on the other. These two primer pairs were joined using the TTAA overlaps and inserted into the SphI and BsiWI sites of the digested pIAO-polh/lacZ plasmid to form the circular pIAO-PIL-TTAA1 plasmid.

The pIAO-P/L-TTAA2 plasmid was constructed in a similar manner by combining the SphI-terminal primer with TTAATTAA-SphI (5'-TTAATTAACCCTAGAAAGATAGTCTGCGTAAAATT GACGCATG-3') (SEQ ID NO: 19), and the BsiWI primer with TTAATTAA-BsiWI (5'-TTAATTAACCCTAGAAAGATAATCATATTGTGAC-3') (SEQ ID NO: 20).

The plasmids pIAO-P/L-2.2 kb, pIAO-P/L-589 bp, pIAO-P/L-354 bp, pIAO-P/L-212 bp and pIAO-P/L-73 bp were constructed by insertion of HindIII or PvuII fragments from the bacteriaphage lambda into the blunt ended XbaI site between the adjacent TTAA target sites of pIAO-polh/lacZ.

Plasmids pIAO-P/L-55 bp, pIAO-P/L40 bp and pIAO-P/L-22 bp plasmids were constructed by annealing oligonucleotide pIAO-4501 (5'-CTAGTACTAGTGCGCCGCGTACG TCTAGAGACGCGCAGTCTAGAAD-3') (SEQ ID NO: 21) and pIAO-4502(5'-TTCTAGACTGCGCGTC TCTAGACGTACGCGGCGCACTAGTACTAGD-3') (SEQ ID NO: 22), forming two XbaI sites and one SpeI site, and ligating them into the blunt ended pIAO-P/L XbaI fragment to generate pIAO-P/L-55 bp. The pIAO-P/L-40 bp plasmid was constructed by cutting pIAO-P/L-55 bp plasmid at the XbaI sites of the inserted fragment and then religating. Cutting pIAO-P/L-40 bp at the XbaI and SpeI sites, and religating formed the pIAO-P/L-22 bp plasmid.

The pIAO-P/L-18 bp plasmid was constructed by PCR amplification of the pIAO-P/L plasmid using the pIAO-18 bp primer (5'-GATGACCTGCAGTAGGAAGACGD-3') (SEQ ID NO: 23) and the TR-18 bp primer (5'-GAC TCTAGACGTACGCGGAGCSSSAACCCTAGAAAGAT AD-3') (SEQ ID NO: 24). The amplified fragment was cut with XbaI and PstI, and ligated to the pIAO-P/L bal and PstI cut fragment.

pCRII-ITR, pCRII-JF03/04 and pBS-ITR plasmids: The oligonucleotide ITR (5'-GGATTCCATGCGTCAATTTTACGCAD-3') (SEQ ID NO: 25), having the piggyBac IR and a terminal BamHI site, was used to PCR amplify the piggyBac 3' and 5' IRs and TRs along with their spacer regions from the pIAO-P/L-589 bp plasmid. The PCR fragment was TA cloned into pCRII (Invitrogen). The resulting plasmid, pCRII-ITR, replaces the entire internal sequence of piggyBac with the pCRII plasmid sequences. A second plasmid, pCRII-JF03/04, was constructed using the same strategy with the primers JF03 (5'-GGATCCTCGATATACAGACCGATAAAAACACATGD-3') (SEQ ID NO: 26) and JF04 (5'-GGTACCATTGCAAACAGCGACGGATTCGCGCTA TD-3') (SEQ ID NO: 27). JF03 is 83 bp internal to the 5' terminus, JF04 is 90 bp internal to the 3' terminus. To construct the pBS-ITR plasmid, the 702 bp BamHI fragment was excised from the pCRII-ITR plasmid and inserted into the BamHI site of the pBlueScript (Stratagene) plasmid.

pXL-Bac plasmid: The 702 bp fragment containing the piggyBac terminal repeats isolated from pCRII-ITR plasmid BamHI digestion was religated to form a circular molecule, followed by BssHII digestion. The pBlueScript II plasmid was also digested by BssHII and the large fragment was band isolated. These two fragments were ligated together to form the pBSII-ITR(Rev) plasmid. The Multiple Cloning Site(MCS) was PCR amplified from the pBSII plasmid using the MCS-for (5'-ACGCGT AGATCTTAATACGACTCACTATAGGG-3') (SEQ ID NO: 28) and MCS-rev (5'-ACGCGT AGATCTAATTAACCCTCACTAAAGGG-3') (SEQ ID NO: 29) primers, and cloned into BamHI site of pBSII-ITR (Rev) to construct the pXL-Bac plasmid.

The pXL-Bac minimum piggyBac vector was constructed by circularizing a ITR BamHI fragment, followed by BssHII digestion; the resulting BssHII fragment was then ligated to the pBlueScript II BssHII AMP/ori containing fragment; the multiple cloning site was PCR amplified from pBSII plasmid and inserted into BamHI site to form pXL-Bac vector; any desired gene can be inserted into the MCS [The BssHII fragment taken from pBSII (Stratagene)] to construct a piggyBac transposon.

Helper plasmid: phspBac (formerly pBhsDSac, Handler et al., 1998) is a transposase-providing helper plasmid that expresses the piggyBac ORF under the control of the *D. melanogaster* hsp 70 promoter.

Target plasmid pGDV1 is a *Bacillus subtilis* plasmid (Sarkar et al., 1997) containing a chloramphenicol resistance gene, and is incapable of replication in *E. coli* unless provided with a *E. coli* origin of replication.

Microinjection: *T. ni* embryos were collected approximately 2 hours post oviposition and microinjected as described by Lobo et al., (1999). After injection, the embryos were allowed to develop for one hour at room temperature, heat shocked at 37° C. for one hour, and allowed to recover at room temperature overnight. Plasmids were recovered using a modified Hirt (1967) extraction procedure.

Excision Assay: The excision assay was performed as described by Thibault et al., (1999). Precise excision events were confirmed by sequencing using a fluorescent labeled M13 reverse primer (Integrated DNA Technologies, Inc.).

Interplasmid Transposition Assay: The interplasmid transposition assay was performed as described by Lobo et al. (1999) and Sarkar et al. (1997). Plasmids isolated from the injected and heat-shocked embryos, as well as those passaged through *E. coli* only, were resuspended in 20 µl of sterile distilled water and 3 µl of the DNAs were then electroporated into of competent *E. coli* DH 10B cells (Gibco-BRL) (Elick et al., 1996a). A 1.0-ml aliquot of SOC (2% w/v Bactotryptone, 0.5% w/v Bacto yeast extract, 8.5 mM NaCl, 2.5 mM Kcl, 10 mM $MgCl_2$, 20 mM glucose) was added to the electroporated cells and the cells were allowed to recover at 37° C. for 15 min. An aliquot (1%) of the transformed bacteria was plated on LB plates containing ampicilin (100 µg/ml) and X-Gal (5-bromo-4-chloro-3-indolyl-β-D-galactosidase; 0.025 µg/ml), and the rest were plated on LB plates containing kanamycin (10 µg/ml), chloramphenicol (10 µg/ml) and X-Gal (0.025 µg/ml). Restriction analysis using HindIII and EcoRV and PCR using outward facing primers specific to piggyBac (JF01:

5'-CCTCGATATACAGACCGATAAAACACATG-3' (SEQ ID NO: 30) and JF02: 5'-GCACGCCTCAGCCGAGCTCCAAGGGCGAC-3') (SEQ ID NO: 31) enabled the preliminary identification of clones with putative interplasmid transposition events. The right insertion site of the clones was sequenced, with the Thermo Sequenase fluorescence-labeled primer sequencing kit (AMersham) and an ALF Express Automated Sequencer (Pharmacia Biotech), using the fluorescence-labeled JF02 primer, while the left insertion site was sequenced with the MF 11 reverse primer (5'-GGATCCCTCAAAATTTCTTCTAAAGTA-3') (SEQ ID NO: 32)

To check for plasmid replication in the embryos, Hirt-extracted plasmid DNAs recovered from injected *D. melanogaster* embryos were digested with the restriction enzyme DpnI (Geier and Modrich, 1979). *E. coli* cells were transformed with equal volumes of the digested and undigested plasmid DNAs and plated on LB plates containing kanamycin, chloramphenicol and X-Gal as above.

The pIAO-P/L series transposition events were sequenced using the fluorescent labeled MF11-recverse primer (5'-GGATCCCTCAAATTTCTTCTAAAGTA-3') (SEQ ID NO: 33) and JF02 primer (5'-GCACGCCTCAGCCCGAGCTCCAAGCGGGGAC-3') (SEQ ID NO: 34), and the pCRII-ITR and pBSII-ITR transposition events were sequenced using fluorescent labeled M13 recerse primer.

Automatic Thermocycle Sequencing: Sequencing was performed using the Thermo Sequenase Fluorescent Labeled Primer Sequencing Kit (Amersham Life Science) and the ALF Express Automated Sequencer (Pharmacia Biotech), following standard protocols provided by the manufacturers.

Figure 12:
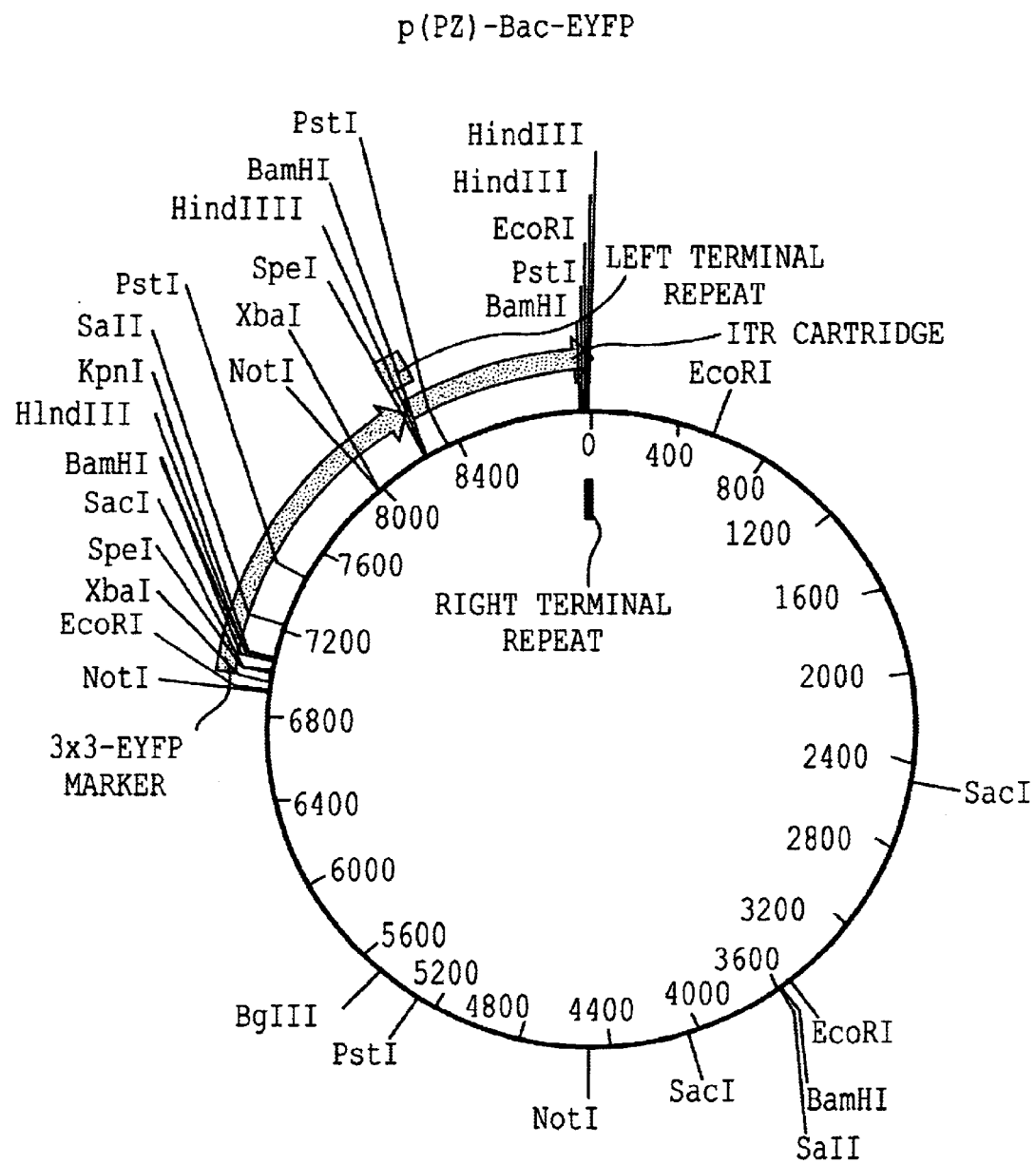
FIG. 12(A) is a plasmid map showing the P element enhancer trap plasmid pP {PZ} (from Dr. O'Tousa, Univ. of Notre Dame) was digested with Hind III then self-ligated to produce the p(PZ)-HindIII plasmid. The ITR cartridge was excised using Sal I and Not I (blunt-ended) from pCRII-ITR and then cloned into the blunt ended Hind III site to form p(PZ)-Bac. The 3xP3-EYFP was PCR amplified as an Spe I fragment from pBac[3xP3-EYFPafm] (Horn and Wimmer, 2000) and cloned into Spe I site of p(PZ)-Bac plasmid to form the p(PZ)-Bac-EYFP plasmid; (B) is the nucleotide sequence (SEQ ID NO: 48) of p(PZ)-Bac-EYFP.
Figure 13A:
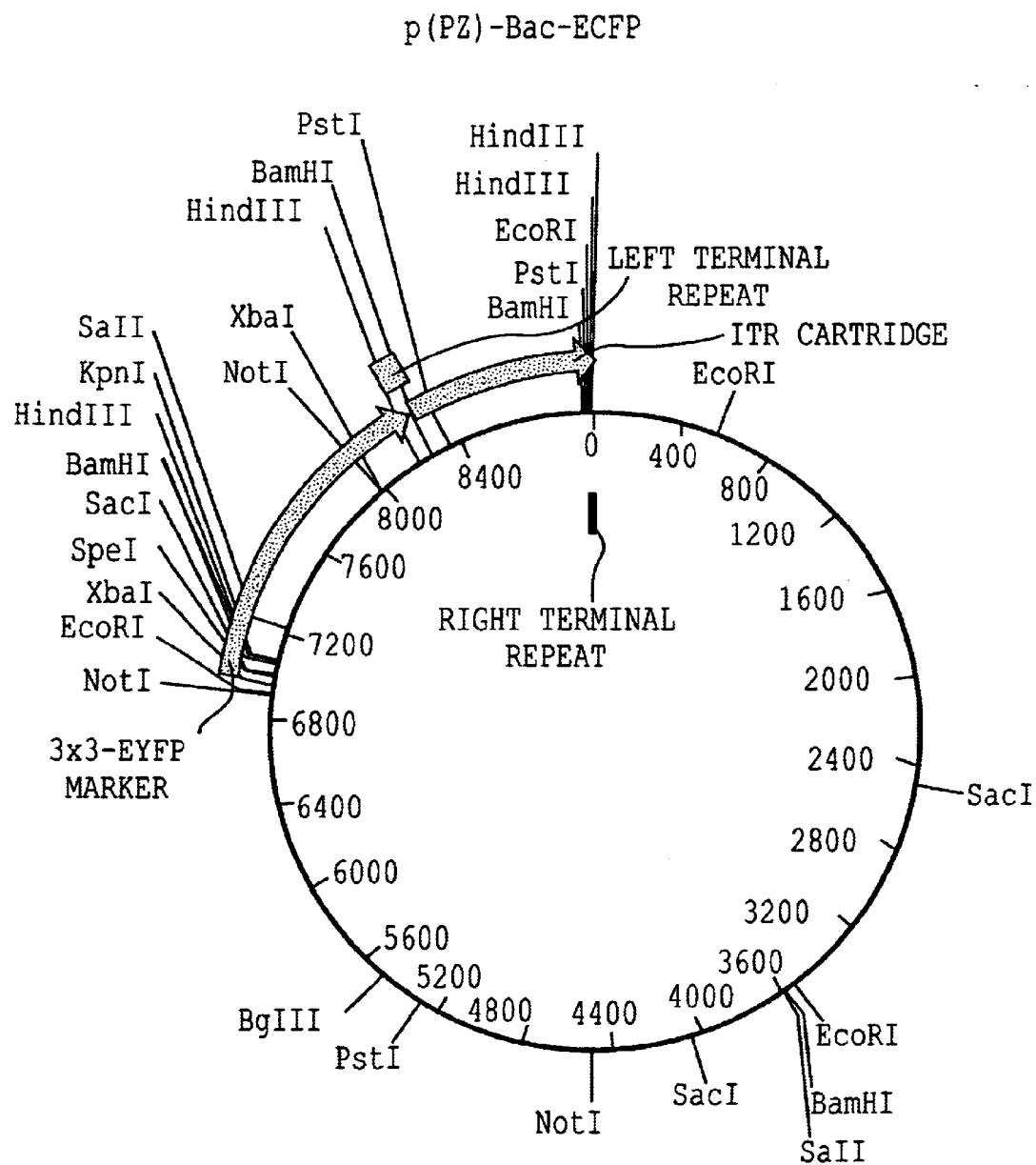
FIG. 13(A) is a plasmid map showing the P element enhancer trap plasmid pP {PZ} (from Dr. O'Tousa, Univ. of Notre Dame) was digested with Hind III then self-ligated to produce the p(PZ)-HindIII plasmid. The ITR cartridge was excised using Sal I and Not I (blunt ended) from pCRII-ITR and then cloned into the blunt ended Hind III site to form p(PZ)-Bac. The 3xP3-ECFP was PCR amplified as an Spe I fragment from pBac[3xP3-ECFPafm] (Horn and Wimmer, 2000) and cloned into the Spe I site of the p(PZ)-Bac plasmid to form the p(PZ)-Bac-ECFP lasmid; (B) is the nucleotide sequence (SEQ ID NO: 49) of p(PZ)-Bac-ECFP.
Figure 14A:
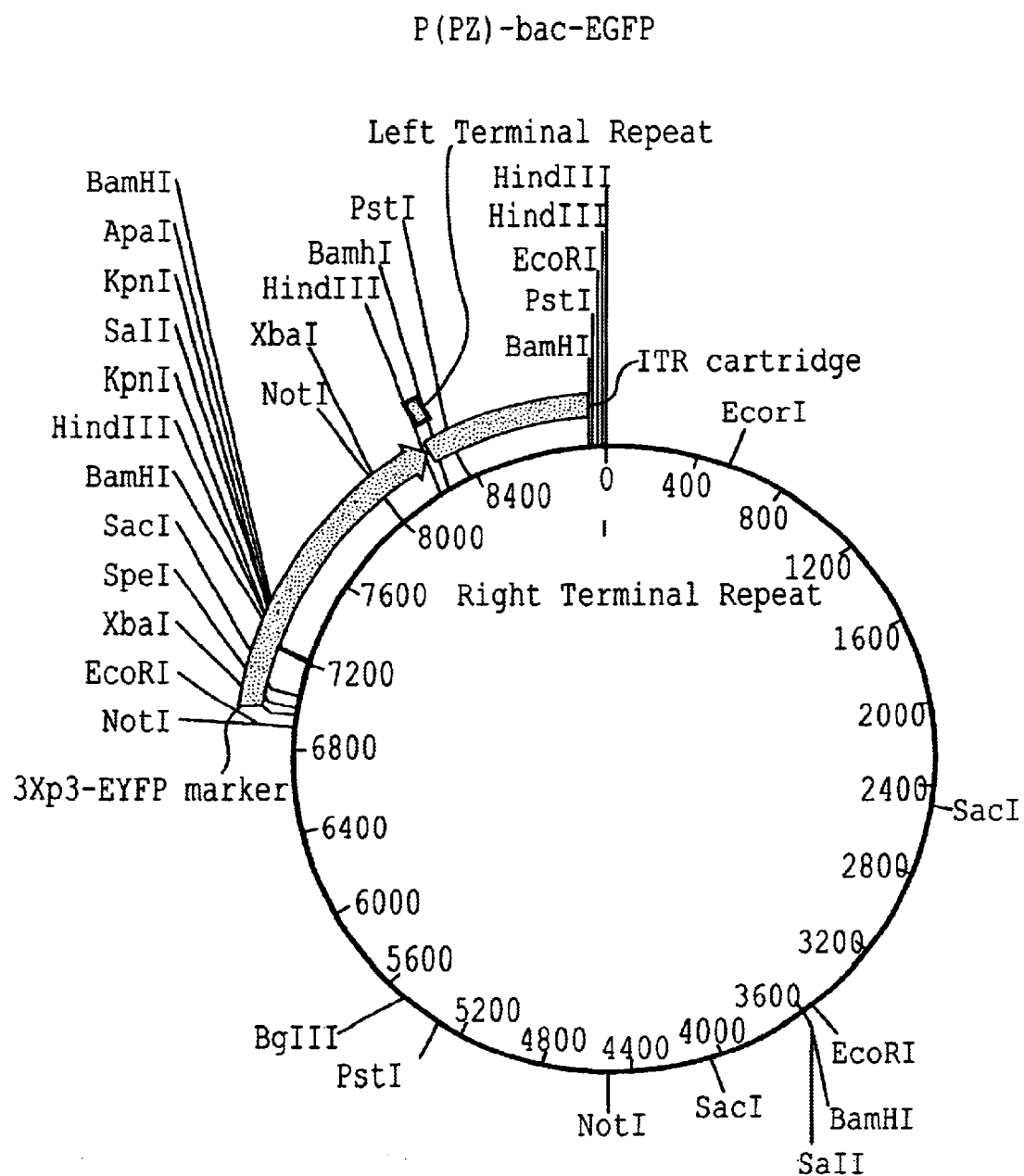
FIG. 14(A) is a plasmid map showing the P element enhancer trap plasmid pP {PZ} (from Dr. O'Tousa, Univ. of Notre Dame) was digested with Hind III then self-ligated to produce the p(PZ)-HindIII plasmid. The ITR cartridge was excised using Sal I and Not I (blunt ended) from pCRII-ITR and then cloned into the blunt ended Hind III site to form p(PZ)-Bac. The 3xP3-EGFP was PCR amplified as an Spe I fragment from pBac[3xP3-EGFPafm] (Horn and Wimmer, 2000) and cloned into the Spe I site of the p(Z)-Bac plasmid to form the p(PZ)-Bac-EGFP plasmid; (B) is the nucleotide sequence (SEQ ID NO: 50) of p(PZ)-Bac-EGFP.

Other Plasmids: FIGS. 12, 13 and 14 present alternative plasmids that may be useful for gene transfer.

DOCUMENTS CITED

Sections of the following that are relevant to the invention are incorporated by reference.

Berghamnmer, A. I., Klingler, M., Wimmer, E. A., 1999 A universal marker for transgenic insects. Nature 402: 370–371.

Cary, L. C., Goebel, M. J., Corsaro, B. G., Wang, H. G., Rosen, E. and Fraser, M. J., 1989 Transposon mutagenesis of Baculoviruses: analysis of *Trichoplusia ni* transposon IFP2 insertions within the FP-locus of nuclear polyhedrosis viruses. Virology 172: 156–169.

Elick, T. A., Bauser, C. A., Principe, N. M., Fraser, M. J., 1996a PCR analysis of insertion site specificity, transcription, and structural uniformity of the Lepidopteran transposable element piggyBac (IFP2) in the TN-368 cell genome. A Genetica 97: 127–139.

Elick, T. A., Bauser, C. A., Fraser, M. J., 1996b Excision of the piggyBac transposable element in vitro is a precise event that is enhanced by the expression of its encoded transposase. Genetica 98: 33–41.

Elick, T. A., Lobo, N, Fraser, M. J., 1997 Analysis of the cis-acting DNA elements required for piggyBac transposable element excision. Mol. Gen. Genet. 255: 605–610.

Fraser, M. J., Smith, G. E. and Summers, M. D., 1983 Acquisition of host cell DNA sequences by baculoviruses: Relationship between host DNA insertions and FP mutants of *Autograplia californica* and *Galleria mellonella* nuclear polyhedrosis viruses. J. Virol. 47: 287–300.

Fraser, M. J., Cary, L., Boonvisudhi, K. and WANG, H. H., 1995 Assay for movement of Lepidopteran transposon IFP2 in insect cells using a baculovirus genome as a target DNA. Virology 221: 397–407.

Fraser, M. J., Ciszczon, T., Elick, T., and BAUSER, C., 1996 Precise excision of TTAA-specific Lepidopteran transposons piggyBac (IFP2) and tagalong (TFP3) from the baculovirus genome in cell lines from two species of Lepidoptera. Insect Mol. Biol. 5: 141–151.

Geier and Modrich, 1979.

Goryshin, I. Y., Kil, Y. V., Reznikoff, W. S., 1994 DNA length, binding, and twisting constraints on IS50 transposition. Proc. Natl. Acad. USA 91: 10834–10838.

Handler, A. M., McCombs, S. D., Fraser, M. J., Saul, S. H., 1998 The Lepidopteran transposon vector piggyBac, mediates germ line transformation in the Mediterranean fruit fly. Proc. Natl. Acad. Sci. USA 95: 7520–7525.

Handler, A. M., Harrell, R. A., 1999 Germline transformation of *Drosophila melanogaster* with the piggyBac transposon vector. Insect Mol. Biol. 8: 449–57.

Hirt, B., 1967. Selective extraction of polyoma DNA from infected mouse cell cultures. *J. Mol. Bio.* 26: 367–369.

Horn, C. and Wimmer, E. A., 2000. A versatile vector set for animal transgenesis. *Dev. Genes Evol.* 210: 630–637.

Jarvis et al., 1990.

Lobo, N., Li, X., Fraser, M. J., 1999 Transposition of the piggyBac element in embryos of *Drosophila melanogaster, Aedes aegypti* and *Trichoplusia ni*. Mol. Gen. Genet. 261: 803–810.

Sambrook, J., Fritsch, E. F., and Maniatis, T., 1989. Molecular Cloning: A Laboratory Manual (New York: Cold Spring Harbor Press).

Sarkar, A., Yardley, K., Atkinson, P. W., James, A. A., O'Brochta, D. A., 1997 Transposition of the Hermes Element in Embryos of the vector mosquito, *Aedes aegypti*. Insect Biochem. Mol. Biol. 27: 359–363.

Sekar, V., 1987 A rapid screening procedure for the identification of recombinant bacterial clones. BioTechniques 5: 11–13.

Tamura, T., Thibert, C., Royer, C., Kanda, T., Abraham, E., Kamba, M., Komoto, N., Thomas, J. L., Mauchamp, B., Chavancy, G., Shirk, P., Fraser, M. J., Prudhomme, J. C., and Couble, P., 2000 Germline transformation of the silkworm *Bombyx mor L*. using a piggyBac transposon-derived vector. Nature Biotechnology 18: 81–84.

Thibault, S. T., Luu, H. T., Vann, N., Miller, T. A., 1999 Precise excision and transposition of piggyBac in pink bollworm embryos. Insect Mol. Biol. 8: 119–23.

Wang, H. H., Fraser, M. J.,1993 TTAA serves as the target site for TFP3 Lepidopteran insertions in both nuclear polyhedrosis virus and *Trichoplusia ni* genomes. Insect Mol. Biol. 1: 109–116.

We claim:
1. A plasmid designated pBSII-IFP2-orf.
2. A plasmid comprising the nuclcotide sequence of SEQ ID NO: 43.
3. A kit comprising a plasmid comprising the nucleotide sequence of SEQ ID NO: 43.

* * * * *